US006482403B1

(12) United States Patent
Sim et al.

(10) Patent No.: US 6,482,403 B1
(45) Date of Patent: Nov. 19, 2002

(54) CANINEY IL-13 IMMUNOREGULATORY PROTEINS AND USES THEREOF

(75) Inventors: Gek-Kee Sim, Fort Collins, CO (US); Shumin Yang, Palo Alto, CA (US); Matthew J. Dreitz; Ramani S. Wonderling, both of Fort Collins, CO (US)

(73) Assignee: Heska Corporation, Fort Collins, CO (US)

( * ) Notice: Subject to any disclaimer, the term of this patent is extended or adjusted under 35 U.S.C. 154(b) by 0 days.

(21) Appl. No.: 09/451,527

(22) Filed: Dec. 1, 1999

(Under 37 CFR 1.47)

Related U.S. Application Data

(63) Continuation-in-part of application No. 09/322,409, filed on May 28, 1999

(60) Provisional application No. 60/087,306, filed on May 29, 1998.

(51) Int. Cl.[7] ........................ A61K 45/00; C12P 21/06; C07K 1/00; C07H 21/04

(52) U.S. Cl. .................... 424/85.2; 424/85.1; 435/69.1; 530/350; 530/351; 536/23.1; 536/23.5

(58) Field of Search .............................. 536/23.1, 23.5; 435/320.1, 325, 69.1, 455; 514/2; 424/85.1, 85.2; 530/350, 351

(56) References Cited

U.S. PATENT DOCUMENTS 5,831,023 A 11/1998 Capon et al. ............... 530/351

FOREIGN PATENT DOCUMENTS

| | | | |
|---|---|---|---|
| EP | 0 186 098 | A1 | 7/1986 |
| EP | 0 322 870 | A2 | 7/1989 |
| EP | 0 414 355 | A1 | 2/1991 |
| EP | 0 759 468 | A1 | 2/1997 |
| EP | 0 875 251 | A1 | 11/1998 |
| WO | WO 99/61618 | | 12/1999 |

OTHER PUBLICATIONS

McKenzie et al., Interleukin 13, a T–cell–derived cytokine that regulates human monocyte and B–cell function, 1993, Proc. Natl. Acad. Sci. USA, vol. 90, pp. 3735–3739.*

A. McKenzie, Regulation of T helper type 2 cell immunity by interleukin–4 and interleukin–13, 2000, Pharmacology & Therapeutics, vol. 88, pp. 143–151.*

Minty et al., Interleukin–13 is a new human lymphokine regulating inflammatory and immune responses, 1993, Nature, vol. 362, pp. 248–250.* van der Kaaij, Molecular cloning and sequencing of the cDNa for dog interleukin–4, 1999, Immunogenetics, vol. 49, pp. 142–143.*

Lakkis, et al., 1997, *Biochemical and Biophysical Research Communications,* vol. 235, pp. 529–532.

de Vries, Jan. E., 1998, *J Allergy Clin Immunol,* vol. 102, pp. 165–169.

Muchamuel, et al., 1997, *The Journal of Immunology,* vol. 158, pp. 2898–2903.

Ueda, et al., 1993, *Journal of Veterinary Medical Science,* vol. 55, No. 2, pp. 251–258, XP001001462.

Armitage et al., *Seminars in Immunology,* vol. 5, 1993, pp. 401–412.

Armitage et al., *Nature,* vol. 357, 1992, pp. 80–82.

Azuma et al., *Nucleic Acids Research,* vol. 14, No. 22, 1986, pp. 9149–9158.

Brown et al., *Journal of Immunology,* vol. 142, No. 2, 1989, pp. 679–687.

Cantrell et al., *Proc. Natl., Acad. Sci. USA,* vol. 82, 1985, pp. 6250–6254.

Daugherty et al., *Journal of Interferon Research,* vol. 4, 1984, pp. 635–643.

Dion et al., *Biochemical and Biophysical Research Communications,* vol. 138, No. 2, 1986, pp. 826–834.

Drexler, *Leukemia,* vol. 10, 1996, pp. 588–599.

Feng et al., *J. Mol. Evol.,* vol. 21, 1985, pp. 112–125.

Gauchat et al., *Res. Immunol.,* vol. 145(3), Mar.–Apr. 1994, pp. 240–249.

Gauchat et al., *FEBS 11964,* vol. 315, No. 3, 1993, pp. 259–266.

Goeddel et al., *Nature,* vol. 290, 1981, pp. 20–26.

Gough et al., *The EMBO Journal,* vol. 4, No. 3, 1985, pp. 645–653.

Graf et al., *Eur. J. Immunol.,* vol. 22, 1992, pp. 3191–3194.

Grimaldi et al., *Journal of Immunology,* vol. 149, No. 12, 1992, pp. 3921–3926.

Hannum et al., *Nature,* vol. 368, 1994, pp. 643–648.

Heussler et al., *Gene,* vol. 114, 1992, pp. 273–278.

Himmler et al., *Journal of Interferon Research,* vol. 7, 1987, pp. 173–183.

Hirano et al., *Immunology,* vol. 90, 1997, pp. 294–300.

Hollenbaugh et al., *The EMBO Journal,* vol. 11, No. 12, 1992, pp. 4313–4321.

(List continued on next page.)

*Primary Examiner*—Scott D. Priebe
*Assistant Examiner*—Sumesh Kausual
(74) *Attorney, Agent, or Firm*—Heska Corporation

(57) ABSTRACT

The present invention relates to canine interleukin-4, canine or feline Flt-3 ligand, canine or feline CD40, canine or feline CD154, canine interleukin-5, canine interleukin-13, feline interferon alpha, and/or feline GM-CSF proteins; to canine interleukin-4, canine or feline Flt-3 ligand, canine or feline CD40, canine or feline CD154, canine interleukin-5, canine interleukin-13, feline interferon alpha, and/or feline GM-CSF nucleic acid molecules, including those that encode canine interleukin-4, canine or feline Flt-3 ligand, canine or feline CD40, canine or feline CD154, canine interleukin-5, canine interleukin-13, feline interferon alpha, and/or feline GM-CSF proteins, respectively; to antibodies raised against such proteins; and to inhibitory compounds that regulate such proteins. The present invention also includes methods to identify and obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to regulate an immune response in an animal.

12 Claims, No Drawings

OTHER PUBLICATIONS

Inumaru et al., *Immunology and Cell Biology,* vol. 73, 1995, pp. 474–476.
Johnson et al., *J. Mol. Biol.,* vol. 233, 1993, pp. 716–738.
Kelley et al., *Nucleic Acids Research,* vol. 13, No. 3, 1985, pp. 805–823.
Lakkis et al., *Biochemical and Biophysical Research Communications,* vol. 197, No. 2, 1993, pp. 612–618.
Leong et al., *Veterinary Immunology and Immunopathology,* vol. 21, 1989, pp. 261–278.
Lerner et al., GenBank Accession No. U39634, submitted Oct. 27, 1995.
Lerner et al., GenBank Accession No. AAB42052 (U39634.1), submitted Oct. 27, 1995.
Lyman et al., *Blood,* vol. 83, No. 10, 1994, pp. 2795–2801.
Lyman et al., *Oncogene,* vol. 10, 1995, pp. 149–157.
Lyman et al., *Cell,* vol. 75, 1993, pp. 1157–1167.
Lyman et al., *Oncogene,* vol. 11, 1995, pp. 1165–1172.
McClanahan et al., *Blood,* vol. 88, No. 9, 1996, pp. 3371–3382.
McInnes et al., *Gene,* vol. 105, 1991, pp. 275–279.
McKenzie et al., *Proc. Natl. Acad. Sci. USA,* vol. 90, 1993, pp. 3735–3739.
Mertens et al., *Immunogenetics,* vol. 42, 1995, pp. 430–431.
Minty et al., *Nature,* vol. 362, 1993, pp. 248–250.
Nagata et al. *Nature,* vol. 287, 1980, pp. 401–408.
Nakamura et al., *Biosci. Biotech. Biochem.,* vol. 56, No. 2, 1992, pp. 211–214.
Nash et al., *Blood,* vol. 78, No. 4, 1991, pp. 930–937.
Navarro et al., *J. Gen. Virol.* vol. 70, 1989, pp. 1381–1389.
O'Brien et al., *Immunology and Cell Biology,* vol. 69, 1991, pp. 51–55.
Osorio et al., *Vaccine,* vol. 17, 1999, pp. 1109–1116.
Padrid et al., *AJVR,* vol. 59, No. 10, 1998, pp. 1263–1269.
Patterson et al., *Journal of Clinical Investigation,* vol. 44, No. 1, 1965, pp. 140–148.
Seow et al., *Gene,* vol. 124, 1993, pp. 291–293.
Sideras et al., *Adv. Exp. Med. Biol.* vol. 213, 1987, pp. 227–236.
Stamenkovic et al., *The EMBO Journal,* vol. 8, No. 5, 1989, pp. 1403–1410.
Torres et al., *Journal of Immunology,* vol. 148, No. 2, 1992, pp. 620–626.
Wong et al., *Science,* vol. 228, 1985, pp. 810–815.
Yokota et al., *Proc. Natl. Acad. Sci. USA,* vol. 83, 1986, pp. 5894–5898.
Zhou et al., GenBank Accession No. L12991.
Van Der Kaaij et al., 1999, "Immunogenetics," vol. 49, pp. 142–143.

* cited by examiner

```
                               SEQUENCE LISTING


<160> NUMBER OF SEQ ID NOS: 174

<210> SEQ ID NO 1
<211> LENGTH: 549
<212> TYPE: DNA
<213> ORGANISM: Canis familiaris
<220> FEATURE:
<221> NAME/KEY: CDS
<222> LOCATION: (43)..(438)

<400> SEQUENCE: 1

ggcacgaggt ctgctattgt cactgcaaat agagatctat ta atg ggt ctc acc        54
                                               Met Gly Leu Thr
                                                 1

tcc caa ctg att cca act ctg gtc tgc tta cta gca ctc acc agc acc      102
Ser Gln Leu Ile Pro Thr Leu Val Cys Leu Leu Ala Leu Thr Ser Thr
  5                  10                  15                  20

ttt gtc cac gga cat aac ttc aat att act att aaa gag atc atc aaa      150
Phe Val His Gly His Asn Phe Asn Ile Thr Ile Lys Glu Ile Ile Lys
                 25                  30                  35

atg ttg aac atc ctc aca gcg aga aac gac tcg tgc atg gag ctg act      198
Met Leu Asn Ile Leu Thr Ala Arg Asn Asp Ser Cys Met Glu Leu Thr
             40                  45                  50

gtc aag gac gtc ttc act gct cca aag aac aca agc gat aag gaa atc      246
Val Lys Asp Val Phe Thr Ala Pro Lys Asn Thr Ser Asp Lys Glu Ile
         55                  60                  65

ttc tgc aga gct gct act gta ctg cgg cag atc tat aca cac aac tgc      294
Phe Cys Arg Ala Ala Thr Val Leu Arg Gln Ile Tyr Thr His Asn Cys
     70                  75                  80

tcc aac aga tat ctc aga gga ctc tac agg aac ctc agc agc atg gca      342
Ser Asn Arg Tyr Leu Arg Gly Leu Tyr Arg Asn Leu Ser Ser Met Ala
 85                  90                  95                 100

aac aag acc tgt tct atg aat gaa atc aag aag agt aca ctg aaa gac      390
Asn Lys Thr Cys Ser Met Asn Glu Ile Lys Lys Ser Thr Leu Lys Asp
                105                 110                 115

ttc ttg gaa agg cta aaa gtg atc atg cag aag aaa tac tac agg cat      438
Phe Leu Glu Arg Leu Lys Val Ile Met Gln Lys Lys Tyr Tyr Arg His
            120                 125                 130

tgaagctgaa tattttaatt tatgagtttt taaatagctt tattttaaaa atatttatat    498

atttataaca taataaaata aaatatatat agaaaaaaaa aaaaaaaaaa a             549


<210> SEQ ID NO 2
<211> LENGTH: 132
<212> TYPE: PRT
<213> ORGANISM: Canis familiaris

<400> SEQUENCE: 2

Met Gly Leu Thr Ser Gln Leu Ile Pro Thr Leu Val Cys Leu Leu Ala
  1               5                  10                  15

Leu Thr Ser Thr Phe Val His Gly His Asn Phe Asn Ile Thr Ile Lys
             20                  25                  30

Glu Ile Ile Lys Met Leu Asn Ile Leu Thr Ala Arg Asn Asp Ser Cys
```

-continued

```
        35                  40                  45

Met Glu Leu Thr Val Lys Asp Val Phe Thr Ala Pro Lys Asn Thr Ser
     50                  55                  60

Asp Lys Glu Ile Phe Cys Arg Ala Ala Thr Val Leu Arg Gln Ile Tyr
 65                  70                  75                  80

Thr His Asn Cys Ser Asn Arg Tyr Leu Arg Gly Leu Tyr Arg Asn Leu
                 85                  90                  95

Ser Ser Met Ala Asn Lys Thr Cys Ser Met Asn Glu Ile Lys Lys Ser
            100                 105                 110

Thr Leu Lys Asp Phe Leu Glu Arg Leu Lys Val Ile Met Gln Lys Lys
        115                 120                 125

Tyr Tyr Arg His
    130


<210> SEQ ID NO 3
<211> LENGTH: 549
<212> TYPE: DNA
<213> ORGANISM: Canis familiaris

<400> SEQUENCE: 3

ttttttttt ttttttttc tatatatatt ttattttatt atgttataaa tatataaata      60

tttttaaaat aaagctattt aaaaactcat aaattaaaat attcagcttc aatgcctgta    120

gtatttcttc tgcatgatca cttttagcct ttccaagaag tctttcagtg tactcttctt    180

gatttcattc atagaacagg tcttgtttgc catgctgctg aggttcctgt agagtcctct    240

gagatatctg ttggagcagt tgtgtgtata gatctgccgc agtacagtag cagctctgca    300

gaagatttcc ttatcgcttg tgttctttgg agcagtgaag acgtccttga cagtcagctc    360

catgcacgag tcgtttctcg ctgtgaggat gttcaacatt ttgatgatct ctttaatagt    420

aatattgaag ttatgtccgt ggacaaaggt gctggtgagt gctagtaagc agaccagagt    480

tggaatcagt tgggaggtga gacccattaa tagatctcta tttgcagtga caatagcaga    540

cctcgtgcc                                                            549


<210> SEQ ID NO 4
<211> LENGTH: 396
<212> TYPE: DNA
<213> ORGANISM: Canis familiaris

<400> SEQUENCE: 4

atgggtctca cctcccaact gattccaact ctggtctgct tactagcact caccagcacc     60

tttgtccacg gacataactt caatattact attaaagaga tcatcaaaat gttgaacatc    120

ctcacagcga gaaacgactc gtgcatggag ctgactgtca aggacgtctt cactgctcca    180

aagaacacaa gcgataagga aatcttctgc agagctgcta ctgtactgcg gcagatctat    240

acacacaact gctccaacag atatctcaga ggactctaca ggaacctcag cagcatggca    300

aacaagacct gttctatgaa tgaaatcaag aagagtacac tgaaagactt cttggaaagg    360

ctaaaagtga tcatgcagaa gaaatactac aggcat                              396


<210> SEQ ID NO 5
<211> LENGTH: 396
<212> TYPE: DNA
<213> ORGANISM: Canis familiaris

<400> SEQUENCE: 5

atgcctgtag tatttcttct gcatgatcac ttttagcctt tccaagaagt ctttcagtgt     60
```

-continued

```
actcttcttg atttcattca tagaacaggt cttgtttgcc atgctgctga ggttcctgta    120

gagtcctctg agatatctgt tggagcagtt gtgtgtatag atctgccgca gtacagtagc    180

agctctgcag aagatttcct tatcgcttgt gttctttgga gcagtgaaga cgtccttgac    240

agtcagctcc atgcacgagt cgtttctcgc tgtgaggatg ttcaacattt tgatgatctc    300

tttaatagta atattgaagt tatgtccgtg gacaaaggtg ctggtgagtg ctagtaagca    360

gaccagagtt ggaatcagtt gggaggtgag acccat                              396


<210> SEQ ID NO 6
<211> LENGTH: 1013
<212> TYPE: DNA
<213> ORGANISM: Canis familiaris
<220> FEATURE:
<221> NAME/KEY: CDS
<222> LOCATION: (35)..(916)

<400> SEQUENCE: 6

atctgaccat aggcatgagg ggcctccggc cgag atg ata gtg ctg gcg cca gcc     55
                                      Met Ile Val Leu Ala Pro Ala
                                        1               5

tgg agc cca act gcc tcc ctg ttg ctg ctg ctg ctg ctc agc ccc ggc      103
Trp Ser Pro Thr Ala Ser Leu Leu Leu Leu Leu Leu Leu Ser Pro Gly
         10                  15                  20

ctc cgc ggg acc ccc gac tgc tcc ttc agc cac agc ccc atc tcc tcc      151
Leu Arg Gly Thr Pro Asp Cys Ser Phe Ser His Ser Pro Ile Ser Ser
     25                  30                  35

acc ttc gcg gtc acc atc cgc aag ctg tct gat tac ctg ctt cag gac      199
Thr Phe Ala Val Thr Ile Arg Lys Leu Ser Asp Tyr Leu Leu Gln Asp
 40                  45                  50                  55

tat cca gtc act gtc gcc tcc aac ctg cag gac gac gag ctc tgc ggg      247
Tyr Pro Val Thr Val Ala Ser Asn Leu Gln Asp Asp Glu Leu Cys Gly
                 60                  65                  70

gcg ttc tgg cgc ctg gtc ctg gcc cag cgc tgg atg gtg cgg ctc cag      295
Ala Phe Trp Arg Leu Val Leu Ala Gln Arg Trp Met Val Arg Leu Gln
             75                  80                  85

gct gtg gct gga tcc caa atg caa atc ctg ctg gag gct gtc aac acg      343
Ala Val Ala Gly Ser Gln Met Gln Ile Leu Leu Glu Ala Val Asn Thr
         90                  95                 100

gag ata cac ttt gtc acc ttc tgt gcc ttc cag ccc ctc ccc agc tgt      391
Glu Ile His Phe Val Thr Phe Cys Ala Phe Gln Pro Leu Pro Ser Cys
    105                 110                 115

ctt cgc ttc gtc cag acc aac atc tcc cac ctc ctg cag gac acc tcc      439
Leu Arg Phe Val Gln Thr Asn Ile Ser His Leu Leu Gln Asp Thr Ser
120                 125                 130                 135

cag cag ctg gcc gcc ctg aag ccc tgg atc acc cgc agg aat ttc tcc      487
Gln Gln Leu Ala Ala Leu Lys Pro Trp Ile Thr Arg Arg Asn Phe Ser
                140                 145                 150

ggg tgc ctg gag ctg cag tgt cag ccc gac tcc tct aca ttg gtg ccc      535
Gly Cys Leu Glu Leu Gln Cys Gln Pro Asp Ser Ser Thr Leu Val Pro
            155                 160                 165

cca agg agc ccc ggg gcc ctg gag gcc act gcc ttg cca gcc cct cag      583
Pro Arg Ser Pro Gly Ala Leu Glu Ala Thr Ala Leu Pro Ala Pro Gln
        170                 175                 180

gca cct cgg ctg ctc ctc ctg ctg ctg ctg ccc gtg gct ctc ctg ctg      631
Ala Pro Arg Leu Leu Leu Leu Leu Leu Leu Pro Val Ala Leu Leu Leu
    185                 190                 195

atg tcc act gcc tgg tgc ctg cat tgg cga agg agg cgg cgg cgg agg      679
Met Ser Thr Ala Trp Cys Leu His Trp Arg Arg Arg Arg Arg Arg Arg
200                 205                 210                 215
```

-continued

```
tca ccc tac cct ggg gag cag agg aca ctg agg ccc agc gag cgg agc      727
Ser Pro Tyr Pro Gly Glu Gln Arg Thr Leu Arg Pro Ser Glu Arg Ser
                220                 225                 230

cat ctg ccc gag gac aca gag ctg gga cct gga ggg agt cag cta gag      775
His Leu Pro Glu Asp Thr Glu Leu Gly Pro Gly Gly Ser Gln Leu Glu
            235                 240                 245

act ggt ccc ttc ctc gac cac gca gcc ccg ctc gct ccc tcc cca gga      823
Thr Gly Pro Phe Leu Asp His Ala Ala Pro Leu Ala Pro Ser Pro Gly
        250                 255                 260

tca agg caa cgc ccg ccc cca acg ccc cca aag cca gcc cca gcc cca      871
Ser Arg Gln Arg Pro Pro Pro Thr Pro Pro Lys Pro Ala Pro Ala Pro
    265                 270                 275

cct ctc ccc ctc tgt aca aag tcc ttg ccc cca aga aat tgt ata          916
Pro Leu Pro Leu Cys Thr Lys Ser Leu Pro Pro Arg Asn Cys Ile
280                 285                 290

taaatcatcc ttttctacca aaaaaaaaaa aaaaaaaaaa aaaaaaaaaa aaaaaaaaaa    976

aaaaaaaaaa aaaaaaaaaa aaaaaaaaaa aaaaaaa                            1013


<210> SEQ ID NO 7
<211> LENGTH: 294
<212> TYPE: PRT
<213> ORGANISM: Canis familiaris

<400> SEQUENCE: 7

Met Ile Val Leu Ala Pro Ala Trp Ser Pro Thr Ala Ser Leu Leu Leu
  1               5                  10                  15

Leu Leu Leu Leu Ser Pro Gly Leu Arg Gly Thr Pro Asp Cys Ser Phe
             20                  25                  30

Ser His Ser Pro Ile Ser Ser Thr Phe Ala Val Thr Ile Arg Lys Leu
         35                  40                  45

Ser Asp Tyr Leu Leu Gln Asp Tyr Pro Val Thr Val Ala Ser Asn Leu
     50                  55                  60

Gln Asp Asp Glu Leu Cys Gly Ala Phe Trp Arg Leu Val Leu Ala Gln
 65                  70                  75                  80

Arg Trp Met Val Arg Leu Gln Ala Val Ala Gly Ser Gln Met Gln Ile
                 85                  90                  95

Leu Leu Glu Ala Val Asn Thr Glu Ile His Phe Val Thr Phe Cys Ala
            100                 105                 110

Phe Gln Pro Leu Pro Ser Cys Leu Arg Phe Val Gln Thr Asn Ile Ser
        115                 120                 125

His Leu Leu Gln Asp Thr Ser Gln Gln Leu Ala Ala Leu Lys Pro Trp
    130                 135                 140

Ile Thr Arg Arg Asn Phe Ser Gly Cys Leu Glu Leu Gln Cys Gln Pro
145                 150                 155                 160

Asp Ser Ser Thr Leu Val Pro Pro Arg Ser Pro Gly Ala Leu Glu Ala
                165                 170                 175

Thr Ala Leu Pro Ala Pro Gln Ala Pro Arg Leu Leu Leu Leu Leu Leu
            180                 185                 190

Leu Pro Val Ala Leu Leu Leu Met Ser Thr Ala Trp Cys Leu His Trp
        195                 200                 205

Arg Arg Arg Arg Arg Arg Arg Ser Pro Tyr Pro Gly Glu Gln Arg Thr
    210                 215                 220

Leu Arg Pro Ser Glu Arg Ser His Leu Pro Glu Asp Thr Glu Leu Gly
225                 230                 235                 240

Pro Gly Gly Ser Gln Leu Glu Thr Gly Pro Phe Leu Asp His Ala Ala
```

-continued

```
                245                 250                 255

Pro Leu Ala Pro Ser Pro Gly Ser Arg Gln Arg Pro Pro Pro Thr Pro
            260                 265                 270

Pro Lys Pro Ala Pro Ala Pro Pro Leu Pro Leu Cys Thr Lys Ser Leu
        275                 280                 285

Pro Pro Arg Asn Cys Ile
    290
```

<210> SEQ ID NO 8
<211> LENGTH: 1013
<212> TYPE: DNA
<213> ORGANISM: Canis familiaris

<400> SEQUENCE: 8

```
tttttttttt tttttttttt tttttttttt tttttttttt tttttttttt tttttttttt     60

tttttttttt ttttttttgg tagaaaagga tgatttatat acaatttctt gggggcaagg    120

actttgtaca gagggggaga ggtggggctg gggctggctt tgggggcgtt gggggcgggc    180

gttgccttga tcctggggag ggagcgagcg gggctgcgtg gtcgaggaag ggaccagtct    240

ctagctgact ccctccaggt cccagctctg tgtcctcggg cagatggctc cgctcgctgg    300

gcctcagtgt cctctgctcc ccagggtagg gtgacctccg ccgccgcctc cttcgccaat    360

gcaggcacca ggcagtggac atcagcagga gagccacggg cagcagcagc aggaggagca    420

gccgaggtgc ctgaggggct ggcaaggcag tggcctccag ggccccgggg ctccttgggg    480

gcaccaatgt agaggagtcg ggctgacact gcagctccag gcacccggag aaattcctgc    540

gggtgatcca gggcttcagg gcggccagct gctgggaggt gtcctgcagg aggtgggaga    600

tgttggtctg gacgaagcga agacagctgg ggaggggctg gaaggcacag aaggtgacaa    660

agtgtatctc cgtgttgaca gcctccagca ggatttgcat ttgggatcca gccacagcct    720

ggagccgcac catccagcgc tgggccagga ccaggcgcca gaacgccccg cagagctcgt    780

cgtcctgcag gttggaggcg acagtgactg gatagtcctg aagcaggtaa tcagacagct    840

tgcggatggt gaccgcgaag gtggaggaga tggggctgtg gctgaaggag cagtcggggg    900

tcccgcggag gccggggctg agcagcagca gcagcaacag ggaggcagtt gggctccagg    960

ctggcgccag cactatcatc tcggccggag gcccctcatg cctatggtca gat          1013
```

<210> SEQ ID NO 9
<211> LENGTH: 882
<212> TYPE: DNA
<213> ORGANISM: Canis familiaris

<400> SEQUENCE: 9

```
atgatagtgc tggcgccagc ctggagccca actgcctccc tgttgctgct gctgctgctc     60

agccccggcc tccgcgggac ccccgactgc tccttcagcc acagccccat ctcctccacc    120

ttcgcggtca ccatccgcaa gctgtctgat tacctgcttc aggactatcc agtcactgtc    180

gcctccaacc tgcaggacga cgagctctgc ggggcgttct ggcgcctggt cctggcccag    240

cgctggatgg tgcggctcca ggctgtggct ggatcccaaa tgcaaatcct gctggaggct    300

gtcaacacgg agatacactt tgtcaccttc tgtgccttcc agcccctccc cagctgtctt    360

cgcttcgtcc agaccaacat ctcccacctc ctgcaggaca cctcccagca gctggccgcc    420

ctgaagccct ggatcacccg caggaatttc tccgggtgcc tggagctgca gtgtcagccc    480

gactcctcta cattggtgcc cccaaggagc cccggggccc tggaggccac tgccttgcca    540
```

-continued

```
gcccctcagg cacctcggct gctcctcctg ctgctgctgc ccgtggctct cctgctgatg    600

tccactgcct ggtgcctgca ttggcgaagg aggcggcggc ggaggtcacc ctaccctggg    660

gagcagagga cactgaggcc cagcgagcgg agccatctgc ccgaggacac agagctggga    720

cctggaggga gtcagctaga gactggtccc ttcctcgacc acgcagcccc gctcgctccc    780

tccccaggat caaggcaacg cccgccccca acgcccccaa agccagcccc agccccacct    840

ctccccctct gtacaaagtc cttgccccca agaaattgta ta                        882
```

<210> SEQ ID NO 10
<211> LENGTH: 882
<212> TYPE: DNA
<213> ORGANISM: Canis familiaris

<400> SEQUENCE: 10

```
tatacaattt cttgggggca aggactttgt acagaggggg agaggtgggg ctggggctgg     60

ctttgggggc gttgggggcg ggcgttgcct tgatcctggg gagggagcga gcggggctgc    120

gtggtcgagg aagggaccag tctctagctg actccctcca ggtcccagct ctgtgtcctc    180

gggcagatgg ctccgctcgc tgggcctcag tgtcctctgc tccccagggt agggtgacct    240

ccgccgccgc ctccttcgcc aatgcaggca ccaggcagtg gacatcagca ggagagccac    300

gggcagcagc agcaggagga gcagccgagg tgcctgaggg gctggcaagg cagtggcctc    360

cagggccccg gggctccttg ggggcaccaa tgtagaggag tcgggctgac actgcagctc    420

caggcacccg gagaaattcc tgcgggtgat ccagggcttc agggcggcca gctgctggga    480

ggtgtcctgc aggaggtggg agatgttggt ctggacgaag cgaagacagc tggggagggg    540

ctggaaggca cagaaggtga caaagtgtat ctccgtgttg acagcctcca gcaggatttg    600

catttgggat ccagccacag cctggagccg caccatccag cgctgggcca ggaccaggcg    660

ccagaacgcc ccgcagagct cgtcgtcctg caggttggag gcgacagtga ctggatagtc    720

ctgaagcagg taatcagaca gcttgcggat ggtgaccgcg aaggtggagg agatggggct    780

gtggctgaag gagcagtcgg gggtcccgcg gaggccgggg ctgagcagca gcagcagcaa    840

cagggaggca gttgggctcc aggctggcgc cagcactatc at                        882
```

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 11

```
ctattaatgg gtctcacctc ccaact                                          26
```

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 12

```
tcaactcggt gcacagagtc ttgg                                            24
```

<210> SEQ ID NO 13
<211> LENGTH: 20

-continued

<212> TYPE: DNA
<213> ORGANISM: Artificial Sequence
<220> FEATURE:
<223> OTHER INFORMATION: Description of Artificial Sequence: Synthetic Primer

<400> SEQUENCE: 13
ctggcgccag cctggagccc 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic Primer

<400> SEQUENCE: 14
gggagatgtt ggtctggacg 20

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic Primer

<400> SEQUENCE: 15
gaccaggcgc cagaacgc 18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic Primer

<400> SEQUENCE: 16
cggtcaccat ccgcaagc 18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic Primer

<400> SEQUENCE: 17
tggcaaggca gtggcctc 18

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic Primer

<400> SEQUENCE: 18
gccgagatga tagtgctggc 20

<210> SEQ ID NO 19
<211> LENGTH: 324
<212> TYPE: DNA

-continued

```
<213> ORGANISM: Canis familiaris
<220> FEATURE:
<221> NAME/KEY: CDS
<222> LOCATION: (1)..(324)

<400> SEQUENCE: 19

cat aac ttc aat att act att aaa gag atc atc aaa atg ttg aac atc       48
His Asn Phe Asn Ile Thr Ile Lys Glu Ile Ile Lys Met Leu Asn Ile
  1               5                  10                  15

ctc aca gcg aga aac gac tcg tgc atg gag ctg act gtc aag gac gtc       96
Leu Thr Ala Arg Asn Asp Ser Cys Met Glu Leu Thr Val Lys Asp Val
             20                  25                  30

ttc act gct cca aag aac aca agc gat aag gaa atc ttc tgc aga gct      144
Phe Thr Ala Pro Lys Asn Thr Ser Asp Lys Glu Ile Phe Cys Arg Ala
         35                  40                  45

gct act gta ctg cgg cag atc tat aca cac aac tgc tcc aac aga tat      192
Ala Thr Val Leu Arg Gln Ile Tyr Thr His Asn Cys Ser Asn Arg Tyr
     50                  55                  60

ctc aga gga ctc tac agg aac ctc agc agc atg gca aac aag acc tgt      240
Leu Arg Gly Leu Tyr Arg Asn Leu Ser Ser Met Ala Asn Lys Thr Cys
 65                  70                  75                  80

tct atg aat gaa atc aag aag agt aca ctg aaa gac ttc ttg gaa agg      288
Ser Met Asn Glu Ile Lys Lys Ser Thr Leu Lys Asp Phe Leu Glu Arg
                 85                  90                  95

cta aaa gtg atc atg cag aag aaa tac tac agg cat                      324
Leu Lys Val Ile Met Gln Lys Lys Tyr Tyr Arg His
            100                 105


<210> SEQ ID NO 20
<211> LENGTH: 108
<212> TYPE: PRT
<213> ORGANISM: Canis familiaris

<400> SEQUENCE: 20

His Asn Phe Asn Ile Thr Ile Lys Glu Ile Ile Lys Met Leu Asn Ile
  1               5                  10                  15

Leu Thr Ala Arg Asn Asp Ser Cys Met Glu Leu Thr Val Lys Asp Val
             20                  25                  30

Phe Thr Ala Pro Lys Asn Thr Ser Asp Lys Glu Ile Phe Cys Arg Ala
         35                  40                  45

Ala Thr Val Leu Arg Gln Ile Tyr Thr His Asn Cys Ser Asn Arg Tyr
     50                  55                  60

Leu Arg Gly Leu Tyr Arg Asn Leu Ser Ser Met Ala Asn Lys Thr Cys
 65                  70                  75                  80

Ser Met Asn Glu Ile Lys Lys Ser Thr Leu Lys Asp Phe Leu Glu Arg
                 85                  90                  95

Leu Lys Val Ile Met Gln Lys Lys Tyr Tyr Arg His
            100                 105


<210> SEQ ID NO 21
<211> LENGTH: 324
<212> TYPE: DNA
<213> ORGANISM: Canis familiaris

<400> SEQUENCE: 21

atgcctgtag tatttcttct gcatgatcac ttttagcctt tccaagaagt ctttcagtgt     60

actcttcttg atttcattca tagaacaggt cttgtttgcc atgctgctga ggttcctgta    120

gagtcctctg agatatctgt tggagcagtt gtgtgtatag atctgccgca gtacagtagc    180

agctctgcag aagatttcct tatcgcttgt gttctttgga gcagtgaaga cgtccttgac    240
```

-continued

```
agtcagctcc atgcacgagt cgtttctcgc tgtgaggatg ttcaacattt tgatgatctc    300

tttaatagta atattgaagt tatg                                           324


<210> SEQ ID NO 22
<211> LENGTH: 804
<212> TYPE: DNA
<213> ORGANISM: Canis familiaris
<220> FEATURE:
<221> NAME/KEY: CDS
<222> LOCATION: (1)..(804)

<400> SEQUENCE: 22

acc ccc gac tgc tcc ttc agc cac agc ccc atc tcc tcc acc ttc gcg       48
Thr Pro Asp Cys Ser Phe Ser His Ser Pro Ile Ser Ser Thr Phe Ala
  1               5                  10                  15

gtc acc atc cgc aag ctg tct gat tac ctg ctt cag gac tat cca gtc       96
Val Thr Ile Arg Lys Leu Ser Asp Tyr Leu Leu Gln Asp Tyr Pro Val
             20                  25                  30

act gtc gcc tcc aac ctg cag gac gac gag ctc tgc ggg gcg ttc tgg      144
Thr Val Ala Ser Asn Leu Gln Asp Asp Glu Leu Cys Gly Ala Phe Trp
         35                  40                  45

cgc ctg gtc ctg gcc cag cgc tgg atg gtg cgg ctc cag gct gtg gct      192
Arg Leu Val Leu Ala Gln Arg Trp Met Val Arg Leu Gln Ala Val Ala
     50                  55                  60

gga tcc caa atg caa atc ctg ctg gag gct gtc aac acg gag ata cac      240
Gly Ser Gln Met Gln Ile Leu Leu Glu Ala Val Asn Thr Glu Ile His
 65                  70                  75                  80

ttt gtc acc ttc tgt gcc ttc cag ccc ctc ccc agc tgt ctt cgc ttc      288
Phe Val Thr Phe Cys Ala Phe Gln Pro Leu Pro Ser Cys Leu Arg Phe
                 85                  90                  95

gtc cag acc aac atc tcc cac ctc ctg cag gac acc tcc cag cag ctg      336
Val Gln Thr Asn Ile Ser His Leu Leu Gln Asp Thr Ser Gln Gln Leu
            100                 105                 110

gcc gcc ctg aag ccc tgg atc acc cgc agg aat ttc tcc ggg tgc ctg      384
Ala Ala Leu Lys Pro Trp Ile Thr Arg Arg Asn Phe Ser Gly Cys Leu
        115                 120                 125

gag ctg cag tgt cag ccc gac tcc tct aca ttg gtg ccc cca agg agc      432
Glu Leu Gln Cys Gln Pro Asp Ser Ser Thr Leu Val Pro Pro Arg Ser
    130                 135                 140

ccc ggg gcc ctg gag gcc act gcc ttg cca gcc cct cag gca cct cgg      480
Pro Gly Ala Leu Glu Ala Thr Ala Leu Pro Ala Pro Gln Ala Pro Arg
145                 150                 155                 160

ctg ctc ctc ctg ctg ctg ctg ccc gtg gct ctc ctg ctg atg tcc act      528
Leu Leu Leu Leu Leu Leu Leu Pro Val Ala Leu Leu Leu Met Ser Thr
                165                 170                 175

gcc tgg tgc ctg cat tgg cga agg agg cgg cgg cgg agg tca ccc tac      576
Ala Trp Cys Leu His Trp Arg Arg Arg Arg Arg Arg Arg Ser Pro Tyr
            180                 185                 190

cct ggg gag cag agg aca ctg agg ccc agc gag cgg agc cat ctg ccc      624
Pro Gly Glu Gln Arg Thr Leu Arg Pro Ser Glu Arg Ser His Leu Pro
        195                 200                 205

gag gac aca gag ctg gga cct gga ggg agt cag cta gag act ggt ccc      672
Glu Asp Thr Glu Leu Gly Pro Gly Gly Ser Gln Leu Glu Thr Gly Pro
    210                 215                 220

ttc ctc gac cac gca gcc ccg ctc gct ccc tcc cca gga tca agg caa      720
Phe Leu Asp His Ala Ala Pro Leu Ala Pro Ser Pro Gly Ser Arg Gln
225                 230                 235                 240

cgc ccg ccc cca acg ccc cca aag cca gcc cca gcc cca cct ctc ccc      768
Arg Pro Pro Pro Thr Pro Pro Lys Pro Ala Pro Ala Pro Pro Leu Pro
                245                 250                 255
```

-continued

```
ctc tgt aca aag tcc ttg ccc cca aga aat tgt ata                   804
Leu Cys Thr Lys Ser Leu Pro Pro Arg Asn Cys Ile
            260                 265


<210> SEQ ID NO 23
<211> LENGTH: 268
<212> TYPE: PRT
<213> ORGANISM: Canis familiaris

<400> SEQUENCE: 23

Thr Pro Asp Cys Ser Phe Ser His Ser Pro Ile Ser Ser Thr Phe Ala
  1               5                  10                  15

Val Thr Ile Arg Lys Leu Ser Asp Tyr Leu Leu Gln Asp Tyr Pro Val
             20                  25                  30

Thr Val Ala Ser Asn Leu Gln Asp Asp Glu Leu Cys Gly Ala Phe Trp
         35                  40                  45

Arg Leu Val Leu Ala Gln Arg Trp Met Val Arg Leu Gln Ala Val Ala
     50                  55                  60

Gly Ser Gln Met Gln Ile Leu Leu Glu Ala Val Asn Thr Glu Ile His
 65                  70                  75                  80

Phe Val Thr Phe Cys Ala Phe Gln Pro Leu Pro Ser Cys Leu Arg Phe
                 85                  90                  95

Val Gln Thr Asn Ile Ser His Leu Leu Gln Asp Thr Ser Gln Gln Leu
            100                 105                 110

Ala Ala Leu Lys Pro Trp Ile Thr Arg Arg Asn Phe Ser Gly Cys Leu
        115                 120                 125

Glu Leu Gln Cys Gln Pro Asp Ser Ser Thr Leu Val Pro Pro Arg Ser
    130                 135                 140

Pro Gly Ala Leu Glu Ala Thr Ala Leu Pro Ala Pro Gln Ala Pro Arg
145                 150                 155                 160

Leu Leu Leu Leu Leu Leu Leu Pro Val Ala Leu Leu Leu Met Ser Thr
                165                 170                 175

Ala Trp Cys Leu His Trp Arg Arg Arg Arg Arg Arg Arg Ser Pro Tyr
            180                 185                 190

Pro Gly Glu Gln Arg Thr Leu Arg Pro Ser Glu Arg Ser His Leu Pro
        195                 200                 205

Glu Asp Thr Glu Leu Gly Pro Gly Gly Ser Gln Leu Glu Thr Gly Pro
    210                 215                 220

Phe Leu Asp His Ala Ala Pro Leu Ala Pro Ser Pro Gly Ser Arg Gln
225                 230                 235                 240

Arg Pro Pro Pro Thr Pro Pro Lys Pro Ala Pro Ala Pro Pro Leu Pro
                245                 250                 255

Leu Cys Thr Lys Ser Leu Pro Pro Arg Asn Cys Ile
            260                 265


<210> SEQ ID NO 24
<211> LENGTH: 804
<212> TYPE: DNA
<213> ORGANISM: Canis familiaris

<400> SEQUENCE: 24

tatacaattt cttgggggca aggactttgt acagaggggg agaggtgggg ctggggctgg     60

ctttgggggc gttgggggcg ggcgttgcct tgatcctggg gagggagcga gcggggctgc    120

gtggtcgagg aagggaccag tctctagctg actccctcca ggtcccagct ctgtgtcctc    180

gggcagatgg ctccgctcgc tgggcctcag tgtcctctgc tccccagggt agggtgacct    240
```

-continued

```
ccgccgccgc ctccttcgcc aatgcaggca ccaggcagtg gacatcagca ggagagccac    300

gggcagcagc agcaggagga gcagccgagg tgcctgaggg gctggcaagg cagtggcctc    360

cagggccccg gggctccttg ggggcaccaa tgtagaggag tcgggctgac actgcagctc    420

caggcacccg gagaaattcc tgcgggtgat ccagggcttc agggcggcca gctgctggga    480

ggtgtcctgc aggaggtggg agatgttggt ctggacgaag cgaagacagc tggggagggg    540

ctggaaggca cagaaggtga caaagtgtat ctccgtgttg acagcctcca gcaggatttg    600

catttgggat ccagccacag cctggagccg caccatccag cgctgggcca ggaccaggcg    660

ccagaacgcc ccgcagagct cgtcgtcctg caggttggag gcgacagtga ctggatagtc    720

ctgaagcagg taatcagaca gcttgcggat ggtgaccgcg aaggtggagg agatggggct    780

gtggctgaag gagcagtcgg gggt                                           804


<210> SEQ ID NO 25
<211> LENGTH: 985
<212> TYPE: DNA
<213> ORGANISM: Canis familiaris
<220> FEATURE:
<221> NAME/KEY: CDS
<222> LOCATION: (74)..(901)

<400> SEQUENCE: 25

ccggcctggc cccttccacg cccagctggg gcaagcctga tctgaccata ggcatgaggg     60

gcctccggcc gag atg ata gtg ctg gcg cca gcc tgg agc cca act gcc       109
               Met Ile Val Leu Ala Pro Ala Trp Ser Pro Thr Ala
                 1               5                  10

tcc ctg ttg ctg ctg ctg ctg ctc agc ccc ggc ctc cgc ggg acc ccc       157
Ser Leu Leu Leu Leu Leu Leu Leu Ser Pro Gly Leu Arg Gly Thr Pro
         15                  20                  25

gac tgc tcc ttc agc cac agc ccc atc tcc tcc acc ttc gcg gtc acc       205
Asp Cys Ser Phe Ser His Ser Pro Ile Ser Ser Thr Phe Ala Val Thr
     30                  35                  40

atc cgc aag ctg tct gat tac ctg ctt cag gac tat cca gtc act gtc       253
Ile Arg Lys Leu Ser Asp Tyr Leu Leu Gln Asp Tyr Pro Val Thr Val
 45                  50                  55                  60

gcc tcc aac ctg cag gac gac gag ctc tgc ggg gcg ttc tgg cgc ctg       301
Ala Ser Asn Leu Gln Asp Asp Glu Leu Cys Gly Ala Phe Trp Arg Leu
                 65                  70                  75

gtc ctg gcc cag cgc tgg atg gtg cgg ctc cag gct gtg gct gga tcc       349
Val Leu Ala Gln Arg Trp Met Val Arg Leu Gln Ala Val Ala Gly Ser
             80                  85                  90

caa atg caa atc ctg ctg gag gct gtc aac acg gag ata cac ttt gtc       397
Gln Met Gln Ile Leu Leu Glu Ala Val Asn Thr Glu Ile His Phe Val
         95                 100                 105

acc ttc tgt gcc ttc cag gac acc tcc cag cag ctg gcc gcc ctg aag       445
Thr Phe Cys Ala Phe Gln Asp Thr Ser Gln Gln Leu Ala Ala Leu Lys
    110                 115                 120

ccc tgg atc acc cgc agg aat ttc tcc ggg tgc ctg gag ctg cag tgt       493
Pro Trp Ile Thr Arg Arg Asn Phe Ser Gly Cys Leu Glu Leu Gln Cys
125                 130                 135                 140

cag ccc gac tcc tct aca ttg gtg ccc cca agg agc ccc ggg gcc ctg       541
Gln Pro Asp Ser Ser Thr Leu Val Pro Pro Arg Ser Pro Gly Ala Leu
                145                 150                 155

gag gcc act gcc ttg cca gcc cct cag gca cct cgg ctg ctc ctc ctg       589
Glu Ala Thr Ala Leu Pro Ala Pro Gln Ala Pro Arg Leu Leu Leu Leu
            160                 165                 170

ctg ctg ctg ccc gtg gct ctc ctg ctg atg tcc act gcc tgg tgc ctg       637
```

-continued

```
Leu Leu Leu Pro Val Ala Leu Leu Leu Met Ser Thr Ala Trp Cys Leu
        175                 180                 185

cat tgg cga agg agg cgg cgg cgg agg tca ccc tac cct ggg gag cag      685
His Trp Arg Arg Arg Arg Arg Arg Arg Ser Pro Tyr Pro Gly Glu Gln
    190                 195                 200

agg aca ctg agg ccc agc gag cgg agc cat ctg ccc gag gac aca gag      733
Arg Thr Leu Arg Pro Ser Glu Arg Ser His Leu Pro Glu Asp Thr Glu
205                 210                 215                 220

ctg gga cct gga ggg agt cag cta gag act ggt ccc ttc ctc gac cac      781
Leu Gly Pro Gly Gly Ser Gln Leu Glu Thr Gly Pro Phe Leu Asp His
                225                 230                 235

gca gcc ccg ctc gct ccc tcc cca gga tca agg caa cgc ccg ccc cca      829
Ala Ala Pro Leu Ala Pro Ser Pro Gly Ser Arg Gln Arg Pro Pro Pro
            240                 245                 250

acg ccc cca aag cca gcc cca gcc cca cct ctc ccc ctc tgt aca aag      877
Thr Pro Pro Lys Pro Ala Pro Ala Pro Pro Leu Pro Leu Cys Thr Lys
        255                 260                 265

tcc ttg ccc cca aga aat tgt ata taaatcatcc ttttctacca gcaaaaaaaa     931
Ser Leu Pro Pro Arg Asn Cys Ile
    270                 275

aaaaaaaaaa aaaaaaaaaa aaaaaaaaaa aaaaaaaaaa aaaaaaaaaa aaaa          985


<210> SEQ ID NO 26
<211> LENGTH: 276
<212> TYPE: PRT
<213> ORGANISM: Canis familiaris

<400> SEQUENCE: 26

Met Ile Val Leu Ala Pro Ala Trp Ser Pro Thr Ala Ser Leu Leu Leu
  1               5                  10                  15

Leu Leu Leu Leu Ser Pro Gly Leu Arg Gly Thr Pro Asp Cys Ser Phe
            20                  25                  30

Ser His Ser Pro Ile Ser Ser Thr Phe Ala Val Thr Ile Arg Lys Leu
        35                  40                  45

Ser Asp Tyr Leu Leu Gln Asp Tyr Pro Val Thr Val Ala Ser Asn Leu
     50                  55                  60

Gln Asp Asp Glu Leu Cys Gly Ala Phe Trp Arg Leu Val Leu Ala Gln
 65                  70                  75                  80

Arg Trp Met Val Arg Leu Gln Ala Val Ala Gly Ser Gln Met Gln Ile
                85                  90                  95

Leu Leu Glu Ala Val Asn Thr Glu Ile His Phe Val Thr Phe Cys Ala
            100                 105                 110

Phe Gln Asp Thr Ser Gln Gln Leu Ala Ala Leu Lys Pro Trp Ile Thr
        115                 120                 125

Arg Arg Asn Phe Ser Gly Cys Leu Glu Leu Gln Cys Gln Pro Asp Ser
    130                 135                 140

Ser Thr Leu Val Pro Pro Arg Ser Pro Gly Ala Leu Glu Ala Thr Ala
145                 150                 155                 160

Leu Pro Ala Pro Gln Ala Pro Arg Leu Leu Leu Leu Leu Leu Leu Pro
                165                 170                 175

Val Ala Leu Leu Leu Met Ser Thr Ala Trp Cys Leu His Trp Arg Arg
            180                 185                 190

Arg Arg Arg Arg Arg Ser Pro Tyr Pro Gly Glu Gln Arg Thr Leu Arg
        195                 200                 205

Pro Ser Glu Arg Ser His Leu Pro Glu Asp Thr Glu Leu Gly Pro Gly
    210                 215                 220
```

-continued

```
Gly Ser Gln Leu Glu Thr Gly Pro Phe Leu Asp His Ala Ala Pro Leu
225                 230                 235                 240

Ala Pro Ser Pro Gly Ser Arg Gln Arg Pro Pro Pro Thr Pro Pro Lys
                245                 250                 255

Pro Ala Pro Ala Pro Pro Leu Pro Leu Cys Thr Lys Ser Leu Pro Pro
            260                 265                 270

Arg Asn Cys Ile
        275


<210> SEQ ID NO 27
<211> LENGTH: 985
<212> TYPE: DNA
<213> ORGANISM: Canis familiaris

<400> SEQUENCE: 27

tttttttttt tttttttttt tttttttttt tttttttttt tttttttttt tttttttttt      60

ttgctggtag aaaaggatga tttatataca atttcttggg ggcaaggact ttgtacagag     120

ggggagaggt ggggctgggg ctggctttgg gggcgttggg ggcgggcgtt gccttgatcc     180

tggggaggga gcgagcgggg ctgcgtggtc gaggaaggga ccagtctcta gctgactccc     240

tccaggtccc agctctgtgt cctcgggcag atggctccgc tcgctgggcc tcagtgtcct     300

ctgctcccca gggtagggtg acctccgccg ccgcctcctt cgccaatgca ggcaccaggc     360

agtggacatc agcaggagag ccacgggcag cagcagcagg aggagcagcc gaggtgcctg     420

aggggctggc aaggcagtgg cctccagggc cccggggctc cttgggggca ccaatgtaga     480

ggagtcgggc tgacactgca gctccaggca cccggagaaa ttcctgcggg tgatccaggg     540

cttcagggcg gccagctgct gggaggtgtc ctggaaggca cagaaggtga caaagtgtat     600

ctccgtgttg acagcctcca gcaggatttg catttgggat ccagccacag cctggagccg     660

caccatccag cgctgggcca ggaccaggcg ccagaacgcc ccgcagagct cgtcgtcctg     720

caggttggag gcgacagtga ctggatagtc ctgaagcagg taatcagaca gcttgcggat     780

ggtgaccgcg aaggtggagg agatggggct gtggctgaag gagcagtcgg gggtcccgcg     840

gaggccgggg ctgagcagca gcagcagcaa cagggaggca gttgggctcc aggctggcgc     900

cagcactatc atctcggccg gaggcccctc atgcctatgg tcagatcagg cttgccccag     960

ctgggcgtgg aaggggccag gccgg                                           985


<210> SEQ ID NO 28
<211> LENGTH: 828
<212> TYPE: DNA
<213> ORGANISM: Canis familiaris

<400> SEQUENCE: 28

atgatagtgc tggcgccagc ctggagccca actgcctccc tgttgctgct gctgctgctc      60

agccccggcc tccgcgggac ccccgactgc tccttcagcc acagccccat ctcctccacc     120

ttcgcggtca ccatccgcaa gctgtctgat tacctgcttc aggactatcc agtcactgtc     180

gcctccaacc tgcaggacga cgagctctgc ggggcgttct ggcgcctggt cctggcccag     240

cgctggatgg tgcggctcca ggctgtggct ggatcccaaa tgcaaatcct gctggaggct     300

gtcaacacgg agatacactt tgtcaccttc tgtgccttcc aggacacctc ccagcagctg     360

gccgccctga agccctggat cacccgcagg aatttctccg ggtgcctgga gctgcagtgt     420

cagcccgact cctctacatt ggtgccccca aggagccccg ggccctgga ggccactgcc      480

ttgccagccc ctcaggcacc tcggctgctc ctcctgctgc tgctgcccgt ggctctcctg     540
```

-continued

```
ctgatgtcca ctgcctggtg cctgcattgg cgaaggaggc ggcggcggag gtcaccctac    600

cctggggagc agaggacact gaggcccagc gagcggagcc atctgcccga ggacacagag    660

ctgggacctg gagggagtca gctagagact ggtcccttcc tcgaccacgc agccccgctc    720

gctccctccc caggatcaag gcaacgcccg cccccaacgc ccccaaagcc agccccagcc    780

ccacctctcc ccctctgtac aaagtccttg cccccaagaa attgtata                 828
```

<210> SEQ ID NO 29
<211> LENGTH: 828
<212> TYPE: DNA
<213> ORGANISM: Canis familiaris

<400> SEQUENCE: 29

```
tatacaattt cttgggggca aggactttgt acagaggggg agaggtgggg ctggggctgg     60

ctttgggggc gttgggggcg ggcgttgcct tgatcctggg gagggagcga gcggggctgc    120

gtggtcgagg aagggaccag tctctagctg actccctcca ggtcccagct ctgtgtcctc    180

gggcagatgg ctccgctcgc tggcctcag tgtcctctgc tccccagggt agggtgacct     240

ccgccgccgc ctccttcgcc aatgcaggca ccaggcagtg gacatcagca ggagagccac    300

gggcagcagc agcaggagga gcagccgagg tgcctgaggg gctggcaagg cagtggcctc    360

cagggccccg gggctccttg ggggcaccaa tgtagaggag tcgggctgac actgcagctc    420

caggcacccg gagaaattcc tgcgggtgat ccagggcttc agggcggcca gctgctggga    480

ggtgtcctgg aaggcacaga aggtgacaaa gtgtatctcc gtgttgacag cctccagcag    540

gatttgcatt tgggatccag ccacagcctg gagccgcacc atccagcgct gggccaggac    600

caggcgccag aacgccccgc agagctcgtc gtcctgcagg ttggaggcga cagtgactgg    660

atagtcctga agcaggtaat cagacagctt gcggatggtg accgcgaagg tggaggagat    720

ggggctgtgg ctgaaggagc agtcgggggt cccgcggagg ccggggctga gcagcagcag    780

cagcaacagg gaggcagttg ggctccaggc tggcgccagc actatcat                 828
```

<210> SEQ ID NO 30
<211> LENGTH: 750
<212> TYPE: DNA
<213> ORGANISM: Canis familiaris
<220> FEATURE:
<221> NAME/KEY: CDS
<222> LOCATION: (1)..(750)

<400> SEQUENCE: 30

```
acc ccc gac tgc tcc ttc agc cac agc ccc atc tcc tcc acc ttc gcg       48
Thr Pro Asp Cys Ser Phe Ser His Ser Pro Ile Ser Ser Thr Phe Ala
  1               5                  10                  15

gtc acc atc cgc aag ctg tct gat tac ctg ctt cag gac tat cca gtc       96
Val Thr Ile Arg Lys Leu Ser Asp Tyr Leu Leu Gln Asp Tyr Pro Val
             20                  25                  30

act gtc gcc tcc aac ctg cag gac gac gag ctc tgc ggg gcg ttc tgg      144
Thr Val Ala Ser Asn Leu Gln Asp Asp Glu Leu Cys Gly Ala Phe Trp
         35                  40                  45

cgc ctg gtc ctg gcc cag cgc tgg atg gtg cgg ctc cag gct gtg gct      192
Arg Leu Val Leu Ala Gln Arg Trp Met Val Arg Leu Gln Ala Val Ala
     50                  55                  60

gga tcc caa atg caa atc ctg ctg gag gct gtc aac acg gag ata cac      240
Gly Ser Gln Met Gln Ile Leu Leu Glu Ala Val Asn Thr Glu Ile His
 65                  70                  75                  80

ttt gtc acc ttc tgt gcc ttc cag gac acc tcc cag cag ctg gcc gcc      288
```

-continued

```
Phe Val Thr Phe Cys Ala Phe Gln Asp Thr Ser Gln Gln Leu Ala Ala
                85                  90                  95

ctg aag ccc tgg atc acc cgc agg aat ttc tcc ggg tgc ctg gag ctg      336
Leu Lys Pro Trp Ile Thr Arg Arg Asn Phe Ser Gly Cys Leu Glu Leu
            100                 105                 110

cag tgt cag ccc gac tcc tct aca ttg gtg ccc cca agg agc ccc ggg      384
Gln Cys Gln Pro Asp Ser Ser Thr Leu Val Pro Pro Arg Ser Pro Gly
        115                 120                 125

gcc ctg gag gcc act gcc ttg cca gcc cct cag gca cct cgg ctg ctc      432
Ala Leu Glu Ala Thr Ala Leu Pro Ala Pro Gln Ala Pro Arg Leu Leu
    130                 135                 140

ctc ctg ctg ctg ctg ccc gtg gct ctc ctg ctg atg tcc act gcc tgg      480
Leu Leu Leu Leu Leu Pro Val Ala Leu Leu Leu Met Ser Thr Ala Trp
145                 150                 155                 160

tgc ctg cat tgg cga agg agg cgg cgg cgg agg tca ccc tac cct ggg      528
Cys Leu His Trp Arg Arg Arg Arg Arg Arg Arg Ser Pro Tyr Pro Gly
                165                 170                 175

gag cag agg aca ctg agg ccc agc gag cgg agc cat ctg ccc gag gac      576
Glu Gln Arg Thr Leu Arg Pro Ser Glu Arg Ser His Leu Pro Glu Asp
            180                 185                 190

aca gag ctg gga cct gga ggg agt cag cta gag act ggt ccc ttc ctc      624
Thr Glu Leu Gly Pro Gly Gly Ser Gln Leu Glu Thr Gly Pro Phe Leu
        195                 200                 205

gac cac gca gcc ccg ctc gct ccc tcc cca gga tca agg caa cgc ccg      672
Asp His Ala Ala Pro Leu Ala Pro Ser Pro Gly Ser Arg Gln Arg Pro
    210                 215                 220

ccc cca acg ccc cca aag cca gcc cca gcc cca cct ctc ccc ctc tgt      720
Pro Pro Thr Pro Pro Lys Pro Ala Pro Ala Pro Pro Leu Pro Leu Cys
225                 230                 235                 240

aca aag tcc ttg ccc cca aga aat tgt ata                              750
Thr Lys Ser Leu Pro Pro Arg Asn Cys Ile
                245                 250


<210> SEQ ID NO 31
<211> LENGTH: 250
<212> TYPE: PRT
<213> ORGANISM: Canis familiaris

<400> SEQUENCE: 31

Thr Pro Asp Cys Ser Phe Ser His Ser Pro Ile Ser Ser Thr Phe Ala
  1               5                  10                  15

Val Thr Ile Arg Lys Leu Ser Asp Tyr Leu Leu Gln Asp Tyr Pro Val
            20                  25                  30

Thr Val Ala Ser Asn Leu Gln Asp Asp Glu Leu Cys Gly Ala Phe Trp
        35                  40                  45

Arg Leu Val Leu Ala Gln Arg Trp Met Val Arg Leu Gln Ala Val Ala
     50                  55                  60

Gly Ser Gln Met Gln Ile Leu Leu Glu Ala Val Asn Thr Glu Ile His
 65                  70                  75                  80

Phe Val Thr Phe Cys Ala Phe Gln Asp Thr Ser Gln Gln Leu Ala Ala
                85                  90                  95

Leu Lys Pro Trp Ile Thr Arg Arg Asn Phe Ser Gly Cys Leu Glu Leu
            100                 105                 110

Gln Cys Gln Pro Asp Ser Ser Thr Leu Val Pro Pro Arg Ser Pro Gly
        115                 120                 125

Ala Leu Glu Ala Thr Ala Leu Pro Ala Pro Gln Ala Pro Arg Leu Leu
    130                 135                 140

Leu Leu Leu Leu Leu Pro Val Ala Leu Leu Leu Met Ser Thr Ala Trp
```

-continued

```
145                 150                 155                 160

Cys Leu His Trp Arg Arg Arg Arg Arg Arg Arg Ser Pro Tyr Pro Gly
                165                 170                 175

Glu Gln Arg Thr Leu Arg Pro Ser Glu Arg Ser His Leu Pro Glu Asp
            180                 185                 190

Thr Glu Leu Gly Pro Gly Gly Ser Gln Leu Glu Thr Gly Pro Phe Leu
        195                 200                 205

Asp His Ala Ala Pro Leu Ala Pro Ser Pro Gly Ser Arg Gln Arg Pro
    210                 215                 220

Pro Pro Thr Pro Pro Lys Pro Ala Pro Ala Pro Pro Leu Pro Leu Cys
225                 230                 235                 240

Thr Lys Ser Leu Pro Pro Arg Asn Cys Ile
                245                 250


<210> SEQ ID NO 32
<211> LENGTH: 750
<212> TYPE: DNA
<213> ORGANISM: Canis familiaris

<400> SEQUENCE: 32

tatacaattt cttgggggca aggactttgt acagaggggg agaggtgggg ctggggctgg     60

ctttgggggc gttgggggcg ggcgttgcct tgatcctggg gagggagcga gcggggctgc    120

gtggtcgagg aagggaccag tctctagctg actccctcca ggtcccagct ctgtgtcctc    180

gggcagatgg ctccgctcgc tgggcctcag tgtcctctgc tccccagggt agggtgacct    240

ccgccgccgc ctccttcgcc aatgcaggca ccaggcagtg gacatcagca ggagagccac    300

gggcagcagc agcaggagga gcagccgagg tgcctgaggg gctggcaagg cagtggcctc    360

cagggccccg gggctccttg gggcgcaccaa tgtagaggag tcgggctgac actgcagctc    420

caggcacccg gagaaattcc tgcgggtgat ccagggcttc agggcggcca gctgctggga    480

ggtgtcctgg aaggcacaga aggtgacaaa gtgtatctcc gtgttgacag cctccagcag    540

gatttgcatt tgggatccag ccacagcctg gagccgcacc atccagcgct gggccaggac    600

caggcgccag aacgccccgc agagctcgtc gtcctgcagg ttggaggcga cagtgactgg    660

atagtcctga agcaggtaat cagacagctt gcggatggtg accgcgaagg tggaggagat    720

ggggctgtgg ctgaaggagc agtcgggggt                                     750


<210> SEQ ID NO 33
<211> LENGTH: 1019
<212> TYPE: DNA
<213> ORGANISM: Canis familiaris
<220> FEATURE:
<221> NAME/KEY: CDS
<222> LOCATION: (74)..(166)

<400> SEQUENCE: 33

ccggcctggc cccttccacg cccagctggg gcaagcctga tctgaccata ggcatgaggg     60

gcctccggcc gag atg ata gtg ctg gcg cca gcc tgg agc cca act gtg       109
               Met Ile Val Leu Ala Pro Ala Trp Ser Pro Thr Val
                 1               5                  10

cgt ata ccc ggg gga caa ggc ggg gga cag gca gag cgc tac cga gct      157
Arg Ile Pro Gly Gly Gln Gly Gly Gly Gln Ala Glu Arg Tyr Arg Ala
         15                  20                  25

ggg cag agc tgagagagca gacggacaga ggcctccctg ttgctgctgc              206
Gly Gln Ser
     30
```

-continued

```
tgctgctcag ccccggcctc cgcgggaccc ccgactgctc cttcagccac agccccatct    266

cctccacctt cgcggtcacc atccgcaagc tgtctgatta cctgcttcag gactatccag    326

tcactgtcgc ctccaacctg caggacgacg agctctgcgg ggcgttctgg cgcctggtcc    386

tggcccagcg ctggatggtg cggctccagg ctgtggctgg atcccaaatg caaatcctgc    446

tggaggctgt caacacggag atacactttg tcaccttctg tgccttccag gacacctccc    506

agcagctggc cgccctgaag ccctggatca cccgcaggaa tttctccggg tgcctggagc    566

tgcagtgtca gcccgactcc tctacattgg tgcccccaag gagccccggg gccctggagg    626

ccactgcctt gccagcccct caggcacctc ggctgctcct cctgctgctg ctgcccgtgg    686

ctctcctgct gatgtccact gcctggtgcc tgcattggcg aaggaggcgg cggcggaggt    746

caccctaccc tggggagcag aggacactga ggcccagcga gcggagccat ctgcccgagg    806

acacagagct gggacctgga gggagtcagc tagagactgg tcccttcctc gaccacgcag    866

ccccgctcgc tccctcccca ggatcaaggc aacgcccgcc cccaacgccc ccaaagccag    926

ccccagcccc acctctcccc ctctgtacaa agtccttgcc cccaagaaat tgtatataaa    986

tcatcctttt ctaccaaaaa aaaaaaaaaa aaa                                1019
```

```
<210> SEQ ID NO 34
<211> LENGTH: 31
<212> TYPE: PRT
<213> ORGANISM: Canis familiaris

<400> SEQUENCE: 34

Met Ile Val Leu Ala Pro Ala Trp Ser Pro Thr Val Arg Ile Pro Gly
  1               5                  10                  15

Gly Gln Gly Gly Gly Gln Ala Glu Arg Tyr Arg Ala Gly Gln Ser
             20                  25                  30


<210> SEQ ID NO 35
<211> LENGTH: 1019
<212> TYPE: DNA
<213> ORGANISM: Canis familiaris

<400> SEQUENCE: 35

tttttttttt tttttttgg tagaaaagga tgatttatat acaatttctt gggggcaagg     60

actttgtaca gaggggggaga ggtggggctg gggctggctt tgggggcgtt gggggcgggc    120

gttgccttga tcctggggag ggagcgagcg gggctgcgtg gtcgaggaag ggaccagtct    180

ctagctgact ccctccaggt cccagctctg tgtcctcggg cagatggctc cgctcgctgg    240

gcctcagtgt cctctgctcc ccagggtagg gtgacctccg ccgccgcctc cttcgccaat    300

gcaggcacca ggcagtggac atcagcagga gagccacggg cagcagcagc aggaggagca    360

gccgaggtgc ctgaggggct ggcaaggcag tggcctccag ggccccgggg ctccttgggg    420

gcaccaatgt agaggagtcg ggctgacact gcagctccag gcacccggag aaattcctgc    480

gggtgatcca gggcttcagg gcggccagct gctgggaggt gtcctggaag gcacagaagg    540

tgacaaagtg tatctccgtg ttgacagcct ccagcaggat ttgcatttgg gatccagcca    600

cagcctggag ccgcaccatc cagcgctggg ccaggaccag gcgccagaac gccccgcaga    660

gctcgtcgtc ctgcaggttg gaggcgacag tgactggata gtcctgaagc aggtaatcag    720

acagcttgcg gatggtgacc gcgaaggtgg aggagatggg gctgtggctg aaggagcagt    780

cgggggtccc gcggaggccg ggctgagca gcagcagcag caacagggag gcctctgtcc    840

gtctgctctc tcagctctgc ccagctcggt agcgctctgc ctgtccccccg ccttgtcccc    900
```

-continued cgggtatacg cacagttggg ctccaggctg gcgccagcac tatcatctcg gccggaggcc 960
cctcatgcct atggtcagat caggcttgcc ccagctgggc gtggaagggg ccaggccgg 1019

<210> SEQ ID NO 36
<211> LENGTH: 93
<212> TYPE: DNA
<213> ORGANISM: Canis familiaris

<400> SEQUENCE: 36
atgatagtgc tggcgccagc ctggagccca actgtgcgta tacccggggg acaaggcggg 60
ggacaggcag agcgctaccg agctgggcag agc 93

<210> SEQ ID NO 37
<211> LENGTH: 93
<212> TYPE: DNA
<213> ORGANISM: Canis familiaris

<400> SEQUENCE: 37
gctctgccca gctcggtagc gctctgcctg tccccgcct tgtcccccgg gtatacgcac 60
agttgggctc caggctggcg ccagcactat cat 93

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 38
tgaattcgga cataacttca atattac 27

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 39
tctcgagatt cagcttcaat gcctgta 27

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 40
cccaagctta tgggtctcac ctcccaac 28

<210> SEQ ID NO 41
<211> LENGTH: 395
<212> TYPE: DNA
<213> ORGANISM: Felis catus

<400> SEQUENCE: 41
ggccataggc atgaagggcc tccggccgag atgatagtgc tggcgccagc ctggagccca 60
actacctccc tgctgctgct gctactgctc agccctggcc tccgcgggtc ccccgactgt 120

-continued

```
tccttcagcc acagccccat ctcctccacc ttcaaggtca ccatccgaaa gctgtctgat    180

tacctgcttc aggattaccc agtcaccgtc gcctccaacc tacaggacga cgagctctgt    240

gggccattct ggcacctggt cctggcccag cgctggatgg gtcggctcaa ggctgtggct    300

gggtcccaga tgcaaagcct gctggaggcg gtcaacaccg agatacattt tgtcaccttg    360

tgtgccttcc agcccctccc cagctgtctt cgatt                               395
```

```
<210> SEQ ID NO 42
<211> LENGTH: 793
<212> TYPE: DNA
<213> ORGANISM: Felis catus

<400> SEQUENCE: 42

cttcaaggtc accatccgaa agctgtctga ttacctgctt caggattacc cagtcaccgt     60

cgcctccaac ctacaggacg acgagctctg tgggccattc tggcacctgg tcctggccca    120

gcgctggatg ggtcggctca aggctgtggc tgggtcccag atgcaaagcc tgctggaggc    180

ggtcaacacc gagatacatt ttgtcacctt gtgtgccttc cagcccctcc ccagctgtct    240

tcgattcgtc cagaccaaca tctcccacct cctgcaggac acctccgagc agctggcggc    300

cttgaagccc tggatcaccc gcaggaattt ctcggggtgc ctggagctac agtgtcagcc    360

cgactcctcc accccactgc ccccaaggag ccccagggcc ttggaggcca cagccctgcc    420

agcccctcag gcccctctgc tgctcctcct gctgctgttg cctgtggctc tcttgctgat    480

gtccgccgcc tggtgcctgc actggcgaag aaggagatgg agaacgccct accccaggga    540

gcagaggaag acactgaggc ccagagagag gaatcacctg cccgaggaca cagagccggg    600

actcggagaa agtcagctag agactggttc cttcctcgac cacgctgccc cgctcactct    660

ccccccggga tggaggcaac gccagccccc aacgccagcc ccagacccac ctatccccct    720

ctgtacaaag tccttgtcct caggaaattg tatataaatc atccttttct accaaaaaaa    780

aaaaaaaaaa aaa                                                       793
```

```
<210> SEQ ID NO 43
<211> LENGTH: 942
<212> TYPE: DNA
<213> ORGANISM: Felis catus
<220> FEATURE:
<221> NAME/KEY: CDS
<222> LOCATION: (31)..(903)

<400> SEQUENCE: 43

ggccataggc atgaagggcc tccggccgag atg ata gtg ctg gcg cca gcc tgg      54
                                 Met Ile Val Leu Ala Pro Ala Trp
                                   1               5

agc cca act acc tcc ctg ctg ctg ctg cta ctg ctc agc cct ggc ctc      102
Ser Pro Thr Thr Ser Leu Leu Leu Leu Leu Leu Leu Ser Pro Gly Leu
     10                  15                  20

cgc ggg tcc ccc gac tgt tcc ttc agc cac agc ccc atc tcc tcc acc      150
Arg Gly Ser Pro Asp Cys Ser Phe Ser His Ser Pro Ile Ser Ser Thr
 25                  30                  35                  40

ttc aag gtc acc atc cga aag ctg tct gat tac ctg ctt cag gat tac      198
Phe Lys Val Thr Ile Arg Lys Leu Ser Asp Tyr Leu Leu Gln Asp Tyr
                 45                  50                  55

cca gtc acc gtc gcc tcc aac cta cag gac gac gag ctc tgt ggg cca      246
Pro Val Thr Val Ala Ser Asn Leu Gln Asp Asp Glu Leu Cys Gly Pro
             60                  65                  70

ttc tgg cac ctg gtc ctg gcc cag cgc tgg atg ggt cgg ctc aag gct      294
```

-continued

```
Phe Trp His Leu Val Leu Ala Gln Arg Trp Met Gly Arg Leu Lys Ala
        75                  80                  85

gtg gct ggg tcc cag atg caa agc ctg ctg gag gcg gtc aac acc gag      342
Val Ala Gly Ser Gln Met Gln Ser Leu Leu Glu Ala Val Asn Thr Glu
    90                  95                  100

ata cat ttt gtc acc ttg tgt gcc ttc cag ccc ctc ccc agc tgt ctt      390
Ile His Phe Val Thr Leu Cys Ala Phe Gln Pro Leu Pro Ser Cys Leu
105                 110                 115                 120

cga ttc gtc cag acc aac atc tcc cac ctc ctg cag gac acc tcc gag      438
Arg Phe Val Gln Thr Asn Ile Ser His Leu Leu Gln Asp Thr Ser Glu
                125                 130                 135

cag ctg gcg gcc ttg aag ccc tgg atc acc cgc agg aat ttc tcg ggg      486
Gln Leu Ala Ala Leu Lys Pro Trp Ile Thr Arg Arg Asn Phe Ser Gly
            140                 145                 150

tgc ctg gag cta cag tgt cag ccc gac tcc tcc acc cca ctg ccc cca      534
Cys Leu Glu Leu Gln Cys Gln Pro Asp Ser Ser Thr Pro Leu Pro Pro
        155                 160                 165

agg agc ccc agg gcc ttg gag gcc aca gcc ctg cca gcc cct cag gcc      582
Arg Ser Pro Arg Ala Leu Glu Ala Thr Ala Leu Pro Ala Pro Gln Ala
    170                 175                 180

cct ctg ctg ctc ctc ctg ctg ctg ttg cct gtg gct ctc ttg ctg atg      630
Pro Leu Leu Leu Leu Leu Leu Leu Leu Pro Val Ala Leu Leu Leu Met
185                 190                 195                 200

tcc gcc gcc tgg tgc ctg cac tgg cga aga agg aga tgg aga acg ccc      678
Ser Ala Ala Trp Cys Leu His Trp Arg Arg Arg Arg Trp Arg Thr Pro
                205                 210                 215

tac ccc agg gag cag agg aag aca ctg agg ccc aga gag agg aat cac      726
Tyr Pro Arg Glu Gln Arg Lys Thr Leu Arg Pro Arg Glu Arg Asn His
            220                 225                 230

ctg ccc gag gac aca gag ccg gga ctc gga gaa agt cag cta gag act      774
Leu Pro Glu Asp Thr Glu Pro Gly Leu Gly Glu Ser Gln Leu Glu Thr
        235                 240                 245

ggt tcc ttc ctc gac cac gct gcc ccg ctc act ctc ccc ccg gga tgg      822
Gly Ser Phe Leu Asp His Ala Ala Pro Leu Thr Leu Pro Pro Gly Trp
    250                 255                 260

agg caa cgc cag ccc cca acg cca gcc cca gac cca cct atc ccc ctc      870
Arg Gln Arg Gln Pro Pro Thr Pro Ala Pro Asp Pro Pro Ile Pro Leu
265                 270                 275                 280

tgt aca aag tcc ttg tcc tca gga aat tgt ata taaatcatcc ttttctacca    923
Cys Thr Lys Ser Leu Ser Ser Gly Asn Cys Ile
                285                 290

aaaaaaaaaa aaaaaaaaa                                                 942


<210> SEQ ID NO 44
<211> LENGTH: 291
<212> TYPE: PRT
<213> ORGANISM: Felis catus

<400> SEQUENCE: 44

Met Ile Val Leu Ala Pro Ala Trp Ser Pro Thr Thr Ser Leu Leu Leu
  1               5                  10                  15

Leu Leu Leu Leu Ser Pro Gly Leu Arg Gly Ser Pro Asp Cys Ser Phe
            20                  25                  30

Ser His Ser Pro Ile Ser Ser Thr Phe Lys Val Thr Ile Arg Lys Leu
        35                  40                  45

Ser Asp Tyr Leu Leu Gln Asp Tyr Pro Val Thr Val Ala Ser Asn Leu
    50                  55                  60

Gln Asp Asp Glu Leu Cys Gly Pro Phe Trp His Leu Val Leu Ala Gln
 65                  70                  75                  80
```

-continued

```
Arg Trp Met Gly Arg Leu Lys Ala Val Ala Gly Ser Gln Met Gln Ser
                85                  90                  95

Leu Leu Glu Ala Val Asn Thr Glu Ile His Phe Val Thr Leu Cys Ala
            100                 105                 110

Phe Gln Pro Leu Pro Ser Cys Leu Arg Phe Val Gln Thr Asn Ile Ser
        115                 120                 125

His Leu Leu Gln Asp Thr Ser Glu Gln Leu Ala Ala Leu Lys Pro Trp
    130                 135                 140

Ile Thr Arg Arg Asn Phe Ser Gly Cys Leu Glu Leu Gln Cys Gln Pro
145                 150                 155                 160

Asp Ser Ser Thr Pro Leu Pro Pro Arg Ser Pro Arg Ala Leu Glu Ala
                165                 170                 175

Thr Ala Leu Pro Ala Pro Gln Ala Pro Leu Leu Leu Leu Leu Leu Leu
            180                 185                 190

Leu Pro Val Ala Leu Leu Leu Met Ser Ala Ala Trp Cys Leu His Trp
        195                 200                 205

Arg Arg Arg Arg Trp Arg Thr Pro Tyr Pro Arg Glu Gln Arg Lys Thr
    210                 215                 220

Leu Arg Pro Arg Glu Arg Asn His Leu Pro Glu Asp Thr Glu Pro Gly
225                 230                 235                 240

Leu Gly Glu Ser Gln Leu Glu Thr Gly Ser Phe Leu Asp His Ala Ala
                245                 250                 255

Pro Leu Thr Leu Pro Pro Gly Trp Arg Gln Arg Gln Pro Pro Thr Pro
            260                 265                 270

Ala Pro Asp Pro Pro Ile Pro Leu Cys Thr Lys Ser Leu Ser Ser Gly
        275                 280                 285

Asn Cys Ile
    290
```

<210> SEQ ID NO 45
<211> LENGTH: 942
<212> TYPE: DNA
<213> ORGANISM: Felis catus

<400> SEQUENCE: 45

```
ttttttttt ttttttttt ggtagaaaag gatgatttat atacaatttc ctgaggacaa     60

ggactttgta cagaggggga taggtgggtc tggggctggc gttgggggct ggcgttgcct    120

ccatcccggg gggagagtga gcggggcagc gtggtcgagg aaggaaccag tctctagctg    180

actttctccg agtcccggct ctgtgtcctc gggcaggtga ttcctctctc tgggcctcag    240

tgtcttcctc tgctccctgg ggtagggcgt tctccatctc cttcttcgcc agtgcaggca    300

ccaggcggcg gacatcagca agagagccac aggcaacagc agcaggagga gcagcagagg    360

ggcctgaggg gctggcaggg ctgtggcctc caaggccctg gggctccttg ggggcagtgg    420

ggtggaggag tcgggctgac actgtagctc caggcacccc gagaaattcc tgcgggtgat    480

ccagggcttc aaggccgcca gctgctcgga ggtgtcctgc aggaggtggg agatgttggt    540

ctggacgaat cgaagacagc tggggagggg ctggaaggca cacaaggtga caaaatgtat    600

ctcggtgttg accgcctcca gcaggctttg catctgggac ccagccacag ccttgagccg    660

acccatccag cgctgggcca ggaccaggtg ccagaatggc ccacagagct cgtcgtcctg    720

taggttggag gcgacggtga ctgggtaatc ctgaagcagg taatcagaca gctttcggat    780

ggtgaccttg aaggtggagg agatggggct gtggctgaag gaacagtcgg gggacccgcg    840
```

-continued

```
gaggccaggg ctgagcagta gcagcagcag cagggaggta gttgggctcc aggctggcgc    900

cagcactatc atctcggccg gaggcccttc atgcctatgg cc                       942


<210> SEQ ID NO 46
<211> LENGTH: 873
<212> TYPE: DNA
<213> ORGANISM: Felis catus

<400> SEQUENCE: 46

atgatagtgc tggcgccagc ctggagccca actacctccc tgctgctgct gctactgctc     60

agccctggcc tccgcgggtc ccccgactgt tccttcagcc acagccccat ctcctccacc    120

ttcaaggtca ccatccgaaa gctgtctgat tacctgcttc aggattaccc agtcaccgtc    180

gcctccaacc tacaggacga cgagctctgt gggccattct ggcacctggt cctggcccag    240

cgctggatgg gtcggctcaa ggctgtggct gggtcccaga tgcaaagcct gctggaggcg    300

gtcaacaccg agatacattt tgtcaccttg tgtgccttcc agcccctccc cagctgtctt    360

cgattcgtcc agaccaacat ctcccacctc ctgcaggaca cctccgagca gctggcggcc    420

ttgaagccct ggatcacccg caggaatttc tcggggtgcc tggagctaca gtgtcagccc    480

gactcctcca ccccactgcc cccaaggagc cccagggcct tggaggccac agccctgcca    540

gcccctcagg cccctctgct gctcctcctg ctgctgttgc ctgtggctct cttgctgatg    600

tccgccgcct ggtgcctgca ctggcgaaga aggagatgga gaacgcccta ccccagggag    660

cagaggaaga cactgaggcc cagagagagg aatcacctgc ccgaggacac agagccggga    720

ctcggagaaa gtcagctaga gactggttcc ttcctcgacc acgctgcccc gctcactctc    780

cccccgggat ggaggcaacg ccagccccca acgccagccc cagacccacc tatccccctc    840

tgtacaaagt ccttgtcctc aggaaattgt ata                                 873


<210> SEQ ID NO 47
<211> LENGTH: 873
<212> TYPE: DNA
<213> ORGANISM: Felis catus

<400> SEQUENCE: 47

tatacaattt cctgaggaca aggactttgt acagaggggg ataggtgggt ctggggctgg     60

cgttgggggc tggcgttgcc tccatcccgg ggggagagtg agcggggcag cgtggtcgag    120

gaaggaacca gtctctagct gactttctcc gagtcccggc tctgtgtcct cgggcaggtg    180

attcctctct ctgggcctca gtgtcttcct ctgctccctg gggtagggcg ttctccatct    240

ccttcttcgc cagtgcaggc accaggcggc ggacatcagc aagagagcca caggcaacag    300

cagcaggagg agcagcagag gggcctgagg ggctggcagg gctgtggcct ccaaggccct    360

ggggctcctt gggggcagtg gggtggagga gtcgggctga cactgtagct ccaggcaccc    420

cgagaaattc ctgcgggtga tccagggctt caaggccgcc agctgctcgg aggtgtcctg    480

caggaggtgg gagatgttgg tctggacgaa tcgaagacag ctggggaggg gctggaaggc    540

acacaaggtg acaaaatgta tctcggtgtt gaccgcctcc agcaggcttt gcatctggga    600

cccagccaca gccttgagcc gacccatcca gcgctgggcc aggaccaggt gccagaatgg    660

cccacagagc tcgtcgtcct gtaggttgga ggcgacggtg actgggtaat cctgaagcag    720

gtaatcagac agctttcgga tggtgacctt gaaggtggag gagatggggc tgtggctgaa    780

ggaacagtcg gggacccgc ggaggccagg gctgagcagt agcagcagca gcagggaggt    840

agttgggctc caggctggcg ccagcactat cat                                 873
```

-continued

```
<210> SEQ ID NO 48
<211> LENGTH: 795
<212> TYPE: DNA
<213> ORGANISM: Felis catus
<220> FEATURE:
<221> NAME/KEY: CDS
<222> LOCATION: (1)..(795)

<400> SEQUENCE: 48

tcc ccc gac tgt tcc ttc agc cac agc ccc atc tcc tcc acc ttc aag       48
Ser Pro Asp Cys Ser Phe Ser His Ser Pro Ile Ser Ser Thr Phe Lys
  1               5                  10                  15

gtc acc atc cga aag ctg tct gat tac ctg ctt cag gat tac cca gtc       96
Val Thr Ile Arg Lys Leu Ser Asp Tyr Leu Leu Gln Asp Tyr Pro Val
             20                  25                  30

acc gtc gcc tcc aac cta cag gac gac gag ctc tgt ggg cca ttc tgg      144
Thr Val Ala Ser Asn Leu Gln Asp Asp Glu Leu Cys Gly Pro Phe Trp
         35                  40                  45

cac ctg gtc ctg gcc cag cgc tgg atg ggt cgg ctc aag gct gtg gct      192
His Leu Val Leu Ala Gln Arg Trp Met Gly Arg Leu Lys Ala Val Ala
     50                  55                  60

ggg tcc cag atg caa agc ctg ctg gag gcg gtc aac acc gag ata cat      240
Gly Ser Gln Met Gln Ser Leu Leu Glu Ala Val Asn Thr Glu Ile His
 65                  70                  75                  80

ttt gtc acc ttg tgt gcc ttc cag ccc ctc ccc agc tgt ctt cga ttc      288
Phe Val Thr Leu Cys Ala Phe Gln Pro Leu Pro Ser Cys Leu Arg Phe
                 85                  90                  95

gtc cag acc aac atc tcc cac ctc ctg cag gac acc tcc gag cag ctg      336
Val Gln Thr Asn Ile Ser His Leu Leu Gln Asp Thr Ser Glu Gln Leu
            100                 105                 110

gcg gcc ttg aag ccc tgg atc acc cgc agg aat ttc tcg ggg tgc ctg      384
Ala Ala Leu Lys Pro Trp Ile Thr Arg Arg Asn Phe Ser Gly Cys Leu
        115                 120                 125

gag cta cag tgt cag ccc gac tcc tcc acc cca ctg ccc cca agg agc      432
Glu Leu Gln Cys Gln Pro Asp Ser Ser Thr Pro Leu Pro Pro Arg Ser
    130                 135                 140

ccc agg gcc ttg gag gcc aca gcc ctg cca gcc cct cag gcc cct ctg      480
Pro Arg Ala Leu Glu Ala Thr Ala Leu Pro Ala Pro Gln Ala Pro Leu
145                 150                 155                 160

ctg ctc ctc ctg ctg ctg ttg cct gtg gct ctc ttg ctg atg tcc gcc      528
Leu Leu Leu Leu Leu Leu Leu Pro Val Ala Leu Leu Leu Met Ser Ala
                165                 170                 175

gcc tgg tgc ctg cac tgg cga aga agg aga tgg aga acg ccc tac ccc      576
Ala Trp Cys Leu His Trp Arg Arg Arg Arg Trp Arg Thr Pro Tyr Pro
            180                 185                 190

agg gag cag agg aag aca ctg agg ccc aga gag agg aat cac ctg ccc      624
Arg Glu Gln Arg Lys Thr Leu Arg Pro Arg Glu Arg Asn His Leu Pro
        195                 200                 205

gag gac aca gag ccg gga ctc gga gaa agt cag cta gag act ggt tcc      672
Glu Asp Thr Glu Pro Gly Leu Gly Glu Ser Gln Leu Glu Thr Gly Ser
    210                 215                 220

ttc ctc gac cac gct gcc ccg ctc act ctc ccc ccg gga tgg agg caa      720
Phe Leu Asp His Ala Ala Pro Leu Thr Leu Pro Pro Gly Trp Arg Gln
225                 230                 235                 240

cgc cag ccc cca acg cca gcc cca gac cca cct atc ccc ctc tgt aca      768
Arg Gln Pro Pro Thr Pro Ala Pro Asp Pro Pro Ile Pro Leu Cys Thr
                245                 250                 255

aag tcc ttg tcc tca gga aat tgt ata                                  795
Lys Ser Leu Ser Ser Gly Asn Cys Ile
            260                 265
```

-continued

<210> SEQ ID NO 49
<211> LENGTH: 265
<212> TYPE: PRT
<213> ORGANISM: Felis catus

<400> SEQUENCE: 49

```
Ser Pro Asp Cys Ser Phe Ser His Ser Pro Ile Ser Ser Thr Phe Lys
  1               5                  10                  15

Val Thr Ile Arg Lys Leu Ser Asp Tyr Leu Leu Gln Asp Tyr Pro Val
             20                  25                  30

Thr Val Ala Ser Asn Leu Gln Asp Asp Glu Leu Cys Gly Pro Phe Trp
         35                  40                  45

His Leu Val Leu Ala Gln Arg Trp Met Gly Arg Leu Lys Ala Val Ala
     50                  55                  60

Gly Ser Gln Met Gln Ser Leu Leu Glu Ala Val Asn Thr Glu Ile His
 65                  70                  75                  80

Phe Val Thr Leu Cys Ala Phe Gln Pro Leu Pro Ser Cys Leu Arg Phe
                 85                  90                  95

Val Gln Thr Asn Ile Ser His Leu Leu Gln Asp Thr Ser Glu Gln Leu
            100                 105                 110

Ala Ala Leu Lys Pro Trp Ile Thr Arg Arg Asn Phe Ser Gly Cys Leu
        115                 120                 125

Glu Leu Gln Cys Gln Pro Asp Ser Ser Thr Pro Leu Pro Pro Arg Ser
    130                 135                 140

Pro Arg Ala Leu Glu Ala Thr Ala Leu Pro Ala Pro Gln Ala Pro Leu
145                 150                 155                 160

Leu Leu Leu Leu Leu Leu Leu Pro Val Ala Leu Leu Leu Met Ser Ala
                165                 170                 175

Ala Trp Cys Leu His Trp Arg Arg Arg Arg Trp Arg Thr Pro Tyr Pro
            180                 185                 190

Arg Glu Gln Arg Lys Thr Leu Arg Pro Arg Glu Arg Asn His Leu Pro
        195                 200                 205

Glu Asp Thr Glu Pro Gly Leu Gly Glu Ser Gln Leu Glu Thr Gly Ser
    210                 215                 220

Phe Leu Asp His Ala Ala Pro Leu Thr Leu Pro Pro Gly Trp Arg Gln
225                 230                 235                 240

Arg Gln Pro Pro Thr Pro Ala Pro Asp Pro Pro Ile Pro Leu Cys Thr
                245                 250                 255

Lys Ser Leu Ser Ser Gly Asn Cys Ile
            260                 265
```

<210> SEQ ID NO 50
<211> LENGTH: 795
<212> TYPE: DNA
<213> ORGANISM: Felis catus

<400> SEQUENCE: 50

```
tatacaattt cctgaggaca aggactttgt acagaggggg ataggtgggt ctggggctgg     60

cgttgggggc tggcgttgcc tccatcccgg ggggagagtg agcggggcag cgtggtcgag    120

gaaggaacca gtctctagct gactttctcc gagtcccggc tctgtgtcct cgggcaggtg    180

attcctctct ctgggcctca gtgtcttcct ctgctccctg gggtagggcg ttctccatct    240

ccttcttcgc cagtgcaggc accaggcggc ggacatcagc aagagagcca caggcaacag    300

cagcaggagg agcagcagag gggcctgagg ggctggcagg gctgtggcct ccaaggccct    360
```

-continued

```
ggggctcctt gggggcagtg gggtggagga gtcgggctga cactgtagct ccaggcaccc    420

cgagaaattc ctgcgggtga tccagggctt caaggccgcc agctgctcgg aggtgtcctg    480

caggaggtgg gagatgttgg tctggacgaa tcgaagacag ctggggaggg gctggaaggc    540

acacaaggtg acaaaatgta tctcggtgtt gaccgcctcc agcaggcttt gcatctggga    600

cccagccaca gccttgagcc gacccatcca gcgctgggcc aggaccaggt gccagaatgg    660

cccacagagc tcgtcgtcct gtaggttgga ggcgacggtg actgggtaat cctgaagcag    720

gtaatcagac agctttcgga tggtgacctt gaaggtggag gagatggggc tgtggctgaa    780

ggaacagtcg gggga                                                     795


<210> SEQ ID NO 51
<211> LENGTH: 321
<212> TYPE: DNA
<213> ORGANISM: Canis familiaris

<400> SEQUENCE: 51

aatgtgtctt ctgctttgga aaagtgtcac ccttggacaa gctgtgaaac caaaggcctg     60

gtgaaggttc aggcgggaac taacaagact gatgttatct gtggtcccca gcctcggtta    120

agagccctag tggtggtccc catcattatg ggatcctgc  ttgttgtcct gttggtgtct    180

gcctgcatcc gaaaggtggt caagaagcca gagaataagg ttatgtatca ggaccctgtg    240

gaggacttgg aggaatttcc tatgcccccg cactccattg ctccggtgca agagacctta    300

catgggtgcc agcccgtcac c                                              321


<210> SEQ ID NO 52
<211> LENGTH: 1425
<212> TYPE: DNA
<213> ORGANISM: Canis familiaris
<220> FEATURE:
<221> NAME/KEY: CDS
<222> LOCATION: (196)..(1017)

<400> SEQUENCE: 52

tagactcccg ggaatattca ggggaactcc cggcgctaag ggtctccagg agctccgccc     60

tgcccaacga agccggccac gattggtccc cgaagacccc gcccatctcc tgggcggggc    120

gggcgggggc aagggctggg gagttactaa agacatcccc gcgcccctac tccgctgcct    180

gctattcacc tcgcc atg gtt ctc ctg cct ctg cgc tgt ctc ttc tgg ggc     231
                 Met Val Leu Leu Pro Leu Arg Cys Leu Phe Trp Gly
                   1               5                  10

tcc ttg ttg acc acc gtc tac cca gaa cca cgc act gca tgc aga gaa      279
Ser Leu Leu Thr Thr Val Tyr Pro Glu Pro Arg Thr Ala Cys Arg Glu
        15                  20                  25

aag caa tac cta gta gac agt cag tgc tgt aat atg tgc cca cca gga      327
Lys Gln Tyr Leu Val Asp Ser Gln Cys Cys Asn Met Cys Pro Pro Gly
    30                  35                  40

gag aaa ctg gtg aat gac tgc cta cat acc att gac acg gaa tgc act      375
Glu Lys Leu Val Asn Asp Cys Leu His Thr Ile Asp Thr Glu Cys Thr
 45                  50                  55                  60

cgt tgc caa aca ggc gaa ttc cta gac act tgg aac gca gag aga cac      423
Arg Cys Gln Thr Gly Glu Phe Leu Asp Thr Trp Asn Ala Glu Arg His
                 65                  70                  75

tgt cac cag cac aaa tac tgc gac ccc aac cta ggg ctc cat gtc gag      471
Cys His Gln His Lys Tyr Cys Asp Pro Asn Leu Gly Leu His Val Glu
             80                  85                  90

aag gag ggc acg tca gaa aca gac acc act tgc aca tgc gat gaa ggt      519
```

-continued

```
Lys Glu Gly Thr Ser Glu Thr Asp Thr Thr Cys Thr Cys Asp Glu Gly
        95                  100                 105

ctg cat tgt acc aac gct gcc tgt gag agc tgc acc atg cac agc ctg      567
Leu His Cys Thr Asn Ala Ala Cys Glu Ser Cys Thr Met His Ser Leu
    110                 115                 120

tgc ccc cct ggc ctg gga gtc aaa cag atc gct aca ggg att tct gat      615
Cys Pro Pro Gly Leu Gly Val Lys Gln Ile Ala Thr Gly Ile Ser Asp
125                 130                 135                 140

acc atc tgc gat ccc tgc ccc atc ggc ttc ttc tcc aat gtg tct tct      663
Thr Ile Cys Asp Pro Cys Pro Ile Gly Phe Phe Ser Asn Val Ser Ser
                145                 150                 155

gct ttg gaa aag tgt cac cct tgg aca agc tgt gaa acc aaa ggc ctg      711
Ala Leu Glu Lys Cys His Pro Trp Thr Ser Cys Glu Thr Lys Gly Leu
            160                 165                 170

gtg aag gtt cag gcg gga act aac aag act gat gtt atc tgt ggt ccc      759
Val Lys Val Gln Ala Gly Thr Asn Lys Thr Asp Val Ile Cys Gly Pro
        175                 180                 185

cag cct cgg tta aga gcc cta gtg gtg gtc ccc atc att atg ggg atc      807
Gln Pro Arg Leu Arg Ala Leu Val Val Val Pro Ile Ile Met Gly Ile
    190                 195                 200

ctg ctt gtt gtc ctg ttg gtg tct gcc tgc atc cga aag gtg gtc aag      855
Leu Leu Val Val Leu Leu Val Ser Ala Cys Ile Arg Lys Val Val Lys
205                 210                 215                 220

aag cca gag aat aag gtt atg tat cag gac cct gtg gag gac ttg gag      903
Lys Pro Glu Asn Lys Val Met Tyr Gln Asp Pro Val Glu Asp Leu Glu
                225                 230                 235

gaa ttt cct atg ccc ccg cac tcc att gct ccg gtg caa gag acc tta      951
Glu Phe Pro Met Pro Pro His Ser Ile Ala Pro Val Gln Glu Thr Leu
            240                 245                 250

cat ggg tgc cag ccc gtc acc cag gag gac ggc aaa gag agc cgc atc      999
His Gly Cys Gln Pro Val Thr Gln Glu Asp Gly Lys Glu Ser Arg Ile
        255                 260                 265

tcc gtg cag gag aga gtg tgaggcagcg tgtgcccagg agtgtgacag            1047
Ser Val Gln Glu Arg Val
    270

cgtgggagag tgggcgcgtg gctggagagc ctggagctgc tggaggggca tgaaggggcg   1107

gtgctcccct gcctgcaccc ctgtgctgca gaaacagaga accttccacc ccacccctgg   1167

agcccattcc acctcccaac ttgcttttaa agatggagat gaaacttttg gggggccaga   1227

tagtaatatc caccaaccca gcatttcagg gccctgaggt gtatatcacg gtggtttcta   1287

cgagcccagg aagacccacg aagagccatt gtggcattgt ttgtgacagt ggacaactgg   1347

aggccactta gctgttcagc agcaggggac tggctaaata aaatttgtaa tatatttata   1407

aaaaaaaaaa aaaaaaa                                                  1425


<210> SEQ ID NO 53
<211> LENGTH: 274
<212> TYPE: PRT
<213> ORGANISM: Canis familiaris

<400> SEQUENCE: 53

Met Val Leu Leu Pro Leu Arg Cys Leu Phe Trp Gly Ser Leu Leu Thr
  1               5                  10                  15

Thr Val Tyr Pro Glu Pro Arg Thr Ala Cys Arg Glu Lys Gln Tyr Leu
            20                  25                  30

Val Asp Ser Gln Cys Cys Asn Met Cys Pro Pro Gly Glu Lys Leu Val
        35                  40                  45

Asn Asp Cys Leu His Thr Ile Asp Thr Glu Cys Thr Arg Cys Gln Thr
```

-continued

```
     50                  55                  60

Gly Glu Phe Leu Asp Thr Trp Asn Ala Glu Arg His Cys His Gln His
 65                 70                  75                  80

Lys Tyr Cys Asp Pro Asn Leu Gly Leu His Val Glu Lys Glu Gly Thr
                85                  90                  95

Ser Glu Thr Asp Thr Thr Cys Thr Cys Asp Glu Gly Leu His Cys Thr
            100                 105                 110

Asn Ala Ala Cys Glu Ser Cys Thr Met His Ser Leu Cys Pro Pro Gly
        115                 120                 125

Leu Gly Val Lys Gln Ile Ala Thr Gly Ile Ser Asp Thr Ile Cys Asp
    130                 135                 140

Pro Cys Pro Ile Gly Phe Phe Ser Asn Val Ser Ser Ala Leu Glu Lys
145                 150                 155                 160

Cys His Pro Trp Thr Ser Cys Glu Thr Lys Gly Leu Val Lys Val Gln
                165                 170                 175

Ala Gly Thr Asn Lys Thr Asp Val Ile Cys Gly Pro Gln Pro Arg Leu
            180                 185                 190

Arg Ala Leu Val Val Val Pro Ile Ile Met Gly Ile Leu Leu Val Val
        195                 200                 205

Leu Leu Val Ser Ala Cys Ile Arg Lys Val Val Lys Lys Pro Glu Asn
    210                 215                 220

Lys Val Met Tyr Gln Asp Pro Val Glu Asp Leu Glu Glu Phe Pro Met
225                 230                 235                 240

Pro Pro His Ser Ile Ala Pro Val Gln Glu Thr Leu His Gly Cys Gln
                245                 250                 255

Pro Val Thr Gln Glu Asp Gly Lys Glu Ser Arg Ile Ser Val Gln Glu
            260                 265                 270

Arg Val


<210> SEQ ID NO 54
<211> LENGTH: 1425
<212> TYPE: DNA
<213> ORGANISM: Canis familiaris

<400> SEQUENCE: 54

ttttttttt ttttttttta taaatatatt acaaatttta tttagccagt cccctgctgc     60

tgaacagcta agtggcctcc agttgtccac tgtcacaaac aatgccacaa tggctcttcg    120

tgggtcttcc tgggctcgta gaaaccaccg tgatatacac ctcagggccc tgaaatgctg    180

ggttggtgga tattactatc tggcccccca aaagtttcat ctccatcttt aaaagcaagt    240

tgggaggtgg aatgggctcc aggggtgggg tggaaggttc tctgtttctg cagcacaggg    300

gtgcaggcag gggagcaccg ccccttcatg cccctccagc agctccaggc tctccagcca    360

cgcgcccact ctcccacgct gtcacactcc tgggcacacg ctgcctcaca ctctctcctg    420

cacggagatg cggctctctt tgccgtcctc ctgggtgacg ggctggcacc catgtaaggt    480

ctcttgcacc ggagcaatgg agtgcggggg cataggaaat tcctccaagt cctccacagg    540

gtcctgatac ataaccttat tctctggctt cttgaccacc tttcggatgc aggcagacac    600

caacaggaca acaagcagga tccccataat gatggggacc accactaggg ctcttaaccg    660

aggctgggga ccacagataa catcagtctt gttagttccc gcctgaacct tcaccaggcc    720

tttggtttca cagcttgtcc aagggtgaca cttttccaaa gcagaagaca cattggagaa    780

gaagccgatg gggcagggat cgcagatggt atcagaaatc cctgtagcga tctgtttgac    840
```

-continued

```
tcccaggcca ggggggcaca ggctgtgcat ggtgcagctc tcacaggcag cgttggtaca    900

atgcagacct tcatcgcatg tgcaagtggt gtctgtttct gacgtgccct ccttctcgac    960

atggagccct aggttggggt cgcagtattt gtgctggtga cagtgtctct ctgcgttcca   1020

agtgtctagg aattcgcctg tttggcaacg agtgcattcc gtgtcaatgg tatgtaggca   1080

gtcattcacc agtttctctc ctggtgggca catattacag cactgactgt ctactaggta   1140

ttgcttttct ctgcatgcag tgcgtggttc tgggtagacg gtggtcaaca aggagcccca   1200

gaagagacag cgcagaggca ggagaaccat ggcgaggtga atagcaggca gcggagtagg   1260

ggcgcgggga tgtctttagt aactccccag cccttgcccc cgcccgcccc gcccaggaga   1320

tgggcggggt cttcggggac caatcgtggc cggcttcgtt gggcagggcg gagctcctgg   1380

agacccttag cgccgggagt tcccctgaat attcccggga gtcta                   1425
```

<210> SEQ ID NO 55
<211> LENGTH: 822
<212> TYPE: DNA
<213> ORGANISM: Canis familiaris

<400> SEQUENCE: 55

```
atggttctcc tgcctctgcg ctgtctcttc tggggctcct tgttgaccac cgtctaccca     60

gaaccacgca ctgcatgcag agaaaagcaa tacctagtag acagtcagtg ctgtaatatg    120

tgcccaccag gagagaaact ggtgaatgac tgcctacata ccattgacac ggaatgcact    180

cgttgccaaa caggcgaatt cctagacact tggaacgcag agagacactg tcaccagcac    240

aaatactgcg accccaacct agggctccat gtcgagaagg agggcacgtc agaaacagac    300

accacttgca catgcgatga aggtctgcat tgtaccaacg ctgcctgtga gagctgcacc    360

atgcacagcc tgtgcccccc tggcctggga gtcaaacaga tcgctacagg gatttctgat    420

accatctgcg atccctgccc catcggcttc ttctccaatg tgtcttctgc tttggaaaag    480

tgtcaccctt ggacaagctg tgaaaccaaa ggcctggtga aggttcaggc gggaactaac    540

aagactgatg ttatctgtgg tccccagcct cggttaagag ccctagtggt ggtccccatc    600

attatgggga tcctgcttgt tgtcctgttg gtgtctgcct gcatccgaaa ggtggtcaag    660

aagccagaga ataaggttat gtatcaggac cctgtggagg acttggagga atttcctatg    720

cccccgcact ccattgctcc ggtgcaagag accttacatg ggtgccagcc cgtcacccag    780

gaggacggca aagagagccg catctccgtg caggagagag tg                       822
```

<210> SEQ ID NO 56
<211> LENGTH: 822
<212> TYPE: DNA
<213> ORGANISM: Canis familiaris

<400> SEQUENCE: 56

```
cactctctcc tgcacggaga tgcggctctc tttgccgtcc tcctgggtga cgggctggca     60

cccatgtaag gtctcttgca ccggagcaat ggagtgcggg ggcataggaa attcctccaa    120

gtcctccaca gggtcctgat acataacctt attctctggc ttcttgacca cctttcggat    180

gcaggcagac accaacagga caacaagcag gatccccata atgatgggga ccaccactag    240

ggctcttaac cgaggctggg gaccacagat aacatcagtc ttgttagttc ccgcctgaac    300

cttcaccagg cctttggttt cacagcttgt ccaagggtga cacttttcca aagcagaaga    360

cacattggag aagaagccga tggggcaggg atcgcagatg gtatcagaaa tccctgtagc    420

gatctgtttg actcccaggc caggggggca caggctgtgc atggtgcagc tctcacaggc    480
```

-continued

```
agcgttggta caatgcagac cttcatcgca tgtgcaagtg gtgtctgttt ctgacgtgcc    540

ctccttctcg acatggagcc ctaggttggg gtcgcagtat ttgtgctggt gacagtgtct    600

ctctgcgttc caagtgtcta ggaattcgcc tgtttggcaa cgagtgcatt ccgtgtcaat    660

ggtatgtagg cagtcattca ccagtttctc tcctggtggg cacatattac agcactgact    720

gtctactagg tattgctttt ctctgcatgc agtgcgtggt tctgggtaga cggtggtcaa    780

caaggagccc cagaagagac agcgcagagg caggagaacc at                       822


<210> SEQ ID NO 57
<211> LENGTH: 765
<212> TYPE: DNA
<213> ORGANISM: Canis familiaris
<220> FEATURE:
<221> NAME/KEY: CDS
<222> LOCATION: (1)..(765)

<400> SEQUENCE: 57

cca gaa cca cgc act gca tgc aga gaa aag caa tac cta gta gac agt       48
Pro Glu Pro Arg Thr Ala Cys Arg Glu Lys Gln Tyr Leu Val Asp Ser
  1               5                  10                  15

cag tgc tgt aat atg tgc cca cca gga gag aaa ctg gtg aat gac tgc       96
Gln Cys Cys Asn Met Cys Pro Pro Gly Glu Lys Leu Val Asn Asp Cys
             20                  25                  30

cta cat acc att gac acg gaa tgc act cgt tgc caa aca ggc gaa ttc      144
Leu His Thr Ile Asp Thr Glu Cys Thr Arg Cys Gln Thr Gly Glu Phe
         35                  40                  45

cta gac act tgg aac gca gag aga cac tgt cac cag cac aaa tac tgc      192
Leu Asp Thr Trp Asn Ala Glu Arg His Cys His Gln His Lys Tyr Cys
     50                  55                  60

gac ccc aac cta ggg ctc cat gtc gag aag gag ggc acg tca gaa aca      240
Asp Pro Asn Leu Gly Leu His Val Glu Lys Glu Gly Thr Ser Glu Thr
 65                  70                  75                  80

gac acc act tgc aca tgc gat gaa ggt ctg cat tgt acc aac gct gcc      288
Asp Thr Thr Cys Thr Cys Asp Glu Gly Leu His Cys Thr Asn Ala Ala
                 85                  90                  95

tgt gag agc tgc acc atg cac agc ctg tgc ccc cct ggc ctg gga gtc      336
Cys Glu Ser Cys Thr Met His Ser Leu Cys Pro Pro Gly Leu Gly Val
            100                 105                 110

aaa cag atc gct aca ggg att tct gat acc atc tgc gat ccc tgc ccc      384
Lys Gln Ile Ala Thr Gly Ile Ser Asp Thr Ile Cys Asp Pro Cys Pro
        115                 120                 125

atc ggc ttc ttc tcc aat gtg tct tct gct ttg gaa aag tgt cac cct      432
Ile Gly Phe Phe Ser Asn Val Ser Ser Ala Leu Glu Lys Cys His Pro
    130                 135                 140

tgg aca agc tgt gaa acc aaa ggc ctg gtg aag gtt cag gcg gga act      480
Trp Thr Ser Cys Glu Thr Lys Gly Leu Val Lys Val Gln Ala Gly Thr
145                 150                 155                 160

aac aag act gat gtt atc tgt ggt ccc cag cct cgg tta aga gcc cta      528
Asn Lys Thr Asp Val Ile Cys Gly Pro Gln Pro Arg Leu Arg Ala Leu
                165                 170                 175

gtg gtg gtc ccc atc att atg ggg atc ctg ctt gtt gtc ctg ttg gtg      576
Val Val Val Pro Ile Ile Met Gly Ile Leu Leu Val Val Leu Leu Val
            180                 185                 190

tct gcc tgc atc cga aag gtg gtc aag aag cca gag aat aag gtt atg      624
Ser Ala Cys Ile Arg Lys Val Val Lys Lys Pro Glu Asn Lys Val Met
        195                 200                 205

tat cag gac cct gtg gag gac ttg gag gaa ttt cct atg ccc ccg cac      672
Tyr Gln Asp Pro Val Glu Asp Leu Glu Glu Phe Pro Met Pro Pro His
    210                 215                 220
```

-continued

```
tcc att gct ccg gtg caa gag acc tta cat ggg tgc cag ccc gtc acc      720
Ser Ile Ala Pro Val Gln Glu Thr Leu His Gly Cys Gln Pro Val Thr
225                 230                 235                 240

cag gag gac ggc aaa gag agc cgc atc tcc gtg cag gag aga gtg          765
Gln Glu Asp Gly Lys Glu Ser Arg Ile Ser Val Gln Glu Arg Val
                245                 250                 255


<210> SEQ ID NO 58
<211> LENGTH: 255
<212> TYPE: PRT
<213> ORGANISM: Canis familiaris

<400> SEQUENCE: 58

Pro Glu Pro Arg Thr Ala Cys Arg Glu Lys Gln Tyr Leu Val Asp Ser
  1               5                  10                  15

Gln Cys Cys Asn Met Cys Pro Pro Gly Glu Lys Leu Val Asn Asp Cys
             20                  25                  30

Leu His Thr Ile Asp Thr Glu Cys Thr Arg Cys Gln Thr Gly Glu Phe
         35                  40                  45

Leu Asp Thr Trp Asn Ala Glu Arg His Cys His Gln His Lys Tyr Cys
     50                  55                  60

Asp Pro Asn Leu Gly Leu His Val Glu Lys Glu Gly Thr Ser Glu Thr
 65                  70                  75                  80

Asp Thr Thr Cys Thr Cys Asp Glu Gly Leu His Cys Thr Asn Ala Ala
                 85                  90                  95

Cys Glu Ser Cys Thr Met His Ser Leu Cys Pro Pro Gly Leu Gly Val
            100                 105                 110

Lys Gln Ile Ala Thr Gly Ile Ser Asp Thr Ile Cys Asp Pro Cys Pro
        115                 120                 125

Ile Gly Phe Phe Ser Asn Val Ser Ser Ala Leu Glu Lys Cys His Pro
    130                 135                 140

Trp Thr Ser Cys Glu Thr Lys Gly Leu Val Lys Val Gln Ala Gly Thr
145                 150                 155                 160

Asn Lys Thr Asp Val Ile Cys Gly Pro Gln Pro Arg Leu Arg Ala Leu
                165                 170                 175

Val Val Val Pro Ile Ile Met Gly Ile Leu Leu Val Val Leu Leu Val
            180                 185                 190

Ser Ala Cys Ile Arg Lys Val Val Lys Lys Pro Glu Asn Lys Val Met
        195                 200                 205

Tyr Gln Asp Pro Val Glu Asp Leu Glu Glu Phe Pro Met Pro Pro His
    210                 215                 220

Ser Ile Ala Pro Val Gln Glu Thr Leu His Gly Cys Gln Pro Val Thr
225                 230                 235                 240

Gln Glu Asp Gly Lys Glu Ser Arg Ile Ser Val Gln Glu Arg Val
                245                 250                 255


<210> SEQ ID NO 59
<211> LENGTH: 765
<212> TYPE: DNA
<213> ORGANISM: Canis familiaris

<400> SEQUENCE: 59

cactctctcc tgcacggaga tgcggctctc tttgccgtcc tcctgggtga cgggctggca     60

cccatgtaag gtctcttgca ccggagcaat ggagtgcggg ggcataggaa attcctccaa    120

gtcctccaca gggtcctgat acataacctt attctctggc ttcttgacca cctttcggat    180
```

-continued

```
gcaggcagac accaacagga caacaagcag gatccccata atgatgggga ccaccactag    240

ggctcttaac cgaggctggg gaccacagat aacatcagtc ttgttagttc ccgcctgaac    300

cttcaccagg cctttggttt cacagcttgt ccaagggtga cacttttcca aagcagaaga    360

cacattggag aagaagccga tggggcaggg atcgcagatg gtatcagaaa tccctgtagc    420

gatctgtttg actcccaggc caggggggca caggctgtgc atggtgcagc tctcacaggc    480

agcgttggta caatgcagac cttcatcgca tgtgcaagtg gtgtctgttt ctgacgtgcc    540

ctccttctcg acatggagcc ctaggttggg gtcgcagtat ttgtgctggt gacagtgtct    600

ctctgcgttc caagtgtcta ggaattcgcc tgtttggcaa cgagtgcatt ccgtgtcaat    660

ggtatgtagg cagtcattca ccagtttctc tcctggtggg cacatattac agcactgact    720

gtctactagg tattgctttt ctctgcatgc agtgcgtggt tctgg                    765
```

```
<210> SEQ ID NO 60
<211> LENGTH: 336
<212> TYPE: DNA
<213> ORGANISM: Felis catus
<220> FEATURE:
<221> NAME/KEY: CDS
<222> LOCATION: (1)..(336)

<400> SEQUENCE: 60

aat gtg tca tct gct tcg gaa aag tgt cac cct tgg acg agg tgt gag       48
Asn Val Ser Ser Ala Ser Glu Lys Cys His Pro Trp Thr Arg Cys Glu
  1               5                  10                  15

acc aaa ggc ctg gtg gag ctt cag gcg ggg acc aac aag acg gat gcc       96
Thr Lys Gly Leu Val Glu Leu Gln Ala Gly Thr Asn Lys Thr Asp Ala
             20                  25                  30

gtc tgc ggt ttc cag gat cgg ata aga gcc ctg gtg gtg atc ccc atc      144
Val Cys Gly Phe Gln Asp Arg Ile Arg Ala Leu Val Val Ile Pro Ile
         35                  40                  45

acg atg gtg gtc ctg ctt gct gtc ttg ttg gtg tct gcg tat atc aga      192
Thr Met Val Val Leu Leu Ala Val Leu Leu Val Ser Ala Tyr Ile Arg
     50                  55                  60

aag gtg acc aag aag cca gag aat aag gtc ctc cag cct aag gct gtg      240
Lys Val Thr Lys Lys Pro Glu Asn Lys Val Leu Gln Pro Lys Ala Val
 65                  70                  75                  80

tcg cag gac cct gtg gag gac ttg gag gtc ctt cct gtc ccc ctc cac      288
Ser Gln Asp Pro Val Glu Asp Leu Glu Val Leu Pro Val Pro Leu His
                 85                  90                  95

ccc att gct ccg gtg cag gag acc tta cac ggg tgc cag ccg gtc acc      336
Pro Ile Ala Pro Val Gln Glu Thr Leu His Gly Cys Gln Pro Val Thr
            100                 105                 110


<210> SEQ ID NO 61
<211> LENGTH: 112
<212> TYPE: PRT
<213> ORGANISM: Felis catus

<400> SEQUENCE: 61

Asn Val Ser Ser Ala Ser Glu Lys Cys His Pro Trp Thr Arg Cys Glu
  1               5                  10                  15

Thr Lys Gly Leu Val Glu Leu Gln Ala Gly Thr Asn Lys Thr Asp Ala
             20                  25                  30

Val Cys Gly Phe Gln Asp Arg Ile Arg Ala Leu Val Val Ile Pro Ile
         35                  40                  45

Thr Met Val Val Leu Leu Ala Val Leu Leu Val Ser Ala Tyr Ile Arg
     50                  55                  60
```

-continued

```
Lys Val Thr Lys Lys Pro Glu Asn Lys Val Leu Gln Pro Lys Ala Val
 65                  70                  75                  80

Ser Gln Asp Pro Val Glu Asp Leu Glu Val Leu Pro Val Pro Leu His
                 85                  90                  95

Pro Ile Ala Pro Val Gln Glu Thr Leu His Gly Cys Gln Pro Val Thr
            100                 105                 110


<210> SEQ ID NO 62
<211> LENGTH: 336
<212> TYPE: DNA
<213> ORGANISM: Felis catus

<400> SEQUENCE: 62

ggtgaccggc tggcacccgt gtaaggtctc ctgcaccgga gcaatggggt ggagggggac     60

aggaaggacc tccaagtcct ccacagggtc ctgcgacaca gccttaggct ggaggacctt    120

attctctggc ttcttggtca cctttctgat atacgcagac accaacaaga cagcaagcag    180

gaccaccatc gtgatgggga tcaccaccag ggctcttatc cgatcctgga aaccgcagac    240

ggcatccgtc ttgttggtcc ccgcctgaag ctccaccagg cctttggtct cacacctcgt    300

ccaagggtga cacttttccg aagcagatga cacatt                              336


<210> SEQ ID NO 63
<211> LENGTH: 390
<212> TYPE: DNA
<213> ORGANISM: Canis familiaris

<400> SEQUENCE: 63

ataagtgagg ctagtagtaa cccagcgtcc gttctgcggt gggcgccaaa agggtactac     60

accataagca gcaacctggt gagcctcgag aatgggaaac agttggccgt gaaaagacaa    120

ggactctatt acgtctatgc ccaagtcacc ttctgctcca atcgggcagc ttcgagtcaa    180

gctccgttcg tcgccagcct atgcctccat tccccgagtg gaacggagag agtcttactc    240

cgcgccgcga gctcccgcgg ctcgtccaaa ccttgcggcc aacagtccat ccacttggga    300

ggagtatttg aattgcatcc aggtgcttcg gtgttcgtca acgtgactga tccaagccaa    360

gtgagccacg ggaccggctt cacgtctttt                                     390


<210> SEQ ID NO 64
<211> LENGTH: 1878
<212> TYPE: DNA
<213> ORGANISM: Canis familiaris
<220> FEATURE:
<221> NAME/KEY: CDS
<222> LOCATION: (284)..(1063)

<400> SEQUENCE: 64

aatgtatgga agaagaaact tgtttcttct ttactaacaa aagggaaagc ctggaagtga     60

atgatatggg tataattaaa aaaaaaaaaa aaaaaaaaaa aaaaccttta cgtaactttt    120

tttgctggga gagaagacta cgaagcacat tttccaggaa gtgtgggctg caacgattgt    180

gcgctcttaa ctaatcctga gtaaggtggc cactttgaca gtgttttcat gctgcctctg    240

ccaccttctc ggtctgaaga tatcatttca actctaacac agc atg atc gaa aca      295
                                                Met Ile Glu Thr
                                                  1

tat agc caa act gct ccc cga tct gtg gcc act gga cca ccc gtc agt      343
Tyr Ser Gln Thr Ala Pro Arg Ser Val Ala Thr Gly Pro Pro Val Ser
  5                  10                  15                  20

atg aaa att ttt atg tat ttg ctt act gtt ttt ctc atc acc cag atg      391
```

-continued

```
Met Lys Ile Phe Met Tyr Leu Leu Thr Val Phe Leu Ile Thr Gln Met
                25                  30                  35

att gga tcg gca ctc ttt gct gta tat ctt cac aga aga ttg gac aag      439
Ile Gly Ser Ala Leu Phe Ala Val Tyr Leu His Arg Arg Leu Asp Lys
            40                  45                  50

ata gaa gat gaa agg aat ctt tat gaa gat ttt gtg ttc atg aaa acg      487
Ile Glu Asp Glu Arg Asn Leu Tyr Glu Asp Phe Val Phe Met Lys Thr
        55                  60                  65

tta cag aaa tgc aac aaa ggg gag ggg tcc ttg tcc tta ctg aac tgt      535
Leu Gln Lys Cys Asn Lys Gly Glu Gly Ser Leu Ser Leu Leu Asn Cys
    70                  75                  80

gag gaa att aaa agc caa ttt gaa gcc ttt ctc aag gag ata atg cta      583
Glu Glu Ile Lys Ser Gln Phe Glu Ala Phe Leu Lys Glu Ile Met Leu
 85                  90                  95                 100

aac aac gaa atg aag aaa gaa gaa aac att gca atg caa aaa ggt gat      631
Asn Asn Glu Met Lys Lys Glu Glu Asn Ile Ala Met Gln Lys Gly Asp
                105                 110                 115

cag gat cct cga att gca gcc cat gtc ata agt gag gct agt agt aac      679
Gln Asp Pro Arg Ile Ala Ala His Val Ile Ser Glu Ala Ser Ser Asn
            120                 125                 130

cca gcg tcc gtt ctg cgg tgg gcg cca aaa ggg tac tac acc ata agc      727
Pro Ala Ser Val Leu Arg Trp Ala Pro Lys Gly Tyr Tyr Thr Ile Ser
        135                 140                 145

agc aac ctg gtg agc ctc gag aat ggg aaa cag ttg gcc gtg aaa aga      775
Ser Asn Leu Val Ser Leu Glu Asn Gly Lys Gln Leu Ala Val Lys Arg
    150                 155                 160

caa gga ctc tat tac gtc tat gcc caa gtc acc ttc tgc tcc aat cgg      823
Gln Gly Leu Tyr Tyr Val Tyr Ala Gln Val Thr Phe Cys Ser Asn Arg
165                 170                 175                 180

gca gct tcg agt caa gct ccg ttc gtc gcc agc cta tgc ctc cat tcc      871
Ala Ala Ser Ser Gln Ala Pro Phe Val Ala Ser Leu Cys Leu His Ser
                185                 190                 195

ccg agt gga acg gag aga gtc tta ctc cgc gcc gcg agc tcc cgc ggc      919
Pro Ser Gly Thr Glu Arg Val Leu Leu Arg Ala Ala Ser Ser Arg Gly
            200                 205                 210

tcg tcc aaa cct tgc ggc caa cag tcc atc cac ttg gga gga gta ttt      967
Ser Ser Lys Pro Cys Gly Gln Gln Ser Ile His Leu Gly Gly Val Phe
        215                 220                 225

gaa ttg cat cca ggt gct tcg gtg ttc gtc aac gtg act gat cca agc     1015
Glu Leu His Pro Gly Ala Ser Val Phe Val Asn Val Thr Asp Pro Ser
    230                 235                 240

caa gtg agc cac ggg acc ggc ttc acg tct ttt ggc tta ctc aaa ctc     1063
Gln Val Ser His Gly Thr Gly Phe Thr Ser Phe Gly Leu Leu Lys Leu
245                 250                 255                 260

tgagtgctgg cacctcacag gctgcagctc agctcctgtt ggtggtcttc gtaatacggc   1123

cgagcagtta agaccaccac ccctgttgaa ctgcctattt ataaccctag gatcctcctc   1183

gtggagaact atttattata cacccccagg cgtggagggc tgcaagaagg gaatgacagg   1243

gcgggggcag cgccaacagg ccccggtcgg taagagttga tattctggaa gcagccgccc   1303

cactgatgca gacatccaga gagtcccatg aaaaagacga gactattatg cacagattga   1363

atcctcagta aacggcagat aattagtcca gtttcgtttt gtttctttgc atgcagtgtc   1423

tttcactgga gaatgtactc gatttccccg cgaagatgct gaagggcaac agggagcctc   1483

agctcacagt cagttacggt tgacccgggg tccccggggc cccgatggag gggacaggct   1543

ccagaaagtc tgatggcgcg gagaactgga aaaccctgcc cccaccagcc accctgacac   1603

tcattctctc cctcctccgc ccccctcccc ccacagtcag gctgttgcta atcggttatc   1663
```

-continued

```
ttatttcaac cctgttgcct ctccaccagt gtaggcggga ggagagagca gaggctgccc   1723

actcctcctc ctgaaatgac tgtatttaaa ggaaatctct cctacctacc tgcagtctcc   1783

attgtttcca gagtgaactt gtgattatct tgttatttat tttttgaata ataaagcgcc   1843

cttaacgtta aaaaaaaaaa aaaaaaaaaa aaaaa                              1878


<210> SEQ ID NO 65
<211> LENGTH: 260
<212> TYPE: PRT
<213> ORGANISM: Canis familiaris

<400> SEQUENCE: 65

Met Ile Glu Thr Tyr Ser Gln Thr Ala Pro Arg Ser Val Ala Thr Gly
  1               5                  10                  15

Pro Pro Val Ser Met Lys Ile Phe Met Tyr Leu Leu Thr Val Phe Leu
             20                  25                  30

Ile Thr Gln Met Ile Gly Ser Ala Leu Phe Ala Val Tyr Leu His Arg
         35                  40                  45

Arg Leu Asp Lys Ile Glu Asp Glu Arg Asn Leu Tyr Glu Asp Phe Val
     50                  55                  60

Phe Met Lys Thr Leu Gln Lys Cys Asn Lys Gly Glu Gly Ser Leu Ser
 65                  70                  75                  80

Leu Leu Asn Cys Glu Glu Ile Lys Ser Gln Phe Glu Ala Phe Leu Lys
                 85                  90                  95

Glu Ile Met Leu Asn Asn Glu Met Lys Lys Glu Glu Asn Ile Ala Met
            100                 105                 110

Gln Lys Gly Asp Gln Asp Pro Arg Ile Ala Ala His Val Ile Ser Glu
        115                 120                 125

Ala Ser Ser Asn Pro Ala Ser Val Leu Arg Trp Ala Pro Lys Gly Tyr
    130                 135                 140

Tyr Thr Ile Ser Ser Asn Leu Val Ser Leu Glu Asn Gly Lys Gln Leu
145                 150                 155                 160

Ala Val Lys Arg Gln Gly Leu Tyr Tyr Val Tyr Ala Gln Val Thr Phe
                165                 170                 175

Cys Ser Asn Arg Ala Ala Ser Ser Gln Ala Pro Phe Val Ala Ser Leu
            180                 185                 190

Cys Leu His Ser Pro Ser Gly Thr Glu Arg Val Leu Leu Arg Ala Ala
        195                 200                 205

Ser Ser Arg Gly Ser Ser Lys Pro Cys Gly Gln Gln Ser Ile His Leu
    210                 215                 220

Gly Gly Val Phe Glu Leu His Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260


<210> SEQ ID NO 66
<211> LENGTH: 1878
<212> TYPE: DNA
<213> ORGANISM: Canis familiaris

<400> SEQUENCE: 66

tttttttttt tttttttttt ttttttaacg ttaagggcgc tttattattc aaaaaataaa     60

taacaagata atcacaagtt cactctggaa acaatggaga ctgcaggtag gtaggagaga    120
```

-continued

```
tttcctttaa atacagtcat ttcaggagga ggagtgggca gcctctgctc tctcctcccg    180

cctacactgg tggagaggca acagggttga aataagataa ccgattagca acagcctgac    240

tgtgggggga ggggggcgga ggagggagag aatgagtgtc agggtggctg gtgggggcag    300

ggttttccag ttctccgcgc catcagactt tctggagcct gtcccctcca tcggggcccc    360

ggggaccccg ggtcaaccgt aactgactgt gagctgaggc tccctgttgc ccttcagcat    420

cttcgcgggg aaatcgagta cattctccag tgaaagacac tgcatgcaaa gaaacaaaac    480

gaaactggac taattatctg ccgtttactg aggattcaat ctgtgcataa tagtctcgtc    540

tttttcatgg gactctctgg atgtctgcat cagtggggcg gctgcttcca gaatatcaac    600

tcttaccgac cggggcctgt tggcgctgcc cccgccctgt cattcccttc ttgcagccct    660

ccacgcctgg gggtgtataa taaatagttc tccacgagga ggatcctagg gttataaata    720

ggcagttcaa caggggtggt ggtcttaact gctcggccgt attacgaaga ccaccaacag    780

gagctgagct gcagcctgtg aggtgccagc actcagagtt tgagtaagcc aaaagacgtg    840

aagccggtcc cgtggctcac ttggcttgga tcagtcacgt tgacgaacac cgaagcacct    900

ggatgcaatt caaatactcc tcccaagtgg atggactgtt ggccgcaagg tttggacgag    960

ccgcgggagc tcgcggcgcg gagtaagact ctctccgttc cactcgggga atggaggcat   1020

aggctggcga cgaacggagc ttgactcgaa gctgcccgat tggagcagaa ggtgacttgg   1080

gcatagacgt aatagagtcc ttgtcttttc acggccaact gtttcccatt ctcgaggctc   1140

accaggttgc tgcttatggt gtagtaccct tttggcgccc accgcagaac ggacgctggg   1200

ttactactag cctcacttat gacatgggct gcaattcgag gatcctgatc accttttttgc  1260

attgcaatgt tttcttcttt cttcatttcg ttgtttagca ttatctcctt gagaaaggct   1320

tcaaattggc ttttaatttc ctcacagttc agtaaggaca aggacccctc ccctttgttg   1380

catttctgta acgttttcat gaacacaaaa tcttcataaa gattcctttc atcttctatc   1440

ttgtccaatc ttctgtgaag atatacagca aagagtgccg atccaatcat ctgggtgatg   1500

agaaaaacag taagcaaata cataaaaatt ttcatactga cgggtggtcc agtggccaca   1560

gatcggggag cagtttggct atatgtttcg atcatgctgt gttagagttg aaatgatatc   1620

ttcagaccga gaaggtggca gaggcagcat gaaaacactg tcaaagtggc caccttactc   1680

aggattagtt aagagcgcac aatcgttgca gcccacactt cctggaaaat gtgcttcgta   1740

gtcttctctc ccagcaaaaa aagttacgta aaggtttttt tttttttttt tttttttttt   1800

taattatacc catatcattc acttccaggc tttccctttt gttagtaaag aagaaacaag   1860

tttcttcttc catacatt                                                 1878
```

<210> SEQ ID NO 67
<211> LENGTH: 780
<212> TYPE: DNA
<213> ORGANISM: Canis familiaris

<400> SEQUENCE: 67

```
atgatcgaaa catatagcca aactgctccc cgatctgtgg ccactggacc acccgtcagt     60

atgaaaattt ttatgtattt gcttactgtt tttctcatca cccagatgat tggatcggca    120

ctctttgctg tatatcttca cagaagattg gacaagatag aagatgaaag gaatctttat    180

gaagattttg tgttcatgaa aacgttacag aaatgcaaca aaggggaggg gtccttgtcc    240

ttactgaact gtgaggaaat taaaagccaa tttgaagcct ttctcaagga gataatgcta    300

aacaacgaaa tgaagaaaga agaaaacatt gcaatgcaaa aaggtgatca ggatcctcga    360
```

-continued

```
attgcagccc atgtcataag tgaggctagt agtaacccag cgtccgttct gcggtgggcg    420

ccaaaagggt actacaccat aagcagcaac ctggtgagcc tcgagaatgg gaaacagttg    480

gccgtgaaaa gacaaggact ctattacgtc tatgcccaag tcaccttctg ctccaatcgg    540

gcagcttcga gtcaagctcc gttcgtcgcc agcctatgcc tccattcccc gagtggaacg    600

gagagagtct tactccgcgc cgcgagctcc cgcggctcgt ccaaaccttg cggccaacag    660

tccatccact tgggaggagt atttgaattg catccaggtg cttcggtgtt cgtcaacgtg    720

actgatccaa gccaagtgag ccacgggacc ggcttcacgt cttttggctt actcaaactc    780


<210> SEQ ID NO 68
<211> LENGTH: 780
<212> TYPE: DNA
<213> ORGANISM: Canis familiaris

<400> SEQUENCE: 68

gagtttgagt aagccaaaag acgtgaagcc ggtcccgtgg ctcacttggc ttggatcagt     60

cacgttgacg aacaccgaag cacctggatg caattcaaat actcctccca agtggatgga    120

ctgttggccg caaggtttgg acgagccgcg ggagctcgcg gcgcggagta agactctctc    180

cgttccactc ggggaatgga ggcataggct ggcgacgaac ggagcttgac tcgaagctgc    240

ccgattggag cagaaggtga cttgggcata gacgtaatag agtccttgtc ttttcacggc    300

caactgtttc ccattctcga ggctcaccag gttgctgctt atggtgtagt acccttttgg    360

cgcccaccgc agaacggacg ctgggttact actagcctca cttatgacat gggctgcaat    420

tcgaggatcc tgatcacctt tttgcattgc aatgttttct tctttcttca tttcgttgtt    480

tagcattatc tccttgagaa aggcttcaaa ttggctttta atttcctcac agttcagtaa    540

ggacaaggac ccctcccctt tgttgcattt ctgtaacgtt ttcatgaaca caaaatcttc    600

ataaagattc ctttcatctt ctatcttgtc caatcttctg tgaagatata cagcaaagag    660

tgccgatcca atcatctggg tgatgagaaa aacagtaagc aaatacataa aaattttcat    720

actgacgggt ggtccagtgg ccacagatcg gggagcagtt tggctatatg tttcgatcat    780


<210> SEQ ID NO 69
<211> LENGTH: 633
<212> TYPE: DNA
<213> ORGANISM: Canis familiaris
<220> FEATURE:
<221> NAME/KEY: CDS
<222> LOCATION: (1)..(633)

<400> SEQUENCE: 69

ttg gac aag ata gaa gat gaa agg aat ctt tat gaa gat ttt gtg ttc       48
Leu Asp Lys Ile Glu Asp Glu Arg Asn Leu Tyr Glu Asp Phe Val Phe
  1               5                  10                  15

atg aaa acg tta cag aaa tgc aac aaa ggg gag ggg tcc ttg tcc tta       96
Met Lys Thr Leu Gln Lys Cys Asn Lys Gly Glu Gly Ser Leu Ser Leu
             20                  25                  30

ctg aac tgt gag gaa att aaa agc caa ttt gaa gcc ttt ctc aag gag      144
Leu Asn Cys Glu Glu Ile Lys Ser Gln Phe Glu Ala Phe Leu Lys Glu
         35                  40                  45

ata atg cta aac aac gaa atg aag aaa gaa gaa aac att gca atg caa      192
Ile Met Leu Asn Asn Glu Met Lys Lys Glu Glu Asn Ile Ala Met Gln
     50                  55                  60

aaa ggt gat cag gat cct cga att gca gcc cat gtc ata agt gag gct      240
Lys Gly Asp Gln Asp Pro Arg Ile Ala Ala His Val Ile Ser Glu Ala
 65                  70                  75                  80
```

-continued

```
agt agt aac cca gcg tcc gtt ctg cgg tgg gcg cca aaa ggg tac tac      288
Ser Ser Asn Pro Ala Ser Val Leu Arg Trp Ala Pro Lys Gly Tyr Tyr
                 85                  90                  95

acc ata agc agc aac ctg gtg agc ctc gag aat ggg aaa cag ttg gcc      336
Thr Ile Ser Ser Asn Leu Val Ser Leu Glu Asn Gly Lys Gln Leu Ala
            100                 105                 110

gtg aaa aga caa gga ctc tat tac gtc tat gcc caa gtc acc ttc tgc      384
Val Lys Arg Gln Gly Leu Tyr Tyr Val Tyr Ala Gln Val Thr Phe Cys
        115                 120                 125

tcc aat cgg gca gct tcg agt caa gct ccg ttc gtc gcc agc cta tgc      432
Ser Asn Arg Ala Ala Ser Ser Gln Ala Pro Phe Val Ala Ser Leu Cys
    130                 135                 140

ctc cat tcc ccg agt gga acg gag aga gtc tta ctc cgc gcc gcg agc      480
Leu His Ser Pro Ser Gly Thr Glu Arg Val Leu Leu Arg Ala Ala Ser
145                 150                 155                 160

tcc cgc ggc tcg tcc aaa cct tgc ggc caa cag tcc atc cac ttg gga      528
Ser Arg Gly Ser Ser Lys Pro Cys Gly Gln Gln Ser Ile His Leu Gly
                165                 170                 175

gga gta ttt gaa ttg cat cca ggt gct tcg gtg ttc gtc aac gtg act      576
Gly Val Phe Glu Leu His Pro Gly Ala Ser Val Phe Val Asn Val Thr
            180                 185                 190

gat cca agc caa gtg agc cac ggg acc ggc ttc acg tct ttt ggc tta      624
Asp Pro Ser Gln Val Ser His Gly Thr Gly Phe Thr Ser Phe Gly Leu
        195                 200                 205

ctc aaa ctc                                                          633
Leu Lys Leu
    210


<210> SEQ ID NO 70
<211> LENGTH: 211
<212> TYPE: PRT
<213> ORGANISM: Canis familiaris

<400> SEQUENCE: 70

Leu Asp Lys Ile Glu Asp Glu Arg Asn Leu Tyr Glu Asp Phe Val Phe
  1               5                  10                  15

Met Lys Thr Leu Gln Lys Cys Asn Lys Gly Glu Gly Ser Leu Ser Leu
             20                  25                  30

Leu Asn Cys Glu Glu Ile Lys Ser Gln Phe Glu Ala Phe Leu Lys Glu
         35                  40                  45

Ile Met Leu Asn Asn Glu Met Lys Lys Glu Glu Asn Ile Ala Met Gln
     50                  55                  60

Lys Gly Asp Gln Asp Pro Arg Ile Ala Ala His Val Ile Ser Glu Ala
 65                  70                  75                  80

Ser Ser Asn Pro Ala Ser Val Leu Arg Trp Ala Pro Lys Gly Tyr Tyr
                 85                  90                  95

Thr Ile Ser Ser Asn Leu Val Ser Leu Glu Asn Gly Lys Gln Leu Ala
            100                 105                 110

Val Lys Arg Gln Gly Leu Tyr Tyr Val Tyr Ala Gln Val Thr Phe Cys
        115                 120                 125

Ser Asn Arg Ala Ala Ser Ser Gln Ala Pro Phe Val Ala Ser Leu Cys
    130                 135                 140

Leu His Ser Pro Ser Gly Thr Glu Arg Val Leu Leu Arg Ala Ala Ser
145                 150                 155                 160

Ser Arg Gly Ser Ser Lys Pro Cys Gly Gln Gln Ser Ile His Leu Gly
                165                 170                 175

Gly Val Phe Glu Leu His Pro Gly Ala Ser Val Phe Val Asn Val Thr
```

-continued

```
            180                 185                 190

Asp Pro Ser Gln Val Ser His Gly Thr Gly Phe Thr Ser Phe Gly Leu
        195                 200                 205

Leu Lys Leu
    210


<210> SEQ ID NO 71
<211> LENGTH: 633
<212> TYPE: DNA
<213> ORGANISM: Canis familiaris

<400> SEQUENCE: 71

gagtttgagt aagccaaaag acgtgaagcc ggtcccgtgg ctcacttggc ttggatcagt     60

cacgttgacg aacaccgaag cacctggatg caattcaaat actcctccca agtggatgga    120

ctgttggccg caaggtttgg acgagccgcg ggagctcgcg gcgcggagta agactctctc    180

cgttccactc ggggaatgga ggcataggct ggcgacgaac ggagcttgac tcgaagctgc    240

ccgattggag cagaaggtga cttgggcata gacgtaatag agtccttgtc ttttcacggc    300

caactgtttc ccattctcga ggctcaccag gttgctgctt atggtgtagt accctttttgg    360

cgcccaccgc agaacggacg ctgggttact actagcctca cttatgacat gggctgcaat    420

tcgaggatcc tgatcacctt tttgcattgc aatgttttct tctttcttca tttcgttgtt    480

tagcattatc tccttgagaa aggcttcaaa ttggctttta atttcctcac agttcagtaa    540

ggacaaggac ccctcccctt tgttgcattt ctgtaacgtt ttcatgaaca caaaatcttc    600

ataaagattc ctttcatctt ctatcttgtc caa                                 633


<210> SEQ ID NO 72
<211> LENGTH: 885
<212> TYPE: DNA
<213> ORGANISM: Felis catus
<220> FEATURE:
<221> NAME/KEY: CDS
<222> LOCATION: (29)..(808)

<400> SEQUENCE: 72

gaagatacca tttcaacttt aacacagc atg atc gaa aca tat agc caa act        52
                               Met Ile Glu Thr Tyr Ser Gln Thr
                                 1               5

gct ccc cgc tcc gtg gcc cct gga cca ccc gtc agt atg aaa att ttt      100
Ala Pro Arg Ser Val Ala Pro Gly Pro Pro Val Ser Met Lys Ile Phe
     10                  15                  20

atg tat tta ctt act gtg ttt ctc atc acc cag atg att ggg tca gca      148
Met Tyr Leu Leu Thr Val Phe Leu Ile Thr Gln Met Ile Gly Ser Ala
 25                  30                  35                  40

ctc ttt gct gtg tat ctt cac aga aga ctg gac aag ata gaa gat gaa      196
Leu Phe Ala Val Tyr Leu His Arg Arg Leu Asp Lys Ile Glu Asp Glu
                 45                  50                  55

agg aat ctt tat gaa gat ttt gtg ttc atg aaa aca tta cag aaa tgc      244
Arg Asn Leu Tyr Glu Asp Phe Val Phe Met Lys Thr Leu Gln Lys Cys
             60                  65                  70

aac aaa gga gag ggg gcc tta tcc tta ctg aac tgt gag gaa att aaa      292
Asn Lys Gly Glu Gly Ala Leu Ser Leu Leu Asn Cys Glu Glu Ile Lys
         75                  80                  85

agc cgg ttt gaa gcc ttt ctc aag gag ata atg cta aac aaa gaa acg      340
Ser Arg Phe Glu Ala Phe Leu Lys Glu Ile Met Leu Asn Lys Glu Thr
     90                  95                 100

aag aaa gaa aaa aat gtt gca atg caa aaa ggc gac cag gat cct cga      388
Lys Lys Glu Lys Asn Val Ala Met Gln Lys Gly Asp Gln Asp Pro Arg
```

-continued

```
105                 110                 115                 120

gtt gca gca cat gtc ata agt gag gcc agc agt agc aca gcg tct gtt      436
Val Ala Ala His Val Ile Ser Glu Ala Ser Ser Ser Thr Ala Ser Val
                125                 130                 135

ctc cag tgg gcc ccc aaa ggc tac tac acc ata agc agc aac ttg gtg      484
Leu Gln Trp Ala Pro Lys Gly Tyr Tyr Thr Ile Ser Ser Asn Leu Val
            140                 145                 150

acc ctc gag aac ggg aag cag ctg gcc gtt aaa aga caa gga ctc tat      532
Thr Leu Glu Asn Gly Lys Gln Leu Ala Val Lys Arg Gln Gly Leu Tyr
        155                 160                 165

tat atc tac gcc caa gtc acc ttc tgt tcc aat cgg gaa gct tcg agt      580
Tyr Ile Tyr Ala Gln Val Thr Phe Cys Ser Asn Arg Glu Ala Ser Ser
    170                 175                 180

caa gct ccg ttc ata gcc agc ctc tgc ctg cat tcc ccg agt gga tcc      628
Gln Ala Pro Phe Ile Ala Ser Leu Cys Leu His Ser Pro Ser Gly Ser
185                 190                 195                 200

gag aga gtc tta ctc aga gct gca aat gcc cgc agt tcc tcc aaa ccc      676
Glu Arg Val Leu Leu Arg Ala Ala Asn Ala Arg Ser Ser Ser Lys Pro
                205                 210                 215

tgt ggg cag caa tcc att cac ttg gga gga gtc ttc gaa ctg cat cca      724
Cys Gly Gln Gln Ser Ile His Leu Gly Gly Val Phe Glu Leu His Pro
            220                 225                 230

ggt gct tcg gtg ttc gtg aac gtg act gat ccg agc caa gtg agc cac      772
Gly Ala Ser Val Phe Val Asn Val Thr Asp Pro Ser Gln Val Ser His
        235                 240                 245

ggg acg ggc ttc acg tct ttt ggc ttg ctc aaa ctc tgaacactgg           818
Gly Thr Gly Phe Thr Ser Phe Gly Leu Leu Lys Leu
    250                 255                 260

cacctcgcag gccgcgaggc ctgcaggccg cggctgagct cacgctggga gtcttcacaa    878

tacagca                                                              885


<210> SEQ ID NO 73
<211> LENGTH: 260
<212> TYPE: PRT
<213> ORGANISM: Felis catus

<400> SEQUENCE: 73

Met Ile Glu Thr Tyr Ser Gln Thr Ala Pro Arg Ser Val Ala Pro Gly
  1               5                  10                  15

Pro Pro Val Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu Tyr Glu Asp Phe Val
    50                  55                  60

Phe Met Lys Thr Leu Gln Lys Cys Asn Lys Gly Glu Gly Ala Leu Ser
 65                  70                  75                  80

Leu Leu Asn Cys Glu Glu Ile Lys Ser Arg Phe Glu Ala Phe Leu Lys
                 85                  90                  95

Glu Ile Met Leu Asn Lys Glu Thr Lys Lys Glu Lys Asn Val Ala Met
            100                 105                 110

Gln Lys Gly Asp Gln Asp Pro Arg Val Ala Ala His Val Ile Ser Glu
        115                 120                 125

Ala Ser Ser Ser Thr Ala Ser Val Leu Gln Trp Ala Pro Lys Gly Tyr
    130                 135                 140

Tyr Thr Ile Ser Ser Asn Leu Val Thr Leu Glu Asn Gly Lys Gln Leu
145                 150                 155                 160
```

-continued

```
Ala Val Lys Arg Gln Gly Leu Tyr Tyr Ile Tyr Ala Gln Val Thr Phe
            165                 170                 175

Cys Ser Asn Arg Glu Ala Ser Ser Gln Ala Pro Phe Ile Ala Ser Leu
            180                 185                 190

Cys Leu His Ser Pro Ser Gly Ser Glu Arg Val Leu Leu Arg Ala Ala
        195                 200                 205

Asn Ala Arg Ser Ser Ser Lys Pro Cys Gly Gln Gln Ser Ile His Leu
    210                 215                 220

Gly Gly Val Phe Glu Leu His Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260


<210> SEQ ID NO 74
<211> LENGTH: 885
<212> TYPE: DNA
<213> ORGANISM: Felis catus

<400> SEQUENCE: 74

tgctgtatta tgaagactcc cagcgtgagc tcagccgcgg cctgcaggcc tcgcggcctg      60

cgaggtgcca gtgttcagag tttgagcaag ccaaaagacg tgaagcccgt cccgtggctc     120

acttggctcg gatcagtcac gttcacgaac accgaagcac ctggatgcag ttcgaagact     180

cctcccaagt gaatggattg ctgcccacag ggtttggagg aactgcgggc atttgcagct     240

ctgagtaaga ctctctcgga tccactcggg gaatgcaggc agaggctggc tatgaacgga     300

gcttgactcg aagcttcccg attggaacag aaggtgactt gggcgtagat ataatagagt     360

ccttgtcttt taacggccag ctgcttcccg ttctcgaggg tcaccaagtt gctgcttatg     420

gtgtagtagc ctttgggggc ccactggaga acagacgctg tgctactgct ggcctcactt     480

atgacatgtg ctgcaactcg aggatcctgg tcgccttttt gcattgcaac atttttttct     540

ttcttcgttt ctttgtttag cattatctcc ttgagaaagg cttcaaaccg gcttttaatt     600

tcctcacagt tcagtaagga taaggccccc tctcctttgt tgcatttctg taatgttttc     660

atgaacacaa aatcttcata aagattcctt tcatcttcta tcttgtccag tcttctgtga     720

agatacacag caaagagtgc tgacccaatc atctgggtga tgagaaacac agtaagtaaa     780

tacataaaaa ttttcatact gacgggtggt ccaggggcca cggagcgggg agcagtttgg     840

ctatatgttt cgatcatgct gtgttaaagt tgaaatggta tcttc                     885


<210> SEQ ID NO 75
<211> LENGTH: 780
<212> TYPE: DNA
<213> ORGANISM: Felis catus

<400> SEQUENCE: 75

atgatcgaaa catatagcca aactgctccc cgctccgtgg cccctggacc acccgtcagt      60

atgaaaattt ttatgtattt acttactgtg tttctcatca cccagatgat tgggtcagca     120

ctctttgctg tgtatcttca cagaagactg gacaagatag aagatgaaag gaatctttat     180

gaagattttg tgttcatgaa aacattacag aaatgcaaca aaggagaggg ggccttatcc     240

ttactgaact gtgaggaaat taaaagccgg tttgaagcct ttctcaagga gataatgcta     300

aacaaagaaa cgaagaaaga aaaaaatgtt gcaatgcaaa aaggcgacca ggatcctcga     360
```

-continued

```
gttgcagcac atgtcataag tgaggccagc agtagcacag cgtctgttct ccagtgggcc    420

cccaaaggct actacaccat aagcagcaac ttggtgaccc tcgagaacgg gaagcagctg    480

gccgttaaaa gacaaggact ctattatatc tacgcccaag tcaccttctg ttccaatcgg    540

gaagcttcga gtcaagctcc gttcatagcc agcctctgcc tgcattcccc gagtggatcc    600

gagagagtct tactcagagc tgcaaatgcc cgcagttcct ccaaaccctg tgggcagcaa    660

tccattcact tgggaggagt cttcgaactg catccaggtg cttcggtgtt cgtgaacgtg    720

actgatccga gccaagtgag ccacgggacg ggcttcacgt cttttggctt gctcaaactc    780


<210> SEQ ID NO 76
<211> LENGTH: 780
<212> TYPE: DNA
<213> ORGANISM: Felis catus

<400> SEQUENCE: 76

gagtttgagc aagccaaaag acgtgaagcc cgtcccgtgg ctcacttggc tcggatcagt     60

cacgttcacg aacaccgaag cacctggatg cagttcgaag actcctccca agtgaatgga    120

ttgctgccca cagggtttgg aggaactgcg ggcatttgca gctctgagta agactctctc    180

ggatccactc ggggaatgca ggcagaggct ggctatgaac ggagcttgac tcgaagcttc    240

ccgattggaa cagaaggtga cttgggcgta gatataatag agtccttgtc ttttaacggc    300

cagctgcttc ccgttctcga gggtcaccaa gttgctgctt atggtgtagt agcctttggg    360

ggcccactgg agaacagacg ctgtgctact gctggcctca cttatgacat gtgctgcaac    420

tcgaggatcc tggtcgcctt tttgcattgc aacatttttt tctttcttcg tttctttgtt    480

tagcattatc tccttgagaa aggcttcaaa ccggctttta atttcctcac agttcagtaa    540

ggataaggcc ccctctcctt tgttgcattt ctgtaatgtt ttcatgaaca caaaatcttc    600

ataaagattc ctttcatctt ctatcttgtc cagtcttctg tgaagataca cagcaaagag    660

tgctgaccca atcatctggg tgatgagaaa cacagtaagt aaatacataa aaattttcat    720

actgacgggt ggtccagggg ccacggagcg gggagcagtt tggctatatg tttcgatcat    780


<210> SEQ ID NO 77
<211> LENGTH: 633
<212> TYPE: DNA
<213> ORGANISM: Felis catus
<220> FEATURE:
<221> NAME/KEY: CDS
<222> LOCATION: (1)..(633)

<400> SEQUENCE: 77

ctg gac aag ata gaa gat gaa agg aat ctt tat gaa gat ttt gtg ttc       48
Leu Asp Lys Ile Glu Asp Glu Arg Asn Leu Tyr Glu Asp Phe Val Phe
  1               5                  10                  15

atg aaa aca tta cag aaa tgc aac aaa gga gag ggg gcc tta tcc tta       96
Met Lys Thr Leu Gln Lys Cys Asn Lys Gly Glu Gly Ala Leu Ser Leu
             20                  25                  30

ctg aac tgt gag gaa att aaa agc cgg ttt gaa gcc ttt ctc aag gag      144
Leu Asn Cys Glu Glu Ile Lys Ser Arg Phe Glu Ala Phe Leu Lys Glu
         35                  40                  45

ata atg cta aac aaa gaa acg aag aaa gaa aaa aat gtt gca atg caa      192
Ile Met Leu Asn Lys Glu Thr Lys Lys Glu Lys Asn Val Ala Met Gln
     50                  55                  60

aaa ggc gac cag gat cct cga gtt gca gca cat gtc ata agt gag gcc      240
Lys Gly Asp Gln Asp Pro Arg Val Ala Ala His Val Ile Ser Glu Ala
 65                  70                  75                  80
```

-continued

```
agc agt agc aca gcg tct gtt ctc cag tgg gcc ccc aaa ggc tac tac      288
Ser Ser Ser Thr Ala Ser Val Leu Gln Trp Ala Pro Lys Gly Tyr Tyr
                85                  90                  95

acc ata agc agc aac ttg gtg acc ctc gag aac ggg aag cag ctg gcc      336
Thr Ile Ser Ser Asn Leu Val Thr Leu Glu Asn Gly Lys Gln Leu Ala
            100                 105                 110

gtt aaa aga caa gga ctc tat tat atc tac gcc caa gtc acc ttc tgt      384
Val Lys Arg Gln Gly Leu Tyr Tyr Ile Tyr Ala Gln Val Thr Phe Cys
        115                 120                 125

tcc aat cgg gaa gct tcg agt caa gct ccg ttc ata gcc agc ctc tgc      432
Ser Asn Arg Glu Ala Ser Ser Gln Ala Pro Phe Ile Ala Ser Leu Cys
    130                 135                 140

ctg cat tcc ccg agt gga tcc gag aga gtc tta ctc aga gct gca aat      480
Leu His Ser Pro Ser Gly Ser Glu Arg Val Leu Leu Arg Ala Ala Asn
145                 150                 155                 160

gcc cgc agt tcc tcc aaa ccc tgt ggg cag caa tcc att cac ttg gga      528
Ala Arg Ser Ser Ser Lys Pro Cys Gly Gln Gln Ser Ile His Leu Gly
                165                 170                 175

gga gtc ttc gaa ctg cat cca ggt gct tcg gtg ttc gtg aac gtg act      576
Gly Val Phe Glu Leu His Pro Gly Ala Ser Val Phe Val Asn Val Thr
            180                 185                 190

gat ccg agc caa gtg agc cac ggg acg ggc ttc acg tct ttt ggc ttg      624
Asp Pro Ser Gln Val Ser His Gly Thr Gly Phe Thr Ser Phe Gly Leu
        195                 200                 205

ctc aaa ctc                                                          633
Leu Lys Leu
    210


<210> SEQ ID NO 78
<211> LENGTH: 211
<212> TYPE: PRT
<213> ORGANISM: Felis catus

<400> SEQUENCE: 78

Leu Asp Lys Ile Glu Asp Glu Arg Asn Leu Tyr Glu Asp Phe Val Phe
  1               5                  10                  15

Met Lys Thr Leu Gln Lys Cys Asn Lys Gly Glu Gly Ala Leu Ser Leu
            20                  25                  30

Leu Asn Cys Glu Glu Ile Lys Ser Arg Phe Glu Ala Phe Leu Lys Glu
        35                  40                  45

Ile Met Leu Asn Lys Glu Thr Lys Lys Glu Lys Asn Val Ala Met Gln
     50                  55                  60

Lys Gly Asp Gln Asp Pro Arg Val Ala Ala His Val Ile Ser Glu Ala
 65                  70                  75                  80

Ser Ser Ser Thr Ala Ser Val Leu Gln Trp Ala Pro Lys Gly Tyr Tyr
                85                  90                  95

Thr Ile Ser Ser Asn Leu Val Thr Leu Glu Asn Gly Lys Gln Leu Ala
            100                 105                 110

Val Lys Arg Gln Gly Leu Tyr Tyr Ile Tyr Ala Gln Val Thr Phe Cys
        115                 120                 125

Ser Asn Arg Glu Ala Ser Ser Gln Ala Pro Phe Ile Ala Ser Leu Cys
    130                 135                 140

Leu His Ser Pro Ser Gly Ser Glu Arg Val Leu Leu Arg Ala Ala Asn
145                 150                 155                 160

Ala Arg Ser Ser Ser Lys Pro Cys Gly Gln Gln Ser Ile His Leu Gly
                165                 170                 175

Gly Val Phe Glu Leu His Pro Gly Ala Ser Val Phe Val Asn Val Thr
```

-continued

```
            180                 185                 190

Asp Pro Ser Gln Val Ser His Gly Thr Gly Phe Thr Ser Phe Gly Leu
        195                 200                 205

Leu Lys Leu
    210


<210> SEQ ID NO 79
<211> LENGTH: 633
<212> TYPE: DNA
<213> ORGANISM: Felis catus

<400> SEQUENCE: 79

gagtttgagc aagccaaaag acgtgaagcc cgtcccgtgg ctcacttggc tcggatcagt     60

cacgttcacg aacaccgaag cacctggatg cagttcgaag actcctccca agtgaatgga    120

ttgctgccca cagggtttgg aggaactgcg ggcatttgca gctctgagta agactctctc    180

ggatccactc ggggaatgca ggcagaggct ggctatgaac ggagcttgac tcgaagcttc    240

ccgattggaa cagaaggtga cttgggcgta gatataatag agtccttgtc ttttaacggc    300

cagctgcttc ccgttctcga gggtcaccaa gttgctgctt atggtgtagt agcctttggg    360

ggcccactgg agaacagacg ctgtgctact gctggcctca cttatgacat gtgctgcaac    420

tcgaggatcc tggtcgcctt tttgcattgc aacatttttt tctttcttcg tttctttgtt    480

tagcattatc tccttgagaa aggcttcaaa ccggctttta atttcctcac agttcagtaa    540

ggataaggcc ccctctcctt tgttgcattt ctgtaatgtt ttcatgaaca caaaatcttc    600

ataaagattc ctttcatctt ctatcttgtc cag                                 633


<210> SEQ ID NO 80
<211> LENGTH: 610
<212> TYPE: DNA
<213> ORGANISM: Canis familiaris
<220> FEATURE:
<221> NAME/KEY: CDS
<222> LOCATION: (29)..(430)

<400> SEQUENCE: 80

caaggcaaac actgaacatt tcagagct atg aga atg ctt ctg aat ttg agt        52
                               Met Arg Met Leu Leu Asn Leu Ser
                                 1               5

ttg cta gct ctt ggg gct gcc tat gtt tct gcc ttt gct gta gaa aat      100
Leu Leu Ala Leu Gly Ala Ala Tyr Val Ser Ala Phe Ala Val Glu Asn
     10                  15                  20

ccc atg aat aga ctg gtg gca gag acc ttg aca ctg ctc tcc act cat      148
Pro Met Asn Arg Leu Val Ala Glu Thr Leu Thr Leu Leu Ser Thr His
 25                  30                  35                  40

cga act tgg ctg ata ggc gat ggg aac ctg atg att cct act cct gaa      196
Arg Thr Trp Leu Ile Gly Asp Gly Asn Leu Met Ile Pro Thr Pro Glu
                 45                  50                  55

aat aaa aat cac caa ctg tgc att aaa gaa gtt ttt cag ggt ata gac      244
Asn Lys Asn His Gln Leu Cys Ile Lys Glu Val Phe Gln Gly Ile Asp
             60                  65                  70

aca ttg aag aac caa act gcc cac ggg gag gct gtg gat aaa cta ttc      292
Thr Leu Lys Asn Gln Thr Ala His Gly Glu Ala Val Asp Lys Leu Phe
         75                  80                  85

caa aac ttg tct tta ata aaa gaa cac ata gag cgc caa aaa aaa agg      340
Gln Asn Leu Ser Leu Ile Lys Glu His Ile Glu Arg Gln Lys Lys Arg
     90                  95                 100

tgt gca gga gaa aga tgg aga gtg aca aag ttc cta gac tac ctg caa      388
Cys Ala Gly Glu Arg Trp Arg Val Thr Lys Phe Leu Asp Tyr Leu Gln
```

-continued

```
105                 110                 115                 120

gta ttt ctt ggt gta ata aac acc gag tgg aca ccg gaa agt             430
Val Phe Leu Gly Val Ile Asn Thr Glu Trp Thr Pro Glu Ser
                125                 130

tgagaacaaa ccggcttatt gtagtggaag attttggaga agaatggttt tttggcgatg    490

agaatgaggg ccaaccaaca gtagggactt aatggccagt ataactaagc ttcagagaca    550

aagtaaatat ttcaggcatc ctactacttt atcacttcac acagatgaaa tatatttgag    610
```

<210> SEQ ID NO 81
<211> LENGTH: 134
<212> TYPE: PRT
<213> ORGANISM: Canis familiaris

<400> SEQUENCE: 81

```
Met Arg Met Leu Leu Asn Leu Ser Leu Leu Ala Leu Gly Ala Ala Tyr
  1               5                  10                  15

Val Ser Ala Phe Ala Val Glu Asn Pro Met Asn Arg Leu Val Ala Glu
             20                  25                  30

Thr Leu Thr Leu Leu Ser Thr His Arg Thr Trp Leu Ile Gly Asp Gly
         35                  40                  45

Asn Leu Met Ile Pro Thr Pro Glu Asn Lys Asn His Gln Leu Cys Ile
     50                  55                  60

Lys Glu Val Phe Gln Gly Ile Asp Thr Leu Lys Asn Gln Thr Ala His
 65                  70                  75                  80

Gly Glu Ala Val Asp Lys Leu Phe Gln Asn Leu Ser Leu Ile Lys Glu
                 85                  90                  95

His Ile Glu Arg Gln Lys Lys Arg Cys Ala Gly Glu Arg Trp Arg Val
            100                 105                 110

Thr Lys Phe Leu Asp Tyr Leu Gln Val Phe Leu Gly Val Ile Asn Thr
        115                 120                 125

Glu Trp Thr Pro Glu Ser
    130
```

<210> SEQ ID NO 82
<211> LENGTH: 610
<212> TYPE: DNA
<213> ORGANISM: Canis familiaris

<400> SEQUENCE: 82

```
ctcaaatata tttcatctgt gtgaagtgat aaagtagtag gatgcctgaa atatttactt     60

tgtctctgaa gcttagttat actggccatt aagtccctac tgttggttgg ccctcattct    120

catcgccaaa aaaccattct tctccaaaat cttccactac aataagccgg tttgttctca    180

actttccggt gtccactcgg tgtttattac accaagaaat acttgcaggt agtctaggaa    240

ctttgtcact ctccatcttt ctcctgcaca cctttttttt tggcgctcta tgtgttcttt    300

tattaaagac aagttttgga atagtttatc cacagcctcc ccgtgggcag tttggttctt    360

caatgtgtct ataccctgaa aaacttcttt aatgcacagt tggtgatttt tattttcagg    420

agtaggaatc atcaggttcc catcgcctat cagccaagtt cgatgagtgg agagcagtgt    480

caaggtctct gccaccagtc tattcatggg attttctaca gcaaaggcag aaacataggc    540

agccccaaga gctagcaaac tcaaattcag aagcattctc atagctctga aatgttcagt    600

gtttgccttg                                                           610
```

<210> SEQ ID NO 83

-continued

<211> LENGTH: 402
<212> TYPE: DNA
<213> ORGANISM: Canis familiaris

<400> SEQUENCE: 83

```
atgagaatgc ttctgaattt gagtttgcta gctcttgggg ctgcctatgt ttctgccttt      60

gctgtagaaa atcccatgaa tagactggtg gcagagacct tgacactgct ctccactcat     120

cgaacttggc tgataggcga tgggaacctg atgattccta ctcctgaaaa taaaaatcac     180

caactgtgca ttaaagaagt ttttcagggt atagacacat tgaagaacca aactgcccac     240

ggggaggctg tggataaact attccaaaac ttgtctttaa taaaagaaca catagagcgc     300

caaaaaaaaa ggtgtgcagg agaaagatgg agagtgacaa agttcctaga ctacctgcaa     360

gtatttcttg gtgtaataaa caccgagtgg acaccggaaa gt                        402
```

<210> SEQ ID NO 84
<211> LENGTH: 402
<212> TYPE: DNA
<213> ORGANISM: Canis familiaris

<400> SEQUENCE: 84

```
actttccggt gtccactcgg tgtttattac accaagaaat acttgcaggt agtctaggaa      60

ctttgtcact ctccatcttt ctcctgcaca cctttttttt tggcgctcta tgtgttcttt     120

tattaaagac aagttttgga atagtttatc cacagcctcc ccgtgggcag tttggttctt     180

caatgtgtct ataccctgaa aaacttcttt aatgcacagt tggtgatttt tattttcagg     240

agtaggaatc atcaggttcc catcgcctat cagccaagtt cgatgagtgg agagcagtgt     300

caaggtctct gccaccagtc tattcatggg attttctaca gcaaaggcag aaacataggc     360

agccccaaga gctagcaaac tcaaattcag aagcattctc at                        402
```

<210> SEQ ID NO 85
<211> LENGTH: 345
<212> TYPE: DNA
<213> ORGANISM: Canis familiaris
<220> FEATURE:
<221> NAME/KEY: CDS
<222> LOCATION: (1)..(345)

<400> SEQUENCE: 85

```
ttt gct gta gaa aat ccc atg aat aga ctg gtg gca gag acc ttg aca       48
Phe Ala Val Glu Asn Pro Met Asn Arg Leu Val Ala Glu Thr Leu Thr
  1               5                  10                  15

ctg ctc tcc act cat cga act tgg ctg ata ggc gat ggg aac ctg atg       96
Leu Leu Ser Thr His Arg Thr Trp Leu Ile Gly Asp Gly Asn Leu Met
             20                  25                  30

att cct act cct gaa aat aaa aat cac caa ctg tgc att aaa gaa gtt      144
Ile Pro Thr Pro Glu Asn Lys Asn His Gln Leu Cys Ile Lys Glu Val
         35                  40                  45

ttt cag ggt ata gac aca ttg aag aac caa act gcc cac ggg gag gct      192
Phe Gln Gly Ile Asp Thr Leu Lys Asn Gln Thr Ala His Gly Glu Ala
     50                  55                  60

gtg gat aaa cta ttc caa aac ttg tct tta ata aaa gaa cac ata gag      240
Val Asp Lys Leu Phe Gln Asn Leu Ser Leu Ile Lys Glu His Ile Glu
 65                  70                  75                  80

cgc caa aaa aaa agg tgt gca gga gaa aga tgg aga gtg aca aag ttc      288
Arg Gln Lys Lys Arg Cys Ala Gly Glu Arg Trp Arg Val Thr Lys Phe
                 85                  90                  95

cta gac tac ctg caa gta ttt ctt ggt gta ata aac acc gag tgg aca      336
Leu Asp Tyr Leu Gln Val Phe Leu Gly Val Ile Asn Thr Glu Trp Thr
```

-continued

```
            100                 105                 110

ccg gaa agt                                                          345
Pro Glu Ser
        115


<210> SEQ ID NO 86
<211> LENGTH: 115
<212> TYPE: PRT
<213> ORGANISM: Canis familiaris

<400> SEQUENCE: 86

Phe Ala Val Glu Asn Pro Met Asn Arg Leu Val Ala Glu Thr Leu Thr
  1               5                  10                  15

Leu Leu Ser Thr His Arg Thr Trp Leu Ile Gly Asp Gly Asn Leu Met
             20                  25                  30

Ile Pro Thr Pro Glu Asn Lys Asn His Gln Leu Cys Ile Lys Glu Val
         35                  40                  45

Phe Gln Gly Ile Asp Thr Leu Lys Asn Gln Thr Ala His Gly Glu Ala
     50                  55                  60

Val Asp Lys Leu Phe Gln Asn Leu Ser Leu Ile Lys Glu His Ile Glu
 65                  70                  75                  80

Arg Gln Lys Lys Arg Cys Ala Gly Glu Arg Trp Arg Val Thr Lys Phe
                 85                  90                  95

Leu Asp Tyr Leu Gln Val Phe Leu Gly Val Ile Asn Thr Glu Trp Thr
            100                 105                 110

Pro Glu Ser
        115


<210> SEQ ID NO 87
<211> LENGTH: 345
<212> TYPE: DNA
<213> ORGANISM: Canis familiaris

<400> SEQUENCE: 87

actttccggt gtccactcgg tgtttattac accaagaaat acttgcaggt agtctaggaa      60

ctttgtcact ctccatcttt ctcctgcaca cctttttttt tggcgctcta tgtgttcttt     120

tattaaagac aagttttgga atagtttatc cacagcctcc ccgtgggcag tttggttctt     180

caatgtgtct ataccctgaa aaacttcttt aatgcacagt tggtgatttt tattttcagg     240

agtaggaatc atcaggttcc catcgcctat cagccaagtt cgatgagtgg agagcagtgt     300

caaggtctct gccaccagtc tattcatggg attttctaca gcaaa                     345


<210> SEQ ID NO 88
<211> LENGTH: 166
<212> TYPE: DNA
<213> ORGANISM: Canis familiaris

<400> SEQUENCE: 88

ctcagcttag gccagcctac gacctgcctg ctcttccctc gctcctcctg cattggctct      60

gggctccatg gcgctctggt tgactgtggt cattgctctc acctgcctcg gtggccttgc     120

ctccccgagc cctgtgactc cctccccaac cctcaaggag ctcatt                    166


<210> SEQ ID NO 89
<211> LENGTH: 272
<212> TYPE: DNA
<213> ORGANISM: Canis familiaris

<400> SEQUENCE: 89
```

-continued

```
tggccttgcc tccccgagcc ctgtgactcc ctccccaacc ctcaaggagc tcattgagga     60

gctggtcaac atcacccaga atcaggcatc cctctgcaac ggcagcatgg tgtggagcgt    120

caacctgacc gccggcatgt actgcgcagc tctagaatct ctgatcaatg tctccgactg    180

cagcgccatc caaaggaccc agaggatgct gaaagcactg tgctctcaaa agcccgcggc    240

agggcagatt tccagtgaac gcagccgaga ca                                  272


<210> SEQ ID NO 90
<211> LENGTH: 278
<212> TYPE: DNA
<213> ORGANISM: Canis familiaris

<400> SEQUENCE: 90

atggcgctct ggttgactgt ggtcattgct ctcacctgcc tcggtggcct tgcctccccg     60

agccctgtga ctccctcccc aaccctcaag gagctcattg aggagctggt caacatcacc    120

cagaatcagg catccctctg caacggcagc atggtgtgga gcgtcaacct gaccgccggc    180

atgtactgcg cagctctaga atctctgatc aatgtctccg actgcagcgc catccaaagg    240

acccagagga tgctgaaagc actgtgctct caaaagcc                            278


<210> SEQ ID NO 91
<211> LENGTH: 1302
<212> TYPE: DNA
<213> ORGANISM: Canis familiaris
<220> FEATURE:
<221> NAME/KEY: CDS
<222> LOCATION: (52)..(444)

<400> SEQUENCE: 91

ctacgacctg cctgctcttc cctcgctcct cctgcattgg ctctgggctc c atg gcg      57
                                                         Met Ala
                                                           1

ctc tgg ttg act gtg gtc att gct ctc acc tgc ctc ggt ggc ctt gcc      105
Leu Trp Leu Thr Val Val Ile Ala Leu Thr Cys Leu Gly Gly Leu Ala
         5                  10                  15

tcc ccg agc cct gtg act ccc tcc cca acc ctc aag gag ctc att gag      153
Ser Pro Ser Pro Val Thr Pro Ser Pro Thr Leu Lys Glu Leu Ile Glu
     20                  25                  30

gag ctg gtc aac atc acc cag aat cag gca tcc ctc tgc aac ggc agc      201
Glu Leu Val Asn Ile Thr Gln Asn Gln Ala Ser Leu Cys Asn Gly Ser
 35                  40                  45                  50

atg gtg tgg agc gtc aac ctg acc gcc ggc atg tac tgc gca gct cta      249
Met Val Trp Ser Val Asn Leu Thr Ala Gly Met Tyr Cys Ala Ala Leu
                 55                  60                  65

gaa tct ctg atc aat gtc tcc gac tgc agc gcc atc caa agg acc cag      297
Glu Ser Leu Ile Asn Val Ser Asp Cys Ser Ala Ile Gln Arg Thr Gln
             70                  75                  80

agg atg ctg aaa gca ctg tgc tct caa aag ccc gcg gca ggg cag att      345
Arg Met Leu Lys Ala Leu Cys Ser Gln Lys Pro Ala Ala Gly Gln Ile
         85                  90                  95

tcc agt gaa cgc agc cga gac acc aaa att gaa gtg atc cag ttg gtg      393
Ser Ser Glu Arg Ser Arg Asp Thr Lys Ile Glu Val Ile Gln Leu Val
    100                 105                 110

aaa aac ctg ctc acc tat gta agg gga gtt tat cgc cat gga aat ttc      441
Lys Asn Leu Leu Thr Tyr Val Arg Gly Val Tyr Arg His Gly Asn Phe
115                 120                 125                 130

aga tgaagcatga aaacttagca tccttatctg tagacccaga cctgaccact           494
Arg
```

-continued

```
taagttccag attcattttt ctttccgacg tcacaaattt cttagggagg tggggggggg    554

ggagaaccat ttcctcagct gggacctcag cctgcaccgc ctgcctccat ggagctgagc    614

ccagccaccc ctgccttggt gcatggggcc cagccgggtg gccctcctcc gtctgcactt    674

catcaacgct gagggaaagc actgcatccc atgactgtcc cctcctcaga gcaaagtgca    734

gcattacagt ggaggcagat atgtgtggga gggggtcttg ctgtacctgg gagtggcaca    794

gacatgtttc ttcttagcct tatttattat tgtgtgttat ttaaacaagt gtctttgttt    854

gtgctgggga cagggagtgg cttggagctg gggcccagt gactcgggtt tagagagtcc     914

ctgggaataa gcactgtgtg taaaattctg ctacctcact gggatcctgg ggccgacaca    974

ggggacagga gaaagggtca gagatgctgc tcttgtctgc cactcagcag ctggccctca   1034

gccaagcagt aatttattgt tttccttgt atttaaagtt aagaaataaa atatgttatc    1094

aaagagttaa taatatatag aagagtagcc taaaaggctg catttggtgt gtgtggccag   1154

gccggggcgg gtgggggga gggtgttgtc actgaatgtg ctctttcact gactttgtca    1214

aactggaagc cagaaataaa gatggtgaca agagaaaaaa aaaaaaaaaa aaaaaaaaaa   1274

aaaaaaaaaa aaaaaaaaaa aaaaaaaa                                      1302
```

<210> SEQ ID NO 92
<211> LENGTH: 131
<212> TYPE: PRT
<213> ORGANISM: Canis familiaris

<400> SEQUENCE: 92

```
Met Ala Leu Trp Leu Thr Val Val Ile Ala Leu Thr Cys Leu Gly Gly
  1               5                  10                  15

Leu Ala Ser Pro Ser Pro Val Thr Pro Ser Pro Thr Leu Lys Glu Leu
             20                  25                  30

Ile Glu Glu Leu Val Asn Ile Thr Gln Asn Gln Ala Ser Leu Cys Asn
         35                  40                  45

Gly Ser Met Val Trp Ser Val Asn Leu Thr Ala Gly Met Tyr Cys Ala
     50                  55                  60

Ala Leu Glu Ser Leu Ile Asn Val Ser Asp Cys Ser Ala Ile Gln Arg
 65                  70                  75                  80

Thr Gln Arg Met Leu Lys Ala Leu Cys Ser Gln Lys Pro Ala Ala Gly
                 85                  90                  95

Gln Ile Ser Ser Glu Arg Ser Arg Asp Thr Lys Ile Glu Val Ile Gln
            100                 105                 110

Leu Val Lys Asn Leu Leu Thr Tyr Val Arg Gly Val Tyr Arg His Gly
        115                 120                 125

Asn Phe Arg
    130
```

<210> SEQ ID NO 93
<211> LENGTH: 1302
<212> TYPE: DNA
<213> ORGANISM: Canis familiaris

<400> SEQUENCE: 93

```
tttttttttt tttttttttt tttttttttt tttttttttt tttttttttt ttttctcttg     60

tcaccatctt tatttctggc ttccagtttg acaaagtcag tgaaagagca cattcagtga    120

caacaccctc ccccccaccc gccccggcct ggccacacac accaaatgca gccttttagg    180

ctactcttct atatattatt aactctttga taacatattt tatttcttaa ctttaaatac    240
```

-continued

```
aaggaaaaac aataaattac tgcttggctg agggccagct gctgagtggc agacaagagc    300

agcatctctg accctttctc ctgtcccctg tgtcggcccc aggatcccag tgaggtagca    360

gaattttaca cacagtgctt attcccaggg actctctaaa cccgagtcac tgggccccca    420

gctccaagcc actccctgtc cccagcacaa acaaagacac ttgtttaaat aacacacaat    480

aataaataag gctaagaaga aacatgtctg tgccactccc aggtacagca agaccccctc    540

ccacacatat ctgcctccac tgtaatgctg cactttgctc tgaggagggg acagtcatgg    600

gatgcagtgc tttccctcag cgttgatgaa gtgcagacgg aggagggcca cccggctggg    660

ccccatgcac caaggcaggg gtggctgggc tcagctccat ggaggcaggc ggtgcaggct    720

gaggtcccag ctgaggaaat ggttctcccc ccccccacc tccctaagaa atttgtgacg    780

tcggaaagaa aaatgaatct ggaacttaag tggtcaggtc tgggtctaca gataaggatg    840

ctaagttttc atgcttcatc tgaaatttcc atggcgataa actcccctta cataggtgag    900

caggtttttc accaactgga tcacttcaat tttggtgtct cggctgcgtt cactggaaat    960

ctgccctgcc gcgggctttt gagagcacag tgctttcagc atcctctggg tcctttggat   1020

ggcgctgcag tcggagacat tgatcagaga ttctagagct gcgcagtaca tgccggcggt   1080

caggttgacg ctccacacca tgctgccgtt gcagagggat gcctgattct gggtgatgtt   1140

gaccagctcc tcaatgagct ccttgagggt tggggaggga gtcacagggc tcggggaggc   1200

aaggccaccg aggcaggtga gagcaatgac cacagtcaac cagagcgcca tggagcccag   1260

agccaatgca ggaggagcga gggaagagca ggcaggtcgt ag                       1302
```

<210> SEQ ID NO 94
<211> LENGTH: 393
<212> TYPE: DNA
<213> ORGANISM: Canis familiaris

<400> SEQUENCE: 94

```
atggcgctct ggttgactgt ggtcattgct ctcacctgcc tcggtggcct tgcctccccg     60

agccctgtga ctccctcccc aaccctcaag gagctcattg aggagctggt caacatcacc    120

cagaatcagg catccctctg caacggcagc atggtgtgga gcgtcaacct gaccgccggc    180

atgtactgcg cagctctaga atctctgatc aatgtctccg actgcagcgc catccaaagg    240

acccagagga tgctgaaagc actgtgctct caaaagcccg cggcagggca gatttccagt    300

gaacgcagcc gagacaccaa aattgaagtg atccagttgg tgaaaaacct gctcacctat    360

gtaaggggag tttatcgcca tggaaatttc aga                                  393
```

<210> SEQ ID NO 95
<211> LENGTH: 393
<212> TYPE: DNA
<213> ORGANISM: Canis familiaris

<400> SEQUENCE: 95

```
tctgaaattt ccatggcgat aaactcccct tacataggtg agcaggtttt tcaccaactg     60

gatcacttca attttggtgt ctcggctgcg ttcactggaa atctgccctg ccgcgggctt    120

ttgagagcac agtgctttca gcatcctctg ggtcctttgg atggcgctgc agtcggagac    180

attgatcaga gattctagag ctgcgcagta catgccggcg gtcaggttga cgctccacac    240

catgctgccg ttgcagaggg atgcctgatt ctgggtgatg ttgaccagct cctcaatgag    300

ctccttgagg gttggggagg gagtcacagg gctcggggag gcaaggccac cgaggcaggt    360
```

-continued

```
gagagcaatg accacagtca accagagcgc cat                           393


<210> SEQ ID NO 96
<211> LENGTH: 333
<212> TYPE: DNA
<213> ORGANISM: Canis familiaris
<220> FEATURE:
<221> NAME/KEY: CDS
<222> LOCATION: (1)..(333)

<400> SEQUENCE: 96

agc cct gtg act ccc tcc cca acc ctc aag gag ctc att gag gag ctg       48
Ser Pro Val Thr Pro Ser Pro Thr Leu Lys Glu Leu Ile Glu Glu Leu
  1               5                  10                  15

gtc aac atc acc cag aat cag gca tcc ctc tgc aac ggc agc atg gtg       96
Val Asn Ile Thr Gln Asn Gln Ala Ser Leu Cys Asn Gly Ser Met Val
             20                  25                  30

tgg agc gtc aac ctg acc gcc ggc atg tac tgc gca gct cta gaa tct      144
Trp Ser Val Asn Leu Thr Ala Gly Met Tyr Cys Ala Ala Leu Glu Ser
         35                  40                  45

ctg atc aat gtc tcc gac tgc agc gcc atc caa agg acc cag agg atg      192
Leu Ile Asn Val Ser Asp Cys Ser Ala Ile Gln Arg Thr Gln Arg Met
     50                  55                  60

ctg aaa gca ctg tgc tct caa aag ccc gcg gca ggg cag att tcc agt      240
Leu Lys Ala Leu Cys Ser Gln Lys Pro Ala Ala Gly Gln Ile Ser Ser
 65                  70                  75                  80

gaa cgc agc cga gac acc aaa att gaa gtg atc cag ttg gtg aaa aac      288
Glu Arg Ser Arg Asp Thr Lys Ile Glu Val Ile Gln Leu Val Lys Asn
                 85                  90                  95

ctg ctc acc tat gta agg gga gtt tat cgc cat gga aat ttc aga          333
Leu Leu Thr Tyr Val Arg Gly Val Tyr Arg His Gly Asn Phe Arg
            100                 105                 110


<210> SEQ ID NO 97
<211> LENGTH: 111
<212> TYPE: PRT
<213> ORGANISM: Canis familiaris

<400> SEQUENCE: 97

Ser Pro Val Thr Pro Ser Pro Thr Leu Lys Glu Leu Ile Glu Glu Leu
  1               5                  10                  15

Val Asn Ile Thr Gln Asn Gln Ala Ser Leu Cys Asn Gly Ser Met Val
             20                  25                  30

Trp Ser Val Asn Leu Thr Ala Gly Met Tyr Cys Ala Ala Leu Glu Ser
         35                  40                  45

Leu Ile Asn Val Ser Asp Cys Ser Ala Ile Gln Arg Thr Gln Arg Met
     50                  55                  60

Leu Lys Ala Leu Cys Ser Gln Lys Pro Ala Ala Gly Gln Ile Ser Ser
 65                  70                  75                  80

Glu Arg Ser Arg Asp Thr Lys Ile Glu Val Ile Gln Leu Val Lys Asn
                 85                  90                  95

Leu Leu Thr Tyr Val Arg Gly Val Tyr Arg His Gly Asn Phe Arg
            100                 105                 110


<210> SEQ ID NO 98
<211> LENGTH: 333
<212> TYPE: DNA
<213> ORGANISM: Canis familiaris

<400> SEQUENCE: 98

tctgaaattt ccatggcgat aaactcccct tacataggtg agcaggtttt tcaccaactg      60
```

-continued

```
gatcacttca attttggtgt ctcggctgcg ttcactggaa atctgccctg ccgcgggctt    120

ttgagagcac agtgctttca gcatcctctg ggtcctttgg atggcgctgc agtcggagac    180

attgatcaga gattctagag ctgcgcagta catgccggcg gtcaggttga cgctccacac    240

catgctgccg ttgcagaggg atgcctgatt ctgggtgatg ttgaccagct cctcaatgag    300

ctccttgagg gttggggagg gagtcacagg gct                                  333


<210> SEQ ID NO 99
<211> LENGTH: 1269
<212> TYPE: DNA
<213> ORGANISM: Canis familiaris
<220> FEATURE:
<221> NAME/KEY: CDS
<222> LOCATION: (57)..(446)

<400> SEQUENCE: 99

ccagcctacg acctgcctgc tcttccctcg ctcctcctgc attggctctg ggctcc atg     59
                                                              Met
                                                                1

gcg ctc tgg ttg act gtg gtc att gct ctc acc tgc ctc ggt ggc ctt      107
Ala Leu Trp Leu Thr Val Val Ile Ala Leu Thr Cys Leu Gly Gly Leu
              5                  10                  15

gcc tcc ccg agc cct gtg act ccc tcc cca acc ctc aag gag ctc att      155
Ala Ser Pro Ser Pro Val Thr Pro Ser Pro Thr Leu Lys Glu Leu Ile
         20                  25                  30

gag gag ctg gtc aac atc acc cag aat cag gca tcc ctc tgc aac ggc      203
Glu Glu Leu Val Asn Ile Thr Gln Asn Gln Ala Ser Leu Cys Asn Gly
     35                  40                  45

agc atg gtg tgg agc gtc aac ctg acc gcc ggc atg tac tgc gca gct      251
Ser Met Val Trp Ser Val Asn Leu Thr Ala Gly Met Tyr Cys Ala Ala
 50                  55                  60                  65

cta gaa tct ctg atc aat gtc tcc gac tgc agc gcc atc caa agg acc      299
Leu Glu Ser Leu Ile Asn Val Ser Asp Cys Ser Ala Ile Gln Arg Thr
                 70                  75                  80

cag agg atg ctg aaa gca ctg tgc tct caa aag ccc gcg gca ggg att      347
Gln Arg Met Leu Lys Ala Leu Cys Ser Gln Lys Pro Ala Ala Gly Ile
             85                  90                  95

tcc agt gaa cgc agc cga gac acc aaa att gaa gtg atc cag ttg gtg      395
Ser Ser Glu Arg Ser Arg Asp Thr Lys Ile Glu Val Ile Gln Leu Val
        100                 105                 110

aaa aac ctg ctc acc tat gta agg gga gtt tat cgc cat gga aat ttc      443
Lys Asn Leu Leu Thr Tyr Val Arg Gly Val Tyr Arg His Gly Asn Phe
    115                 120                 125

aga tgaagcatga aaacttagca tccttatctg tagacccaga cctgaccact           496
Arg
130

taagttccag attcattttt ctttccgacg tcacaaattt cttagggagg tggggggggg    556

ggagaaccat ttcctcagct gggacctcag cctgcaccgc ctgcctccat ggagctgagc    616

ccagccaccc ctgccttggt gcatggggcc cagccgggtg gccctcctcc gtctgcactt    676

catcaacgct gagggaaagc actgcatccc atgactgtcc cctcctcaga gcaaagtgca    736

gcattacagt ggaggcagat atgtgtggga gggggtcttg ctgtacctgg gagtggcaca    796

gacatgtttc ttcttagcct tatttattat tgtgtgttat ttaaacaagt gtctttgttt    856

gtgctgggga cagggagtgg cttggagctg ggggcccagt gactcgggtt tagagagtcc    916

ctgggaataa gcactgtgtg taaaattctg ctacctcact gggatcctgg ggccgacaca    976

ggggacagga gaaagggtca gagatgctgc tcttgtctgc cactcagcag ctggccctca   1036
```

```
gccaagcagt aatttattgt ttttccttgt atttaaagtt aagaaataaa atatgttatc   1096

aaagagttaa taatatatag aagagtagcc taaaaggctg catttggtgt gtgtggccag   1156

gccggggcgg gtgggggga gggtgttgtc actgaatgtg ctctttcact gactttgtca   1216

aactggaagc cagaaataaa gatggtgaca agagaaaaaa aaaaaaaaaa aaa          1269


<210> SEQ ID NO 100
<211> LENGTH: 130
<212> TYPE: PRT
<213> ORGANISM: Canis familiaris

<400> SEQUENCE: 100

Met Ala Leu Trp Leu Thr Val Val Ile Ala Leu Thr Cys Leu Gly Gly
  1               5                  10                  15

Leu Ala Ser Pro Ser Pro Val Thr Pro Ser Pro Thr Leu Lys Glu Leu
             20                  25                  30

Ile Glu Glu Leu Val Asn Ile Thr Gln Asn Gln Ala Ser Leu Cys Asn
         35                  40                  45

Gly Ser Met Val Trp Ser Val Asn Leu Thr Ala Gly Met Tyr Cys Ala
     50                  55                  60

Ala Leu Glu Ser Leu Ile Asn Val Ser Asp Cys Ser Ala Ile Gln Arg
 65                  70                  75                  80

Thr Gln Arg Met Leu Lys Ala Leu Cys Ser Gln Lys Pro Ala Ala Gly
                 85                  90                  95

Ile Ser Ser Glu Arg Ser Arg Asp Thr Lys Ile Glu Val Ile Gln Leu
            100                 105                 110

Val Lys Asn Leu Leu Thr Tyr Val Arg Gly Val Tyr Arg His Gly Asn
        115                 120                 125

Phe Arg
    130


<210> SEQ ID NO 101
<211> LENGTH: 1269
<212> TYPE: DNA
<213> ORGANISM: Canis familiaris

<400> SEQUENCE: 101

tttttttttt tttttttttc tcttgtcacc atctttattt ctggcttcca gtttgacaaa     60

gtcagtgaaa gagcacattc agtgacaaca ccctcccccc cacccgcccc ggcctggcca    120

cacacaccaa atgcagcctt ttaggctact cttctatata ttattaactc tttgataaca    180

tattttattt cttaacttta aatacaagga aaaacaataa attactgctt ggctgagggc    240

cagctgctga gtggcagaca agagcagcat ctctgaccct ttctcctgtc ccctgtgtcg    300

gccccaggat cccagtgagg tagcagaatt ttacacacag tgcttattcc cagggactct    360

ctaaacccga gtcactgggc ccccagctcc aagccactcc ctgtccccag cacaaacaaa    420

gacacttgtt taaataacac acaataataa ataaggctaa gaagaaacat gtctgtgcca    480

ctcccaggta cagcaagacc ccctcccaca catatctgcc tccactgtaa tgctgcactt    540

tgctctgagg aggggacagt catgggatgc agtgctttcc ctcagcgttg atgaagtgca    600

gacggaggag ggccacccgg ctgggcccca tgcaccaagg caggggtggc tgggctcagc    660

tccatggagg caggcggtgc aggctgaggt cccagctgag gaaatggttc tccccccccc    720

ccacctccct aagaaatttg tgacgtcgga aagaaaaatg aatctggaac ttaagtggtc    780

aggtctgggt ctacagataa ggatgctaag ttttcatgct tcatctgaaa tttccatggc    840
```

-continued

```
gataaactcc ccttacatag gtgagcaggt ttttcaccaa ctggatcact tcaattttgg    900

tgtctcggct gcgttcactg gaaatccctg ccgcgggctt ttgagagcac agtgctttca    960

gcatcctctg ggtcctttgg atggcgctgc agtcggagac attgatcaga gattctagag   1020

ctgcgcagta catgccggcg gtcaggttga cgctccacac catgctgccg ttgcagaggg   1080

atgcctgatt ctgggtgatg ttgaccagct cctcaatgag ctccttgagg gttggggagg   1140

gagtcacagg gctcggggag gcaaggccac cgaggcaggt gagagcaatg accacagtca   1200

accagagcgc catggagccc agagccaatg caggaggagc gagggaagag caggcaggtc   1260

gtaggctgg                                                           1269
```

```
<210> SEQ ID NO 102
<211> LENGTH: 390
<212> TYPE: DNA
<213> ORGANISM: Canis familiaris

<400> SEQUENCE: 102

atggcgctct ggttgactgt ggtcattgct ctcacctgcc tcggtggcct tgcctccccg     60

agccctgtga ctccctcccc aaccctcaag gagctcattg aggagctggt caacatcacc    120

cagaatcagg catccctctg caacggcagc atggtgtgga gcgtcaacct gaccgccggc    180

atgtactgcg cagctctaga atctctgatc aatgtctccg actgcagcgc catccaaagg    240

acccagagga tgctgaaagc actgtgctct caaaagcccg cggcagggat ttccagtgaa    300

cgcagccgag acaccaaaat tgaagtgatc cagttggtga aaaacctgct cacctatgta    360

aggggagttt atcgccatgg aaatttcaga                                     390
```

```
<210> SEQ ID NO 103
<211> LENGTH: 390
<212> TYPE: DNA
<213> ORGANISM: Canis familiaris

<400> SEQUENCE: 103

tctgaaattt ccatggcgat aaactcccct tacataggtg agcaggtttt tcaccaactg     60

gatcacttca attttggtgt ctcggctgcg ttcactggaa atccctgccg cgggcttttg    120

agagcacagt gctttcagca tcctctgggt cctttggatg gcgctgcagt cggagacatt    180

gatcagagat tctagagctg cgcagtacat gccggcggtc aggttgacgc tccacaccat    240

gctgccgttg cagagggatg cctgattctg ggtgatgttg accagctcct caatgagctc    300

cttgagggtt ggggagggag tcacagggct cggggaggca aggccaccga ggcaggtgag    360

agcaatgacc acagtcaacc agagcgccat                                     390
```

```
<210> SEQ ID NO 104
<211> LENGTH: 330
<212> TYPE: DNA
<213> ORGANISM: Canis familiaris
<220> FEATURE:
<221> NAME/KEY: CDS
<222> LOCATION: (1)..(330)

<400> SEQUENCE: 104

agc cct gtg act ccc tcc cca acc ctc aag gag ctc att gag gag ctg       48
Ser Pro Val Thr Pro Ser Pro Thr Leu Lys Glu Leu Ile Glu Glu Leu
  1               5                  10                  15

gtc aac atc acc cag aat cag gca tcc ctc tgc aac ggc agc atg gtg       96
Val Asn Ile Thr Gln Asn Gln Ala Ser Leu Cys Asn Gly Ser Met Val
             20                  25                  30
```

-continued

```
tgg agc gtc aac ctg acc gcc ggc atg tac tgc gca gct cta gaa tct      144
Trp Ser Val Asn Leu Thr Ala Gly Met Tyr Cys Ala Ala Leu Glu Ser
        35                  40                  45

ctg atc aat gtc tcc gac tgc agc gcc atc caa agg acc cag agg atg      192
Leu Ile Asn Val Ser Asp Cys Ser Ala Ile Gln Arg Thr Gln Arg Met
    50                  55                  60

ctg aaa gca ctg tgc tct caa aag ccc gcg gca ggg att tcc agt gaa      240
Leu Lys Ala Leu Cys Ser Gln Lys Pro Ala Ala Gly Ile Ser Ser Glu
 65                  70                  75                  80

cgc agc cga gac acc aaa att gaa gtg atc cag ttg gtg aaa aac ctg      288
Arg Ser Arg Asp Thr Lys Ile Glu Val Ile Gln Leu Val Lys Asn Leu
                85                  90                  95

ctc acc tat gta agg gga gtt tat cgc cat gga aat ttc aga              330
Leu Thr Tyr Val Arg Gly Val Tyr Arg His Gly Asn Phe Arg
            100                 105                 110


<210> SEQ ID NO 105
<211> LENGTH: 110
<212> TYPE: PRT
<213> ORGANISM: Canis familiaris

<400> SEQUENCE: 105

Ser Pro Val Thr Pro Ser Pro Thr Leu Lys Glu Leu Ile Glu Glu Leu
  1               5                  10                  15

Val Asn Ile Thr Gln Asn Gln Ala Ser Leu Cys Asn Gly Ser Met Val
            20                  25                  30

Trp Ser Val Asn Leu Thr Ala Gly Met Tyr Cys Ala Ala Leu Glu Ser
        35                  40                  45

Leu Ile Asn Val Ser Asp Cys Ser Ala Ile Gln Arg Thr Gln Arg Met
    50                  55                  60

Leu Lys Ala Leu Cys Ser Gln Lys Pro Ala Ala Gly Ile Ser Ser Glu
 65                  70                  75                  80

Arg Ser Arg Asp Thr Lys Ile Glu Val Ile Gln Leu Val Lys Asn Leu
                85                  90                  95

Leu Thr Tyr Val Arg Gly Val Tyr Arg His Gly Asn Phe Arg
            100                 105                 110


<210> SEQ ID NO 106
<211> LENGTH: 330
<212> TYPE: DNA
<213> ORGANISM: Canis familiaris

<400> SEQUENCE: 106

tctgaaattt ccatggcgat aaactcccct tacataggtg agcaggtttt tcaccaactg     60

gatcacttca attttggtgt ctcggctgcg ttcactggaa atccctgccg cgggcttttg    120

agagcacagt gctttcagca tcctctgggt cctttggatg gcgctgcagt cggagacatt    180

gatcagagat tctagagctg cgcagtacat gccggcggtc aggttgacgc tccacaccat    240

gctgccgttg cagagggatg cctgattctg ggtgatgttg accagctcct caatgagctc    300

cttgagggtt ggggagggag tcacagggct                                     330


<210> SEQ ID NO 107
<211> LENGTH: 567
<212> TYPE: DNA
<213> ORGANISM: Felis catus
<220> FEATURE:
<221> NAME/KEY: CDS
<222> LOCATION: (1)..(567)
```

-continued

<400> SEQUENCE: 107 atg gcg ctg ccc tct tcc ttc ttg gtg gcc ctg gtg gcg ctg ggc tgc 48
Met Ala Leu Pro Ser Ser Phe Leu Val Ala Leu Val Ala Leu Gly Cys
1 5 10 15 aac tcc gtc tgc tct ctg ggc tgt gac ctg cct cag acc cac ggc ctg 96
Asn Ser Val Cys Ser Leu Gly Cys Asp Leu Pro Gln Thr His Gly Leu
20 25 30 ctg aac agg agg gcc ttg acg ctc ctg gga caa atg agg aga ctc cct 144
Leu Asn Arg Arg Ala Leu Thr Leu Leu Gly Gln Met Arg Arg Leu Pro
35 40 45 gcc agc tcc tgt cag aag gac aga aat gac ttc gcc ttc ccc cag gac 192
Ala Ser Ser Cys Gln Lys Asp Arg Asn Asp Phe Ala Phe Pro Gln Asp
50 55 60 gtg ttt ggt gga gac cag tcc cac aag gcc caa gcc ctc tcg gtg gtg 240
Val Phe Gly Gly Asp Gln Ser His Lys Ala Gln Ala Leu Ser Val Val
65 70 75 80 cac gtg acg aac cag aag atc ttc cac ttc ttc tgc aca gag gcg tcc 288
His Val Thr Asn Gln Lys Ile Phe His Phe Phe Cys Thr Glu Ala Ser
85 90 95 tcg tct gct gct tgg aac acc acc ctc ctg gag gaa ttc tgc acg gga 336
Ser Ser Ala Ala Trp Asn Thr Thr Leu Leu Glu Glu Phe Cys Thr Gly
100 105 110 ctt gat tgg cag ctg acc cgc ctg gaa gcc tgt gtc atg cag gag gtg 384
Leu Asp Trp Gln Leu Thr Arg Leu Glu Ala Cys Val Met Gln Glu Val
115 120 125 ggg gag gga gag gct ccc ctc acg aac gag gac tcc atc ctg agg aac 432
Gly Glu Gly Glu Ala Pro Leu Thr Asn Glu Asp Ser Ile Leu Arg Asn
130 135 140 tac ttc caa aga ctc tcc ctc tac ctg caa gag aag aaa tac agc cct 480
Tyr Phe Gln Arg Leu Ser Leu Tyr Leu Gln Glu Lys Lys Tyr Ser Pro
145 150 155 160 tgt gcc tgg gag atc gtc aga gca gaa atc atg aga tcc ttg tat tat 528
Cys Ala Trp Glu Ile Val Arg Ala Glu Ile Met Arg Ser Leu Tyr Tyr
165 170 175 tca tca aca gcc ttg cag aaa aga tta agg agc gag aaa 567
Ser Ser Thr Ala Leu Gln Lys Arg Leu Arg Ser Glu Lys
180 185

<210> SEQ ID NO 108
<211> LENGTH: 189
<212> TYPE: PRT
<213> ORGANISM: Felis catus

<400> SEQUENCE: 108

Met Ala Leu Pro Ser Ser Phe Leu Val Ala Leu Val Ala Leu Gly Cys
1 5 10 15

Asn Ser Val Cys Ser Leu Gly Cys Asp Leu Pro Gln Thr His Gly Leu
20 25 30

Leu Asn Arg Arg Ala Leu Thr Leu Leu Gly Gln Met Arg Arg Leu Pro
35 40 45

Ala Ser Ser Cys Gln Lys Asp Arg Asn Asp Phe Ala Phe Pro Gln Asp
50 55 60

Val Phe Gly Gly Asp Gln Ser His Lys Ala Gln Ala Leu Ser Val Val
65 70 75 80

His Val Thr Asn Gln Lys Ile Phe His Phe Phe Cys Thr Glu Ala Ser
85 90 95

Ser Ser Ala Ala Trp Asn Thr Thr Leu Leu Glu Glu Phe Cys Thr Gly
100 105 110

-continued

```
Leu Asp Trp Gln Leu Thr Arg Leu Glu Ala Cys Val Met Gln Glu Val
        115                 120                 125

Gly Glu Gly Glu Ala Pro Leu Thr Asn Glu Asp Ser Ile Leu Arg Asn
    130                 135                 140

Tyr Phe Gln Arg Leu Ser Leu Tyr Leu Gln Glu Lys Lys Tyr Ser Pro
145                 150                 155                 160

Cys Ala Trp Glu Ile Val Arg Ala Glu Ile Met Arg Ser Leu Tyr Tyr
                165                 170                 175

Ser Ser Thr Ala Leu Gln Lys Arg Leu Arg Ser Glu Lys
            180                 185


<210> SEQ ID NO 109
<211> LENGTH: 567
<212> TYPE: DNA
<213> ORGANISM: Felis catus

<400> SEQUENCE: 109

tttctcgctc cttaatcttt tctgcaaggc tgttgatgaa taatacaagg atctcatgat      60

ttctgctctg acgatctccc aggcacaagg gctgtatttc ttctcttgca ggtagaggga     120

gagtctttgg aagtagttcc tcaggatgga gtcctcgttc gtgaggggag cctctccctc     180

ccccacctcc tgcatgacac aggcttccag gcgggtcagc tgccaatcaa gtcccgtgca     240

gaattcctcc aggagggtgg tgttccaagc agcagacgag gacgcctctg tgcagaagaa     300

gtggaagatc ttctggttcg tcacgtgcac caccgagagg gcttgggcct tgtgggactg     360

gtctccacca aacacgtcct gggggaaggc gaagtcattt ctgtccttct gacaggagct     420

ggcagggagt ctcctcattt gtcccaggag cgtcaaggcc ctcctgttca gcaggccgtg     480

ggtctgaggc aggtcacagc ccagagagca gacggagttg cagcccagcg ccaccagggc     540

caccaagaag gaagagggca gcgccat                                         567


<210> SEQ ID NO 110
<211> LENGTH: 567
<212> TYPE: DNA
<213> ORGANISM: Felis catus
<220> FEATURE:
<221> NAME/KEY: CDS
<222> LOCATION: (1)..(567)

<400> SEQUENCE: 110

atg gcg ctg ccc tct tcc ttc ttg gtg gcc ctg gtg gcg ctg ggc tgc       48
Met Ala Leu Pro Ser Ser Phe Leu Val Ala Leu Val Ala Leu Gly Cys
  1               5                  10                  15

aac tcc gtc tgc tct ctg ggc tgt gac ctg cct cag acc cac ggc ctg       96
Asn Ser Val Cys Ser Leu Gly Cys Asp Leu Pro Gln Thr His Gly Leu
             20                  25                  30

ctg aac agg agg gcc ttg acg ctc ctg gga caa atg agg aga ctc cct      144
Leu Asn Arg Arg Ala Leu Thr Leu Leu Gly Gln Met Arg Arg Leu Pro
         35                  40                  45

gcc agc tcc tgt cag aag gac agg aat gac ttc gcc ttc ccc cag gac      192
Ala Ser Ser Cys Gln Lys Asp Arg Asn Asp Phe Ala Phe Pro Gln Asp
     50                  55                  60

gtg ttc ggt gga gac cag tcc cac aag gct caa gcc ctc tcg gtg gtg      240
Val Phe Gly Gly Asp Gln Ser His Lys Ala Gln Ala Leu Ser Val Val
 65                  70                  75                  80

cac gtg acg aac cag gag atc ttc cac ttc ttc tgc aca gag gcg tcc      288
His Val Thr Asn Gln Glu Ile Phe His Phe Phe Cys Thr Glu Ala Ser
                 85                  90                  95

tcg tct gct gct tgg aac acc acc ctc ctg gag gaa ttc tgc acg gga      336
```

-continued

```
Ser Ser Ala Ala Trp Asn Thr Thr Leu Leu Glu Glu Phe Cys Thr Gly
            100                 105                 110

ctt gat cgg cag ctg acc cgc ctg gaa gcc tgt gtc gtg cag gag gtg      384
Leu Asp Arg Gln Leu Thr Arg Leu Glu Ala Cys Val Val Gln Glu Val
        115                 120                 125

ggg gag gga gag gct ccc ctc acg aac gag gac tcc ctc ctg agg aac      432
Gly Glu Gly Glu Ala Pro Leu Thr Asn Glu Asp Ser Leu Leu Arg Asn
    130                 135                 140

tac ttc caa aga ctc tcc ctc tac ctg caa gag aag aaa tac agc cct      480
Tyr Phe Gln Arg Leu Ser Leu Tyr Leu Gln Glu Lys Lys Tyr Ser Pro
145                 150                 155                 160

tgt gcc tgg gag atc gtc aga gca gaa atc atg aga tcc ttg tat tat      528
Cys Ala Trp Glu Ile Val Arg Ala Glu Ile Met Arg Ser Leu Tyr Tyr
                165                 170                 175

tca tca aca gcc ttg caa aaa aga tta agg agc gag aaa                  567
Ser Ser Thr Ala Leu Gln Lys Arg Leu Arg Ser Glu Lys
            180                 185


<210> SEQ ID NO 111
<211> LENGTH: 189
<212> TYPE: PRT
<213> ORGANISM: Felis catus

<400> SEQUENCE: 111

Met Ala Leu Pro Ser Ser Phe Leu Val Ala Leu Val Ala Leu Gly Cys
  1               5                  10                  15

Asn Ser Val Cys Ser Leu Gly Cys Asp Leu Pro Gln Thr His Gly Leu
            20                  25                  30

Leu Asn Arg Arg Ala Leu Thr Leu Leu Gly Gln Met Arg Arg Leu Pro
        35                  40                  45

Ala Ser Ser Cys Gln Lys Asp Arg Asn Asp Phe Ala Phe Pro Gln Asp
    50                  55                  60

Val Phe Gly Gly Asp Gln Ser His Lys Ala Gln Ala Leu Ser Val Val
 65                  70                  75                  80

His Val Thr Asn Gln Glu Ile Phe His Phe Phe Cys Thr Glu Ala Ser
                85                  90                  95

Ser Ser Ala Ala Trp Asn Thr Thr Leu Leu Glu Glu Phe Cys Thr Gly
            100                 105                 110

Leu Asp Arg Gln Leu Thr Arg Leu Glu Ala Cys Val Val Gln Glu Val
        115                 120                 125

Gly Glu Gly Glu Ala Pro Leu Thr Asn Glu Asp Ser Leu Leu Arg Asn
    130                 135                 140

Tyr Phe Gln Arg Leu Ser Leu Tyr Leu Gln Glu Lys Lys Tyr Ser Pro
145                 150                 155                 160

Cys Ala Trp Glu Ile Val Arg Ala Glu Ile Met Arg Ser Leu Tyr Tyr
                165                 170                 175

Ser Ser Thr Ala Leu Gln Lys Arg Leu Arg Ser Glu Lys
            180                 185


<210> SEQ ID NO 112
<211> LENGTH: 567
<212> TYPE: DNA
<213> ORGANISM: Felis catus

<400> SEQUENCE: 112

tttctcgctc cttaatcttt tttgcaaggc tgttgatgaa taatacaagg atctcatgat     60

ttctgctctg acgatctccc aggcacaagg gctgtatttc ttctcttgca ggtagaggga    120
```

-continued

```
gagtctttgg aagtagttcc tcaggaggga gtcctcgttc gtgaggggag cctctccctc    180

ccccacctcc tgcacgacac aggcttccag gcgggtcagc tgccgatcaa gtcccgtgca    240

gaattcctcc aggagggtgg tgttccaagc agcagacgag gacgcctctg tgcagaagaa    300

gtggaagatc tcctggttcg tcacgtgcac caccgagagg gcttgagcct tgtgggactg    360

gtctccaccg aacacgtcct gggggaaggc gaagtcattc ctgtccttct gacaggagct    420

ggcagggagt ctcctcattt gtcccaggag cgtcaaggcc ctcctgttca gcaggccgtg    480

ggtctgaggc aggtcacagc ccagagagca gacggagttg cagcccagcg ccaccagggc    540

caccaagaag gaagagggca gcgccat                                        567


<210> SEQ ID NO 113
<211> LENGTH: 498
<212> TYPE: DNA
<213> ORGANISM: Felis catus
<220> FEATURE:
<221> NAME/KEY: CDS
<222> LOCATION: (1)..(498)

<400> SEQUENCE: 113

tgt gac ctg cct cag acc cac ggc ctg ctg aac agg agg gcc ttg acg       48
Cys Asp Leu Pro Gln Thr His Gly Leu Leu Asn Arg Arg Ala Leu Thr
  1               5                  10                  15

ctc ctg gga caa atg agg aga ctc cct gcc agc tcc tgt cag aag gac       96
Leu Leu Gly Gln Met Arg Arg Leu Pro Ala Ser Ser Cys Gln Lys Asp
             20                  25                  30

aga aat gac ttc gcc ttc ccc cag gac gtg ttt ggt gga gac cag tcc      144
Arg Asn Asp Phe Ala Phe Pro Gln Asp Val Phe Gly Gly Asp Gln Ser
         35                  40                  45

cac aag gcc caa gcc ctc tcg gtg gtg cac gtg acg aac cag aag atc      192
His Lys Ala Gln Ala Leu Ser Val Val His Val Thr Asn Gln Lys Ile
     50                  55                  60

ttc cac ttc ttc tgc aca gag gcg tcc tcg tct gct gct tgg aac acc      240
Phe His Phe Phe Cys Thr Glu Ala Ser Ser Ser Ala Ala Trp Asn Thr
 65                  70                  75                  80

acc ctc ctg gag gaa ttc tgc acg gga ctt gat tgg cag ctg acc cgc      288
Thr Leu Leu Glu Glu Phe Cys Thr Gly Leu Asp Trp Gln Leu Thr Arg
                 85                  90                  95

ctg gaa gcc tgt gtc atg cag gag gtg ggg gag gga gag gct ccc ctc      336
Leu Glu Ala Cys Val Met Gln Glu Val Gly Glu Gly Glu Ala Pro Leu
            100                 105                 110

acg aac gag gac tcc atc ctg agg aac tac ttc caa aga ctc tcc ctc      384
Thr Asn Glu Asp Ser Ile Leu Arg Asn Tyr Phe Gln Arg Leu Ser Leu
        115                 120                 125

tac ctg caa gag aag aaa tac agc cct tgt gcc tgg gag atc gtc aga      432
Tyr Leu Gln Glu Lys Lys Tyr Ser Pro Cys Ala Trp Glu Ile Val Arg
    130                 135                 140

gca gaa atc atg aga tcc ttg tat tat tca tca aca gcc ttg cag aaa      480
Ala Glu Ile Met Arg Ser Leu Tyr Tyr Ser Ser Thr Ala Leu Gln Lys
145                 150                 155                 160

aga tta agg agc gag aaa                                              498
Arg Leu Arg Ser Glu Lys
                165


<210> SEQ ID NO 114
<211> LENGTH: 166
<212> TYPE: PRT
<213> ORGANISM: Felis catus

<400> SEQUENCE: 114
```

-continued

```
Cys Asp Leu Pro Gln Thr His Gly Leu Leu Asn Arg Arg Ala Leu Thr
  1               5                  10                  15

Leu Leu Gly Gln Met Arg Arg Leu Pro Ala Ser Ser Cys Gln Lys Asp
             20                  25                  30

Arg Asn Asp Phe Ala Phe Pro Gln Asp Val Phe Gly Gly Asp Gln Ser
         35                  40                  45

His Lys Ala Gln Ala Leu Ser Val Val His Val Thr Asn Gln Lys Ile
     50                  55                  60

Phe His Phe Phe Cys Thr Glu Ala Ser Ser Ser Ala Ala Trp Asn Thr
 65                  70                  75                  80

Thr Leu Leu Glu Glu Phe Cys Thr Gly Leu Asp Trp Gln Leu Thr Arg
                 85                  90                  95

Leu Glu Ala Cys Val Met Gln Glu Val Gly Glu Gly Glu Ala Pro Leu
            100                 105                 110

Thr Asn Glu Asp Ser Ile Leu Arg Asn Tyr Phe Gln Arg Leu Ser Leu
        115                 120                 125

Tyr Leu Gln Glu Lys Lys Tyr Ser Pro Cys Ala Trp Glu Ile Val Arg
    130                 135                 140

Ala Glu Ile Met Arg Ser Leu Tyr Tyr Ser Ser Thr Ala Leu Gln Lys
145                 150                 155                 160

Arg Leu Arg Ser Glu Lys
                165


<210> SEQ ID NO 115
<211> LENGTH: 498
<212> TYPE: DNA
<213> ORGANISM: Felis catus

<400> SEQUENCE: 115

tttctcgctc cttaatcttt tctgcaaggc tgttgatgaa taatacaagg atctcatgat     60

ttctgctctg acgatctccc aggcacaagg gctgtatttc ttctcttgca ggtagaggga    120

gagtctttgg aagtagttcc tcaggatgga gtcctcgttc gtgaggggag cctctccctc    180

ccccacctcc tgcatgacac aggcttccag gcgggtcagc tgccaatcaa gtcccgtgca    240

gaattcctcc aggagggtgg tgttccaagc agcagacgag gacgcctctg tgcagaagaa    300

gtggaagatc ttctggttcg tcacgtgcac caccgagagg gcttgggcct tgtgggactg    360

gtctccacca aacacgtcct gggggaaggc gaagtcattt ctgtccttct gacaggagct    420

ggcagggagt ctcctcattt gtcccaggag cgtcaaggcc ctcctgttca gcaggccgtg    480

ggtctgaggc aggtcaca                                                  498


<210> SEQ ID NO 116
<211> LENGTH: 498
<212> TYPE: DNA
<213> ORGANISM: Felis catus
<220> FEATURE:
<221> NAME/KEY: CDS
<222> LOCATION: (1)..(498)

<400> SEQUENCE: 116

tgt gac ctg cct cag acc cac ggc ctg ctg aac agg agg gcc ttg acg       48
Cys Asp Leu Pro Gln Thr His Gly Leu Leu Asn Arg Arg Ala Leu Thr
  1               5                  10                  15

ctc ctg gga caa atg agg aga ctc cct gcc agc tcc tgt cag aag gac       96
Leu Leu Gly Gln Met Arg Arg Leu Pro Ala Ser Ser Cys Gln Lys Asp
             20                  25                  30

agg aat gac ttc gcc ttc ccc cag gac gtg ttc ggt gga gac cag tcc      144
```

-continued

```
Arg Asn Asp Phe Ala Phe Pro Gln Asp Val Phe Gly Gly Asp Gln Ser
         35                  40                  45

cac aag gct caa gcc ctc tcg gtg gtg cac gtg acg aac cag gag atc      192
His Lys Ala Gln Ala Leu Ser Val Val His Val Thr Asn Gln Glu Ile
     50                  55                  60

ttc cac ttc ttc tgc aca gag gcg tcc tcg tct gct gct tgg aac acc      240
Phe His Phe Phe Cys Thr Glu Ala Ser Ser Ser Ala Ala Trp Asn Thr
 65                  70                  75                  80

acc ctc ctg gag gaa ttc tgc acg gga ctt gat cgg cag ctg acc cgc      288
Thr Leu Leu Glu Glu Phe Cys Thr Gly Leu Asp Arg Gln Leu Thr Arg
                 85                  90                  95

ctg gaa gcc tgt gtc gtg cag gag gtg ggg gag gga gag gct ccc ctc      336
Leu Glu Ala Cys Val Val Gln Glu Val Gly Glu Gly Glu Ala Pro Leu
            100                 105                 110

acg aac gag gac tcc ctc ctg agg aac tac ttc caa aga ctc tcc ctc      384
Thr Asn Glu Asp Ser Leu Leu Arg Asn Tyr Phe Gln Arg Leu Ser Leu
        115                 120                 125

tac ctg caa gag aag aaa tac agc cct tgt gcc tgg gag atc gtc aga      432
Tyr Leu Gln Glu Lys Lys Tyr Ser Pro Cys Ala Trp Glu Ile Val Arg
    130                 135                 140

gca gaa atc atg aga tcc ttg tat tat tca tca aca gcc ttg caa aaa      480
Ala Glu Ile Met Arg Ser Leu Tyr Tyr Ser Ser Thr Ala Leu Gln Lys
145                 150                 155                 160

aga tta agg agc gag aaa                                              498
Arg Leu Arg Ser Glu Lys
                165


<210> SEQ ID NO 117
<211> LENGTH: 166
<212> TYPE: PRT
<213> ORGANISM: Felis catus

<400> SEQUENCE: 117

Cys Asp Leu Pro Gln Thr His Gly Leu Leu Asn Arg Arg Ala Leu Thr
  1               5                  10                  15

Leu Leu Gly Gln Met Arg Arg Leu Pro Ala Ser Ser Cys Gln Lys Asp
             20                  25                  30

Arg Asn Asp Phe Ala Phe Pro Gln Asp Val Phe Gly Gly Asp Gln Ser
         35                  40                  45

His Lys Ala Gln Ala Leu Ser Val Val His Val Thr Asn Gln Glu Ile
     50                  55                  60

Phe His Phe Phe Cys Thr Glu Ala Ser Ser Ser Ala Ala Trp Asn Thr
 65                  70                  75                  80

Thr Leu Leu Glu Glu Phe Cys Thr Gly Leu Asp Arg Gln Leu Thr Arg
                 85                  90                  95

Leu Glu Ala Cys Val Val Gln Glu Val Gly Glu Gly Glu Ala Pro Leu
            100                 105                 110

Thr Asn Glu Asp Ser Leu Leu Arg Asn Tyr Phe Gln Arg Leu Ser Leu
        115                 120                 125

Tyr Leu Gln Glu Lys Lys Tyr Ser Pro Cys Ala Trp Glu Ile Val Arg
    130                 135                 140

Ala Glu Ile Met Arg Ser Leu Tyr Tyr Ser Ser Thr Ala Leu Gln Lys
145                 150                 155                 160

Arg Leu Arg Ser Glu Lys
                165


<210> SEQ ID NO 118
<211> LENGTH: 498
```

-continued

```
<212> TYPE: DNA
<213> ORGANISM: Felis catus

<400> SEQUENCE: 118

tttctcgctc cttaatcttt tttgcaaggc tgttgatgaa taatacaagg atctcatgat     60

ttctgctctg acgatctccc aggcacaagg gctgtatttc ttctcttgca ggtagaggga    120

gagtctttgg aagtagttcc tcaggaggga gtcctcgttc gtgaggggag cctctccctc    180

ccccacctcc tgcacgacac aggcttccag gcgggtcagc tgccgatcaa gtcccgtgca    240

gaattcctcc aggagggtgg tgttccaagc agcagacgag gacgcctctg tgcagaagaa    300

gtggaagatc tcctggttcg tcacgtgcac caccgagagg gcttgagcct tgtgggactg    360

gtctccaccg aacacgtcct gggggaaggc gaagtcattc ctgtccttct gacaggagct    420

ggcagggagt ctcctcattt gtcccaggag cgtcaaggcc ctcctgttca gcaggccgtg    480

ggtctgaggc aggtcaca                                                  498


<210> SEQ ID NO 119
<211> LENGTH: 444
<212> TYPE: DNA
<213> ORGANISM: Felis catus
<220> FEATURE:
<221> NAME/KEY: CDS
<222> LOCATION: (10)..(441)

<400> SEQUENCE: 119

ggatccacc atg tgg ctg cag aac ctg ctt ttc ctg ggc act gtg gtc tgc      51
          Met Trp Leu Gln Asn Leu Leu Phe Leu Gly Thr Val Val Cys
            1               5                  10

agc atc tct gca ccc acc agt tca ccc agc tct gtc act cgg ccc tgg        99
Ser Ile Ser Ala Pro Thr Ser Ser Pro Ser Ser Val Thr Arg Pro Trp
 15                  20                  25                  30

caa cac gtg gat gcc atc aag gag gcc ctg agc ctt ctg aac aac agt       147
Gln His Val Asp Ala Ile Lys Glu Ala Leu Ser Leu Leu Asn Asn Ser
                 35                  40                  45

agt gaa ata act gct gtg atg aat gaa gca gta gaa gtc gtc tct gaa       195
Ser Glu Ile Thr Ala Val Met Asn Glu Ala Val Glu Val Val Ser Glu
             50                  55                  60

atg ttt gac cct gag gag ccg aaa tgc ctg cag act cac cta aag ctg       243
Met Phe Asp Pro Glu Glu Pro Lys Cys Leu Gln Thr His Leu Lys Leu
         65                  70                  75

tac gag cag ggc cta cgg ggc agc ctc atc agc ctc aag gag cct ctg       291
Tyr Glu Gln Gly Leu Arg Gly Ser Leu Ile Ser Leu Lys Glu Pro Leu
     80                  85                  90

aga atg atg gcc aac cat tac aag cag cac tgc ccc ctt act ccg gaa       339
Arg Met Met Ala Asn His Tyr Lys Gln His Cys Pro Leu Thr Pro Glu
 95                 100                 105                 110

acg ccc tgt gaa acc cag act atc acc ttc aaa aat ttc aaa gag aat       387
Thr Pro Cys Glu Thr Gln Thr Ile Thr Phe Lys Asn Phe Lys Glu Asn
                115                 120                 125

ctg aag gat ttt ctg ttt aac aac ccc ttt gac tgc tgg gga cca gac       435
Leu Lys Asp Phe Leu Phe Asn Asn Pro Phe Asp Cys Trp Gly Pro Asp
            130                 135                 140

cag aag taa                                                           444
Gln Lys


<210> SEQ ID NO 120
<211> LENGTH: 144
<212> TYPE: PRT
<213> ORGANISM: Felis catus
```

-continued

<400> SEQUENCE: 120

```
Met Trp Leu Gln Asn Leu Leu Phe Leu Gly Thr Val Val Cys Ser Ile
  1               5                  10                  15

Ser Ala Pro Thr Ser Ser Pro Ser Ser Val Thr Arg Pro Trp Gln His
             20                  25                  30

Val Asp Ala Ile Lys Glu Ala Leu Ser Leu Leu Asn Asn Ser Ser Glu
         35                  40                  45

Ile Thr Ala Val Met Asn Glu Ala Val Glu Val Val Ser Glu Met Phe
     50                  55                  60

Asp Pro Glu Glu Pro Lys Cys Leu Gln Thr His Leu Lys Leu Tyr Glu
 65                  70                  75                  80

Gln Gly Leu Arg Gly Ser Leu Ile Ser Leu Lys Glu Pro Leu Arg Met
                 85                  90                  95

Met Ala Asn His Tyr Lys Gln His Cys Pro Leu Thr Pro Glu Thr Pro
            100                 105                 110

Cys Glu Thr Gln Thr Ile Thr Phe Lys Asn Phe Lys Glu Asn Leu Lys
        115                 120                 125

Asp Phe Leu Phe Asn Asn Pro Phe Asp Cys Trp Gly Pro Asp Gln Lys
    130                 135                 140
```

<210> SEQ ID NO 121
<211> LENGTH: 444
<212> TYPE: DNA
<213> ORGANISM: Felis catus

<400> SEQUENCE: 121

```
ttacttctgg tctggtcccc agcagtcaaa ggggttgtta aacagaaaat ccttcagatt     60

ctctttgaaa tttttgaagg tgatagtctg ggtttcacag ggcgtttccg gagtaagggg    120

gcagtgctgc ttgtaatggt tggccatcat tctcagaggc tccttgaggc tgatgaggct    180

gccccgtagg ccctgctcgt acagctttag gtgagtctgc aggcatttcg gctcctcagg    240

gtcaaacatt tcagagacga cttctactgc ttcattcatc acagcagtta tttcactact    300

gttgttcaga aggctcaggg cctccttgat ggcatccacg tgttgccagg gccgagtgac    360

agagctgggt gaactggtgg gtgcagagat gctgcagacc acagtgccca ggaaaagcag    420

gttctgcagc cacatggtgg atcc                                           444
```

<210> SEQ ID NO 122
<211> LENGTH: 432
<212> TYPE: DNA
<213> ORGANISM: Felis catus

<400> SEQUENCE: 122

```
atgtggctgc agaacctgct tttcctgggc actgtggtct gcagcatctc tgcacccacc     60

agttcaccca gctctgtcac tcggccctgg caacacgtgg atgccatcaa ggaggccctg    120

agccttctga acaacagtag tgaaataact gctgtgatga atgaagcagt agaagtcgtc    180

tctgaaatgt ttgaccctga ggagccgaaa tgcctgcaga ctcacctaaa gctgtacgag    240

cagggcctac ggggcagcct catcagcctc aaggagcctc tgagaatgat ggccaaccat    300

tacaagcagc actgcccccct tactccggaa acgccctgtg aaacccagac tatcaccttc    360

aaaaatttca aagagaatct gaaggatttt ctgtttaaca accccttga ctgctgggga    420

ccagaccaga ag                                                        432
```

<210> SEQ ID NO 123

-continued

<211> LENGTH: 432
<212> TYPE: DNA
<213> ORGANISM: Felis catus

<400> SEQUENCE: 123

```
cttctggtct ggtccccagc agtcaaaggg gttgttaaac agaaaatcct tcagattctc     60

tttgaaattt ttgaaggtga tagtctgggt ttcacagggc gtttccggag taagggggca    120

gtgctgcttg taatggttgg ccatcattct cagaggctcc ttgaggctga tgaggctgcc    180

ccgtaggccc tgctcgtaca gctttaggtg agtctgcagg catttcggct cctcagggtc    240

aaacatttca gagacgactt ctactgcttc attcatcaca gcagttattt cactactgtt    300

gttcagaagg ctcagggcct ccttgatggc atccacgtgt tgccagggcc gagtgacaga    360

gctgggtgaa ctggtgggtg cagagatgct gcagaccaca gtgcccagga aaagcaggtt    420

ctgcagccac at                                                        432
```

<210> SEQ ID NO 124
<211> LENGTH: 381
<212> TYPE: DNA
<213> ORGANISM: Felis catus
<220> FEATURE:
<221> NAME/KEY: CDS
<222> LOCATION: (1)..(381)

<400> SEQUENCE: 124

```
gca ccc acc agt tca ccc agc tct gtc act cgg ccc tgg caa cac gtg       48
Ala Pro Thr Ser Ser Pro Ser Ser Val Thr Arg Pro Trp Gln His Val
  1               5                  10                  15

gat gcc atc aag gag gcc ctg agc ctt ctg aac aac agt agt gaa ata       96
Asp Ala Ile Lys Glu Ala Leu Ser Leu Leu Asn Asn Ser Ser Glu Ile
             20                  25                  30

act gct gtg atg aat gaa gca gta gaa gtc gtc tct gaa atg ttt gac      144
Thr Ala Val Met Asn Glu Ala Val Glu Val Val Ser Glu Met Phe Asp
         35                  40                  45

cct gag gag ccg aaa tgc ctg cag act cac cta aag ctg tac gag cag      192
Pro Glu Glu Pro Lys Cys Leu Gln Thr His Leu Lys Leu Tyr Glu Gln
     50                  55                  60

ggc cta cgg ggc agc ctc atc agc ctc aag gag cct ctg aga atg atg      240
Gly Leu Arg Gly Ser Leu Ile Ser Leu Lys Glu Pro Leu Arg Met Met
 65                  70                  75                  80

gcc aac cat tac aag cag cac tgc ccc ctt act ccg gaa acg ccc tgt      288
Ala Asn His Tyr Lys Gln His Cys Pro Leu Thr Pro Glu Thr Pro Cys
                 85                  90                  95

gaa acc cag act atc acc ttc aaa aat ttc aaa gag aat ctg aag gat      336
Glu Thr Gln Thr Ile Thr Phe Lys Asn Phe Lys Glu Asn Leu Lys Asp
            100                 105                 110

ttt ctg ttt aac aac ccc ttt gac tgc tgg gga cca gac cag aag          381
Phe Leu Phe Asn Asn Pro Phe Asp Cys Trp Gly Pro Asp Gln Lys
        115                 120                 125
```

<210> SEQ ID NO 125
<211> LENGTH: 127
<212> TYPE: PRT
<213> ORGANISM: Felis catus

<400> SEQUENCE: 125

```
Ala Pro Thr Ser Ser Pro Ser Ser Val Thr Arg Pro Trp Gln His Val
  1               5                  10                  15

Asp Ala Ile Lys Glu Ala Leu Ser Leu Leu Asn Asn Ser Ser Glu Ile
             20                  25                  30
```

-continued

```
Thr Ala Val Met Asn Glu Ala Val Glu Val Val Ser Glu Met Phe Asp
        35                  40                  45

Pro Glu Glu Pro Lys Cys Leu Gln Thr His Leu Lys Leu Tyr Glu Gln
    50                  55                  60

Gly Leu Arg Gly Ser Leu Ile Ser Leu Lys Glu Pro Leu Arg Met Met
 65                  70                  75                  80

Ala Asn His Tyr Lys Gln His Cys Pro Leu Thr Pro Glu Thr Pro Cys
                 85                  90                  95

Glu Thr Gln Thr Ile Thr Phe Lys Asn Phe Lys Glu Asn Leu Lys Asp
            100                 105                 110

Phe Leu Phe Asn Asn Pro Phe Asp Cys Trp Gly Pro Asp Gln Lys
        115                 120                 125


<210> SEQ ID NO 126
<211> LENGTH: 381
<212> TYPE: DNA
<213> ORGANISM: Felis catus

<400> SEQUENCE: 126

cttctggtct ggtccccagc agtcaaaggg gttgttaaac agaaaatcct tcagattctc     60

tttgaaattt ttgaaggtga tagtctgggt ttcacagggc gtttccggag taagggggca    120

gtgctgcttg taatggttgg ccatcattct cagaggctcc ttgaggctga tgaggctgcc    180

ccgtaggccc tgctcgtaca gctttaggtg agtctgcagg catttcggct cctcagggtc    240

aaacatttca gagacgactt ctactgcttc attcatcaca gcagttattt cactactgtt    300

gttcagaagg ctcagggcct ccttgatggc atccacgtgt tgccagggcc gagtgacaga    360

gctgggtgaa ctggtgggtg c                                               381


<210> SEQ ID NO 127
<211> LENGTH: 28
<212> TYPE: DNA
<213> ORGANISM: Artificial Sequence

<400> SEQUENCE: 127

cctcgagatt cagctttcaa tgcctgta                                        28


<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 128

tgcccrstcg gcttcttctc c                                               21


<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 129

cgactctctt trccrtcctc ctg                                             23


<210> SEQ ID NO 130
<211> LENGTH: 21
```

-continued

<212> TYPE: DNA
<213> ORGANISM: Artificial Sequence
<220> FEATURE:
<223> OTHER INFORMATION: Description of Artificial Sequence: Synthetic Primer

<400> SEQUENCE: 130
cctcaaattg cggcacatgt c 21

<210> SEQ ID NO 131
<211> LENGTH: 22
<212> TYPE: DNA
<213> ORGANISM: Artificial Sequence
<220> FEATURE:
<223> OTHER INFORMATION: Description of Artificial Sequence: Synthetic Primer

<400> SEQUENCE: 131
ctgttcagag tttgagtaag cc 22

<210> SEQ ID NO 132
<211> LENGTH: 28
<212> TYPE: DNA
<213> ORGANISM: Artificial Sequence
<220> FEATURE:
<223> OTHER INFORMATION: Description of Artificial Sequence: Synthetic Primer

<400> SEQUENCE: 132
gaagatacca tttcaacttt aacacagc 28

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic Primer

<400> SEQUENCE: 133
tgctgtattg tgaagactcc cagc 24

<210> SEQ ID NO 134
<211> LENGTH: 16
<212> TYPE: DNA
<213> ORGANISM: Artificial Sequence
<220> FEATURE:
<223> OTHER INFORMATION: Description of Artificial Sequence: Synthetic Primer

<400> SEQUENCE: 134
atgcactttc tttgcc 16

<210> SEQ ID NO 135
<211> LENGTH: 42
<212> TYPE: DNA
<213> ORGANISM: Artificial Sequence
<220> FEATURE:
<223> OTHER INFORMATION: Description of Artificial Sequence: Synthetic Primer

<400> SEQUENCE: 135
ctggaggaaa akacttcrat gattctgata tctgaaatat at 42

<210> SEQ ID NO 136
<211> LENGTH: 27
<212> TYPE: DNA

```
<213> ORGANISM: Artificial Sequence
<220> FEATURE:
<223> OTHER INFORMATION: Description of Artificial Sequence:  Synthetic
      Primer

<400> SEQUENCE: 136

ctgacycttk sttggscctc attctca                                          27

<210> SEQ ID NO 137
<211> LENGTH: 36
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 137

gggctcgaga aaagatttgc tgtagaaaat cccatg                                36

<210> SEQ ID NO 138
<211> LENGTH: 32
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 138

cccgcggccg ctcaactttc cggtgtccac tc                                    32

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 139

gtcmtggctc tyrcttgcct tgg                                              23

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 140

aaastgggcy acytcgattt tgg                                              23

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 141

gtgatgttgm ycagctcctc                                                  20

<210> SEQ ID NO 142
<211> LENGTH: 20
<212> TYPE: DNA
<213> ORGANISM: Artificial Sequence
```

-continued

<220> FEATURE:
<223> OTHER INFORMATION: Description of Artificial Sequence: Synthetic
Primer

<400> SEQUENCE: 142
aattaaccct cactaaaggg 20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 143
atggcgctct ggttgactgt 20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 144
ggcttttgag agcacagtgc 20

<210> SEQ ID NO 145
<211> LENGTH: 29
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 145
ccccatatga gccctgtgac tccctcccc 29

<210> SEQ ID NO 146
<211> LENGTH: 30
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 146
ggggaattct catctgaaat ttccatggcg 30

<210> SEQ ID NO 147
<211> LENGTH: 24
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 147
atggcgctgc cctcttcctt cttg 24

<210> SEQ ID NO 148
<211> LENGTH: 28
<212> TYPE: DNA
<213> ORGANISM: Artificial Sequence
<220> FEATURE:

-continued

```
<223> OTHER INFORMATION: Description of Artificial Sequence:  Synthetic
      Primer

<400> SEQUENCE: 148

tcatttctcg ctccttaatc ttttctgc                                          28


<210> SEQ ID NO 149
<211> LENGTH: 37
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 149

cagggatcca ccatgtggct gcagaacctg cttttcc                               37


<210> SEQ ID NO 150
<211> LENGTH: 50
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 150

ttacttctgg tctggtcccc agcagtcaaa ggggttgtta aacagaaaat                 50


<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 151

cacagyccca tctcctcc                                                     18


<210> SEQ ID NO 152
<211> LENGTH: 22
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 152

gtaatacgac tcactatagg gc                                                22


<210> SEQ ID NO 153
<211> LENGTH: 26
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 153

acggaattcg agatgatagt gctggc                                            26


<210> SEQ ID NO 154
<211> LENGTH: 28
<212> TYPE: DNA
<213> ORGANISM: Artificial Sequence
<220> FEATURE:
<223> OTHER INFORMATION: Description of Artificial Sequence:  Synthetic
```

-continued

Primer

<400> SEQUENCE: 154

```
gtgtctagat ttggtagaaa aggatgat                                        28
```

```
<210> SEQ ID NO 155
<211> LENGTH: 567
<212> TYPE: DNA
<213> ORGANISM: Felis catus
<220> FEATURE:
<221> NAME/KEY: CDS
<222> LOCATION: (1)..(567)

<400> SEQUENCE: 155

atg gcg ctg ccc tct tcc ttc ttg gtg gcc ctg gtg gcg ctg ggc tgc       48
Met Ala Leu Pro Ser Ser Phe Leu Val Ala Leu Val Ala Leu Gly Cys
  1               5                  10                  15

aac tcc gtc tgc tct ctg ggc tgt gac ctg cct cag acc cac ggc ctg       96
Asn Ser Val Cys Ser Leu Gly Cys Asp Leu Pro Gln Thr His Gly Leu
             20                  25                  30

ctg aac agg agg gcc ttg acg ctc ctg gga caa atg agg aga ctc cct      144
Leu Asn Arg Arg Ala Leu Thr Leu Leu Gly Gln Met Arg Arg Leu Pro
         35                  40                  45

gcc agc tcc tgt cag aag gac aga agt gac ttc gcc ttc ccc cag gac      192
Ala Ser Ser Cys Gln Lys Asp Arg Ser Asp Phe Ala Phe Pro Gln Asp
     50                  55                  60

gtg ttt ggt gga gac cag tcc cac aag gcc caa gcc ctc tcg gtg gtg      240
Val Phe Gly Gly Asp Gln Ser His Lys Ala Gln Ala Leu Ser Val Val
 65                  70                  75                  80

cac gtg acg aac cag aag atc ttc cac ttc ttc tgc aca gag gcg tcc      288
His Val Thr Asn Gln Lys Ile Phe His Phe Phe Cys Thr Glu Ala Ser
                 85                  90                  95

tcg tct gct gct tgg aac acc acc ctc ctg gag gaa ttc tgc acg gga      336
Ser Ser Ala Ala Trp Asn Thr Thr Leu Leu Glu Glu Phe Cys Thr Gly
            100                 105                 110

ctt gat tgg cag ctg acc cgc ctg gaa gcc tgt gtc atg cag gag gtg      384
Leu Asp Trp Gln Leu Thr Arg Leu Glu Ala Cys Val Met Gln Glu Val
        115                 120                 125

ggg gag gga gag gct ccc ctc acg aac gag gac tcc atc ctg agg aac      432
Gly Glu Gly Glu Ala Pro Leu Thr Asn Glu Asp Ser Ile Leu Arg Asn
    130                 135                 140

tac ttc caa aga ctc tcc ctc tac ctg caa gag aag aaa tac agc cct      480
Tyr Phe Gln Arg Leu Ser Leu Tyr Leu Gln Glu Lys Lys Tyr Ser Pro
145                 150                 155                 160

tgt gcc tgg gag atc gtc aga gca gaa atc atg aga tcc ttg tat tat      528
Cys Ala Trp Glu Ile Val Arg Ala Glu Ile Met Arg Ser Leu Tyr Tyr
                165                 170                 175

tca tca aca gcc ttg cag aaa aga tta agg agc gag aaa                  567
Ser Ser Thr Ala Leu Gln Lys Arg Leu Arg Ser Glu Lys
            180                 185


<210> SEQ ID NO 156
<211> LENGTH: 189
<212> TYPE: PRT
<213> ORGANISM: Felis catus

<400> SEQUENCE: 156

Met Ala Leu Pro Ser Ser Phe Leu Val Ala Leu Val Ala Leu Gly Cys
  1               5                  10                  15

Asn Ser Val Cys Ser Leu Gly Cys Asp Leu Pro Gln Thr His Gly Leu
             20                  25                  30
```

-continued

```
Leu Asn Arg Arg Ala Leu Thr Leu Leu Gly Gln Met Arg Arg Leu Pro
        35                  40                  45

Ala Ser Ser Cys Gln Lys Asp Arg Ser Asp Phe Ala Phe Pro Gln Asp
    50                  55                  60

Val Phe Gly Gly Asp Gln Ser His Lys Ala Gln Ala Leu Ser Val Val
65                  70                  75                  80

His Val Thr Asn Gln Lys Ile Phe His Phe Phe Cys Thr Glu Ala Ser
                85                  90                  95

Ser Ser Ala Ala Trp Asn Thr Thr Leu Leu Glu Glu Phe Cys Thr Gly
            100                 105                 110

Leu Asp Trp Gln Leu Thr Arg Leu Glu Ala Cys Val Met Gln Glu Val
        115                 120                 125

Gly Glu Gly Glu Ala Pro Leu Thr Asn Glu Asp Ser Ile Leu Arg Asn
    130                 135                 140

Tyr Phe Gln Arg Leu Ser Leu Tyr Leu Gln Glu Lys Lys Tyr Ser Pro
145                 150                 155                 160

Cys Ala Trp Glu Ile Val Arg Ala Glu Ile Met Arg Ser Leu Tyr Tyr
                165                 170                 175

Ser Ser Thr Ala Leu Gln Lys Arg Leu Arg Ser Glu Lys
            180                 185


<210> SEQ ID NO 157
<211> LENGTH: 567
<212> TYPE: DNA
<213> ORGANISM: Felis catus

<400> SEQUENCE: 157

tttctcgctc cttaatcttt tctgcaaggc tgttgatgaa taatacaagg atctcatgat     60

ttctgctctg acgatctccc aggcacaagg gctgtatttc ttctcttgca ggtagaggga    120

gagtctttgg aagtagttcc tcaggatgga gtcctcgttc gtgaggggag cctctccctc    180

ccccacctcc tgcatgacac aggcttccag gcgggtcagc tgccaatcaa gtcccgtgca    240

gaattcctcc aggagggtgg tgttccaagc agcagacgag gacgcctctg tgcagaagaa    300

gtggaagatc ttctggttcg tcacgtgcac caccgagagg gcttgggcct tgtgggactg    360

gtctccacca aacacgtcct gggggaaggc gaagtcactt ctgtccttct gacaggagct    420

ggcagggagt ctcctcattt gtcccaggag cgtcaaggcc ctcctgttca gcaggccgtg    480

ggtctgaggc aggtcacagc ccagagagca gacggagttg cagcccagcg ccaccagggc    540

caccaagaag gaagagggca gcgccat                                        567


<210> SEQ ID NO 158
<211> LENGTH: 498
<212> TYPE: DNA
<213> ORGANISM: Felis catus
<220> FEATURE:
<221> NAME/KEY: CDS
<222> LOCATION: (1)..(498)

<400> SEQUENCE: 158

tgt gac ctg cct cag acc cac ggc ctg ctg aac agg agg gcc ttg acg       48
Cys Asp Leu Pro Gln Thr His Gly Leu Leu Asn Arg Arg Ala Leu Thr
  1               5                  10                  15

ctc ctg gga caa atg agg aga ctc cct gcc agc tcc tgt cag aag gac       96
Leu Leu Gly Gln Met Arg Arg Leu Pro Ala Ser Ser Cys Gln Lys Asp
            20                  25                  30

aga agt gac ttc gcc ttc ccc cag gac gtg ttt ggt gga gac cag tcc      144
Arg Ser Asp Phe Ala Phe Pro Gln Asp Val Phe Gly Gly Asp Gln Ser
```

-continued

```
        35                  40                  45

cac aag gcc caa gcc ctc tcg gtg gtg cac gtg acg aac cag aag atc      192
His Lys Ala Gln Ala Leu Ser Val Val His Val Thr Asn Gln Lys Ile
     50                  55                  60

ttc cac ttc ttc tgc aca gag gcg tcc tcg tct gct gct tgg aac acc      240
Phe His Phe Phe Cys Thr Glu Ala Ser Ser Ser Ala Ala Trp Asn Thr
 65                  70                  75                  80

acc ctc ctg gag gaa ttc tgc acg gga ctt gat tgg cag ctg acc cgc      288
Thr Leu Leu Glu Glu Phe Cys Thr Gly Leu Asp Trp Gln Leu Thr Arg
                 85                  90                  95

ctg gaa gcc tgt gtc atg cag gag gtg ggg gag gga gag gct ccc ctc      336
Leu Glu Ala Cys Val Met Gln Glu Val Gly Glu Gly Glu Ala Pro Leu
            100                 105                 110

acg aac gag gac tcc atc ctg agg aac tac ttc caa aga ctc tcc ctc      384
Thr Asn Glu Asp Ser Ile Leu Arg Asn Tyr Phe Gln Arg Leu Ser Leu
        115                 120                 125

tac ctg caa gag aag aaa tac agc cct tgt gcc tgg gag atc gtc aga      432
Tyr Leu Gln Glu Lys Lys Tyr Ser Pro Cys Ala Trp Glu Ile Val Arg
    130                 135                 140

gca gaa atc atg aga tcc ttg tat tat tca tca aca gcc ttg cag aaa      480
Ala Glu Ile Met Arg Ser Leu Tyr Tyr Ser Ser Thr Ala Leu Gln Lys
145                 150                 155                 160

aga tta agg agc gag aaa                                              498
Arg Leu Arg Ser Glu Lys
                165


<210> SEQ ID NO 159
<211> LENGTH: 166
<212> TYPE: PRT
<213> ORGANISM: Felis catus

<400> SEQUENCE: 159

Cys Asp Leu Pro Gln Thr His Gly Leu Leu Asn Arg Arg Ala Leu Thr
  1               5                  10                  15

Leu Leu Gly Gln Met Arg Arg Leu Pro Ala Ser Ser Cys Gln Lys Asp
             20                  25                  30

Arg Ser Asp Phe Ala Phe Pro Gln Asp Val Phe Gly Gly Asp Gln Ser
         35                  40                  45

His Lys Ala Gln Ala Leu Ser Val Val His Val Thr Asn Gln Lys Ile
     50                  55                  60

Phe His Phe Phe Cys Thr Glu Ala Ser Ser Ser Ala Ala Trp Asn Thr
 65                  70                  75                  80

Thr Leu Leu Glu Glu Phe Cys Thr Gly Leu Asp Trp Gln Leu Thr Arg
                 85                  90                  95

Leu Glu Ala Cys Val Met Gln Glu Val Gly Glu Gly Glu Ala Pro Leu
            100                 105                 110

Thr Asn Glu Asp Ser Ile Leu Arg Asn Tyr Phe Gln Arg Leu Ser Leu
        115                 120                 125

Tyr Leu Gln Glu Lys Lys Tyr Ser Pro Cys Ala Trp Glu Ile Val Arg
    130                 135                 140

Ala Glu Ile Met Arg Ser Leu Tyr Tyr Ser Ser Thr Ala Leu Gln Lys
145                 150                 155                 160

Arg Leu Arg Ser Glu Lys
                165


<210> SEQ ID NO 160
<211> LENGTH: 498
<212> TYPE: DNA
```

-continued

<213> ORGANISM: Felis catus

<400> SEQUENCE: 160

```
tttctcgctc cttaatcttt tctgcaaggc tgttgatgaa taatacaagg atctcatgat      60

ttctgctctg acgatctccc aggcacaagg gctgtatttc ttctcttgca ggtagaggga     120

gagtctttgg aagtagttcc tcaggatgga gtcctcgttc gtgaggggag cctctccctc     180

ccccacctcc tgcatgacac aggcttccag gcgggtcagc tgccaatcaa gtcccgtgca     240

gaattcctcc aggagggtgg tgttccaagc agcagacgag gacgcctctg tgcagaagaa     300

gtggaagatc ttctggttcg tcacgtgcac caccgagagg gcttgggcct tgtgggactg     360

gtctccacca aacacgtcct gggggaaggc gaagtcactt ctgtccttct gacaggagct     420

ggcagggagt ctcctcattt gtcccaggag cgtcaaggcc ctcctgttca gcaggccgtg     480

ggtctgaggc aggtcaca                                                   498
```

<210> SEQ ID NO 161
<211> LENGTH: 582
<212> TYPE: DNA
<213> ORGANISM: Felis catus
<220> FEATURE:
<221> NAME/KEY: CDS
<222> LOCATION: (1)..(582)

<400> SEQUENCE: 161

```
atg gcg ctg ccc tct tcc ttc ttg gtg gcc ctg gtg gcg ctg ggc tgc       48
Met Ala Leu Pro Ser Ser Phe Leu Val Ala Leu Val Ala Leu Gly Cys
  1               5                  10                  15

aac tcc gtc tgc tct ctg ggc tgt gat ctg cct cag acc cac ggc ctg       96
Asn Ser Val Cys Ser Leu Gly Cys Asp Leu Pro Gln Thr His Gly Leu
             20                  25                  30

ctg aac agg agg gcc ttg acg ctc ctg gga caa atg agg aga ctc cct      144
Leu Asn Arg Arg Ala Leu Thr Leu Leu Gly Gln Met Arg Arg Leu Pro
         35                  40                  45

gcc agc tcc tgt cag aag gac aga agt gac ttc gcc ttc ccc cag gac      192
Ala Ser Ser Cys Gln Lys Asp Arg Ser Asp Phe Ala Phe Pro Gln Asp
     50                  55                  60

gtg ttc ggt gga gac cag tcc cac aag gcc caa gcc ctc tcg gtg gtg      240
Val Phe Gly Gly Asp Gln Ser His Lys Ala Gln Ala Leu Ser Val Val
 65                  70                  75                  80

cac gtg acg aac cag aag atc ttc cac ttc ttc tgc aca gag gcg tcc      288
His Val Thr Asn Gln Lys Ile Phe His Phe Phe Cys Thr Glu Ala Ser
                 85                  90                  95

tcg tct gct gct tgg aac acc acc ctc ctg gag gaa ttc tgc acg gga      336
Ser Ser Ala Ala Trp Asn Thr Thr Leu Leu Glu Glu Phe Cys Thr Gly
            100                 105                 110

ctt gat cgg cag ctg acc cgc ctg gaa gcc tgt gtc gtg cag gag gtg      384
Leu Asp Arg Gln Leu Thr Arg Leu Glu Ala Cys Val Val Gln Glu Val
        115                 120                 125

ggg gag gga gag gct ccc ctg acg aac gag gac att cat ccc gag gac      432
Gly Glu Gly Glu Ala Pro Leu Thr Asn Glu Asp Ile His Pro Glu Asp
    130                 135                 140

tcc atc ctg agg aac tac ttc caa aga ctc tcc ctc tac ctg caa gag      480
Ser Ile Leu Arg Asn Tyr Phe Gln Arg Leu Ser Leu Tyr Leu Gln Glu
145                 150                 155                 160

aag aaa tac agc cct tgt gcc tgg gag atc gtc aga gca gaa atc atg      528
Lys Lys Tyr Ser Pro Cys Ala Trp Glu Ile Val Arg Ala Glu Ile Met
                165                 170                 175

aga tcc ttg tat tat tca tca aca gcc ttg cag aaa aga tta agg agc      576
Arg Ser Leu Tyr Tyr Ser Ser Thr Ala Leu Gln Lys Arg Leu Arg Ser
```

-continued

```
            180                 185                 190

gag aaa                                                              582
Glu Lys


<210> SEQ ID NO 162
<211> LENGTH: 194
<212> TYPE: PRT
<213> ORGANISM: Felis catus

<400> SEQUENCE: 162

Met Ala Leu Pro Ser Ser Phe Leu Val Ala Leu Val Ala Leu Gly Cys
  1               5                  10                  15

Asn Ser Val Cys Ser Leu Gly Cys Asp Leu Pro Gln Thr His Gly Leu
            20                  25                  30

Leu Asn Arg Arg Ala Leu Thr Leu Leu Gly Gln Met Arg Arg Leu Pro
        35                  40                  45

Ala Ser Ser Cys Gln Lys Asp Arg Ser Asp Phe Ala Phe Pro Gln Asp
     50                  55                  60

Val Phe Gly Gly Asp Gln Ser His Lys Ala Gln Ala Leu Ser Val Val
 65                  70                  75                  80

His Val Thr Asn Gln Lys Ile Phe His Phe Phe Cys Thr Glu Ala Ser
                 85                  90                  95

Ser Ser Ala Ala Trp Asn Thr Thr Leu Leu Glu Glu Phe Cys Thr Gly
            100                 105                 110

Leu Asp Arg Gln Leu Thr Arg Leu Glu Ala Cys Val Val Gln Glu Val
        115                 120                 125

Gly Glu Gly Glu Ala Pro Leu Thr Asn Glu Asp Ile His Pro Glu Asp
    130                 135                 140

Ser Ile Leu Arg Asn Tyr Phe Gln Arg Leu Ser Leu Tyr Leu Gln Glu
145                 150                 155                 160

Lys Lys Tyr Ser Pro Cys Ala Trp Glu Ile Val Arg Ala Glu Ile Met
                165                 170                 175

Arg Ser Leu Tyr Tyr Ser Ser Thr Ala Leu Gln Lys Arg Leu Arg Ser
            180                 185                 190

Glu Lys


<210> SEQ ID NO 163
<211> LENGTH: 582
<212> TYPE: DNA
<213> ORGANISM: Felis catus

<400> SEQUENCE: 163

tttctcgctc cttaatcttt tctgcaaggc tgttgatgaa taatacaagg atctcatgat      60

ttctgctctg acgatctccc aggcacaagg gctgtatttc ttctcttgca ggtagaggga     120

gagtctttgg aagtagttcc tcaggatgga gtcctcggga tgaatgtcct cgttcgtcag     180

gggagcctct ccctccccca cctcctgcac gacacaggct tccaggcggg tcagctgccg     240

atcaagtccc gtgcagaatt cctccaggag ggtggtgttc caagcagcag acgaggacgc     300

ctctgtgcag aagaagtgga agatcttctg gttcgtcacg tgcaccaccg agagggcttg     360

ggccttgtgg gactggtctc caccgaacac gtcctggggg aaggcgaagt cacttctgtc     420

cttctgacag gagctggcag ggagtctcct catttgtccc aggagcgtca aggccctcct     480

gttcagcagg ccgtgggtct gaggcagatc acagcccaga gagcagacgg agttgcagcc     540

cagcgccacc agggccacca agaaggaaga gggcagcgcc at                        582
```

-continued

<210> SEQ ID NO 164
<211> LENGTH: 513
<212> TYPE: DNA
<213> ORGANISM: Felis catus
<220> FEATURE:
<221> NAME/KEY: CDS
<222> LOCATION: (1)..(513)

<400> SEQUENCE: 164 tgt gat ctg cct cag acc cac ggc ctg ctg aac agg agg gcc ttg acg 48
Cys Asp Leu Pro Gln Thr His Gly Leu Leu Asn Arg Arg Ala Leu Thr
1 5 10 15 ctc ctg gga caa atg agg aga ctc cct gcc agc tcc tgt cag aag gac 96
Leu Leu Gly Gln Met Arg Arg Leu Pro Ala Ser Ser Cys Gln Lys Asp
20 25 30 aga agt gac ttc gcc ttc ccc cag gac gtg ttc ggt gga gac cag tcc 144
Arg Ser Asp Phe Ala Phe Pro Gln Asp Val Phe Gly Gly Asp Gln Ser
35 40 45 cac aag gcc caa gcc ctc tcg gtg gtg cac gtg acg aac cag aag atc 192
His Lys Ala Gln Ala Leu Ser Val Val His Val Thr Asn Gln Lys Ile
50 55 60 ttc cac ttc ttc tgc aca gag gcg tcc tcg tct gct gct tgg aac acc 240
Phe His Phe Phe Cys Thr Glu Ala Ser Ser Ser Ala Ala Trp Asn Thr
65 70 75 80 acc ctc ctg gag gaa ttc tgc acg gga ctt gat cgg cag ctg acc cgc 288
Thr Leu Leu Glu Glu Phe Cys Thr Gly Leu Asp Arg Gln Leu Thr Arg
85 90 95 ctg gaa gcc tgt gtc gtg cag gag gtg ggg gag gga gag gct ccc ctg 336
Leu Glu Ala Cys Val Val Gln Glu Val Gly Glu Gly Glu Ala Pro Leu
100 105 110 acg aac gag gac att cat ccc gag gac tcc atc ctg agg aac tac ttc 384
Thr Asn Glu Asp Ile His Pro Glu Asp Ser Ile Leu Arg Asn Tyr Phe
115 120 125 caa aga ctc tcc ctc tac ctg caa gag aag aaa tac agc cct tgt gcc 432
Gln Arg Leu Ser Leu Tyr Leu Gln Glu Lys Lys Tyr Ser Pro Cys Ala
130 135 140 tgg gag atc gtc aga gca gaa atc atg aga tcc ttg tat tat tca tca 480
Trp Glu Ile Val Arg Ala Glu Ile Met Arg Ser Leu Tyr Tyr Ser Ser
145 150 155 160 aca gcc ttg cag aaa aga tta agg agc gag aaa 513
Thr Ala Leu Gln Lys Arg Leu Arg Ser Glu Lys
165 170

<210> SEQ ID NO 165
<211> LENGTH: 171
<212> TYPE: PRT
<213> ORGANISM: Felis catus

<400> SEQUENCE: 165

Cys Asp Leu Pro Gln Thr His Gly Leu Leu Asn Arg Arg Ala Leu Thr
1 5 10 15

Leu Leu Gly Gln Met Arg Arg Leu Pro Ala Ser Ser Cys Gln Lys Asp
20 25 30

Arg Ser Asp Phe Ala Phe Pro Gln Asp Val Phe Gly Gly Asp Gln Ser
35 40 45

His Lys Ala Gln Ala Leu Ser Val Val His Val Thr Asn Gln Lys Ile
50 55 60

Phe His Phe Phe Cys Thr Glu Ala Ser Ser Ser Ala Ala Trp Asn Thr
65 70 75 80

Thr Leu Leu Glu Glu Phe Cys Thr Gly Leu Asp Arg Gln Leu Thr Arg

-continued

```
                 85                  90                  95

Leu Glu Ala Cys Val Val Gln Glu Val Gly Glu Gly Glu Ala Pro Leu
            100                 105                 110

Thr Asn Glu Asp Ile His Pro Glu Asp Ser Ile Leu Arg Asn Tyr Phe
        115                 120                 125

Gln Arg Leu Ser Leu Tyr Leu Gln Glu Lys Lys Tyr Ser Pro Cys Ala
    130                 135                 140

Trp Glu Ile Val Arg Ala Glu Ile Met Arg Ser Leu Tyr Tyr Ser Ser
145                 150                 155                 160

Thr Ala Leu Gln Lys Arg Leu Arg Ser Glu Lys
                165                 170


<210> SEQ ID NO 166
<211> LENGTH: 513
<212> TYPE: DNA
<213> ORGANISM: Felis catus

<400> SEQUENCE: 166

tttctcgctc cttaatcttt tctgcaaggc tgttgatgaa taatacaagg atctcatgat      60

ttctgctctg acgatctccc aggcacaagg gctgtatttc ttctcttgca ggtagaggga     120

gagtctttgg aagtagttcc tcaggatgga gtcctcggga tgaatgtcct cgttcgtcag     180

gggagcctct ccctccccca cctcctgcac gacacaggct tccaggcggg tcagctgccg     240

atcaagtccc gtgcagaatt cctccaggag ggtggtgttc caagcagcag acgaggacgc     300

ctctgtgcag aagaagtgga agatcttctg gttcgtcacg tgcaccaccg agagggcttg     360

ggccttgtgg gactggtctc caccgaacac gtcctggggg aaggcgaagt cacttctgtc     420

cttctgacag gagctggcag ggagtctcct catttgtccc aggagcgtca aggccctcct     480

gttcagcagg ccgtgggtct gaggcagatc aca                                   513


<210> SEQ ID NO 167
<211> LENGTH: 567
<212> TYPE: DNA
<213> ORGANISM: Felis catus
<220> FEATURE:
<221> NAME/KEY: CDS
<222> LOCATION: (1)..(567)

<400> SEQUENCE: 167

atg gcg ctg ccc tct tcc ttc ttg gtg gcc ctg gtg gcg ctg ggc tgc        48
Met Ala Leu Pro Ser Ser Phe Leu Val Ala Leu Val Ala Leu Gly Cys
  1               5                  10                  15

aac tct gtc tgc tct ctg ggc tgt gac ctg cct cag acc cac ggc ctg        96
Asn Ser Val Cys Ser Leu Gly Cys Asp Leu Pro Gln Thr His Gly Leu
            20                  25                  30

ctg aac agg agg gcc ttg acg ctc ctg gga caa atg agg aga ctc cct       144
Leu Asn Arg Arg Ala Leu Thr Leu Leu Gly Gln Met Arg Arg Leu Pro
        35                  40                  45

gcc agc tcc tgc cag aag gac aga aat gac ttc gcc ttc ccc cag gac       192
Ala Ser Ser Cys Gln Lys Asp Arg Asn Asp Phe Ala Phe Pro Gln Asp
     50                  55                  60

gtg ttc ggt gga gac cag tcc cac aag gcc caa gcc ctc tcg gtg gtg       240
Val Phe Gly Gly Asp Gln Ser His Lys Ala Gln Ala Leu Ser Val Val
 65                  70                  75                  80

cac gtg acg aac cag aag atc ttc cac ttc ttc tgc aca gag gcg tcc       288
His Val Thr Asn Gln Lys Ile Phe His Phe Phe Cys Thr Glu Ala Ser
                 85                  90                  95

tcg tct gct gct tgg aac acc acc ctc ctg gag gaa ttc tgc acg gga       336
```

-continued

```
Ser Ser Ala Ala Trp Asn Thr Thr Leu Leu Glu Glu Phe Cys Thr Gly
            100                 105                 110

ctt gat cgg cag ctg acc cgc ctg gaa gcc tgt gtc gtg cag gag gtg      384
Leu Asp Arg Gln Leu Thr Arg Leu Glu Ala Cys Val Val Gln Glu Val
        115                 120                 125

ggg gag gga gag gct ccc ctc acg aac gag gac tcc atc ctg agg aac      432
Gly Glu Gly Glu Ala Pro Leu Thr Asn Glu Asp Ser Ile Leu Arg Asn
    130                 135                 140

tac ttc caa aga ctc tcc ctc tac ctg caa gag aag aaa tac agc cct      480
Tyr Phe Gln Arg Leu Ser Leu Tyr Leu Gln Glu Lys Lys Tyr Ser Pro
145                 150                 155                 160

tgt gcc tgg gag atc gtc aga gca gaa atc atg aga tcc ttg tat tat      528
Cys Ala Trp Glu Ile Val Arg Ala Glu Ile Met Arg Ser Leu Tyr Tyr
                165                 170                 175

tca tca aca gcc ttg cag aaa aga tta agg agc gag aaa                  567
Ser Ser Thr Ala Leu Gln Lys Arg Leu Arg Ser Glu Lys
            180                 185


<210> SEQ ID NO 168
<211> LENGTH: 189
<212> TYPE: PRT
<213> ORGANISM: Felis catus

<400> SEQUENCE: 168

Met Ala Leu Pro Ser Ser Phe Leu Val Ala Leu Val Ala Leu Gly Cys
  1               5                  10                  15

Asn Ser Val Cys Ser Leu Gly Cys Asp Leu Pro Gln Thr His Gly Leu
            20                  25                  30

Leu Asn Arg Arg Ala Leu Thr Leu Leu Gly Gln Met Arg Arg Leu Pro
        35                  40                  45

Ala Ser Ser Cys Gln Lys Asp Arg Asn Asp Phe Ala Phe Pro Gln Asp
    50                  55                  60

Val Phe Gly Gly Asp Gln Ser His Lys Ala Gln Ala Leu Ser Val Val
 65                  70                  75                  80

His Val Thr Asn Gln Lys Ile Phe His Phe Phe Cys Thr Glu Ala Ser
                 85                  90                  95

Ser Ser Ala Ala Trp Asn Thr Thr Leu Leu Glu Glu Phe Cys Thr Gly
            100                 105                 110

Leu Asp Arg Gln Leu Thr Arg Leu Glu Ala Cys Val Val Gln Glu Val
        115                 120                 125

Gly Glu Gly Glu Ala Pro Leu Thr Asn Glu Asp Ser Ile Leu Arg Asn
    130                 135                 140

Tyr Phe Gln Arg Leu Ser Leu Tyr Leu Gln Glu Lys Lys Tyr Ser Pro
145                 150                 155                 160

Cys Ala Trp Glu Ile Val Arg Ala Glu Ile Met Arg Ser Leu Tyr Tyr
                165                 170                 175

Ser Ser Thr Ala Leu Gln Lys Arg Leu Arg Ser Glu Lys
            180                 185


<210> SEQ ID NO 169
<211> LENGTH: 567
<212> TYPE: DNA
<213> ORGANISM: Felis catus

<400> SEQUENCE: 169

tttctcgctc cttaatcttt tctgcaaggc tgttgatgaa taatacaagg atctcatgat     60

ttctgctctg acgatctccc aggcacaagg gctgtatttc ttctcttgca ggtagaggga    120
```

-continued

```
gagtctttgg aagtagttcc tcaggatgga gtcctcgttc gtgaggggag cctctccctc    180

ccccacctcc tgcacgacac aggcttccag gcgggtcagc tgccgatcaa gtcccgtgca    240

gaattcctcc aggagggtgg tgttccaagc agcagacgag gacgcctctg tgcagaagaa    300

gtggaagatc ttctggttcg tcacgtgcac caccgagagg gcttgggcct tgtgggactg    360

gtctccaccg aacacgtcct gggggaaggc gaagtcattt ctgtccttct ggcaggagct    420

ggcagggagt ctcctcattt gtcccaggag cgtcaaggcc ctcctgttca gcaggccgtg    480

ggtctgaggc aggtcacagc ccagagagca gacagagttg cagcccagcg ccaccagggc    540

caccaagaag gaagagggca gcgccat                                        567


<210> SEQ ID NO 170
<211> LENGTH: 498
<212> TYPE: DNA
<213> ORGANISM: Felis catus
<220> FEATURE:
<221> NAME/KEY: CDS
<222> LOCATION: (1)..(498)

<400> SEQUENCE: 170

tgt gac ctg cct cag acc cac ggc ctg ctg aac agg agg gcc ttg acg       48
Cys Asp Leu Pro Gln Thr His Gly Leu Leu Asn Arg Arg Ala Leu Thr
  1               5                  10                  15

ctc ctg gga caa atg agg aga ctc cct gcc agc tcc tgc cag aag gac       96
Leu Leu Gly Gln Met Arg Arg Leu Pro Ala Ser Ser Cys Gln Lys Asp
             20                  25                  30

aga aat gac ttc gcc ttc ccc cag gac gtg ttc ggt gga gac cag tcc      144
Arg Asn Asp Phe Ala Phe Pro Gln Asp Val Phe Gly Gly Asp Gln Ser
         35                  40                  45

cac aag gcc caa gcc ctc tcg gtg gtg cac gtg acg aac cag aag atc      192
His Lys Ala Gln Ala Leu Ser Val Val His Val Thr Asn Gln Lys Ile
     50                  55                  60

ttc cac ttc ttc tgc aca gag gcg tcc tcg tct gct gct tgg aac acc      240
Phe His Phe Phe Cys Thr Glu Ala Ser Ser Ser Ala Ala Trp Asn Thr
 65                  70                  75                  80

acc ctc ctg gag gaa ttc tgc acg gga ctt gat cgg cag ctg acc cgc      288
Thr Leu Leu Glu Glu Phe Cys Thr Gly Leu Asp Arg Gln Leu Thr Arg
                 85                  90                  95

ctg gaa gcc tgt gtc gtg cag gag gtg ggg gag gga gag gct ccc ctc      336
Leu Glu Ala Cys Val Val Gln Glu Val Gly Glu Gly Glu Ala Pro Leu
            100                 105                 110

acg aac gag gac tcc atc ctg agg aac tac ttc caa aga ctc tcc ctc      384
Thr Asn Glu Asp Ser Ile Leu Arg Asn Tyr Phe Gln Arg Leu Ser Leu
        115                 120                 125

tac ctg caa gag aag aaa tac agc cct tgt gcc tgg gag atc gtc aga      432
Tyr Leu Gln Glu Lys Lys Tyr Ser Pro Cys Ala Trp Glu Ile Val Arg
    130                 135                 140

gca gaa atc atg aga tcc ttg tat tat tca tca aca gcc ttg cag aaa      480
Ala Glu Ile Met Arg Ser Leu Tyr Tyr Ser Ser Thr Ala Leu Gln Lys
145                 150                 155                 160

aga tta agg agc gag aaa                                              498
Arg Leu Arg Ser Glu Lys
                165


<210> SEQ ID NO 171
<211> LENGTH: 166
<212> TYPE: PRT
<213> ORGANISM: Felis catus

<400> SEQUENCE: 171
```

-continued

```
Cys Asp Leu Pro Gln Thr His Gly Leu Leu Asn Arg Arg Ala Leu Thr
  1               5                  10                  15

Leu Leu Gly Gln Met Arg Arg Leu Pro Ala Ser Ser Cys Gln Lys Asp
            20                  25                  30

Arg Asn Asp Phe Ala Phe Pro Gln Asp Val Phe Gly Gly Asp Gln Ser
        35                  40                  45

His Lys Ala Gln Ala Leu Ser Val Val His Val Thr Asn Gln Lys Ile
     50                  55                  60

Phe His Phe Phe Cys Thr Glu Ala Ser Ser Ser Ala Ala Trp Asn Thr
 65                  70                  75                  80

Thr Leu Leu Glu Glu Phe Cys Thr Gly Leu Asp Arg Gln Leu Thr Arg
                85                  90                  95

Leu Glu Ala Cys Val Val Gln Glu Val Gly Glu Gly Glu Ala Pro Leu
            100                 105                 110

Thr Asn Glu Asp Ser Ile Leu Arg Asn Tyr Phe Gln Arg Leu Ser Leu
        115                 120                 125

Tyr Leu Gln Glu Lys Lys Tyr Ser Pro Cys Ala Trp Glu Ile Val Arg
    130                 135                 140

Ala Glu Ile Met Arg Ser Leu Tyr Tyr Ser Ser Thr Ala Leu Gln Lys
145                 150                 155                 160

Arg Leu Arg Ser Glu Lys
                165
```

<210> SEQ ID NO 172
<211> LENGTH: 498
<212> TYPE: DNA
<213> ORGANISM: Felis catus

<400> SEQUENCE: 172

```
tttctcgctc cttaatcttt tctgcaaggc tgttgatgaa taatacaagg atctcatgat     60

ttctgctctg acgatctccc aggcacaagg gctgtatttc ttctcttgca ggtagaggga    120

gagtctttgg aagtagttcc tcaggatgga gtcctcgttc gtgaggggag cctctccctc    180

ccccacctcc tgcacgacac aggcttccag gcgggtcagc tgccgatcaa gtcccgtgca    240

gaattcctcc aggagggtgg tgttccaagc agcagacgag gacgcctctg tgcagaagaa    300

gtggaagatc ttctggttcg tcacgtgcac caccgagagg gcttgggcct tgtgggactg    360

gtctccaccg aacacgtcct gggggaaggc gaagtcattt ctgtccttct ggcaggagct    420

ggcagggagt ctcctcattt gtcccaggag cgtcaaggcc ctcctgttca gcaggccgtg    480

ggtctgaggc aggtcaca                                                  498
```

<210> SEQ ID NO 173
<211> LENGTH: 29
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 173

```
attaggatcc atggcgctgc cctcttcct                                       29
```

<210> SEQ ID NO 174
<211> LENGTH: 40
<212> TYPE: DNA
<213> ORGANISM: Artificial Sequence
<220> FEATURE:
<223> OTHER INFORMATION: Description of Artificial Sequence: Synthetic -continued

```
      Primer

<400> SEQUENCE: 174

gcctctagac tgtcatttct cgctccttaa tcttttctgc                          40
```

CANINEY IL-13 IMMUNOREGULATORY PROTEINS AND USES THEREOF

CROSS-REFERENCE TO RELATED APPLICATIONS

This application is a continuation-in-part of U.S. patent application Ser. No. 09/322,409, filed May 28, 1999, entitled "CANINE AND FELINE IMMUNOREGULATORY PROTEINS, NUCLEIC ACID MOLECULES, AND USES THEREOF"; which claims priority to U.S. Provisional Patent Application Serial No. 60/087,306, filed May 29, 1998, entitled "CANINE INTERLEUKIN-4 AND FLT-3 LIGAND PROTEINS, NUCLEIC ACID MOLECULES, AND USES THEREOF"; each of which is incorporated herein by reference in its entirety.

FIELD OF THE INVENTION

The present invention relates to canine interleukin-4, canine or feline Flt-3 ligand, canine or feline CD40, canine or feline CD154, canine interleukin-5, canine interleukin-13, feline interferon alpha, or feline GM-CSF nucleic acid molecules, proteins encoded by such nucleic acid molecules, antibodies raised against such proteins and/or inhibitors of such proteins or nucleic acid molecules. The present invention also includes therapeutic compositions comprising such nucleic acid molecules, proteins, antibodies and/or inhibitors, as well as their use to regulate an immune response in an animal.

BACKGROUND OF THE INVENTION

Regulating immune responses in animals is important in disease management. Immune responses can be regulated by modifying the activity of immunoregulatory molecules and immune cells.

Several immunoregulatory molecules have been found in humans and other mammal species. Interleukin-4, produced by activated type 2 helper cells ($T_H2$ cells), has a number of functions. These functions include promotion of naive T cells and B cells to differentiate and proliferate. IL-4 promotes $T_H2$ differentiation and inhibits $T_H1$ development. FMS-like tyrosine kinase 3, (Flt-3 ligand) stimulates the expansion and mobilization of hematopoetic precursor cell stimulating activity. CD40 is a type I transmembrane protein expressed on antigen presenting cells, such as B lymphocytes, and other types of cells such as endothelial cells, epithelial cells, and fibroblasts. CD40 ligand (also known as CD154) is a type II transmembrane protein that is preferentially expressed on activated T lymphocytes. The CD40-CD154 interaction regulates diverse pathways of the immune system, including B cell proliferation, immunoglobulin production and class switching by B cells, activation and clonal expansion of T cells, activity of antigen presenting cells, growth and differentiation of epithelial cells, and regulation of inflammatory responses at mucosal and cutaneous sites. Interleukin-5 is produced by activated type 2 helper cells ($T_H2$), mast cells, and eosinophils. Its main functions include promotion of growth and differentiation of eosinophils and generation of cytotoxic T cells from thymocytes. Interleukin-13 is produced by $T_H1$ and $T_H2$ cells, and promotes growth and differentiation of B cells, up-regulation of MHC class II and CD23 expression on monocytes/macrophages and B cells; and inhibition of production of inflammatory cytokines such as IL-1$\alpha$, IL-1$\beta$, IL-6, IL-8, IL-10, IL-12, among others. Interferon alpha is an antiviral protein that has three major functions: it inhibits viral replication by activating cellular genes that destroy mRNA and inhibit protein translation, it induces MHC class I expression in non virally-infected cells, increasing resistance to NK cells, and can activate NK cells. GM-CSF, (granulocyte-macrophage colony-stimulating factor) stimulates the production of granulocytes and macrophages.

Prior investigators have disclosed sequences encoding feline IL-4 (Lerner et al., Genbank Accession No. U39634); porcine L-4 (Zhou et al., Genbank Accession No. L12991); bovine IL-4 (Heussler, V.T., et al., *Gene*. vol. 114, pp. 273–278, 1992); ovine IL-4 (Seow, H.-F., et al., *Gene*, vol. 124, pp. 291–293, 1993); human IL-4 (Yokota, T., et al., *Proc. Natl. Acad. Sci. U.S.A.*, vol. 83(16), pp. 5894–5898, 1986); and murine IL-4 (Sideras, P., et al., *Adv. Exp. Med. Biol.*, vol. 213, pp. 227–236, 1987). Prior investigators have disclosed sequences encoding murine Flt-3 ligand (McClanahan et al., Genbank Accession No. U44024); and human Flt-3 ligand (Lyman et al., *Blood*, vol. 83, pp. 2795–2801, 1994). Prior investigators have disclosed sequences encoding human CD40 (Stamenkovic et al., *EMBO J.*, vol. 8:1403–1410, 1989, GenBank Accession No. (X60592), bovine CD40 (Hirano et al., *Immunology*, vol. 90, pp. 294–300, 1997, GenBank Accession No. U57745), and murine CD40 (Grimaldi et al., *J. Immunol.*, vol. 143, pp.3921–3926. 1992; Torres and Clark, *J. Immunol.*, vol. 148, pp. 620–626, 1992, GenBank Accession No. M83312). Prior investigators have disclosed sequences encoding human CD154 (Graf et al., *Eur. J. Immunol.*, vol. 22, pp. 3191–3194, 1992; Hollenbaugh, et al., *EMBO J.*, vol. 11:4313–4321, 1992; Gauchat et al., *FEBS lett.*, vol., 315, pp. 259–266, 1993; GenBank Accession Nos L07414, X68550, Z15017, X67878, respectively); bovine CD154 (Mertens et al., *Immunogenetics*, vol. 42, pp. 430–431, GenBank Accession No. Z48468); and murine CD154 (Armitage et al., *Nature*, vol. 357, pp. 80–82; 1992, GenBank Accession No. X65453). Prior investigators have disclosed sequences encoding feline interleukin-5 (Padrid et al., *Am. J. Vet. Res.*, vol. 59, pp. 1263–1269, 1998, GenBank Accession No. AF025436) and human interleukin-5 (Azuma et al., *Nucleic Acids Res.*, vol. 14, pp. 9149–9158, 1986, GenBank Accession No. X04688). Prior investigators have disclosed sequences encoding human interleukin-13 (McKenzie et al., *Proc. Natl Acad. Sci. USA*, vol. 90, pp. 3735–3739, 1993; Minty et al., *Nature*, vol. 362, pp. 248–250, 1993, GenBank Accession Nos L06801 and X69079, respectively); murine interleukin-13 (Brown et al., *J. Immunol.*, vol. 142, pp. 679–687, 1989, GenBank Accession No M23504); and rat interleukin-13 (Lakkis et al., *Biochem. Biophys. Res. Commun.*, Vol. 197, pp. 612–618, 1993, GenBank Accession No. L26913). Prior investigators have disclosed sequences encoding feline interferon (Nakamura, N., Sudo, T., Matsuda, S., Yanai, A., *Biosci. Biotechnol. Biochem.* (1992)Vol: 56 pp 211–214, GenBank accession # E02521). Prior investigators have also disclosed sequences encoding feline GM-CSF (direct submission to GenBank, Accession No. AF053007)

There remains a need for compounds and methods to regulate an immune response by manipulation of the function of canine interleukin-4, canine or feline Flt-3 ligand, canine or feline CD40, canine or feline CD154, canine interleukin-5, canine interleukin-13, feline interferon alpha, or feline GM-CSF.

SUMMARY OF THE INVENTION

The present invention relates to canine interleukin-4, canine or feline Flt-3 ligand, canine or feline CD40, canine or feline CD154, canine interleukin-5, canine interleukin-13, feline interferon alpha, or feline GM-CSF nucleic acid molecules, proteins encoded by such nucleic acid molecules, antibodies raised against such proteins and/or inhibitors of such proteins or nucleic acid molecules. Identification of the nucleic acid molecules of the present invention is unexpected because initial attempts to obtain nucleic acid molecules using PCR were unsuccessful. After numerous attempts, the inventors discovered specific primers that were useful for isolating such nucleic acid molecules.

One embodiment of the present invention is an isolated nucleic acid molecule selected from the group consisting of: (a) an isolated nucleic acid molecule comprising a nucleic acid sequence selected from the group consisting of SEQ ID NO:1, SEQ ID NO:3, SEQ ID NO:4, SEQ ID NO:5, SEQ ID NO:19, and/or SEQ ID NO:21 or a homolog thereof, wherein said homolog has an at least about 50 contiguous nucleotide region identical in sequence to a 50 contiguous nucleotide region of a nucleic acid sequence selected from the group consisting of SEQ ID NO:1, SEQ ID NO:3, SEQ ID NO:4, SEQ ID NO:5, SEQ ID NO:19, and/or SEQ ID NO:21; (b) an isolated nucleic acid molecule comprising a nucleic acid sequence selected from the group consisting of SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, and/or SEQ ID NO:37 or a homolog thereof, wherein said homolog has an at least 40 contiguous nucleotide region identical in sequence to a 40 contiguous nucleotide region of a nucleic acid molecule having a nucleic acid sequence selected from the group consisting of SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, and/or SEQ ID NO:37; (c) an isolated nucleic acid molecule comprising a nucleic acid sequence selected from the group consisting of SEQ ID NO:41, SEQ ID NO:42, SEQ ID NO:43, SEQ ID NO:45, SEQ ID NO:46, SEQ ID NO:47, SEQ ID NO:48, and/or SEQ ID NO:50, and/or a homolog thereof, wherein said homolog has an at least 30 contiguous nucleotide region identical in sequence to a 30 contiguous nucleotide region of a nucleic acid molecule having a nucleic acid sequence selected from the group consisting of SEQ ID NO:41, SEQ ID NO:42, SEQ ID NO:43, SEQ ID NO:45, SEQ ID NO:46, SEQ ID NO:47, SEQ ID NO:48, and/or SEQ ID NO:50; (d) an isolated nucleic acid molecule comprising a nucleic acid sequence selected from the group consisting of SEQ ID NO:51, SEQ ID NO:52, SEQ ID NO:54, SEQ ID NO:55, SEQ ID NO:56, SEQ ID NO:57, and/or SEQ ID NO:59, and/or a homolog thereof, wherein said homolog has an at least 40 contiguous nucleotide region identical in sequence to a 40 contiguous nucleotide region of a nucleic acid sequence selected from the group consisting of SEQ ID NO:51, SEQ ID NO:52, SEQ ID NO:54, SEQ ID NO:55, SEQ ID NO:56, SEQ ID NO:57, and/or SEQ ID NO:59; (e) an isolated nucleic acid molecule comprising a nucleic acid sequence selected from the group consisting of SEQ ID NO:60 and/or SEQ ID NO:62, and/or a homolog thereof, wherein said homolog has an at least 30 contiguous nucleotide region identical in sequence to a 30 contiguous nucleotide region of a nucleic acid molecule having a 3 nucleic acid sequence selected from the group consisting of SEQ ID NO:60 and/or SEQ ID NO:62; (f) an isolated nucleic acid molecule comprising a nucleic acid sequence selected from the group consisting of SEQ ID NO:63, SEQ ID NO:64, SEQ ID NO:66, SEQ ID NO:67, SEQ ID NO:68, SEQ ID NO:69 and/or SEQ ID NO:71, and/or a homolog thereof, wherein said homolog has an at least 45 contiguous nucleotide region identical in sequence to a 45 nucleotide region of a nucleic acid molecule having a nucleic acid sequence selected from the group consisting of SEQ ID NO:63, SEQ ID NO:64, SEQ ID NO:66, SEQ ID NO:67, SEQ ID NO:68, SEQ ID NO:69 and/or SEQ ID NO:71; (g) an isolated nucleic acid molecule comprising a nucleic acid sequence selected from the group consisting of SEQ ID NO:72, SEQ ID NO:74, SEQ ID NO:75, SEQ ID NO:76, SEQ ID NO:77, and/or SEQ ID NO:79, and/or a homolog thereof, wherein said homolog has an at least 35 contiguous nucleotide region identical in sequence to a 35 contiguous nucleotide region of a nucleic acid molecule having a nucleic acid sequence selected from the group consisting of SEQ ID NO:72, SEQ ID NO:74, SEQ ID NO:75, SEQ ID NO:76, SEQ ID NO:77, and/or SEQ ID NO:79; (h) an isolated nucleic acid molecule comprising a nucleic acid sequence selected from the group consisting of SEQ ID NO:80, SEQ ID NO:82, SEQ ID NO:83, SEQ ID NO:84, SEQ ID NO:85, and/or SEQ ID NO:87, and/or a homolog thereof, wherein said homolog has an at least 45 contiguous nucleotide region identical in sequence to a 45 contiguous nucleotide region of a nucleic acid molecule having a nucleic acid sequence selected from the group consisting of SEQ ID NO:80, SEQ ID NO:82, SEQ ID NO:83, SEQ ID NO:84, SEQ ID NO:85, and/or SEQ ID NO:87; (i) an isolated nucleic acid molecule comprising a nucleic acid sequence selected from the group consisting of SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, and/or SEQ ID NO:106, and/or a homolog thereof, wherein said homolog has an at least 15 contiguous nucleotide region identical to a 15 contiguous nucleotide region of a nucleic acid molecule having a nucleic acid sequence selected from the group consisting of SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, and/or SEQ ID NO:106; (j) an isolated nucleic acid molecule having a nucleic acid sequence selected from the group consisting of SEQ ID NO:107, SEQ ID NO:109, SEQ ID NO:110, SEQ ID NO:112, SEQ ID NO:113, SEQ ID NO:115, SEQ ID NO:116, SEQ ID NO:118, SEQ ID NO:155, SEQ ID NO:157, SEQ ID NO:158, SEQ ID NO:160, SEQ ID NO:161, SEQ ID NO:163, SEQ ID NO:164, SEQ ID NO:166, SEQ ID NO:167, SEQ ID NO:169, SEQ ID NO:170, and SEQ ID NO:172; and/or (k) an isolated nucleic acid molecule having a nucleic acid sequence selected from the group consisting of SEQ ID NO:119, SEQ ID NO:121, SEQ ID NO:122, SEQ ID NO:123, SEQ ID NO:124, SEQ ID NO:126.

Another embodiment of the present invention is an isolated nucleic acid molecule selected from the group consisting of: (a) a nucleic acid molecule having a nucleic acid sequence that is at least about 92 percent identical to a nucleic acid sequence selected from the group consisting of SEQ ID NO:1, SEQ ID NO:3, SEQ ID NO:4, SEQ ID NO:5, SEQ ID NO:19, and/or SEQ ID NO:21; (b) a nucleic acid molecule having a nucleic acid sequence that is at least about 75 percent identical to a nucleic acid sequence selected from the group consisting of SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, and/or SEQ ID NO:37; (c) a nucleic acid molecule having a nucleic acid sequence that is at least about 75 percent identical to a nucleic acid sequence selected from the group consisting of SEQ ID NO:41, SEQ ID NO:42, SEQ ID NO:43, SEQ ID NO:45, SEQ ID NO:46, SEQ ID NO:47, SEQ ID NO:48, and/or SEQ ID NO:50; (d) a nucleic acid molecule having a nucleic acid sequence that is at least about 70 percent identical to a nucleic acid sequence selected from the group consisting of SEQ ID NO:51, SEQ ID NO:52, SEQ ID NO:54, SEQ ID NO:55, SEQ ID NO:56, SEQ ID NO:57, and/or SEQ ID NO:59; (e) a nucleic acid molecule having a nucleic acid sequence that is at least about 70 percent identical to a nucleic acid sequence selected from the group consisting of SEQ ID NO:60 and/or SEQ ID NO:62; (f) a nucleic acid molecule having a nucleic acid sequence that is at least about 85 percent identical to a nucleic acid sequence selected from the group consisting of SEQ ID NO:63, SEQ ID NO:64, SEQ ID NO:66, SEQ ID NO:67, SEQ ID NO:68, SEQ ID NO:69, and/or SEQ ID NO:71; (g) a nucleic acid molecule having a nucleic acid sequence that is at least about 91 percent identical to a nucleic acid sequence selected from the group consisting of SEQ ID NO:72, SEQ ID NO:74, SEQ ID NO:75, SEQ ID NO:76, SEQ ID NO:77, and/or SEQ ID NO:79; (h) a nucleic acid molecule having a nucleic acid sequence that is at least about 90 percent identical to a nucleic acid sequence selected from the group consisting of SEQ ID NO:80, SEQ ID NO:82, SEQ ID NO:83, SEQ ID NO:84, SEQ ID NO:85, and/or SEQ ID NO:87; (i) a nucleic acid molecule having a nucleic acid sequence that is at least about 65 percent identical to a nucleic acid sequence selected from the group consisting of SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, and/or SEQ ID NO:106; (j) a nucleic acid molecule having a nucleic acid sequence that is selected from the group consisting of SEQ ID NO:107, SEQ ID NO:109, SEQ ID NO:110, SEQ ID NO:112, SEQ ID NO:113, SEQ ID NO:115, SEQ ID NO:116, SEQ ID NO:118, SEQ ID NO:155, SEQ ID NO:157, SEQ ID NO:158, SEQ ID NO:160, SEQ ID NO:161, SEQ ID NO:163, SEQ ID NO:164, SEQ ID NO:166, SEQ ID NO:167, SEQ ID NO:169, SEQ ID NO:170 and/or SEQ ID NO:172; and/or (k) a nucleic acid molecule having a nucleic acid sequence that is selected from the group consisting of SEQ ID NO:119, SEQ ID NO:121, SEQ ID NO:122, SEQ ID NO:123, SEQ ID NO:124, and/or SEQ ID NO:126.

Yet another embodiment of the present invention is an isolated nucleic acid molecule selected from the group consisting of: (a) a nucleic acid molecule having a nucleic acid sequence encoding an IL-4 protein selected from the group consisting of (i) a protein having an amino acid sequence that is at least about 85 percent identical to an amino acid sequence selected from the group consisting of SEQ ID NO:2 and/or SEQ ID NO:20 and/or (ii) a protein comprising a fragment of at least 20 amino acids of an amino acid sequence selected from the group consisting of SEQ ID NO:2 and/or SEQ ID NO:20; (b) a nucleic acid molecule having a nucleic acid sequence encoding a Flt-3 ligand protein selected from the group consisting of (i) a protein having an amino acid sequence that is at least about 75 percent identical to an amino acid sequence selected from the group consisting of SEQ ID NO:7, SEQ ID NO:23, SEQ ID NO:26, SEQ ID NO:31, and/or SEQ ID NO:34 and/or (ii) a protein comprising a fragment of at least 25 amino acids of an amino acid sequence selected from the group consisting of SEQ ID NO:7, SEQ ID NO:23, SEQ ID NO:26, SEQ ID NO:3 1, and/or SEQ ID NO:34; (c) a nucleic acid molecule having a nucleic acid sequence encoding a Flt-3 ligand protein selected from the group consisting of (i) a protein having an amino acid sequence that is at least about 75 percent identical to an amino acid sequence selected from the group consisting of SEQ ID NO:44 and/or SEQ ID NO:49 and/or (ii) a protein comprising a fragment of at least 25 amino acids of an amino acid sequence selected from the group consisting of SEQ ID NO:44 and/or SEQ ID NO:49; (d) a nucleic acid molecule having a nucleic acid sequence encoding a CD40 protein selected from the group consisting of (i) a protein having an amino acid sequence that is at least about 70 percent identical to an amino acid sequence selected from the group consisting of SEQ ID NO:53 and/or SEQ ID NO:58 and/or (ii) a protein comprising a fragment of at least 30 amino acids of an amino acid sequence selected from the group consisting of SEQ ID NO:53 and/or SEQ ID NO:58; (e) a nucleic acid molecule having a nucleic acid sequence encoding a CD40 protein selected from the group consisting of (i) a protein having an amino acid sequence that is at least about 60 percent identical to an amino acid sequence comprising SEQ ID NO:61 and/or (ii) a protein comprising a fragment of at least 20 amino acids of an amino acid sequence comprising SEQ ID NO:61; (f) a nucleic acid molecule having a nucleic acid sequence encoding a CD154 protein selected from the group consisting of (i) a protein having an amino acid sequence that is at least about 80 percent identical to an amino acid sequence selected from the group consisting of SEQ ID NO:65 and/or SEQ ID NO:70, and/or (ii) a protein comprising a fragment of at least 35 amino acids of an amino acid sequence selected from the group consisting of SEQ ID NO:65 and/or SEQ ID NO:70; (g) a nucleic acid molecule having a nucleic acid sequence encoding a CD154 protein selected from the group consisting of (i) a protein having an amino acid sequence that is at least about 85 percent identical to an amino acid sequence selected from the group consisting of SEQ ID NO:73 and/or SEQ ID NO:78, and/or (ii) a protein comprising a fragment of at least 50 amino acids of an amino acid sequence selected from the group consisting of SEQ ID NO:73 and/or SEQ ID NO:78; (h) a nucleic acid molecule having a nucleic acid sequence encoding an IL-5 protein selected from the group consisting of (i) a protein having an amino acid sequence that is at least about 85 percent identical to an amino acid sequence selected from the group consisting of SEQ ID NO:81 and/or SEQ ID NO:86 and/or (ii) a protein comprising a fragment of at least 20 amino acids of an amino acid sequence selected from the group consisting of SEQ ID NO:81 and/or SEQ ID NO:86; (i) a nucleic acid molecule having a nucleic acid sequence encoding an IL-13 protein selected from the group consisting of (i) a protein having an amino acid sequence that is at least about 70 percent identical to an amino acid sequence selected from the group consisting of SEQ ID NO:92, SEQ ID NO:97, SEQ ID NO:100, and/or SEQ ID NO:105 and/or (ii) a protein comprising a fragment of at least 15 amino acids of an amino acid sequence selected from the group consisting of SEQ ID NO:92, SEQ ID NO:97, SEQ ID NO:100, and/or SEQ ID NO:105; (j) a nucleic acid molecule having a nucleic acid sequence encoding an interferon alpha protein having an amino acid sequence that is selected from the group consisting of amino acid sequence SEQ ID NO:108, SEQ ID NO:111, SEQ ID NO:114, SEQ ID NO:117, SEQ ID NO:156, SEQ ID NO:159, SEQ ID NO:162, SEQ ID NO:165, SEQ ID NO:168, and/or SEQ ID NO:171; (k) a nucleic acid molecule having a nucleic acid sequence encoding a GMCSF protein having an amino acid sequence that is selected from the group consisting of amino acid sequence SEQ ID NO:120, SEQ ID NO:125, and/or (1) a nucleic acid molecule comprising a complement of any of said nucleic acid molecules as set forth in (a), (b), (c), (d), (e), (f), (g), (h), (i), 0), and/or (k), wherein said IL-4 protein elicits an immune response against an IL-4 protein selected from the group consisting of SEQ ID NO:2 and/or SEQ ID NO:20 and/or is a protein with interleukin-4 activity, said Flt-3 ligand protein elicits an immune response against a Flt-3 ligand protein selected from the group consisting of SEQ ID NO:7, SEQ ID NO:23, SEQ ID NO:26, SEQ ID NO:31, SEQ ID NO:34, SEQ ID NO:44, and/or SEQ ID NO:49 and/or is a protein with Flt-3 ligand activity, said CD40 protein elicits an immune response against a CD40 protein selected from the group consisting of SEQ ID NO:53, SEQ ID NO:58, and/or SEQ ID NO:61 and/or is a protein with CD40 activity, said CD154 protein elicits an immune response against a CD154 protein selected from the group consisting of SEQ ID NO:65, SEQ ID NO:70, SEQ ID NO:73, and/or SEQ ID NO:78 and/or is a protein with CD154 activity, said IL-5 protein elicits an immune response against a IL-5 protein selected from the group consisting of SEQ ID NO:81 and/or SEQ ID NO:86 and/or is a protein with IL-5 activity, said IL-13 protein elicits an immune response against an IL-13 protein selected from the group consisting of SEQ ID NO:92, SEQ ID NO:97, SEQ ID NO:100, and/or SEQ ID NO:105 and/or is a protein with IL-13 activity, said interferon alpha protein elicits an immune response against an interferon alpha protein selected from the group consisting of SEQ ID NO:108, SEQ ID NO:111, SEQ ID NO:114, SEQ ID NO:117, SEQ ID NO:156, SEQ ID NO:159, SEQ ID NO:162, SEQ ID NO:165, SEQ ID NO:168, and/or SEQ ID NO:171 and/or is a protein with interferon alpha activity, and/or said GMCSF protein elicits an immune response against a GMCSF protein selected from the group consisting of SEQ ID NO:120 and/or SEQ ID NO:125 and/or is a protein with GM-CSF activity.

The present invention also includes methods to produce any of the proteins of the present invention using nucleic acid molecules of the present invention and recombinantly using such nucleic acid molecules.

The present invention also includes an isolated protein selected from the group consisting of: (a) (i) an isolated protein of at least about 20 amino acids in length, wherein said protein is encoded by a nucleic acid molecule, wherein said nucleic acid molecule has an at least60 contiguous nucleotide region identical in sequence to a 60 contiguous nucleotide region of a nucleic acid sequence selected from the group consisting of SEQ ID NO:1, SEQ ID NO:4, and/or SEQ ID NO:19; and/or (ii) an isolated protein of at least about 20 amino acids in length, wherein said protein has an at least 20 contiguous amino acid region identical in sequence to a 20 contiguous amino acid region selected from the group consisting of SEQ ID NO:2 and/or SEQ ID NO:20, wherein said isolated protein elicits an immune response against a canine IL-4 protein and/or has IL-4 activity; (b) (i) an isolated protein of at least about 20 amino acids in length, wherein said protein is encoded by a nucleic acid molecule, wherein said nucleic acid molecule has an at least60 contiguous nucleotide region identical in sequence to a 60 contiguous nucleotide region of a nucleic acid sequence selected from the group consisting of SEQ ID NO:6, SEQ ID NO:9, SEQ ID NO:22, SEQ ID NO:25, SEQ ID NO:28, SEQ ID NO:30, SEQ ID NO:33, and/or SEQ ID NO:36; and/or (ii) an isolated protein of at least about 20 amino acids in length, wherein said protein has an at least 20 contiguous amino acid region identical in sequence to a 20 contiguous amino acid region selected from the group consisting of SEQ ID NO:7, SEQ ID NO:23, SEQ ID NO:26, SEQ ID NO:31, and/or SEQ ID NO:34, wherein said isolated protein is capable of eliciting an immune response against a canine Flt-3 ligand protein and/or has Flt-3 activity; (c) (i) an isolated protein of at least about 20 amino acids in length, wherein said protein is encoded by a nucleic acid molecule, wherein said nucleic acid molecule has an at least60 contiguous nucleotide region identical in sequence to a 60 contiguous nucleotide region of a nucleic acid sequence selected from the group consisting of SEQ ID NO:41, SEQ ID NO:42, SEQ ID NO:43, SEQ ID NO:46, and/or SEQ ID NO:48; and/or (ii) an isolated protein of at least about 20 amino acids in length, wherein said protein has an at least 20 contiguous amino acid region identical in sequence to a 20 contiguous amino acid region selected from the group consisting of SEQ ID NO:44 and/or SEQ ID NO:49, wherein said isolated protein is capable of eliciting an immune response against a feline Flt-3 ligand protein and/or has Flt-3 activity; (d)(i) an isolated protein of at least about 30 amino acids in length, wherein said protein is encoded by a nucleic acid molecule, wherein said nucleic acid molecule has an at least90 contiguous nucleotide region identical in sequence to a 90 contiguous nucleotide region of a nucleic acid sequence selected from the group consisting of SEQ ID NO:51, SEQ ID NO:52, SEQ ID NO:55, and/or SEQ ID NO:57; and/or (ii) an isolated protein of at least about 30 amino acids in length, wherein said protein has an at least 30 contiguous amino acid region identical in sequence to a 30 contiguous amino acid region selected from the group consisting of SEQ ID NO:53, SEQ ID NO:58, wherein said isolated protein is capable of eliciting an immune response against a canine CD40 protein and/or has CD40 activity; (e) (i) an isolated protein of at least about 20 amino acids in length, wherein said protein is encoded by a nucleic acid molecule, wherein said nucleic acid molecule has an at least60 contiguous nucleotide region identical in sequence to a 60 contiguous nucleotide region of a nucleic acid sequence comprising SEQ ID NO:60; and/or (ii) an isolated protein of at least about 20 amino acids in length, wherein said protein has an at least 20 contiguous amino acid region identical in sequence to a 20 contiguous amino acid region comprising the amino acid sequence SEQ ID NO:61, wherein said isolated protein is capable of eliciting an immune response against a feline CD40 protein and/or has CD40 activity; (f)(i) an isolated protein of at least about 35 amino acids in length, wherein said protein is encoded by a nucleic acid molecule, wherein said nucleic acid molecule has an at least105 contiguous nucleotide region identical in sequence to a 105 contiguous nucleotide region of a nucleic acid sequence selected from the group consisting of SEQ ID NO:63, SEQ ID NO:64, SEQ ID NO:67, and/or SEQ ID NO:69; and/or (ii) an isolated protein of at least about 35 amino acids in length, wherein said protein has an at least 35 contiguous amino acid region identical in sequence to a 35 contiguous amino acid region selected from the group consisting of SEQ ID NO:65 and/or SEQ ID NO:70, wherein said isolated protein is capable of eliciting an immune response against a canine CD154 protein and/or has CD154 activity; (g)(i) an isolated protein of at least about 50 amino acids in length, wherein said protein is encoded by a nucleic acid molecule, wherein said nucleic acid molecule has an at least150 contiguous nucleotide region identical in sequence to a 150 contiguous nucleotide region of a nucleic acid sequence selected from the group consisting of SEQ ID NO:72, SEQ ID NO:75, and/or SEQ ID NO:77; and/or (ii) an isolated protein of at least about 50 amino acids in length, wherein said protein has an at least 50 contiguous amino acid region identical in sequence to a 50 contiguous amino acid region selected from the group consisting of SEQ ID NO:73 and/or SEQ ID NO:78, wherein said isolated protein is capable of eliciting an immune response against a feline CD154 protein and/or has CD154 activity; (h)(i) an isolated protein of at least about 20 amino acids in length, wherein said protein is encoded by a nucleic acid molecule, wherein said nucleic acid molecule has an at least60 contiguous nucleotide region identical in sequence to a 60 contiguous nucleotide region of a nucleic acid sequence selected from the group consisting of SEQ ID NO:80, SEQ ID NO:83, and/or SEQ ID NO:85; and/or (ii) an isolated protein of at least about 20 amino acids in length, wherein said protein has an at least 20 contiguous amino acid region identical in sequence to a 20 contiguous amino acid region selected from the group consisting of SEQ ID NO:81 and/or SEQ ID NO:86, wherein said isolated protein is capable of eliciting an immune response against a canine IL-5 protein and/or has IL-5 activity; (i)(i) an isolated protein of at least about 15 amino acids in length, wherein said protein is encoded by a nucleic acid molecule, wherein said nucleic acid molecule has an at least45 contiguous nucleotide region identical in sequence to a 45 contiguous nucleotide region of a nucleic acid sequence selected from the group consisting of SEQ ID NO:88, SEQ ID NO:89, SEQ ID NO:90, SEQ ID NO:91, SEQ ID NO:94, SEQ ID NO:96, SEQ ID NO:99, SEQ ID NO:102, and/or SEQ ID NO:104; and/or (ii) an isolated protein of at least about 15 amino acids in length, wherein said protein has an at least 15 contiguous amino acid region identical in sequence to a 15 contiguous amino acid region selected from the group consisting of SEQ ID NO:92, SEQ ID NO:97, SEQ ID NO:100, and/or SEQ ID NO:105, wherein said isolated protein is capable of eliciting an immune response against a canine IL-13 protein and/or has IL-13 activity; (j) (i) an isolated protein encoded by a nucleic acid molecule selected from the group consisting of SEQ ID NO:107, SEQ ID NO:110, SEQ ID NO:113, SEQ ID NO:116, SEQ ID NO:155, SEQ ID NO:158, SEQ ID NO:161, SEQ ID NO:164, SEQ ID NO:167, and/or SEQ ID NO:170, and/or (ii) an isolated protein selected from the group consisting of SEQ ID NO:108, SEQ ID NO:111, SEQ ID NO:114, SEQ ID NO:117, SEQ ID NO:156, SEQ ID NO:159, SEQ ID NO:162, SEQ ID NO:165, SEQ ID NO:168, and/or SEQ ID NO:171, wherein said isolated protein is capable of eliciting an immune response against a feline interferon alpha protein and/or has interferon alpha activity; (k) (i) an isolated protein encoded by a nucleic acid molecule selected from the group consisting of SEQ ID NO:119, SEQ ID NO:122, and/or SEQ ID NO:124, and/or (ii) an isolated protein selected from the group consisting of SEQ ID NO:120 and/or SEQ ID NO:125, wherein said isolated protein is capable of eliciting an immune response against a feline GM-CSF and/or has GM-CSF activity.

The present invention also includes an isolated protein selected from the group consisting of: (a) a protein having an amino acid sequence that is at least about 85 percent identical to an amino acid sequence selected from the group consisting of SEQ ID NO:2 and/or SEQ ID NO:20; (b) a protein having an amino acid sequence that is at least about 75 percent identical to an amino acid sequence selected from the group consisting of SEQ ID NO:7, SEQ ID NO:23, SEQ ID NO:26, SEQ ID NO:31, and/or SEQ ID NO:34; (c) a protein having an amino acid sequence that is at least about 75 percent identical to an amino acid sequence selected from the group consisting of SEQ ID NO:44 and/or SEQ ID NO:49; (d) a protein having an amino acid sequence that is at least about 70 percent identical to an amino acid sequence selected from the group consisting of SEQ ID NO:53 and/or SEQ ID NO:58; (e) a protein having an amino acid sequence that is at least about 60 percent identical to an amino acid sequence comprising SEQ ID NO:61; (f) a protein having an amino acid sequence that is at least about 80 percent identical to an amino acid sequence selected from the group consisting of SEQ ID NO:65 and/or SEQ ID NO:70; (g) a protein having an amino acid sequence that is at least about 85 percent identical to the amino acid sequence SEQ ID NO:73 and/or SEQ ID NO:78; (h) a protein having an amino acid sequence that is at least about 85 percent identical to an amino acid sequence selected from the group consisting of SEQ ID NO:81 and/or SEQ ID NO:86; (i) a protein having an amino acid sequence that is at least about 70 percent identical to an amino acid sequence selected from the group consisting of SEQ ID NO:92, SEQ ID NO:97, SEQ ID NO:100, and/or SEQ ID NO:105; (j) a protein having an amino acid sequence selected from the group consisting of SEQ ID NO:108, SEQ ID NO:111, SEQ ID NO:114, SEQ ID NO:117, SEQ ID NO:156, SEQ ID NO:159, SEQ ID NO:162, SEQ ID NO:165, SEQ ID NO:168, and/or SEQ ID NO:171; and/or (k) a protein having an amino acid sequence selected from the group consisting of SEQ ID NO:120, and/or SEQ ID NO:125.

The present invention also includes isolated antibodies that selectively bind to a protein of the present invention.

One aspect of the present invention is a therapeutic composition that, when administered to an animal, regulates an immune response in said animal, said therapeutic composition comprising a therapeutic compound selected from the group consisting of: an immunoregulatory protein of the present invention; a mimetope of any of said immunoregulatory proteins; and a multimeric form of any of said immunoregulatory proteins; an isolated nucleic acid molecule of the present invention; an antibody that selectively binds to any of said immunoregulatory proteins; and/or an inhibitor of a immunoregulatory protein activity identified by its ability to inhibit the activity of any of said immunoregulatory proteins. Yet another aspect of the present invention is a method to regulate an immune response in an animal comprising administering to the animal a therapeutic composition of the present invention.

The present invention also includes a method to produce an immunoregulatory protein, said method comprising culturing a cell capable of expressing said protein, said protein being encoded by a nucleic acid molecule of the present invention.

One embodiment of the present invention is a method to identify a compound capable of regulating an immune response in an animal, said method comprising: (a) contacting an isolated canine IL-4 protein of the present invention with a putative inhibitory compound under conditions in which, in the absence of said compound, said protein has T cell proliferation stimulating activity; and determining if said putative inhibitory compound inhibits said activity; (b) contacting an isolated canine Flt-3 ligand protein of the present invention with a putative inhibitory compound under conditions in which, in the absence of said compound, said protein has dendritic precursor cell proliferation stimulating activity; and determining if said putative inhibitory compound inhibits said activity; (c) contacting an isolated feline Flt-3 ligand protein of the present invention with a putative inhibitory compound under conditions in which, in the absence of said compound, said protein has dendritic precursor cell proliferation stimulating activity; and determining if said putative inhibitory compound inhibits said activity; (d) contacting an isolated canine CD40 protein of the present invention with a putative inhibitory compound under conditions in which, in the absence of said compound, said protein has CD40 ligand binding activity; and determining if said putative inhibitory compound inhibits said activity; (e) contacting an isolated feline CD40 protein of the present invention with a putative inhibitory compound under conditions in which, in the absence of said compound, said protein has CD40 ligand binding activity; and determining if said putative inhibitory compound inhibits said activity; (f) contacting an isolated canine CD154 protein of the present invention with a putative inhibitory compound under conditions in which, in the absence of said compound, said protein has B cell proliferation activity; and determining if said putative inhibitory compound inhibits said activity; (g) contacting an isolated feline CD154 protein of the present invention with a putative inhibitory compound under conditions in which, in the absence of said compound, said protein has B cell proliferation activity; and determining if said putative inhibitory compound inhibits said activity; (h) contacting an isolated canine IL-5 protein of the present invention with a putative inhibitory compound under conditions in which, in the absence of said compound, said protein has TF-1 cell proliferation activity; and determining if said putative inhibitory compound inhibits said activity; (i) contacting an isolated canine IL-13 protein of the present invention with a putative inhibitory compound under conditions in which, in the absence of said compound, said protein has TF-1 cell proliferation activity; and determining if said putative inhibitory compound inhibits said activity; (j) contacting an isolated feline IFNα protein of the present invention with a putative inhibitory compound under conditions in which, in the absence of said compound, said protein has inhibition of proliferation of GM-CSF stimulated TF-1 cell activity; and determining if said putative inhibitory compound inhibits said activity; or (k) contacting an isolated feline GMCSF protein of the present invention with a putative inhibitory compound under conditions in which, in the absence of said compound, said protein has TF-1 cell proliferation activity; and determining if said putative inhibitory compound inhibits said activity.

DETAILED DESCRIPTION OF THE INVENTION

The present invention provides for isolated canine interleukin-4, canine or feline Flt-3 ligand, canine or feline CD40, canine or feline CD154, canine interleukin-5, canine interleukin-13, feline interferon alpha, or feline GM-CSF proteins, isolated canine interleukin-4, canine or feline Flt-3 ligand, canine or feline CD40, canine or feline CD154, canine interleukin-5, canine interleukin-13, feline interferon alpha, or feline GM-CSF nucleic acid molecules, antibodies directed against canine interleukin-4, canine or feline Flt-3 ligand, canine or feline CD40, canine or feline CD154, canine interleukin-5, canine interleukin-13, feline interferon alpha, or feline GM-CSF proteins, and compounds derived therefrom that regulate the immune response of an animal (e.g. inhibitors, antibodies and peptides).

Canine IL-4 protein can refer to a canine IL-4 protein, including homologs thereof. Canine Flt-3 ligand protein can refer to a canine Flt-3 ligand, including homologs thereof, and feline Flt-3 ligand can refer to feline Flt-3 ligand, including homologs thereof. Canine CD40 can refer to a canine CD4-, including homologs thereof; feline CD40 can refer to a feline CD40, including homologs thereof. Canine CD154 can refer to a canine CD154, including homo logs thereof; feline CD154 can refer to a feline CD154, including homologs thereof. Canine IL-5 can refer to canine IL-5, including homologs thereof; canine IL-13 can refer to canine IL-13, including homologs thereof. Feline IFNα can refer to a feline IFNα, including homologs thereof, and feline GM-CSF can refer to a feline GM-CSF, including homologs thereof. As used herein, the phrase "regulate an immune response" refers to modulating the activity of cells or molecules involved in an immune response. The term "regulate" can refer to increasing or decreasing an immune response. Regulation of an immune response can be determined using methods known in the art as well as methods disclosed herein. The term, "immunoregulatory protein" refers to a protein that can modulate the activity of cells or of molecules involved in an immune response. An immunoregulatory protein of the present invention refers to a canine IL-4, a canine and/or feline CD40, a canine and/or feline Flt3 ligand, a canine and/or feline CD154, a canine IL-5, a canine IL-13, a feline IFNα and/or a feline GM-CSF protein as described herein. As used herein, the terms isolated canine interleukin-4, canine or feline Flt-3 ligand, canine or feline CD40, canine or feline CD154, canine interleukin-5, canine interleukin-13, feline interferon alpha, or feline GM-CSF proteins and/or isolated canine interleukin-4, canine or feline Flt-3 ligand, canine or feline CD40, canine or feline CD1 54, canine interleukin-5, canine interleukin-13, feline interferon alpha, or feline GM-CSF nucleic acid molecules refer to canine interleukin-4, canine or feline Flt-3 ligand, canine or feline CD40, canine or feline CD154, canine interleukin-5, canine interleukin-13, feline interferon alpha, or feline GM-CSF proteins and/or canine interleukin-4, canine or feline Flt-3 ligand, canine or feline CD40, canine or feline CD154, canine interleukin-5, canine interleukin-13, feline interferon alpha, or feline GM-CSF nucleic acid molecules derived from mammals and, as such, can be obtained from their natural source, or can be produced using, for example, recombinant nucleic acid technology or chemical synthesis. Also included in the present invention is the use of these proteins, nucleic acid molecules, antibodies, and/or compounds derived therefrom as therapeutic compositions to regulate the immune response of an animal as well as in other applications, such as those disclosed below.

One embodiment of the present invention is an isolated protein that includes a canine IL-4 protein, a canine and/or feline Flt-3 ligand protein, a canine and/or feline CD40 protein, a canine and/or feline CD154 protein, a canine interleukin-5 protein, a canine interleukin-13 protein, a feline interferon alpha protein, and/or a feline GM-CSF protein. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and/or "biologically pure" do not necessarily reflect the extent to which the protein has been purified. An isolated protein of the present invention can be obtained from its natural source, can be produced using recombinant DNA technology, or can be produced by chemical synthesis. Nucleic acid molecules of the present invention of known length isolated from Canis familiaris are denoted as follows:

IL-4 is denoted as nCaIL-$4_x$, for example, nCaIL-$4_{549}$, wherein "#" refers to the number of nucleotides in that molecule; and in a similar fashion, Flt-3 ligand nucleic acid molecules are referred to as nCaFlt3$L_x$; CD40, nCaCD$40_x$; CD154, nCaCD$154_x$; IL-5, nCaIL-$5_x$; and IL-13, nCaIL-$13_x$. In a similar fashion, Flt-3 ligand nucleic acid molecules of the present invention of known length isolated from Felis catus are denoted as nFeFlt3$L_x$, CD40, nFeCD$40_x$; CD154, nFeCD$154_x$; IFNα, nFeIFN$\alpha_x$; and GM-CSF (also denoted GMCSF), nFeGM-$CSF_x$. Similarly, proteins of the present invention of known length isolated from Felis catus are denoted as PFeFlt3$1_x$, PFeCD$40_x$, PFeCD$154_x$, PFeIFN$\alpha_x$, and/or PFeGM-$CSF_x$; and proteins of the present invention of known length isolated from Canis familiaris are denoted PCaIL-$4_x$, PCaFlt3$L_x$, PCaCD$40_x$, PCaCD$154_x$, PCaIL-$5_x$, and/or PCaIL-$13_x$.

As used herein, an isolated canine interleukin-4, canine or feline Flt-3 ligand, canine or feline CD40, canine or feline CD154, canine interleukin-5, canine interleukin-13, feline interferon alpha, and/or feline GM-CSF ligand protein of the present invention (i.e., an canine interleukin-4, canine or feline Flt-3 ligand, canine or feline CD40, canine or feline CD154, canine interleukin-5, canine interleukin-13, feline interferon alpha, or feline GM-CSF protein, respectively) can be a full-length protein or any homolog of such a protein. An isolated IL-4 protein of the present invention, including a homolog, can be identified in a straight-forward manner by the protein's ability to elicit an immune response against, (or to) an IL-4 protein, bind to an IL-4 receptor, stimulate B cell differentiation or activation or stimulate production of immunoglobulin by a B cell. An isolated Flt-3 ligand protein of the present invention, including a homolog, can be identified in a straight-forward manner by the protein's ability to elicit an immune response against a Flt-3 ligand protein, bind to Flt-3 receptor or stimulate Flt-3 receptor-bearing hematopoietic stem cells, early hematopoietic progenitor cells or immature lymphocytes. An isolated CD40 protein of the present invention, including a homolog, can be identified in a straight-forward manner by the protein's ability to elicit an immune response against a CD40 protein, bind to CD154 or stimulate CD1 54-bearing B cells, T cells, and/or epithelial cells. An isolated CD154 protein of the present invention, including a homolog, can be identified in a straight-forward manner by the protein's ability to elicit an immune response to a CD154 protein, bind to CD40 or stimulate CD40-bearing B cells, T cells, and/or epithelial cells. An isolated IL-5 protein of the present invention, including a homolog, can be identified in a straight-forward manner by the protein's ability to elicit an immune response to an IL-5 protein, bind to an IL-5 receptor, and/or stimulate eosinophils and/or cause thymocytes to produce cytotoxic T cells. An isolated IL-13 protein of the present invention, including a homolog, can be identified in a straight-forward maner by the protein's ability to elicit an immune response to an IL-13 protein, bind to an IL-13 receptor, and/or stimulate B cells, up-regulate expression of MHC class II and/or CD23 on monocytes, macrophages and/or B cells; and/or inhibition of proinflammatory cytokines. An isolated interferon alpha protein of the present invention, including a homolog, can be identified in a straight-forward manner by the protein's ability to elicit an immune response to an interferon alpha protein, bind to an interferon alpha receptor, and/or activate NK cells and/or inhibit viral replication. An isolated GM-CSF protein of the present invention, including a homolog, can be identified in a straight-forward manner by the protein's ability to elicit an immune response to a GM-CSF protein, bind to a GM-CSF receptor, and/or activate granulocytes and/or macrophages. Examples of protein homologs of the present invention include immunoregulatory proteins of the present invention in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the protein homolog includes at least one epitope capable of eliciting an immune response against the parent protein, of binding to an antibody directed against the parent protein and/or of binding to the parent's receptor, where the term parent refers to the longer and/or full-length protein that the homolog is derived from. That is, when the homolog is administered to an animal as an immunogen, using techniques known to those skilled in the art, the animal will produce an immune response against at least one epitope of an immunoregulatory protein of the present invention, depending upon which protein is administered to an animal. The ability of a protein to effect an immune response can be measured using techniques known to those skilled in the art. As used herein, the term "epitope" refers to the smallest portion of a protein capable of selectively binding to the antigen binding site of an antibody. It is well accepted by those skilled in the art that the minimal size of a protein epitope capable of selectively binding to the antigen binding site of an antibody is about five or six to seven amino acids.

Homologs of immunoregulatory proteins of the present invention can be the result of natural allelic variation, including natural mutation. Protein homologs of the present invention can also be produced using techniques known in the art including, but not limited to, direct modifications to the protein and/or modifications to the gene encoding the protein using, for example, classic or recombinant DNA techniques to effect random or targeted mutagenesis.

Immunoregulatory proteins of the present invention include variants of a full-length protein of a protein of the present invention. Such variants include proteins that are less than full-length. As used herein, variants of the present invention refer to nucleic acid molecules that are naturally-occurring as defined below, and may result from alternative RNA splicing, alternative termination of an amino acid sequence or DNA recombination. Examples of variants include allelic variants as defined below. It is to be noted that a variant is an example of a homolog of the present invention.

Immunoregulatory proteins of the present invention are encoded by nucleic acid molecules of the present invention. As used herein, an IL-4 nucleic acid molecule includes nucleic acid sequences related to a natural canine IL-4 gene. As used herein, a Flt-3 ligand nucleic acid molecule includes nucleic acid sequences related to a natural canine Flt-3 ligand gene. As used herein, a CD40 nucleic acid molecule includes nucleic acid sequences related to a natural CD40 gene. As used herein, a CD154 nucleic acid molecule includes nucleic acid sequences related to a natural CD154 gene. As used herein, an IL-5 nucleic acid molecule includes nucleic acid sequences related to a natural IL-5 gene. As used herein, an IL-13 nucleic acid molecule includes nucleic acid sequences related to a natural IL-13 gene. As used herein, an IFNα nucleic acid molecule includes nucleic acid sequences related to a natural IFNα gene. As used herein, a GM-CSF nucleic acid molecule includes nucleic acid sequences related to a natural GM-CSF gene. As used herein, a canine IL-4, a canine and/or feline CD40, a canine and/or feline Flt3 ligand, a canine and/or feline CD154, a canine IL-5, a canine IL-13, a feline IFNα, and/or a feline GM-CSF gene refers to the natural genomic elements that encode an canine IL-4, a canine and/or feline CD40, a canine and/or feline Flt3 ligand, a canine and/or feline CD154, a canine IL-5, a canine IL-13, a feline IFNα, and/or a feline GM-CSF protein, respectively, and includes all regions such as regulatory regions that control production of the protein encoded by the gene (such as, but not limited to, transcription, translation or post-translation control regions) as well as the coding region itself, and any introns or non-translated coding regions. As used herein, a gene that "includes" or "comprises" a sequence may include that sequence in one contiguous array, or may include the sequence as fragmented exons. As used herein, the term "coding region" refers to a continuous linear array of nucleotides that translates into a protein. A full-length coding region is that region that is translated into a full-length, i.e., a complete, protein as would be initially translated in its natural milieu, prior to any post-translational modifications.

In one embodiment, an IL-4 gene of the present invention includes the nucleic acid sequence SEQ ID NO:1, as well as the complement of SEQ ID NO:1. Nucleic acid sequence SEQ ID NO:1 represents the deduced sequence of the coding strand of a cDNA (complementary DNA) denoted herein as nucleic acid molecule nCaIL-$4_{549}$, the production of which is disclosed in the Examples. Nucleic acid molecule nCaIL-$4_{549}$ comprises an apparently full-length coding region of canine IL-4. The complement of SEQ ID NO:1 (represented herein by SEQ ID NO:3) refers to the nucleic acid sequence of the strand fully complementary to the strand having SEQ ID NO:1, which can easily be determined by those skilled in the art. Likewise, a nucleic acid sequence complement of any nucleic acid sequence of the present invention refers to the nucleic acid sequence of the nucleic acid strand that is fully complementary to (i.e., can form a double helix with) the strand for which the sequence is cited. It should be noted that since nucleic acid sequencing technology is not entirely error-free, SEQ ID NO:1 (as well as other nucleic acid and protein sequences presented herein) represents an apparent nucleic acid sequence of the nucleic acid molecule encoding an immunoregulatory protein of the present invention.

In another embodiment, a Flt-3 ligand gene of the present invention includes the nucleic acid sequence SEQ ID NO:6, as well as the complement represented by SEQ ID NO:8. Nucleic acid sequence SEQ ID NO:6 represents the deduced sequence of the coding strand of a cDNA denoted herein as nucleic acid molecule nCaFlt3$L_{1013}$, the production of which is disclosed in the Examples. Nucleic acid molecule nCaFlt3$L_{1013}$ comprises an apparently full-length coding region of canine Flt-3 ligand.

In another embodiment, a Flt-3 ligand gene of the present invention includes the nucleic acid sequence SEQ ID NO:43, as well as the complement represented by SEQ ID NO:45. Nucleic acid sequence SEQ ID NO:43 represents the deduced sequence of the coding strand of a cDNA denoted herein as nucleic acid molecule nFeFlt3$L_{942}$, the production of which is disclosed in the Examples. Nucleic acid molecule nFeFlt3$L_{942}$ comprises an apparently full-length coding region of feline Flt-3 ligand.

In another embodiment, a CD40 gene of the present invention includes the nucleic acid sequence SEQ ID NO:52, as well as the complement represented by SEQ ID NO:54. Nucleic acid sequence SEQ ID NO:52 represents the deduced sequence of the coding strand of a cDNA denoted herein as nucleic acid molecule nCaCD$40_{1425}$, the production of which is disclosed in the Examples. Nucleic acid molecule nCaCD$40_{1425}$ comprises an apparently full-length coding region of canine CD40.

In another embodiment, a CD40 gene of the present invention includes the nucleic acid sequence SEQ ID NO:60, as well as the complement represented by SEQ ID NO:62. Nucleic acid sequence SEQ ID NO:60 represents the deduced sequence of the coding strand of a cDNA denoted herein as nucleic acid molecule nFeCD$40_{336}$, the production of which is disclosed in the Examples. Nucleic acid molecule nFeCD$40_{336}$ comprises an apparent portion of the coding region of feline CD40.

In another embodiment, a CD154 gene of the present invention includes the nucleic acid sequence SEQ ID NO:64, as well as the complement represented by SEQ ID NO:66. Nucleic acid sequence SEQ ID NO:64 represents the deduced sequence of the coding strand of a cDNA denoted herein as nucleic acid molecule nCaCD$154_{1878}$, the production of which is disclosed in the Examples. Nucleic acid molecule nCaCD$154_{1878}$ comprises an apparently full-length coding region of canine CD154.

In another embodiment, a CD154 gene of the present invention includes the nucleic acid sequence SEQ ID NO:72, as well as the complement represented by SEQ ID NO:74. Nucleic acid sequence SEQ ID NO:72 represents the deduced sequence of the coding strand of a cDNA denoted herein as nucleic acid molecule nFeCD$154_{885}$, the production of which is disclosed in the Examples. Nucleic acid molecule nFeCD$154_{885}$ comprises an apparently full-length coding region of feline CD154.

In another embodiment, an IL-5 gene of the present invention includes the nucleic acid sequence SEQ ID NO:80, as well as the complement represented by SEQ ID NO:82. Nucleic acid sequence SEQ ID NO:80 represents the deduced sequence of the coding strand of a cDNA denoted herein as nucleic acid molecule nCaIL-$5_{610}$, the production of which is disclosed in the Examples. Nucleic acid molecule nCaIL-$5_{610}$ comprises an apparently full-length coding region of canine IL-5.

In another embodiment, an IL-13 gene of the present invention includes the nucleic acid sequence SEQ ID NO:91, as well as the complement represented by SEQ ID NO:93. Nucleic acid sequence SEQ ID NO:91 represents the deduced sequence of the coding strand of a cDNA denoted herein as nucleic acid molecule nCaIL-$13_{1302}$, the production of which is disclosed in the Examples. Nucleic acid molecule nCaIL-$13_{1302}$ comprises an apparently full-length coding region of canine IL-13.

In another embodiment, an IFNα gene of the present invention includes the nucleic acid sequence SEQ ID NO:107, SEQ ID NO:110, SEQ ID NO:155, SEQ ID NO:158, SEQ ID NO:161, SEQ ID NO:164, SEQ ID NO:167, or SEQ ID NO:170, as well as the complement represented by, respectively, SEQ ID NO:109, SEQ ID NO:112, SEQ ID NO:157, SEQ ID NO:160, SEQ ID NO:163, or SEQ ID NO:166, SEQ ID NO:169, and SEQ ID NO:172. Nucleic acid sequences SEQ ID NO:107, SEQ ID NO:110, SEQ ID NO:155, SEQ ID NO:158, SEQ ID NO:161, SEQ ID NO:164, SEQ ID NO:167, and SEQ ID NO:170 represent the deduced sequences of the coding strands of cDNAs denoted herein as nucleic acid molecules nFeIFN$\alpha_{567a}$, nFeIFN$\alpha_{567b}$, nFeIFN$\alpha_{567c}$, nFeIFN$\alpha_{498c}$, nFeIFN$\alpha_{582d}$, nFeIFN$\alpha_{513d}$, nFeIFN$\alpha_{567e}$ and nFeIFN$\alpha_{498e}$, respectively. Each of these nucleic acid molecules, the production of which is disclosed in the Examples, comprises an apparently full-length coding region of a feline IFNα protein.

In another embodiment, a GM-CSF gene of the present invention includes the nucleic acid sequence SEQ ID NO:119, as well as the complement represented by SEQ ID NO:121. Nucleic acid sequence SEQ ID NO:119 represents the deduced sequence of the coding strand of a cDNA denoted herein as nucleic acid molecule nFeGM-CSF$_{444}$, the production of which is disclosed in the Examples. Nucleic acid molecule nFeGM-CSF$_{444}$ comprises an apparently full-length coding region of feline GM-CSF.

Additional immunoregulatory nucleic acid molecules and proteins of the present invention having specific sequence identifiers are described in Table 1.

TABLE 1

Sequence identification numbers (SEQ ID NOs) and their corresponding nucleic acid molecules or proteins.

| SEQ ID NO: | DESCRIPTION |
|---|---|
| 1 | nCaIL-4$_{549}$ coding strand |
| 2 | PCaIL-4$_{132}$ |
| 3 | nCaIL-4$_{549}$ complementary strand |
| 4 | nCaIL-4$_{396}$ coding strand |
| 5 | nCaIL-4$_{396}$ complementary strand |
| 6 | nCaFlt3L$_{1013}$ coding strand |
| 7 | PCaFlt3L$_{294}$ |
| 8 | nCaFlt3L$_{1013}$ complementary strand |
| 9 | nCaFlt3L$_{882}$ coding strand |
| 10 | nCaFlt3L$_{882}$ complementary strand |
| 19 | nCaIL-4$_{324}$ coding strand |
| 20 | PCaIL-4$_{108}$ |
| 21 | nCaIL-4$_{324}$ complementary strand |
| 22 | nCaFlt3L$_{804}$ coding strand |
| 23 | PCaFlt3L$_{268}$ |
| 24 | nCaFlt3L$_{804}$ complementary strand |
| 25 | nCaFlt3L$_{985}$ coding strand |
| 26 | PCaFlt3L$_{276}$ |
| 27 | nCaFlt3L$_{985}$ complementary strand |
| 28 | nCaFlt3L$_{828}$ coding strand |
| 29 | nCaFlt3L$_{828}$ complementary strand |
| 30 | nCaFlt3L$_{750}$ coding strand |
| 31 | PCaFlt3L$_{250}$ |
| 32 | nCaFlt3L$_{750}$ complementary strand |
| 33 | nCaFlt3L$_{1019}$ coding strand |
| 34 | PCaFlt3L$_{31}$ |
| 35 | nCaFlt3L$_{1019}$ complementary strand |
| 36 | nCaFlt3L$_{93}$ coding strand |
| 37 | nCaFlt3L$_{93}$ complementary strand |
| 41 | nFeFlt3L$_{395}$ coding strand |
| 42 | nFeFlt3L$_{793}$ coding strand |
| 43 | nFeFlt3L$_{942}$ coding strand |
| 44 | PFeFlt3L$_{291}$ |
| 45 | nFeFlt3L$_{942}$ complementary strand |
| 46 | nFeFlt3L$_{873}$ coding strand |
| 47 | nFeFlt3L$_{873}$ complementary strand |
| 48 | nFeFlt3L$_{795}$ coding strand |
| 49 | PFeFlt3L$_{265}$ |
| 50 | nFeFlt3L$_{795}$ complementary strand |
| 51 | nCaCD40$_{321}$ coding strand |
| 52 | nCaCD40$_{1425}$ coding strand |
| 53 | PCaCD40$_{274}$ |
| 54 | nCaCD40$_{1425}$ complementary strand |
| 55 | nCaCD40$_{822}$ coding strand |
| 56 | nCaCD40$_{822}$ complementary strand |
| 57 | nCaCD40$_{765}$ coding strand |
| 58 | PCaCD40$_{255}$ |
| 59 | nCaCD40$_{765}$ complementary strand |
| 60 | nFeCD40$_{336}$ coding strand |
| 61 | PFeCD40$_{112}$ |
| 62 | nFeCD40$_{336}$ complementary strand |
| 63 | nCaCD154$_{390}$ coding strand |
| 64 | nCaCD154$_{1878}$ coding strand |
| 65 | PCaCD154$_{260}$ |
| 66 | nCaCD154$_{1878}$ complementary strand |
| 67 | nCaCD154$_{780}$ coding strand |
| 68 | nCaCD154$_{780}$ complementary strand |
| 69 | nCaCD154$_{633}$ coding strand |
| 70 | PCaCD154$_{211}$ |
| 71 | nCaCD154$_{633}$ complementary strand |
| 72 | nFeCD154$_{885}$ coding strand |
| 73 | PFeCD154$_{260}$ |
| 74 | nFeCD154$_{885}$ complementary strand |
| 75 | nFeCD154$_{780}$ coding strand |
| 76 | nFeCD154$_{780}$ complementary strand |
| 77 | nFeCD154$_{633}$ coding strand |
| 78 | PFeCD154$_{211}$ |
| 79 | nFeCD154$_{633}$ complementary strand |
| 80 | nCAIL-5$_{610}$ coding strand |
| 81 | PCaIL-5$_{134}$ |
| 82 | nCaIL-5$_{610}$ complementary strand |
| 83 | nCaIL-5$_{402}$ coding strand |
| 84 | nIL-5$_{402}$ complementary strand |
| 85 | nCaIL-5$_{345}$ coding strand |
| 86 | PCaIL-5$_{115}$ |
| 87 | nCaIL-5$_{345}$ complementary strand |
| 88 | nCaIL-13$_{166}$ coding strand |
| 89 | nCaIL-13$_{272}$ coding strand |
| 90 | nCaIL-13$_{278}$ coding strand |
| 91 | nCaIL-13$_{1302}$ coding strand |
| 92 | PCaIL-13$_{131}$ |
| 93 | nCaIL-13$_{1302}$ complementary strand |
| 94 | nCaIL-13$_{393}$ coding strand |
| 95 | nCaIL-13$_{393}$ complementary strand |
| 96 | nCaIL-13$_{333}$ coding strand |
| 97 | PaIL-13$_{111}$ |
| 98 | nCaIL-13$_{333}$ complementary strand |
| 99 | nCaIL-13$_{1269}$ coding strand |
| 100 | PCaIL-13$_{130}$ |
| 101 | nCaIL-13$_{1269}$ complementary strand |
| 102 | nCaIL-13$_{390}$ coding strand |
| 103 | nCaIL-13$_{390}$ complementary strand |
| 104 | nCaIL-13$_{330}$ coding strand |
| 105 | PCaIL-13$_{110}$ |
| 106 | nCaIL-13$_{330}$ complementary strand |
| 107 | nFeIFN$\alpha_{567a}$ coding strand |
| 108 | PFeIFN$\alpha_{189a}$ |
| 109 | nFeIFN$\alpha_{567a}$ complementary strand |
| 110 | nFeIFN$\alpha_{567b}$ coding strand |
| 111 | PFeIFN$\alpha_{189b}$ |
| 112 | nFeIFN$\alpha_{567b}$ complementary strand |
| 113 | nFeIFN$\alpha_{498a}$ coding strand |
| 114 | PFeIFN$\alpha_{166a}$ |
| 115 | nFeIFN$\alpha_{498a}$ complementary strand |
| 116 | nFeFeIFN$\alpha_{498b}$ coding strand |
| 117 | PFeIFN$\alpha_{166b}$ |
| 118 | nFeIFN$\alpha_{498b}$ complementary strand |
| 119 | nFeGMCSF$_{444}$ coding strand |
| 120 | PFeGMCSF$_{144}$ |
| 121 | nFeGMCSF$_{444}$ complementary strand |
| 122 | nFeGMCSF$_{432}$ coding strand |
| 123 | nFeGMCSF$_{432}$ complementary strand |
| 124 | nFeGMCSF$_{381}$ coding strand |
| 125 | PFeGMCSF$_{127}$ |
| 126 | nFeGMCSF$_{381}$ complementary strand |
| 155 | nFeIFN$\alpha_{567c}$ |
| 156 | PFeIFN$\alpha_{189c}$ |
| 157 | nFeIFN$\alpha_{567a}$ complementary strand |
| 158 | nFeIFN$\alpha_{498c}$ |
| 159 | PFeIFN$\alpha_{166c}$ |
| 160 | nFeIFN$\alpha_{498c}$ complementary strand |
| 161 | nFeIFN$\alpha_{582d}$ |
| 162 | PFeIFN$\alpha_{194d}$ |
| 163 | nFeIFN$\alpha_{582d}$ complementary strand |
| 164 | nFeIFN$\alpha_{513d}$ |
| 165 | PFeIFN$\alpha_{171d}$ |
| 166 | nFeIFN$\alpha_{513d}$ complementary strand |
| 167 | nFeIFN$\alpha_{567e}$ |
| 168 | PFeIFN$\alpha_{189e}$ |
| 169 | nFeIFN$\alpha_{567e}$ complementary strand |
| 170 | nFeIFN$\alpha_{498e}$ |
| 171 | PFeIFN$\alpha_{166e}$ |
| 172 | nFeIFN$\alpha_{498e}$ complementary strand |

In another embodiment, an IL-4 gene or nucleic acid molecule can be an allelic variant that includes a similar but not identical sequence to SEQ ID NO:1, SEQ ID NO:3, SEQ ID NO:4, SEQ ID NO:5, SEQ ID NO:19, SEQ ID NO:2 1, and/or any other IL-4 nucleic acid sequence cited herein. In another embodiment, a Flt-3 ligand gene or nucleic acid molecule can be an allelic variant that includes a similar but not identical sequence to SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, SEQ ID NO:37, SEQ ID NO:41, SEQ ID NO:42, SEQ ID NO:43, SEQ ID NO:45, SEQ ID NO:46, SEQ ID NO:47, SEQ ID NO:48, SEQ ID NO:50 and/or any other Flt-3 ligand nucleic acid sequence cited herein. In another embodiment, a CD40 gene or nucleic acid molecule can be an allelic variant that includes a similar but not identical sequence to SEQ ID NO:51, SEQ ID NO:52, SEQ ID NO:54, SEQ ID NO:55, SEQ ID NO:56, SEQ ID NO:57, SEQ ID NO:59, SEQ ID NO:60, SEQ ID NO:62 and/or any other CD40 nucleic acid sequence cited herein. In another embodiment, a CD154 gene or nucleic acid molecule can be an allelic variant that includes a similar but not identical sequence to SEQ ID NO:63, SEQ ID NO:64, SEQ ID NO:66, SEQ ID NO:67, SEQ ID NO:68, SEQ ID NO:69, SEQ ID NO:71, SEQ ID NO:72, SEQ ID NO:74, SEQ ID NO:75, SEQ ID NO:76, SEQ ID NO:77, SEQ ID NO:79 and/or any other CD154 nucleic acid sequence cited herein. In another embodiment, an IL-5 gene or nucleic acid molecule can be an allelic variant that includes a similar but not identical sequence to SEQ ID NO:80, SEQ ID NO:82, SEQ ID NO:83, SEQ ID NO:84, SEQ ID NO:85, SEQ ID NO:87 and/or any other IL-5 nucleic acid sequence cited herein. In another embodiment, an IL-13 gene or nucleic acid molecule can be an allelic variant that includes a similar but not identical sequence to SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, SEQ ID NO:106 and/or any other IL-13 nucleic acid sequence cited herein. In another embodiment, an IFNα gene or nucleic acid molecule can be an allelic variant that includes a similar but not identical sequence to SEQ ID NO:107, SEQ ID NO:109, SEQ ID NO:110, SEQ ID NO:112, SEQ ID NO:113, SEQ ID NO:115, SEQ ID NO:116, SEQ ID NO:118, SEQ ID NO:155, SEQ ID NO:157, SEQ ID NO:158, SEQ ID NO:160, SEQ ID NO:161, SEQ ID NO:163, SEQ ID NO:164, SEQ ID NO:166, SEQ ID NO:167, SEQ ID NO:169, SEQ ID NO:170 and/or SEQ ID NO:172, and/or any other IFNα nucleic acid sequence cited herein. In another embodiment, a GM-CSF gene or nucleic acid molecule can be an allelic variant that includes a similar but not identical sequence to SEQ ID NO:119, SEQ ID NO:121, SEQ ID NO:122, SEQ ID NO:123, SEQ ID NO:124, and/or SEQ ID NO:126 and/or any other GM-CSF nucleic acid cited herein. An allelic variant of a canine interleukin-4, canine or feline Flt-3 ligand, canine or feline CD40, canine or feline CD154, canine interleukin-5, canine interleukin-13, feline interferon alpha, or feline GM-CSF gene, including the particular SEQ ID NO's cited herein, is a gene that occurs at essentially the same locus (or loci) in the genome as the gene including the particular SEQ ID NO's cited herein, but which, due to natural variations caused by, for example, mutation or recombination, has a similar but not identical sequence. Also included in the term allelic variant are allelic variants of cDNAs derived from such genes. Because natural selection typically selects against alterations that affect function, allelic variants usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to be found within a given animal, since the respective genomes are diploid, and sexual reproduction will result in the reassortment of alleles.

The minimal size of an canine interleukin-4, canine or feline Flt-3 ligand, canine or feline CD40, canine or feline CD154, canine interleukin-5, canine interleukin-13, feline interferon alpha, or feline GM-CSF protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267–284, each of which is incorporated herein by this reference. As explained in detail in the cited references, the determination of hybridization conditions involves the manipulation of a set of variables including the ionic strength (M, in moles/liter), the hybridization temperature (° C.), the concentration of nucleic acid helix destabilizing agents, such as formamide, the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m=81.5° \text{ C.}+16.6 \log M+0.41(\%G+C)-500/n-0.61(\%\text{formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d=4(G+C)+2(A+T).$$

A temperature of 5° C. below $T_d$ is used to detect hybridization between perfectly matched molecules.

Also well known to those skilled in the art is how base pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art. These simple procedures allow one skilled in the art to set the hybridization conditions, by altering, for example, the salt concentration, the formamide concentration or the temperature, so that only nucleic acid hybrids with greater than a specified % base pair mismatch will hybridize. Stringent hybridization conditions are commonly understood by those skilled in the art to be those experimental conditions that will allow about 30% base pair mismatch, i.e., about 70% identity. Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene or specified nucleic acid molecule under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

Preferred portions, or fragments, of a canine interleukin-4, canine or feline Flt-3 ligand, canine or feline CD40, canine or feline CD154, canine interleukin-5, canine interleukin-13, feline interferon alpha, or feline GM-CSF, protein of the present invention include at least 15 amino acids, at least 20 amino acids, at least 25 amino acids, at least 30 amino acids, at least 35 amino acids, at least 40 amino acids, at least 45 amino acids, at least 50 amino acids, at least 60 amino acids, at least 75 amino acids or at least 100 amino acids. An IL-4, IL-5, and/or IL-13 protein of the present invention can include at least a portion of an IL-4, IL-5, and/or IL-13 protein that is capable of binding to an IL-4, IL-5, and/or IL-13 receptor, respectively. IL-4, IL-5, and IL-13 receptors are known to those of skill in the art, and are described in Janeway et al., in *Immunobiology, the Immune System in Health and Disease*, Garland Publishing, Inc., N.Y., 1996 (which is incorporated herein by this reference in its entirety). The IL-4, IL-5, and/or IL-13 receptor-binding portion of an IL-4, IL-5, and/or IL-13 protein, respectively, can be determined by incubating the protein with an isolated IL-4, IL-5, and/or IL-13 receptor, as appropriate, or a cell having an IL-4, IL-5, and/or IL-13 receptor on its surface, as appropriate. IL-4, IL-5, and/or IL-13 protein binding to purified IL-4, IL-5, and/or IL-13 receptor, respectively, can be determined using methods known in the art including Biacore® screening, confocal immunofluorescent microscopy, immunoprecipitation, gel chromatography, determination of inhibition of binding of antibodies that bind specifically to the IL-4, IL-5, and/or IL-13 binding domain of an IL-4, IL-5, and/or IL-13 receptor, ELISA using an IL-4, IL-5, and/or IL-13 receptor, respectively, labeled with a detectable tag such as an enzyme or chemiluminescent tag or yeast-2 hybrid technology. A Flt-3 ligand protein of the present invention can include at least a portion of a Flt-3 ligand protein that is capable of binding to Flt-3 receptor or stimulating Flt-3 receptor-bearing hematopoietic stem cells, early hematopoietic progenitor cells or immature lymphocytes. Flt-3 receptors are known to those of skill in the art, and are described in Drexler, *Leukemia*, vol. 10, pp. 588–599, 1996 (which is incorporated herein in its entirety by this reference). The Flt-3 receptor-binding portion of a Flt-3 ligand protein can be determined by incubating the protein with isolated Flt-3 receptor or a cell having a Flt-3 receptor on its surface. Flt-3 ligand protein binding to purified Flt-3 receptor can be determined using methods known in the art including Biacore® screening, confocal immunofluorescent microscopy, immunoprecipitation, gel chromatography, determination of inhibition of binding of antibodies that bind specifically to the Flt-3 ligand binding domain of a Flt-3 receptor, ELISA using a Flt-3 receptor labeled with a detectable tag such as an enzyme or chemiluminescent tag or yeast-2 hybrid technology. A CD40 and/or CD154 protein of the present invention can include at least a portion of a CD40 and/or CD154 protein that is capable of binding to a CD40 and/or CD154 receptor, respectively, or stimulating CD40 and/or CD154 receptor-bearing hematopoietic stem cells, early hematopoietic progenitor cells or immature lymphocytes. The CD40 and/or CD154 receptor-binding portion of a CD40 and/or CD154 protein can be determined by incubating the protein with isolated CD40 and/or CD154 receptor, as appropriate, or a cell having a CD40 and/or CD154 receptor on its surface, as appropriate. CD40 and/or CD154 protein binding to CD154 and/or CD40, respectively, can be determined using methods known in the art including Biacore® screening, confocal immunofluorescent microscopy, immunoprecipitation, gel chromatography, determination of inhibition of binding of antibodies that bind specifically to the CD40 and/or CD154 binding domain of CD40 and/or CD154, as appropriate, ELISA using a CD40 and/or CD154 labeled with a detectable tag such as an enzyme or chemiluminescent tag or yeast-2 hybrid technology.

The present invention also includes mimetopes of canine interleukin-4, canine or feline Flt-3 ligand, canine or feline CD40, canine or feline CD154, canine interleukin-5, canine interleukin-13, feline interferon alpha, or feline GM-CSF proteins of the present invention. As used herein, a mimetope of an immunoregulatory protein of the present invention refers to any compound that is able to mimic the activity of such a canine interleukin-4, canine or feline Flt-3 ligand, canine or feline CD40, canine or feline CD1 54, canine interleukin-5, canine interleukin-13, feline interferon alpha, or feline GM-CSF protein, respectively, often because the mimetope has a structure that mimics the particular protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and/or synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of an immunoregulatory protein of the present invention is a fusion protein that includes either a canine interleukin-4, canine or feline Flt-3 ligand, canine or feline CD40, canine or feline CD154, canine interleukin-5, canine interleukin-13, feline interferon alpha, or feline GM-CSF protein-containing domain, each attached to one or more fusion segments. Suitable fusion segments for use with the present invention include, but are not limited to, segments that can: link two or more immunoregulatory proteins of the present invention, to form multimeric forms of an immunoregulatory protein of the present invention; enhance a protein's stability; act as an immunopotentiator to enhance an immune response against an canine interleukin-4, canine or feline Flt-3 ligand, canine or feline CD40, canine or feline CD154, canine interleukin-5, canine interleukin-13, feline interferon alpha, or feline GM-CSF protein; and/or assist in purification of an canine interleukin-4, canine or feline Flt-3 ligand, canine or feline CD40, canine or feline CD154, canine interleukin-5, canine interleukin-13, feline interferon alpha, or feline GM-CSF protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the IL-4-containing domain, or the Flt-3 ligand-containing domain, or the CD40-containing domain, or the CD154-containing domain, or the IL-5-containing domain, or the IL-3-containing domain, or the IFNα-containing domain, or GM-CSF-containing domain, of a protein and can be susceptible to cleavage in order to enable straightforward recovery of either canine interleukin-4, canine or feline Flt-3 ligand, canine or feline CD40, canine or feline CD154, canine interleukin-5, canine interleukin-13, feline interferon alpha, or feline GM-CSF protein, respectively. Fusion proteins are preferably produced by culturing a recombinant cell transformed with a fusion nucleic acid molecule that encodes a protein including the fuision segment attached to either the carboxyl and/or amino terminal end of an canine interleukin-4-, canine or feline Flt-3 ligand-, canine or feline CD40-, canine or feline CD154-, canine interleukin-5-, canine interleukin-13-, feline interferon alpha-, or feline GM-CSF-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of -galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

A suitable fusion segment that links one IL-4 protein to another IL-4 protein, or one Flt-3 ligand protein to another Flt-3 ligand protein, or one CD40 protein to another CD40 protein, or one CD154 protein to another CD154 protein, or one IL-5 protein to another IL-5 protein to another IL-5 protein, or one IL-13 protein to another IL-13 protein, or one IFNα protein to another IFNα protein, or one GM-CSF protein to another GM-CSF protein, includes any amino acid sequence that enables such proteins to be linked while maintaining the biological function of either the canine interleukin-4, canine or feline Flt-3 ligand, canine or feline CD40, canine or feline CD154, canine interleukin-5, canine interleukin-13, feline interferon alpha, or feline GM-CSF, proteins, respectively. Selection of a suitable linker is dependent upon how many proteins are to be linked to form one multimeric molecule and from where on either the canine interleukin-4, canine or feline Flt-3 ligand, canine or feline CD40, canine or feline CD154, canine interleukin-5, canine interleukin-13, feline interferon alpha, or feline GM-CSF molecule the linker extends. Preferably, a linker fusion segment of the present invention comprises a peptide of from about 6 amino acid residues to about 40 residues, more preferably from about 6 residues to about 30 residues in length.

In another embodiment, an canine interleukin-4, canine or feline Flt-3 ligand, canine or feline CD40, canine or feline CD154, canine interleukin-5, canine interleukin-13, feline interferon alpha, or feline GM-CSF protein of the present invention also includes at least one additional protein segment that is capable of targeting either canine interleukin-4, canine or feline Flt-3 ligand, canine or feline CD40, canine or feline CD154, canine interleukin-5, canine interleukin-13, feline interferon alpha, or feline GM-CSF protein, respectively, to a desired cell or receptive molecule. Such a multivalent targeting protein can be produced by culturing a cell transformed with a nucleic acid molecule comprising two or more nucleic acid domains joined together in such a manner that the resulting nucleic acid molecule is expressed as a multivalent targeting protein containing a canine interleukin-4, canine or feline Flt-3 ligand, canine or feline CD40, canine or feline CD1 54, canine interleukin-5, canine interleukin-13, feline interferon alpha, or feline GM-CSF protein or portion thereof and/or at least one targeting compound capable of delivering the canine interleukin-4, canine or feline Flt-3 ligand, canine or feline CD40, canine or feline CD154, canine interleukin-5, canine interleukin-13, feline interferon alpha, or feline GM-CSF protein, respectively, to a desired site in an animal.

Examples of multivalent targeting proteins include, but are not limited to, a canine interleukin-4, canine or feline Flt-3 ligand, canine or feline CD40, canine or feline CD154, canine interleukin-5, canine interleukin-13, feline interferon alpha, or feline GM-CSF protein of the present invention attached to one or more compounds that can bind to a receptive molecule on the surface of a cell located in an area of an animal where regulation of an immune response is desired. One of skill in the art can select appropriate targeting fusion segments depending upon the cell or receptive molecule being targeted.

Another example of a multivalent protein of the present invention includes, but is not limited to, a canine interleukin-4, canine or feline Flt-3 ligand, canine or feline CD40, canine or feline CD154, canine interleukin-5, canine interleukin-13, feline interferon alpha, or feline GM-CSF protein of the present invention attached to one or more proteins that are potentially antigenic in mammals. Thus, immunogenicity of the potentially antigenic protein could be enhanced by administering to a mammal together with an immunoregulatory protein of the present invention.

A naturally-occurring variant of a canine interleukin-4, canine or feline Flt-3 ligand, canine or feline CD40, canine or feline CD154, canine interleukin-5, canine interleukin-13, feline interferon alpha, or feline GM-CSF protein of the present invention is preferably isolated from (including isolation of the natural protein or production of the protein by recombinant or synthetic techniques) from mammals, including but not limited to dogs (i.e., canids), cats (i.e., felids), horses (i.e., equids), humans, cattle, chinchillas, ferrets, goats, mice, minks, rabbits, raccoons, rats, sheep, squirrels, swine, chickens, ostriches, quail and/or turkeys as well as other furry animals, pets, zoo animals, work animals and/or food animals. Particularly preferred animals from which to isolate canine interleukin-4, canine or feline Flt-3 ligand, canine or feline CD40, canine or feline CD154, canine interleukin-5, canine interleukin-13, feline interferon alpha, or feline GM-CSF proteins are dogs, cats, horses and/or humans.

A preferred isolated protein of the present invention is a protein encoded by at least one of the following nucleic acid molecules:$nCaIL\text{-}4_{549}$, $nCaIL\text{-}4_{396}$, $nCaIL\text{-}4_{324}$, $nCaFlt3L_{1013}$, $nCaFlt3L_{882}$, $nCaFlt3L_{804}$, $nCaFlt3L_{828}$, $nCaFlt3L_{985}$, $nCaFlt3L_{1019}$, $nCaFlt3L_{93}$, $nCaFlt3L_{750}$, $nFeFlt3L_{395}$, $nFeFlt3L_{793}$, $nFeFlt3L_{942}$, $nFeFlt3L_{873}$, $nFeFlt3L_{795}$, $nCaCD40_{321}$, $nCaCD40_{1425}$, $nCaCD40_{822}$, $nCaCD40_{765}$, $nFeCD40_{336}$, $nCaCD154_{390}$, $nCaCD1541_{878}$, $nCaCD154_{780}$, $nCaCD154_{633}$, $nFeCD154_{885}$, $nFeCD154_{780}$, $nFeCD154_{633}$, $nCaIL\text{-}5_{610}$, $nCaIL\text{-}5_{402}$, $nCaIL\text{-}5_{345}$, $nCaIL\text{-}13_{166}$, $nCaIL\text{-}13_{272}$, $nCaIL\text{-}13_{278}$, $nCaIL\text{-}13_{1302}$, $nCaIL\text{-}13_{393}$, $nCaIL\text{-}13_{333}$, $nCaIL\text{-}13_{1269}$, $nCaIL\text{-}13_{390}$, $nCaIL\text{-}13_{330}$, $nFeIFN\alpha_{567a}$, $nFeIFN\alpha_{567b}$, $nFeIFN\alpha_{567c}$, $nFeIFN\alpha_{498a}$, $nFeIFN\alpha_{498b}$, $nFeIFN\alpha_{498c}$, $nFeIFN\alpha_{582d}$, $nFeIFN\alpha_{513d}$, $nFeIFN\alpha_{567e}$, $nFeIFN\alpha_{498e}$, $nFeGMCSF_{444}$, $nFeGMCSF_{432}$, $nFeGMCSF_{38}$, and/or allelic variants of any of these nucleic acid molecules. Also preferred is an isolated protein that is encoded by a nucleic acid molecule the having nucleic acid sequence SEQ ID NO:1, SEQ ID NO:4, SEQ ID NO:19, SEQ ID NO:6, SEQ ID NO:9, SEQ ID NO:22, SEQ ID NO:25, SEQ ID NO:28, SEQ ID NO:30, SEQ ID NO:33, SEQ ID NO:36, SEQ ID NO:41, SEQ ID NO:42, SEQ ID NO:43, SEQ ID NO:46, SEQ ID NO:48, SEQ ID NO:51, SEQ ID NO:52, SEQ ID NO:55, SEQ ID NO:57, SEQ ID NO:60, SEQ ID NO:63, SEQ ID NO:64, SEQ ID NO:67, SEQ ID NO:69, SEQ ID NO:72, SEQ ID NO:75, SEQ ID NO:77, SEQ ID NO:80, SEQ ID NO:83, SEQ ID NO:85, SEQ ID NO:88, SEQ ID NO:89, SEQ ID NO:90, SEQ ID NO:91, SEQ ID NO:94, SEQ ID NO:96, SEQ ID NO:99, SEQ ID NO:102, SEQ ID NO:104, SEQ ID NO:107, SEQ ID NO:110, SEQ ID NO:113, SEQ ID NO:116, SEQ ID NO:119, SEQ ID NO:122, SEQ ID NO:124, SEQ ID NO:155, SEQ ID NO:158, SEQ ID NO:161, SEQ ID NO:164, SEQ ID NO:167, and SEQ ID NO:170; and/or an allelic variant of such a nucleic acid molecule.

Translation of SEQ ID NO:1, the coding strand of $nCaIL\text{-}4_{549}$, yields a protein of about 132 amino acids, denoted herein as $PCaIL\text{-}4_{132}$, the amino acid sequence of which is presented in SEQ ID NO:2, assuming an open reading frame having an initiation codon spanning from nucleotide 43 through nucleotide 45 of SEQ ID NO:1 and a stop codon spanning from nucleotide 439 through nucleotide 441 of SEQ ID NO:1.

Translation of SEQ ID NO:6, the coding strand of $nCaFlt3L_{1013}$, yields a protein of about 294 amino acids, denoted herein as $PCaFlt3L_{294}$, the amino acid sequence of which is presented in SEQ ID NO:7, assuming an open reading frame having an initiation codon spanning from nucleotide 35 through nucleotide 37 of SEQ ID NO:6 and a stop codon spanning from nucleotide 917 through nucleotide 919 of SEQ ID NO:6.

Translation of SEQ ID NO:43, the coding strand for $nFeFlt3L_{942}$, yields a protein of about 291 amino acids, denoted herein as $PFeFlt3L_{291}$, the amino acid sequence of which is presented in SEQ ID NO:44, assuming an open reading frame having an initiation codon spanning from nucleotide 31 through nucleotide 33 of SEQ ID NO:43 and a stop codon spanning from nucleotide 904 through nucleotide 906 of SEQ ID NO:43.

Translation of SEQ ID NO:52, the coding strand for $nCaCD40_{1425}$, yields a protein of about 274 amino acids, denoted herein as $PCaCD40_{274}$, the amino acid sequence of which is presented in SEQ ID NO:53, assuming an open reading frame having an initation codon spanning from nucleotide 196 through nucleotide 198 of SEQ ID NO:52 and a stop codon spanning from about nucleotide 1018 through nucleotide 1020 of SEQ ID NO:52.

Translation of SEQ ID NO:60, the coding strand for $nFeCD40_{336}$, yields a protein of about 112 amino acids, denoted herein as $PFeCD40_{112}$, the amino acid sequence of which is presented in SEQ ID NO:61, assuming an open reading frame having an initiation codon spanning from nucleotide 1 through nucleotide 3 of SEQ ID NO:60.

Translation of SEQ ID NO:64, the coding strand for $nCaCD154_{1878}$, yields a protein of about 260 amino acids, denoted herein as $PCaCD154_{260}$, the amino acid sequence of which is presented in SEQ ID NO:65, assuming an open reading frame having an initiation codon spanning from nucleotide 284 through nucleotide 286 of SEQ ID NO:64 and a stop codon spanning from nucleotide 1064 through nucleotide 1066 of SEQ ID NO:64.

Translation of SEQ ID NO:72, the coding strand for $nFeCD154_{885}$, yields a protein of about 260 amino acids, denoted herein as $PFeCD154_{260}$, the amino acid sequence of which is presented in SEQ ID NO:73, assuming an open reading frame having an initiation codon spanning from nucleotide 29 through nucleotide 31 of SEQ ID NO:72, and a stop codon spanning from nucleotide 809 through nucleotide 811 of SEQ ID NO:72.

Translation of SEQ ID NO:80, the coding strand for $nCaIL\text{-}5_{610}$, yields a protein of about 134 amino acids, denoted herein as $PCaIL\text{-}5_{134}$, the amino acid sequence of which is presented in SEQ ID NO:81, assuming an open reading frame having an initiation codon spanning from nucleotide 29 through nucleotide 31 of SEQ ID NO:80, and a stop codon spanning from nucleotide 431 through nucleotide 433 of SEQ ID NO:80.

Translation of SEQ ID NO:91, the coding strand for $nCaIL\text{-}13_{1302}$, yields a protein of about 131 amino acids, denoted herein as $PCaIL\text{-}13_{131}$, the amino acid sequence of which is presented in SEQ ID NO:92, assuming an open reading frame having an initiation codon spanning from nucleotide 52 through nucleotide 54 of SEQ ID NO:91 and a stop codon spanning from nucleotide 445 through nucleotide 447 of SEQ ID NO:91.

Translation of SEQ ID NO:107, the coding strand for $nFeIFN\alpha_{567a}$, yields a protein of about 189 amino acids, denoted herein as $PFeIFN\alpha_{189a}$, the amino acid sequence of which is presented in SEQ ID NO:108, assuming an open reading frame having an initiation codon spanning from nucleotide 1 through nucleotide 3 and a last codon prior to a stop codon spanning from nucleotide 565 through nucleotide 567 of SEQ ID NO:107.

Translation of SEQ ID NO:110, the coding strand for $nFeIFN\alpha_{567b}$, yields a protein of about 189 amino acids, denoted herein as $PFeIFN\alpha_{189b}$, the amino acid sequence of which is presented in SEQ ID NO:111, assuming an open reading frame having an initiation codon spanning from nucleotide 1 through nucleotide 3 and a last codon prior to a stop codon spanning from nucleotide 565 through nucleotide 567 of SEQ ID NO:110.

Translation of SEQ ID NO:155, the coding strand for nFeIFN$\alpha_{567c}$, yields a protein of about 189 amino acids, denoted herein as PFeIFN$\alpha_{189c}$, the amino acid sequence of which is presented in SEQ ID NO:156, assuming an open reading frame having an initiation codon spanning from nucleotide 1 through nucleotide 3 and a last codon prior to a stop codon spanning from nucleotide 565 through nucleotide 567 of SEQ ID NO:155.

Translation of SEQ ID NO:161, the coding strand for nFeIFN$\alpha_{582d}$, yields a protein of about 194 amino acids, denoted herein as PFeIFN$\alpha_{194d}$, the amino acid sequence of which is presented in SEQ ID NO:162, assuming an open reading frame having an initiation codon spanning from nucleotide 1 through nucleotide 3 and a last codon prior to a stop codon spanning from nucleotide 565 through nucleotide 567 of SEQ ID NO:161.

Translation of SEQ ID NO:167, the coding strand for nFeIFN$\alpha_{567e}$, yields a protein of about 189 amino acids, denoted herein as PFeIFN$\alpha_{189e}$, the amino acid sequence of which is presented in SEQ ID NO:168, assuming an open reading frame having an initiation codon spanning from nucleotide 1 through nucleotide 3 and a last codon prior to a stop codon spanning from nucleotide 565 through nucleotide 567 of SEQ ID NO:167.

Translation of SEQ ID NO:119, the coding strand for nFeGMCSF$_{444}$, yields a protein of about 144 amino acids, denoted herein as PFeGMCSF$_{144}$, the amino acid sequence of which is presented in SEQ ID NO:120, assuming an open reading frame having an initiation codon spanning from nucleotide 10 through nucleotide 12 of SEQ ID NO:119 and a stop codon spanning from nucleotide 442 through nucleotide 444 of SEQ ID NO:119.

Preferred IL-4 proteins of the present invention include proteins that are at least about 85%, preferably at least about 90%, and even more preferably at least about 95% identical to PCaIL-4$_{132}$, PCaIL-4$_{108}$, or fragments thereof. Preferred Flt-3 ligand proteins of the present invention include proteins that are at least about 75%, even more preferably at least about 80%, even more preferably at least about 85%, even more preferably at least about 90%, and even more preferably at least about 95% identical to PCaFlt3L$_{294}$, PCaFlt3L$_{268}$, PCaFlt3L$_{276}$, PCaFlt3L$_{250}$, PCaFlt3L$_{31}$, and/or fragments thereof. Additional preferred Flt-3 ligand proteins of the present invention includes proteins that are at least about 75%, even more preferably at least about 80%, even more preferably at least about 85%, even more preferably at least about 90%, and even more preferably at least about 95% identical to PFeFlt3L$_{291}$, PFeFlt3L$_{265}$ and/or fragments thereof. Preferred CD40 proteins of the present invention includes proteins that are at least about 70%, preferably at least about 75%, even more preferably at least about 80%, even more preferably at least about 85%, even more preferably at least about 90%, and even more preferably at least about 95% identical to PCaCD40$_{274}$, PCaCD40$_{255}$ and/or fragments thereof Additional preferred CD40 proteins of the present invention includes proteins that are at least about 60%, at least about 65%, preferably at least about 70%, preferably at least about 75%, even more preferably at least about 80%, even more preferably at least about 85%, even more preferably at least about 90%, and even more preferably at least about 95% identical to PFeCD40$_{112}$ and/or fragments thereof. Preferred CD154 proteins of the present invention includes proteins that are at least about 80% identical, preferably at least about 85% identical, even more preferably at least about 90%, and even more preferably at least about 95% identical to PCaCD154$_{260}$, PCaCD154$_{211}$ and/or fragments thereof. Additional preferred CD154 proteins of the present invention includes proteins that are at least about 85% identical, even more preferably at least about 90%, and even more preferably at least about 95% identical to PFeCD154$_{260}$, PFeCD154$_{211}$ and/or fragments thereof. Preferred IL-5 proteins of the present invention includes proteins that are at least about 85% identical, even more preferably at least about 90%, and even more preferably at least about 95% identical to PCaIL-5$_{134}$, PCaIL-5$_{115}$ and/or fragments thereof Preferred IL-13 proteins of the present invention includes proteins that are at least about 70% identical, preferably at least about 75% identical, more preferably at least about 80% identical, more preferably at least about 85% identical, even more preferably at least about 90%, and even more preferably at least about 95% identical to PCaIL-13$_{131}$, PCaIL-13$_{111}$, PCaEL-13$_{130}$, PCaIL-13$_{110}$, and/or fragments thereof. Preferred IFN$\alpha$ proteins of the present invention include PFeIFN$\alpha_{189a}$, PFeIFN$\alpha_{189b}$, PFeIFN$\alpha_{189c}$, PFeIFN$\alpha_{166a}$, PFeIFN$\alpha_{166c}$, PFeIFN$\alpha_{194d}$, PFeIFN$\alpha_{171d}$, PFeIFN$\alpha_{189e}$, PFeIFN$\alpha_{166e}$, and/or PFeIFN$\alpha_{166b}$. Preferred GM-CSF proteins of the present invention include PFeGMCSF$_{144}$, and/or PFeGMCSF$_{127}$.

More preferred are IL-4 proteins comprising PCaIL-4$_{132}$, PCaIL-4$_{108}$, and/or proteins encoded by allelic variants of a nucleic acid molecule encoding proteins PCaIL-4$_{132}$ and/or PCaEL-4$_{108}$. More preferred are Flt-3 ligand proteins comprising PCaFlt3L$_{294}$, PCaFlt3L$_{268}$, PCaFlt3L$_{276}$, PCaFlt3L$_{250}$, PCaFlt3L$_{31}$, PFeFlt3L$_{291}$, PFeFlt3L$_{265}$ and/or proteins encoded by allelic variants of a nucleic acid molecule encoding proteins PCaFlt3L$_{294}$, PCaFlt3L$_{268}$, PCaFlt3L$_{276}$, PCaFlt3L$_{250}$ PCaFlt3L$_{31}$, PFeFlt3L$_{291}$, and/or PFeFlt3L$_{265}$. More preferred are CD40 proteins comprising PCaCD40$_{274}$, PCaCD40$_{255}$, and/or PFeCD40$_{112}$ and/or proteins encoded by allelic variants of a nucleic acid molecule encoding proteins PCaCD40$_{274}$, PCaCD40$_{255}$, and/or PFeCD40$_{112}$. More preferred are CD154 proteins comprising PCaCD154$_{260}$, PCaCD154$_{211}$, PFeCD154$_{260}$, PFeCD154$_{211}$ and/or proteins encoded by allelic variants of a nucleic acid molecule encoding one of proteins PCaCD154$_{260}$, PCaCD154$_{211}$ PFeCD154$_{260}$, PFeCD154$_{211}$. More preferred are IL-5 proteins comprising PCaEL-5$_{134}$, PCaIL-5$_{115}$ and/or proteins encoded by allelic variants of a nucleic acid molecule encoding one of the proteins PCaIL-5$_{134}$ and/or PCaIL-5$_{115}$. More preferred are IL-13 proteins comprising PCaIL-13$_{131}$, PCaIL-13$_{111}$, PCaIL-13$_{130}$, PCaIL-13$_{110}$, and/or proteins encoded by allelic variants of anucleic acid molecule encoding one of the proteins PCaIL-13$_{131}$, PCaIL-13$_{111}$, PCaIL-13$_{130}$, PCaIL-13$_{110}$.

Also preferred are IL-4 proteins of the present invention having amino acid sequences that are at least about 85%, preferably at least about 90%, and even more preferably at least about 95% identical to SEQ ID NO:2, SEQ ID NO:20 and/or fragments thereof Also preferred are Flt-3 ligand proteins of the present invention having amino acid sequences that are at least about 75%, even more preferably at least about 80%, even more preferably at least about 85%, even more preferably at least about 90%, and even more preferably at least about 95% identical to SEQ ID NO:7, SEQ ID NO:23, SEQ ID NO:26, SEQ ID NO:31, and/or SEQ ID NO:34 and/or fragments thereof. Additional preferred Flt-3 ligand proteins of the present invention includes proteins that are at least about 75%, even more preferably at least about 80%, even more preferably at least about 85%, even more preferably at least about 90%, and/or even more preferably at least about 95% identical to SEQ ID NO:44, SEQ ID NO:49 and/or fragments thereof. Preferred CD40 proteins of the present invention includes proteins that are at least about 70%, preferably at least about 75%, even more preferably at least about 80%, even more preferably at least about 85%, even more preferably at least about 90%, and/or even more preferably at least about 95% identical to SEQ ID NO:53, SEQ ID NO:58 and/or fragments thereof. Additional preferred CD40 proteins of the present invention includes proteins that are at least about 60%, at least about 65%, preferably at least about 70%, preferably at least about 75%, even more preferably at least about 80%, even more preferably at least about 85%, even more preferably at least about 90%, and even more preferably at least about 95% identical to SEQ ID NO:61 and/or fragments thereof. Preferred CD154 proteins of the present invention includes proteins that are at least about 80% identical, preferably at least about 85% identical, even more preferably at least about 90%, and even more preferably at least about 95% identical to SEQ ID NO:65, SEQ ID NO:70 and/or fragments thereof. Additional preferred CD154 proteins of the present invention includes proteins that are at least about 85% identical, even more preferably at least about 90%, and even more preferably at least about 95% identical to SEQ ID NO:73, SEQ ID NO:78 and/or fragments thereof. Preferred IL-5 proteins of the present invention includes proteins that are at least about 85% identical, even more preferably at least about 90%, and even more preferably at least about 95% identical to SEQ ID NO:81, SEQ ID NO:86 and/or fragments thereof. Preferred IL-13 proteins of the present invention includes proteins that are at least about 70% identical, preferably at least about 75% identical, more preferably at least about 80% identical, more preferably at least about 85% identical, even more preferably at least about 90%, and even more preferably at least about 95% identical to SEQ ID NO:92, SEQ ID NO:97, SEQ ID NO:100, SEQ ID NO:105, and/or fragments thereof. Preferred IFNα proteins of the present invention include SEQ ID NO:108, SEQ ID NO:111, SEQ ID NO:114, SEQ ID NO:117, SEQ ID NO:156, SEQ ID NO:159, SEQ ID NO:162, SEQ ID NO:165, SEQ ID NO:168, and SEQ ID NO:171. Preferred GM-CSF proteins of the present invention include SEQ ID NO:120, SEQ ID NO:125.

More preferred are IL-4 proteins comprising the amino acid sequence SEQ ID NO:2, SEQ ID NO:20; and/or L-4 proteins encoded by allelic variants of nucleic acid molecules encoding IL-4 proteins having the amino acid sequence SEQ ID NO:2, SEQ ID NO:20. More preferred are Flt-3 ligand proteins comprising SEQ ID NO:7, SEQ ID NO:23, SEQ ID NO:26, SEQ ID NO:31, and/or SEQ ID NO:34, SEQ ID NO:44, SEQ ID NO:49 and/or proteins encoded by allelic variants of a nucleic acid molecule encoding proteins SEQ ID NO:7, SEQ ID NO:23, SEQ ID NO:26, SEQ ID NO:31, SEQ ID NO:34, SEQ ID NO:44, and/or SEQ ID NO:49. More preferred are CD40 proteins comprising SEQ ID NO:53, SEQ ID NO:58 SEQ ID NO:61 and/or proteins encoded by allelic variants of a nucleic acid molecule encoding proteins SEQ ID NO:53, SEQ ID NO:58 and/or SEQ ID NO:61. More preferred are CD154 proteins comprising SEQ ID NO:65, SEQ ID NO:70 SEQ ID NO:73, SEQ ID NO:78 and/or proteins encoded by allelic variants of a nucleic acid molecule encoding one of proteins SEQ ID NO:65, SEQ ID NO:70, SEQ ID NO:73, and/or SEQ ID NO:78. More preferred are IL-5 proteins comprising SEQ ID NO:81, SEQ ID NO:86 and/or proteins encoded by allelic variants of a nucleic acid molecule encoding one of the proteins SEQ ID NO:81, and/or SEQ ID NO:86. More preferred are IL-13 proteins comprising SEQ ID NO:92, SEQ ID NO:97, SEQ ID NO:100, SEQ ID NO:105, and/or proteins encoded by allelic variants of anucleic acid molecule encoding one of the proteins SEQ ID NO:92, SEQ ID NO:97, SEQ ID NO:100, and/or SEQ ID NO:105.

Percent identities between amino acid or nucleic acid sequences can be determined using standard methods known to those of skill in the art. It is known in the art that methods to determine the percentage identity and the number of gaps are substantially similar when different methods for determining sequence similarity are used and when the degree of similarity is greater than 30% amino acid identity, as described by Johnson et al., *J. Mol. Biol.*, vol. 233, pages 716–738, 1993, and Feng et al., *J. Mol. Evol.*, vol. 21, pages 112–125, 1985, which are incorporated by reference herein in their entirety. Preferred methods to determine percentage identities between amino acid sequences and between nucleic acid sequences include comparisons using various computer programs such as GCG™ program (available from Genetics Computer Group, Madison, Wis.), DNAsis™ program (available from Hitachi Software, San Bruno, Calif.) or the MacVector™ program (available from the Eastman Kodak Company, New Haven, Conn.). Preferred settings for sequence comparisons using the DNAsis™ computer program or the GAP GCG™ program are disclosed herein in the Examples section.

Additional preferred L-4 proteins of the present invention include proteins encoded by nucleic acid molecules comprising at least a portion of $nCaIL\text{-}4_{549}$, $nCaIL\text{-}4_{396}$, and/or $nCaIL\text{-}4_{324}$, as well as IL-4 proteins encoded by allelic variants of such nucleic acid molecules. Additional preferred Flt-3 ligand proteins of the present invention include proteins encoded by nucleic acid molecules comprising at least a portion of $nCaFlt3L_{1013}$, $nCaFlt3L_{882}$, $nCaFlt3L_{804}$, $nCaFlt3L_{828}$, $nCaFlt3L_{985}$, $CaFlt3L_{109}$, $nCaFlt3L_{93}$, $nCaFlt3L_{750}$, $nFeFlt3L_{395}$, $nFeFlt3L_{793}$, $nFeFlt3L_{942}$, $nFeFlt3L_{873}$, and/or $nFeFlt3L_{795}$ as well as Flt-3 ligand proteins encoded by allelic variants of such nucleic acid molecules. Additional preferred CD40 proteins of the present invention include proteins encoded by nucleic acid molecules encoding at least a portion of $nCaCD40_{321}$, $nCaCD40_{1425}$, $nCaCD40_{822}$, $nCaCD40_{765}$, and/or $nFeCD40_{336}$ as well as CD40 proteins encoded by allelic variants of such nucleic acid molecules. Additional preferred CD154 proteins of the present invention include proteins encoded by nucleic acid molecules encoding at least a portion of $nCaCD154_{390}$, $nCaCD1541_{878}$, $nCaCD154_{780}$, $nCaCD154_{633}$, $nFeCD154_{885}$, $nFeCD154_{780}$, and/or $nFeCD154_{633}$ as well as CD154 proteins encoded by allelic variants of such nucleic acid molecules. Additional preferred IL-5 proteins of the present invention include proteins encoded by nucleic acid molecules encoding at least a portion of $nCaIL\text{-}5_{610}$, $nCaIL\text{-}5_{402}$, and/or $nCaIL\text{-}5_{345}$ as well as IL-5 proteins encoded by allelic variants of such nucleic acid molecules. Additional preferred IL-13 proteins of the present invention include proteins encoded by nucleic acid molecules encoding at least a portion of $nCaIL\text{-}5_{610}$, $nCaIL\text{-}5_{402}$, and/or $nCaIL\text{-}5_{345}$ as well as IL-13 proteins encoded by allelic variants of such nucleic acid molecules.

Also preferred are IL-4 proteins encoded by nucleic acid molecules having nucleic acid sequences comprising at least a portion of SEQ ID NO:1, SEQ ID NO:4, and/or SEQ ID NO:19, as well as allelic variants of these nucleic acid molecules. Also preferred are Flt-3 ligand proteins encoded by nucleic acid molecules having nucleic acid sequences comprising at least a portion of SEQ ID NO:6, SEQ ID NO:9, SEQ ID NO:22, SEQ ID NO:25, SEQ ID NO:28, SEQ ID NO:30, SEQ ID NO:33, SEQ ID NO:36, SEQ ID NO:41, SEQ ID NO:42, SEQ ID NO:43, SEQ ID NO:46, and/or SEQ ID NO:48, as well as allelic variants of these nucleic acid molecules. Also preferred are CD40 proteins encoded by nucleic acid molecules having nucleic acid sequences comprising at least a portion of SEQ ID NO:51, SEQ ID NO:52, SEQ ID NO:55, SEQ ID NO:57, and/or SEQ ID NO:60, as well as allelic variants of these nucleic acid molecules. Also preferred are CD154 proteins encoded by nucleic acid molecules having nucleic acid sequences comprising at least a portion of SEQ ID NO:63, SEQ ID NO:64, SEQ ID NO:67, SEQ ID NO:69, SEQ ID NO:72, SEQ ID NO:75, and/or SEQ ID NO:77, as well as allelic variants of these nucleic acid molecules. Also preferred are IL-5 proteins encoded by nucleic acid molecules having nucleic acid sequences comprising at least a portion of SEQ ID NO:80, SEQ ID NO:83, and/or SEQ ID NO:85, as well as allelic variants of these nucleic acid molecules. Also preferred are EL-13 proteins encoded by nucleic acid molecules having nucleic acid sequences comprising at least a portion of SEQ ID NO:88, SEQ ID NO:89, SEQ ID NO:90, SEQ ID NO:91, SEQ ID NO:94, SEQ ID NO:96, SEQ ID NO:99, SEQ ID NO:102, and/or SEQ ID NO:104, as well as allelic variants of these nucleic acid molecules.

Another embodiment of the present invention is a canine interleukin-4, canine or feline Flt-3 ligand, canine or feline CD40, canine or feline CD154, canine interleukin-5, canine interleukin-13, feline interferon alpha, or feline GM-CSF nucleic acid molecule that includes one or more regulatory regions, full-length or partial coding regions, or combinations thereof The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of a canine interleukin-4, canine or feline Flt-3 ligand, canine or feline CD40, canine or feline CD154, canine interleukin-5, canine interleukin-13, feline interferon alpha, or feline GM-CSF nucleic acid molecule of the present invention is from about 12 to about 18 nucleotides in length.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. An isolated canine interleukin-4, canine or feline Flt-3 ligand, canine or feline CD40, canine or feline CD154, canine interleukin-5, canine interleukin-13, feline interferon alpha, or feline GM-CSF nucleic acid molecule of the present invention can be isolated from its natural source or produced using recombinant DNA technology (e.g., polymerase chain reaction (PCR) amplification or cloning) or chemical synthesis. Isolated canine interleukin-4, canine or feline Flt-3 ligand, canine or feline CD40, canine or feline CD154, canine interleukin-5, canine interleukin-13, feline interferon alpha, and/or feline GM-CSF, nucleic acid molecules can include, for example, natural allelic variants and/or nucleic acid molecules modified by nucleotide insertions, deletions, substitutions, and/or inversions in a manner such that the modifications do not substantially interfere with the nucleic acid molecule's ability to encode an canine interleukin-4, canine or feline Flt-3 ligand, canine or feline CD40, canine or feline CD154, canine interleukin-5, canine interleukin-13, feline interferon alpha, and/or feline GM-CSF protein of the present invention.

A canine interleukin-4, canine or feline Flt-3 ligand, canine or feline CD40, canine or feline CD154, canine interleukin-5, canine interleukin-13, feline interferon alpha, and/or feline GM-CSF ligand nucleic acid molecule homolog can be produced using a number of methods known to those skilled in the art, see, for example, Sambrook et al., 1989*, Molecular Cloning: A Laboratory Manual*, Cold Spring Harbor Labs Press; Sambrook et al., ibid., is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologs can be selected by hybridization with either a canine interleukin-4, canine or feline Flt-3 ligand, canine or feline CD40, canine or feline CD154, canine interleukin-5, canine interleukin-13, feline interferon alpha, or feline GM-CSF nucleic acid molecule or by screening the function of a protein encoded by the nucleic acid molecule (e.g., ability to elicit an immune response against at least one epitope of a canine interleukin-4, canine or feline Flt-3 ligand, canine or feline CD40, canine or feline CD154, canine interleukin-5, canine interleukin-13, feline interferon alpha, or feline GM-CSF protein, respectively).

An isolated nucleic acid molecule of the present invention can include a nucleic acid sequence that encodes at least one canine interleukin-4, canine or feline Flt-3 ligand, canine or feline CD40, canine or feline CD154, canine interleukin-5, canine interleukin-13, feline interferon alpha, or feline GM-CSF protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a canine interleukin-4, canine or feline Flt-3 ligand, canine or feline CD40, canine or feline CD154, canine interleukin-5, canine interleukin-13, feline interferon alpha, or feline GM-CSF ligand protein.

A preferred nucleic acid molecule of the present invention, when administered to an animal, is capable of regulating an immune response in an animal. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode an immunoregulatory protein (e.g., a cell-bound or soluble protein of the present invention), the nucleic acid molecule being delivered to the animal, for example, by direct injection (i.e., as a genetic vaccine) or in a vehicle such as a recombinant virus vaccine or a recombinant cell vaccine.

One embodiment of the present invention is an IL-4 nucleic acid molecule comprising all or part (i.e., a fragment of the IL-4 nucleic acid molecule) of nucleic acid molecules $nCaIL-4_{549}$, $nCaIL-4_{396}$, and/or $nCaIL-4_{324}$, or allelic variants of these nucleic acid molecules. One embodiment of the present invention is a Flt-3 ligand nucleic acid molecule comprising all or part (i.e., a fragment of the Flt-3 ligand nucleic acid molecule) of nucleic acid molecules $nCaFlt3L_{1013}$, $nCaFlt3L_{882}$, $nCaFlt3L_{804}$, $nCaFlt3L_{828}$, $nCaFlt3L_{985}$, $nCaFlt3L_{1019}$, $nCaFlt3L_{93}$, $nCaFlt3L_{750}$, $nFeFlt3L_{395}$, $nFeFlt3L_{793}$, $nFeFlt3L_{942}$, $nFeFlt3L_{873}$, and/or $nFeFlt3L_{795}$, and/or allelic variants of these nucleic acid molecules. One embodiment of the present invention is a CD40 nucleic acid molecule comprising all or part (i.e. a fragment of the CD40 nucleic acid molecule) of nucleic acid molecules $nCaCD40_{321}$, $nCaCD40_{1425}$, $nCaCD40_{822}$, $nCaCD40_{765}$, and/or $nFeCD40_{336}$ and/or allelic variants of these nucleic acid molecules. One embodiment of the present invention is a CCD154 nucleic acid molecule comprising all or part of nucleic acid molecules $nCaCD154_{390}$, $nCaCD1541_{878}$, $nCaCD154_{780}$, $nCaCD154_{633}$, $nFeCD154_{885}$, $nFeCD154_{780}$, and/or $nFeCD154_{633}$, and/or allelic variants of these nucleic acid molecules. One embodiment of the present invention is an IL-5 nucleic acid molecule comprising all or part of nucleic acid molecules $nCaIL\text{-}5_{610}$, $nCaIL\text{-}5_{402}$, and/or $nCaIL\text{-}5_{345}$, and/or allelic variants of these nucleic acid molecules. One embodiment of the present invention is an IL-13 nucleic acid molecule comprising all or part of nucleic acid molecules $nCaIL\text{-}13_{166}$, $nCaIL\text{-}13_{272}$, $nCaIL\text{-}13_{278}$, $nCaIL\text{-}13_{1302}$, $nCaIL\text{-}13_{393}$, $nCaIL\text{-}13_{333}$, $nCaIL\text{-}13_{1269}$, $nCaIL\text{-}13_{390}$, and/or $nCaIL\text{-}13_{330}$, and/or allelic variants of these nucleic acid molecules. Another preferred nucleic acid molecule of the present invention includes at least a portion of (i.e., a fragment of the nucleic acid molecule) nucleic acid sequence SEQ ID NO:1, SEQ ID NO:3, SEQ ID NO:4, SEQ ID NO:5, SEQ ID NO:19, SEQ ID NO:21, SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, SEQ ID NO:37, SEQ ID NO:41, SEQ ID NO:42, SEQ ID NO:43, SEQ ID NO:45, SEQ ID NO:46, SEQ ID NO:47, SEQ ID NO:48, SEQ ID NO:50, SEQ ID NO:51, SEQ ID NO:52, SEQ ID NO:54, SEQ ID NO:55, SEQ ID NO:56, SEQ ID NO:57, SEQ ID NO:59, SEQ ID NO:60, SEQ ID NO:62, SEQ ID NO:63, SEQ ID NO:64, SEQ ID NO:66, SEQ ID NO:67, SEQ ID NO:68, SEQ ID NO:69, SEQ ID NO:71, SEQ ID NO:72, SEQ ID NO:74, SEQ ID NO:75, SEQ ID NO:76, SEQ ID NO:77, SEQ ID NO:79, SEQ ID NO:80, SEQ ID NO:82, SEQ ID NO:83, SEQ ID NO:84, SEQ ID NO:85, SEQ ID NO:87, SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, SEQ ID NO:106, SEQ ID NO:107, SEQ ID NO:109, SEQ ID NO:110, SEQ ID NO:112, SEQ ID NO:113, SEQ ID NO:115, SEQ ID NO:116, SEQ ID NO:118, SEQ ID NO:119, SEQ ID NO:121, SEQ ID NO:122, SEQ ID NO:123, SEQ ID NO:124, SEQ ID NO:126, SEQ ID NO:155, SEQ ID NO:157, SEQ ID NO:158, SEQ ID NO:160, SEQ ID NO:161, SEQ ID NO:163, SEQ ID NO:164, SEQ ID NO:166, SEQ ID NO:167, SEQ ID NO:169, SEQ ID NO:170, and/or SEQ ID NO:172, as well as allelic variants of nucleic acid molecules having these nucleic acid sequences. Such nucleic acid molecules can include nucleotides in addition to those included in the SEQ ID NOs, such as, but not limited to, a full-length gene, a full-length coding region, a nucleic acid molecule encoding a fusion protein, and/or a nucleic acid molecule encoding a multivalent therapeutic compound.

One embodiment of an isolated nucleic acid molecule of the present invention is a nucleic acid molecule that can be any of the following: (a) an isolated nucleic acid molecule comprising a nucleic acid sequence selected from the group consisting of SEQ ID NO:1, SEQ ID NO:3, SEQ ID NO:4, SEQ ID NO:5, SEQ ID NO:19, and/or SEQ ID NO:21 and/or a homolog thereof, wherein said homolog has an at least 50 contiguous nucleotide region identical in sequence to a 50 contiguous nucleotide region of a nucleic acid sequence selected from the group consisting of SEQ ID NO:1, SEQ ID NO:3, SEQ ID NO:4, SEQ ID NO:5, SEQ ID NO:19, and/or SEQ ID NO:21; (b) an isolated nucleic acid molecule comprising a nucleic acid sequence selected from the group consisting of SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ED NO:28, SEQ ID NO:29, SEQ ID NO:30, SEQ ID NO:32, SEQ ID NO:33, SEQ ID NO:35, SEQ ID NO:36, and/or SEQ ID NO:37, and/or a homolog thereof, wherein said homolog has an at least 40 contiguous nucleotide region identical in sequence to a 40 contiguous nucleotide region of a nucleic acid molecule having a nucleic acid sequence selected from the group consisting of SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, and/or SEQ ID NO:37; (c) an isolated nucleic acid molecule comprising a nucleic acid sequence selected from the group consisting of SEQ ID NO:41, SEQ ID NO:42, SEQ ID NO:43, SEQ ID NO:45, SEQ ID NO:46, SEQ ID NO:47, SEQ ID NO:48, and/or SEQ ID NO:50, and/or a homolog thereof, wherein said homolog has an at least 30 contiguous nucleotide region identical in sequence to a 30 contiguous nucleotide region of a nucleic acid molecule having a nucleic acid sequence selected from the group consisting of SEQ ID NO:41, SEQ ID NO:42, SEQ ID NO:43, SEQ ID NO:45, SEQ ID NO:46, SEQ ID NO:47, SEQ ID NO:48, and/or SEQ ID NO:50; (d) an isolated nucleic acid molecule comprising a nucleic acid sequence selected from the group consisting of SEQ ID NO:51, SEQ ID NO:52, SEQ ID NO:54, SEQ ID NO:55, SEQ ID NO:56, SEQ ID NO:57, and/or SEQ ID NO:59, and/or a homolog thereof, wherein said homolog has an at least 40 contiguous nucleotide region identical in sequence to a 40 contiguous nucleotide region of a nucleic acid molecule having a nucleic acid sequence selected from the group consisting of SEQ ID NO:51, SEQ ID NO:52, SEQ ID NO:54, SEQ ID NO:55, SEQ ID NO:56, SEQ ID NO:57, and/or SEQ ID NO:59; (e) an isolated nucleic acid molecule comprising a nucleic acid sequence selected from the group consisting of SEQ ID NO:60 and/or SEQ ID NO:62, and/or a homolog thereof, wherein said homolog has an at least 30 contiguous nucleotide region identical in sequence to a 30 contiguous nucleotide region of a nucleic acid molecule having a nucleic acid sequence selected from the group consisting of SEQ ID NO:60 and/or SEQ ID NO:62; (f) an isolated nucleic acid molecule comprising a nucleic acid sequence selected from the group consisting of SEQ ID NO:63, SEQ ID NO:64, SEQ ID NO:66, SEQ ID NO:67, SEQ ID NO:68, SEQ ID NO:69 and/or SEQ ID NO:71, and/or a homolog thereof, wherein said homolog has an at least 45 contiguous nucleotide region identical in sequence to a 45 contiguous nucleotide region of a nucleic acid molecule having a nucleic acid sequence selected from the group consisting of SEQ ID NO:63, SEQ ID NO:64, SEQ ID NO:66, SEQ ID NO:67, SEQ ID NO:68, SEQ ID NO:69 and/or SEQ ID NO:71; (g) an isolated nucleic acid molecule comprising a nucleic acid sequence selected from the group consisting of SEQ ID NO:72, SEQ ID NO:74, SEQ ID NO:75, SEQ ID NO:76, SEQ ID NO:77, and/or SEQ ID NO:79, and/or a homolog thereof, wherein said homolog has an at least 35 contiguous nucleotide region identical in sequence to a 35 contiguous nucleotide region of a nucleic acid molecule having a nucleic acid sequence selected from the group consisting of SEQ ID NO:72, SEQ ID NO:74, SEQ ID NO:75, SEQ ID NO:76, SEQ ID NO:77, and/or SEQ ID NO:79; (h) an isolated nucleic acid molecule comprising a nucleic acid sequence selected from the group consisting of SEQ ID NO:80, SEQ ID NO:82, SEQ ID NO:83, SEQ ID NO:84, SEQ ID NO:85, and/or SEQ ID NO:87, and/or a homolog thereof, wherein said homolog has an at least 45 contiguous nucleotide region identical in sequence to a 45 contiguous nucleotide region of a nucleic acid molecule having a nucleic acid sequence selected from the group consisting of SEQ ID NO:80, SEQ ID NO:82, SEQ ID NO:83, SEQ ID NO:84, SEQ ID NO:85, and/or SEQ ID NO:87; (i) an isolated nucleic acid molecule comprising a nucleic acid sequence selected from the group consisting of SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, and/or SEQ ID NO:106, and/or a homolog thereof, wherein said homolog has an at least 15 contiguous nucleotide region identical in sequence to a 15 contiguous nucleotide region of a nucleic acid molecule having a nucleic acid sequence selected from the group consisting of SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, and/or SEQ ID NO:106; (j) an isolated nucleic acid molecule having a nucleic acid sequence selected from the group consisting of SEQ ID NO:107, SEQ ID NO:109, SEQ ID NO:110, SEQ ID NO:112, SEQ ID NO:113, SEQ ID NO:115, SEQ ID NO:116, SEQ ID NO:118, SEQ ID NO:155, SEQ ID NO:157, SEQ ID NO:158, SEQ ID NO:160, SEQ ID NO:161, SEQ ID NO:163, SEQ ID NO:164, SEQ ID NO:166, SEQ ID NO:167, SEQ ID NO:169, SEQ ID NO:170 and/or SEQ ID NO:172; and/or (k) an isolated nucleic acid molecule having a nucleic acid sequence selected from the group consisting of SEQ ID NO:119, SEQ ID NO:121, SEQ ID NO:122, SEQ ID NO:123, SEQ ID NO:124, and/or SEQ ID NO:126. The phrase, a homolog having an at least "x" contiguous nucleotide region identical in sequence to an "x" contiguous nucleotide region of a nucleic acid molecule selected from the group consisting of SEQ ID NO:"y", refers to an "x"-nucleotide in length nucleic acid molecule that is identical in sequence to an "x"-nucleotide portion of SEQ ID NO:"y", as well as to nucleic acid molecules that are longer in length than "x". The additional length may be in the form of nucleotides that extend from either the 5' or the 3' end(s) of the contiguous identical "x"-nucleotide portion. The 5' and/or 3' extensions can include one or more extensions that have no identity to an immunoregulatory molecule of the present invention, as well as extensions that show similarity or identity to cited nucleic acids sequences or portions thereof.

In another embodiment, an isolated nucleic acid molecule of the present invention can be any of the following: (a) a nucleic acid molecule having a nucleic acid sequence encoding an IL-4 protein selected from the group consisting of (i) a protein having an amino acid sequence that is at least about 85 percent identical to an amino acid sequence selected from the group consisting of SEQ ID NO:2 and/or SEQ ID NO:20 and/or (ii) a protein comprising a fragment of at least 20 amino acids of an amino acid sequence selected from the group consisting of SEQ ID NO:2 and/or SEQ ID NO:20; (b) a nucleic acid molecule having a nucleic acid sequence encoding a Flt-3 ligand protein selected from the group consisting of (i) a protein having an amino acid sequence that is at least about 75 percent identical to an amino acid sequence selected from the group consisting of SEQ ID NO:7, SEQ ID NO:23, SEQ ID NO:26, SEQ ID NO:31, and/or SEQ ID NO:34, and/or (ii) a protein comprising a fragment of at least 25 amino acids of an amino acid sequence selected from the group consisting of SEQ ID NO:7, SEQ ID NO:23, SEQ ID NO:26, SEQ ID NO:3 1, and/or SEQ ID NO:34; (c) a nucleic acid molecule having a nucleic acid sequence encoding a Flt-3 ligand protein selected from the group consisting of (i) a protein having an amino acid sequence that is at least about 75 percent identical to an amino acid sequence selected from the group consisting of SEQ ID NO:44 and/or SEQ ID NO:49 and/or (ii) a protein comprising a fragment of at least 25 amino acids of an amino acid sequence selected from the group consisting of SEQ ID NO:44 and/or SEQ ID NO:49; (d) a nucleic acid molecule having a nucleic acid sequence encoding a CD40 protein selected from the group consisting of (i) a protein having an amino acid sequence that is at least about 70 percent identical to an amino acid sequence selected from the group consisting of SEQ ID NO:53 and/or SEQ ID NO:58 and/or (ii) a protein comprising a fragment of at least 30 amino acids of an amino acid sequence selected from the group consisting of SEQ ID NO:53 and/or SEQ ID NO:58; (e) a nucleic acid molecule having a nucleic acid sequence encoding a CD40 protein selected from the group consisting of (i) a protein having an amino acid sequence that is at least about 60 percent identical to an amino acid sequence comprising SEQ ID NO:61 and/or (ii) a protein comprising a fragment of at least 20 amino acids of an amino acid sequence comprising SEQ ID NO:61; (f) a nucleic acid molecule having a nucleic acid sequence encoding a CD154 protein selected from the group consisting of (i) a protein having an amino acid sequence that is at least about 80 percent identical to an amino acid sequence selected from the group consisting of SEQ ID NO:65 and/or SEQ ID NO:70, and/or (ii) a protein comprising a fragment of at least 35 amino acids of an amino acid sequence selected from the group consisting of SEQ ID NO:65 and/or SEQ ID NO:70; (g) a nucleic acid molecule having a nucleic acid sequence encoding a CD154 protein selected from the group consisting of (i) a protein having an amino acid sequence that is at least about 85 percent identical to an amino acid sequence selected from the group consisting of SEQ ID NO:73 and/or SEQ ID NO:78, and/or (ii) a protein comprising a fragment of at least 50 amino acids of an amino acid sequence selected from the group consisting of SEQ ID NO:73 and/or SEQ ID NO:78; (h) a nucleic acid molecule having a nucleic acid sequence encoding an IL-5 protein selected from the group consisting of (i) a protein having an amino acid sequence that is at least about 85 percent identical to an amino acid sequence selected from the group consisting of SEQ ID NO:81 and/or SEQ ID NO:86 and/or (ii) a protein comprising a fragment of at least 20 amino acids of an amino acid sequence selected from the group consisting of SEQ ID NO:81 and/or SEQ ID NO:86; (i) a nucleic acid molecule having a nucleic acid sequence encoding an IL-13 protein selected from the group consisting of (i) a protein having an amino acid sequence that is at least about 70 percent identical to an amino acid sequence selected from the group consisting of SEQ ID NO:92, SEQ ID NO:97, SEQ ID NO:100, and/or SEQ ID NO:105 and/or (ii) a protein comprising a fragment of at least 15 amino acids of an amino acid sequence selected from the group consisting of SEQ ID NO:92, SEQ ID NO:97, SEQ ID NO:100, and/or SEQ ID NO:105; (j) a nucleic acid molecule having a nucleic acid sequence encoding an interferon alpha protein having an amino acid sequence that is selected from the group consisting of amino acid sequence SEQ ID NO:108, SEQ ID NO:111, SEQ ID NO:114, SEQ ID NO:117, SEQ ID NO:156, SEQ ID NO:159, SEQ ID NO:162, SEQ ID NO:165, SEQ ID NO:168, and/or SEQ ID NO:171; (k) a nucleic acid molecule having a nucleic acid sequence encoding a GMCSF protein having an amino acid sequence that is selected from the group consisting of amino acid sequence SEQ ID NO:120, SEQ ID NO:125, and/or (l) a nucleic acid molecule comprising a complement of any of the before-mentioned nucleic acid sequences; wherein said IL-4 protein elicits an immune response against an IL-4 protein selected from the group consisting of SEQ ID NO:2 and/or SEQ ID NO:20 and/or is a protein with interleukin-4 activity, said Flt-3 ligand protein elicits an immune response against a Flt-3 ligand protein selected from the group consisting of SEQ ID NO:7, SEQ ID NO:23, SEQ ID NO:26, SEQ ID NO:31, SEQ ID NO:34, SEQ ID NO:44, and/or SEQ ID NO:49 and/or is a protein with Flt-3 ligand activity, said CD40 protein elicits an immune response against a CD40 protein selected from the group consisting of SEQ ID NO:53, SEQ ID NO:58, and/or SEQ ID NO:61 and/or is a protein with CD40 activity, said CD154 protein elicits an immune response against a CD154 protein selected from the group consisting of SEQ ID NO:65, SEQ ID NO:70, SEQ ID NO:73, and/or SEQ ID NO:78 and/or is a protein with CD154 activity, said IL-5 protein elicits an immune response against a IL-5 protein selected from the group consisting of SEQ ID NO:81 and/or SEQ ID NO:86 and/or is a protein with IL-5 activity, said IL-13 protein elicits an immune response against an IL-13 protein selected from the group consisting of SEQ ID NO:92, SEQ ID NO:97, SEQ ID NO:100, and/or SEQ ID NO:105 and/or is a protein with IL-13 activity, said interferon alpha protein elicits an immune response against an interferon alpha protein selected from the group consisting of SEQ ID NO:108, SEQ ID NO:111, SEQ ID NO:114, SEQ ID NO:117, SEQ ID NO:156, SEQ ID NO:159, SEQ ID NO:162, SEQ ID NO:165, SEQ ID NO:168, and/or SEQ ID NO:171 and/or is a protein with interferon alpha activity, and said GMCSF protein elicits an immune response against a GMCSF protein selected from the group consisting of SEQ ID NO:120 and/or SEQ ID NO:125 and/or is a protein with GM-CSF activity.

In one embodiment, an IL-4 nucleic acid molecule of the present invention encodes a protein that is at least about 85%, preferably at least about 90%, preferably at least about 92%, and even more preferably at least about 95% identical to PCaIL-$4_{132}$ and/or PCaIL-$4_{108}$ In one embodiment, a Flt-3 ligand nucleic acid molecule of the present invention encodes a protein that is at least about 75%, even more preferably at least about 80%, even more preferably at least about 85%, even more preferably at least about 90%, and even more preferably at least about 95% identical to $PCaFlt3L_{294}$, $PCaFlt3L_{268}$, $PCaFlt3L_{276}$, $PCaFlt3L_{250}$, and/or $PCaFlt3L_{31}$. In one embodiment, a Flt-3 ligand nucleic acid molecule of the present invention encodes a protein that is at least about 75%, more preferably at least about 80%, even more preferably at least about 85%, even more preferably at least about 90%, and even more preferably at least about 95% identical to $PFeFlt3L_{291}$, and/or $PFeFlt3L_{265}$. In one embodiment, a CD40 nucleic acid molecule of the present invention encodes a protein that is at least about $PCaCD40_{274}$, and/or $PCaCD40_{255}$. In one embodiment, a CD40 nucleic acid molecule of the present invention encodes a protein that is at least about 60%, preferably at least about 65%, preferably at least about 70%, preferably at least about 75%, even more preferably at least about 80%, even more preferably at least about 85%, even more preferably at least about 90%, and even more preferably at least about 95% identical to $PFeCD40_{112}$. In one embodiment, a CD154 nucleic acid molecule of the present invention encodes a protein that is at least about 80%, at least about 85%, more preferably at least about 90%, and even more preferably at least about 95% identical to $PCaCD154_{260}$, and/or $PCaCD154_{211}$. In one embodiment, a CD154 nucleic acid molecule of the present invention encodes a protein that is at least about 85%, more preferably at least about 90%, and even more preferably at least about 95% identical to $PFeCD154_{260}$, $PFeCD154_{211}$. In one embodiment, an IL-5 nucleic acid molecule of the present invention encodes a protein that is at least about 85%, more preferably at least about 90%, and even more preferably at least about 95% identical to PCaIL-$5_{134}$, and/or PCaIL-$5_{115}$. In one embodiment, an IL-13 nucleic acid molecule of the present invention encodes a protein that is at least about 70%, at least about 75%, at least about 80%, preferably at least about 85%, more preferably at least about 90%, and even more preferably at least about 95% identical to PCaIL-$13_{131}$, PCaIL-$13_{111}$, PCaIL-$13_{130}$, PCaIL-$13_{110}$. Even more preferred is a nucleic acid molecule encoding PCaIL-$4_{132}$, PCaIL-$4_{108}$, $PCaFlt3L_{294}$, $PCaFlt3L_{268}$, $PCaFlt3L_{276}$, $PCaFlt3L_{250}$, $PCaFlt3L_{31}$, $PFeFlt3L_{291}$, PFeFlt3L265, $PCaCD40_{274}$, $PCaCD40_{255}$, $PFeCD40_{112}$, $PCaCD154_{260}$, $PCaCD154_{211}$, $PFeCD154_{260}$, $PFeCD154_{211}$, PCaIL-$5_{134}$, PCaIL-$5_{115}$, PCaIL-$13_{131}$, PCaIL-$13_{111}$, PCaIL-$13_{130}$, PCaIL-$13_{110}$ and/or an allelic variant of such a nucleic acid molecule.

In another embodiment, an IL-4 nucleic acid molecule of the present invention encodes a protein having an amino acid sequence that is at least about 85%, preferably at least about 90%, and even more preferably at least about 95% identical to SEQ ID NO:2, SEQ ID NO:20. The present invention also includes an IL-4 nucleic acid molecule encoding a protein having at least a portion of SEQ ID NO:2, and/or SEQ ID NO:20, as well as allelic variants of an IL-4 nucleic acid molecule encoding a protein having these sequences, including nucleic acid molecules that have been modified to accommodate codon usage properties of the cells in which such nucleic acid molecules are to be expressed.

In another embodiment, a Flt-3 ligand nucleic acid molecule of the present invention encodes a protein having an amino acid sequence that is at least about 75%, even more preferably at least about 80%, even more preferably at least about 85%, even more preferably at least about 90%, and even more preferably at least about 95% identical to SEQ ID NO:7, SEQ ID NO:23, SEQ ID NO:26, SEQ ID NO:31, and/or SEQ ID NO:34. The present invention also includes a Flt-3 ligand nucleic acid molecule encoding a protein having at least a portion of SEQ ID NO:7, SEQ ID NO:23, SEQ ID NO:26, SEQ ID NO:31, and/or SEQ ID NO:34, as well as allelic variants of a Flt-3 ligand nucleic acid molecule encoding a protein having these sequences, including nucleic acid molecules that have been modified to accommodate codon usage properties of the cells in which such nucleic acid molecules are to be expressed.

In another embodiment, a Flt-3 ligand nucleic acid molecule of the present invention encodes a protein having an amino acid sequence that is at least about 75%, more preferably at least about 80%, even more preferably at least about 85%, even more preferably at least about 90%, and even more preferably at least about 95% identical to SEQ ID NO:44, and/or SEQ ID NO:49. The present invention also includes a Flt-3 ligand nucleic acid molecule encoding a protein having at least a portion of SEQ ID NO:44, and/or SEQ ID NO:49, as well as allelic variants of a Flt-3 ligand nucleic acid molecule encoding a protein having these sequences, including nucleic acid molecules that have been modified to accommodate codon usage properties of the cells in which such nucleic acid molecules are to be expressed.

In another embodiment, a CD40 nucleic acid molecule of the present invention encodes a protein having an amino acid sequence that is at least about 70%, preferably at least about 75%, even more preferably at least about 80%, even more preferably at least about 85%, even more preferably at least about 90%, and even more preferably at least about 95% identical to SEQ ID NO:53 and/or SEQ ID NO:58. The present invention also includes a CD40 nucleic acid molecule encoding a protein having at least a portion of SEQ ID NO:53 and/or SEQ ID NO:58, as well as allelic variants of a CD40 nucleic acid molecule encoding a protein having these sequences, including nucleic acid molecules that have been modified to accommodate codon usage properties of the cells in which such nucleic acid molecules are to be expressed.

In another embodiment, a CD40 nucleic acid molecule of the present invention encodes a protein having an amino acid sequence that is at least about 60%, preferably at least about 65%, preferably at least about 70%, preferably at least about 75%, even more preferably at least about 80%, even more preferably at least about 85%, even more preferably at least about 90%, and even more preferably at least about 95% identical to SEQ ID NO:60. The present invention also includes a CD40 nucleic acid molecule encoding a protein having at least a portion of SEQ ID NO:60, as well as allelic variants of a CD40 nucleic acid molecule encoding a protein having these sequences, including nucleic acid molecules that have been modified to accommodate codon usage properties of the cells in which such nucleic acid molecules are to be expressed.

In another embodiment, a CD154 nucleic acid molecule of the present invention encodes a protein having an amino acid sequence that is at least about at least about 80%, at least about 85%, more preferably at least about 90%, and even more preferably at least about 95% identical to SEQ ID NO:63, SEQ ID NO:64, SEQ ID NO:67, and/or SEQ ID NO:69. The present invention also includes a CD154 nucleic acid molecule encoding a protein having at least a portion of SEQ ID NO:63, SEQ ID NO:64, SEQ ID NO:67, and/or SEQ ID NO:69, as well as allelic variants of a CD154 nucleic acid molecule encoding a protein having these sequences, including nucleic acid molecules that have been modified to accommodate codon usage properties of the cells in which such nucleic acid molecules are to be expressed.

In another embodiment, a CD154 nucleic acid molecule of the present invention encodes a protein having an amino acid sequence that is at least about at least about 85%, more preferably at least about 90%, and even more preferably at least about 95% identical to SEQ ID NO:72, SEQ ID NO:75, and/or SEQ ID NO:77. The present invention also includes a CD154 nucleic acid molecule encoding a protein having at least a portion of SEQ ID NO:72, SEQ ID NO:75, and/or SEQ ID NO:77, as well as allelic variants of a CD154 nucleic acid molecule encoding a protein having these sequences, including nucleic acid molecules that have been modified to accommodate codon usage properties of the cells in which such nucleic acid molecules are to be expressed.

In another embodiment, an IL-5 nucleic acid molecule of the present invention encodes a protein having an amino acid sequence that is at least about at least about 85%, at least about 85%, more preferably at least about 90%, and even more preferably at least about 95% identical to SEQ ID NO:80, SEQ ID NO:83, and/or SEQ ID NO:85. The present invention also includes an IL-5 nucleic acid molecule encoding a protein having at least a portion of SEQ ID NO:80, SEQ ID NO:83, and/or SEQ ID NO:85, as well as allelic variants of an IL-5 nucleic acid molecule encoding a protein having these sequences, including nucleic acid molecules that have been modified to accommodate codon usage properties of the cells in which such nucleic acid molecules are to be expressed.

In another embodiment, an IL-13 nucleic acid molecule of the present invention encodes a protein having an amino acid sequence that is at least about at least about 70%, at least about 75%, at least about 80%, preferably at least about 85%, more preferably at least about 90%, and even more preferably at least about 95% identical to SEQ ID NO:88, SEQ ID NO:89, SEQ ID NO:90, SEQ ID NO:91, SEQ ID NO:94, SEQ ID NO:96, SEQ ID NO:99, SEQ ID NO:102, and/or SEQ ID NO:104. The present invention also includes an IL-13 nucleic acid molecule encoding a protein having at least a portion of SEQ ID NO:88, SEQ ID NO:89, SEQ ID NO:90, SEQ ID NO:91, SEQ ID NO:94, SEQ ID NO:96, SEQ ID NO:99, SEQ ID NO:102, and/or SEQ ID NO:104, as well as allelic variants of an IL-13 nucleic acid molecule encoding a protein having these sequences, including nucleic acid molecules that have been modified to accommodate codon usage properties of the cells in which such nucleic acid molecules are to be expressed.

In one embodiment, an IL-4 nucleic acid molecule of the present invention is at least about 90%, and preferably at least about 95% identical to nCaIL-$4_{549}$. Even more preferred is a nucleic acid molecule comprising nCaIL-$4_{549}$, nCaIL-$4_{396}$, nCaIL-$4_{324}$, and/or an allelic variant of such a nucleic acid molecule. In another embodiment, a Flt-3 ligand nucleic acid molecule of the present invention is at least about 75%, more preferably at least about 80%, more preferably at least about 85%, more preferably at least about 90% and even more preferably at least about 95% identical to nCaFlt3$L_{1013}$. Even more preferred is a nucleic acid molecule comprising nCaFlt3$L_{1013}$, nCaFlt3$L_{882}$, nCaFlt3$L_{804}$, nCaFlt3$L_{828}$, nCaFlt3$L_{985}$, nCaFlt3$L_{1019}$, nCaFlt3$L_{93}$, and/or nCaFlt3$L_{750}$, and/or an alleic variant of such a nucleic acid molecule. In one embodiment, a Flt-3 ligand nucleic acid molecule of the present invention is at least about 75%, more preferably at least about 80%, more preferably at least about 85%, more preferably at least about 90% and even more preferably at least about 95% identical to nFeFlt3$L_{942}$. Even more preferred is a nucleic acid molecule comprising nFeFlt3$L_{395}$, nFeFlt3$L_{793}$, nFeFlt3$L_{942}$, nFeFlt3$L_{873}$, and/or nFeFlt3$L_{795}$, and/or an allelic variant of such a nucleic acid molecule. In one embodiment, a CD40 nucleic acid molecule of the present invention is at least about 70%, at least about 75%, more preferably at least about 80%, more preferably at least about 85%, more preferably at least about 90% and even more preferably at least about 95% identical to nCaCD$40_{321}$, nCaCD$40_{1425}$, nCaCD$40_{822}$, and/or nCaCD$40_{765}$, and/or an allelic variant of such a nucleic acid molecule. In one embodiment, a CD40 nucleic acid molecule of the present invention is at least about 70%, at least about 75%, more preferably at least about 80%, more preferably at least about 85%, more preferably at least about 90% and even more preferably at least about 95% identical to nFeCD$40_{336}$, and/or an allelic variant of such a nucleic acid molecule. In one embodiment, a CD154 nucleic acid molecule of the present invention is at least about 85%, preferably at least about 85%, more preferably at least about 90% and even more preferably at least about 95% identical to $nCaCD154_{390}$, $nCaCD154_{878}$, $nCaCD154_{780}$, and/or $nCaCD1541_{633}$, and/or an allelic variant of such a nucleic acid molecule. In one embodiment, a CD154 nucleic acid molecule of the present invention is at least about 91%, and preferably about 95% identical to $nFeCD154_{885}$, $nFeCD154_{780}$, and/or $nFeCD154_{633}$, and/or an allelic variant of such a nucleic acid molecule. In one embodiment, an IL-5 molecule of the present invention is at least about 90% and preferably at least about 95% identical to nCaIL-$5_{610}$, nCaIL-$5_{402}$, and/or nCaIL-$5_{345}$, and/or an allelic variant of such a nucleic acid molecule. In another embodiment, an IL-13 molecule of the present invention is at least about 65%, at least about 70%, preferably at least about 75%, more preferably at least about 80%, more preferably at least about 85%, more preferably at least about 90% and even more preferably at least about 95% identical to nCaIL-$13_{166}$, nCaIL-$13_{272}$, nCaIL-$13_{278}$, nCaIL-$13_{1302}$, nCaIL-$13_{393}$, nCaIL-$13_{333}$, nCaIL-$13_{1269}$, nCaIL-$13_{390}$, and/or nCaIL-$13_{330}$, and/or an allelic variant of such a nucleic acid molecule.

In another embodiment, an IL-4 nucleic acid molecule of the present invention comprises a nucleic acid sequence that is at least about 90%, and preferably at least about 95% identical to SEQ ID NO:1, SEQ ID NO:3, SEQ ID NO:4, SEQ ID NO:5, SEQ ID NO:19, and/or SEQ ID NO:21. The present invention also includes an IL-4 nucleic acid molecule comprising at least a portion of SEQ ID NO:1, SEQ ID NO:3, SEQ ID NO:4, SEQ ID NO:5, SEQ ID NO:19, and/or SEQ ID NO:21, as well as allelic variants of such IL-4 nucleic acid molecules, including nucleic acid molecules that have been modified to accommodate codon usage properties of the cells in which such nucleic acid molecules are to be expressed.

In another embodiment, a Flt-3 ligand nucleic acid molecule of the present invention comprises a nucleic acid sequence that is at least about 75%, preferably at least about 80%, more preferably at least about 85%, more preferably at least about 90% and even more preferably at least about 95% identical to SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, and/or SEQ ID NO:37. The present invention also includes a Flt-3 ligand- nucleic acid molecule comprising at least a portion of SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, and/or SEQ ID NO:37, as well as allelic variants of such Flt-3 ligand nucleic acid molecules, including nucleic acid molecules that have been modified to accommodate codon usage properties of the cells in which such nucleic acid molecules are to be expressed.

In one embodiment, a Flt-3 ligand nucleic acid molecule of the present invention comprises a nucleic acid sequence that is at least about 75%, more preferably at least about 80%, more preferably at least about 85%, more preferably at least about 90% and even more preferably at least about 95% identical to SEQ ID NO:41, SEQ ID NO:42, SEQ ID NO:43, SEQ ID NO:45, SEQ ID NO:46, SEQ ID NO:47, SEQ ID NO:48, and/or SEQ ID NO:50. The present invention also includes a Flt-3 ligand- nucleic acid molecule comprising at least a portion of SEQ ID NO:41, SEQ ID NO:42, SEQ ID NO:43, SEQ ID NO:45, SEQ ID NO:46, SEQ ID NO:47, SEQ ID NO:48, and/or SEQ ID NO:50, as well as allelic variants of such Flt-3 ligand nucleic acid molecules, including nucleic acid molecules that have been modified to accommodate codon usage properties of the cells in which such nucleic acid molecules are to be expressed.

In one embodiment, a CD40 nucleic acid molecule of the present invention comprises a nucleic acid sequence that is at least about 70%, at least about 75%, more preferably at least about 80%, more preferably at least about 85%, more preferably at least about 90% and even more preferably at least about 95% identical to SEQ ID NO:51, SEQ ID NO:52, SEQ ID NO:54, SEQ ID NO:55, SEQ ID NO:56, SEQ ID NO:57, and/or SEQ ID NO:59. The present invention also includes a CD40 nucleic acid molecule comprising at least a portion of SEQ ID NO:51, SEQ ID NO:52, SEQ ID NO:54, SEQ ID NO:55, SEQ ID NO:56, SEQ ID NO:57, and/or SEQ ID NO:59, as well as allelic variants of such CD40 nucleic acid molecules, including nucleic acid molecules that have been modified to accommodate codon usage properties of the cells in which such nucleic acid molecules are to be expressed.

In one embodiment, a CD40 nucleic acid molecule of the present invention comprises a nucleic acid sequence that is at least about 70%, at least about 75%, more preferably at least about 80%, more preferably at least about 85%, more preferably at least about 90% and even more preferably at least about 95% identical to SEQ ID NO:60 and/or SEQ ID NO:62. The present invention also includes a CD40 nucleic acid molecule comprising at least a portion of SEQ ID NO:60 and/or SEQ ID NO:62, as well as allelic variants of such CD40 nucleic acid molecules, including nucleic acid molecules that have been modified to accommodate codon usage properties of the cells in which such nucleic acid molecules are to be expressed.

In one embodiment, a CD154 nucleic acid molecule of the present invention comprises a nucleic acid sequence that is at least about 85%, preferably at least about 85%, more preferably at least about 90% and even more preferably at least about 95% identical to SEQ ID NO:63, SEQ ID NO:64, SEQ ID NO:66, SEQ ID NO:67, SEQ ID NO:68, SEQ ID NO:69, and/or SEQ ID NO:71. The present invention also includes a CD154 nucleic acid molecule comprising at least a portion of SEQ ID NO:63, SEQ ID NO:64, SEQ ID NO:66, SEQ ID NO:67, SEQ ID NO:68, SEQ ID NO:69, and/or SEQ ID NO:71, as well as allelic variants of such CD154 nucleic acid molecules, including nucleic acid molecules that have been modified to accommodate codon usage properties of the cells in which such nucleic acid molecules are to be expressed.

In one embodiment, a CD154 nucleic acid molecule of the present invention comprises a nucleic acid sequence that is at least about 91%, and preferably about 95% identical to SEQ ID NO:72, SEQ ID NO:74, SEQ ID NO:75, SEQ ID NO:76, SEQ ID NO:77, and/or SEQ ID NO:79. The present invention also includes a CD154 nucleic acid molecule comprising at least a portion of SEQ ID NO:72, SEQ ID NO:74, SEQ ID NO:75, SEQ ID NO:76, SEQ ID NO:77, and/or SEQ ID NO:79, as well as allelic variants of such CD154 nucleic acid molecules, including nucleic acid molecules that have been modified to accommodate codon usage properties of the cells in which such nucleic acid molecules are to be expressed.

In one embodiment, an IL-5 nucleic acid molecule of the present invention comprises a nucleic acid sequence that is at least about 90% and preferably at least about 95% identical to SEQ ID NO:80, SEQ ID NO:82, SEQ ID NO:83, SEQ ID NO:84, SEQ ID NO:85, and/or SEQ ID NO:87. The present invention also includes an IL-5 nucleic acid molecule comprising at least a portion of SEQ ID NO:80, SEQ ID NO:82, SEQ ID NO:83, SEQ ID NO:84, SEQ ID NO:85, and/or SEQ ID NO:87, as well as allelic variants of such IL-5 nucleic acid molecules, including nucleic acid molecules that have been modified to accommodate codon usage properties of the cells in which such nucleic acid molecules are to be expressed.

In one embodiment, an IL-13 nucleic acid molecule of the present invention comprises a nucleic acid sequence that is at least about 65%, at least about 70%, preferably at least about 75%, more preferably at least about 80%, more preferably at least about 85%, more preferably at least about 90% and even more preferably at least about 95% identical to SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, and/or SEQ ID NO:106. The present invention also includes an IL-13 nucleic acid molecule comprising at least a portion of SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:94, SEQ ID NO:102, SEQ ID NO:103, SEQ ID NO:104, and/or SEQ ID NO:106, as well as allelic variants of such IL-13 nucleic acid molecules, including nucleic acid molecules that have been modified to accommodate codon usage properties of the cells in which such nucleic acid molecules are to be expressed.

In one embodiment, an IFNα nucleic acid molecule of the present invention is identical to SEQ ID NO:107, SEQ ID NO:109, SEQ ID NO:110, SEQ ID NO:112, SEQ ID NO:113, SEQ ID NO:115, SEQ ID NO:116, SEQ ID NO:118, SEQ ID NO:155, SEQ ID NO:157, SEQ ID NO:158, SEQ ID NO:160, SEQ ID NO:161, SEQ ID NO:163, SEQ ID NO:164, SEQ ID NO:166, SEQ ID NO:167, SEQ ID NO:169, SEQ ID NO:170, and/or SEQ ID NO:172.

In another embodiment, a GM-CSF nucleic acid molecule of the present invention is identical to SEQ ID NO:119, SEQ ID NO:121, SEQ ID NO:122, SEQ ID NO:123, SEQ ID NO:124, and/or SEQ ID NO:126.

Knowing the nucleic acid sequences of certain immunoregulatory nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and/or (c) obtain other immunoregulatory nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include mammalian cDNA libraries as well as genomic DNA libraries. Similarly, preferred DNA sources from which to amplify nucleic acid molecules include mammalian cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising canine interleukin-4, canine or feline Flt-3 ligand, canine or feline CD40, canine or feline CD154, canine interleukin-5, canine interleukin-13, feline interferon alpha, or feline GM-CSF nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of about 100 nucleotides. The present invention includes oligonucleotides that can be used as, for example, probes to identify nucleic acid molecules, primers to produce nucleic acid molecules, or therapeutic reagents to inhibit canine interleukin-4, canine or feline Flt-3 ligand, canine or feline CD40, canine or feline CD154, canine interleukin-5, canine interleukin-13, feline interferon alpha, or feline GM-CSF protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating immunoregulatory nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, insect and mammalian cells, and more preferably in the cell types disclosed herein, more preferably in vivo.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth and/or other endoparasite, insect and mammalian cells, such as, but not limited to, tac, lac, trp, trc, oxy-pro, omp/lpp, rmB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with mammals, such as dog, cat, horse or human transcription control sequences.

Suitable and preferred nucleic acid molecules to include in recombinant vectors of the present invention are as disclosed herein. Preferred nucleic acid molecules to include in recombinant vectors, and particularly in recombinant molecules, include nCaIL-$4_{549}$, nCaIL-$4_{396}$, nCaIL-$4_{324}$, nCaFlt3$L_{1013}$, nCaFlt3$L_{882}$, nCaFlt3$L_{804}$, nCaFlt3$L_{828}$, nCaFlt3$L_{985}$, nCaFlt3$L_{1019}$, nCaFlt3$L_{93}$, nCaFlt3$L_{750}$, nFeFlt3$L_{395}$, nFeFlt3$L_{793}$, nFeFlt3$L_{942}$, nFeFlt3$L_{873}$, nFeFlt3$L_{795}$, nCaCD$40_{321}$, nCaCD$40_{1425}$, nCaCD$40_{822}$, nCaCD$40_{765}$, nFeCD$40_{336}$, nCaCD$154_{390}$, nCaCD$1541_{878}$, nCaCD$154_{780}$, nCaCD$154_{633}$, nFeCD$154_{885}$, nFeCD$154_{780}$, nFeCD$154_{633}$, nCaIL-$5_{610}$, nCaIL-$5_{402}$, nCaIL-$5_{345}$, nCaIL-$13_{166}$, nCaIL-$13_{272}$, nCaIL-$13_{278}$, nCaIL-$13_{1302}$, nCaIL-$13_{393}$, nCaIL-$13_{333}$, nCaIL-$13_{1269}$, nCaIL-$13_{390}$, nCaIL-$13_{330}$, nFeIFN$\alpha_{567a}$, nFeIFN$\alpha_{567b}$, nFeIFN$\alpha_{567c}$, nFeIFN$\alpha_{498a}$, nFeIFN$\alpha_{498b}$, nFeIFN$\alpha_{498c}$, nFeIFN$\alpha_{582d}$, nFeIFN$\alpha_{513d}$, nFeIFN$\alpha_{567e}$, nFeIFN$\alpha_{498e}$, nFeGMCS$F_{444}$, nFeGMCS$F_{432}$, and/or nFeGMCS$F_{381}$.

Recombinant molecules of the present invention may also (a) contain secretory signals (i.e., signal segment nucleic acid sequences) to enable an expressed parasitic helminth protein of the present invention to be secreted from the cell that produces the protein and/or (b) contain fuision sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include immunoregulatory nucleic acid molecules of the present invention disclosed herein. Particularly preferred nucleic acid molecules with which to transform a cell include nCaIL-$4_{549}$, nCaIL-$4_{396}$, nCaIL-$4_{324}$, nCaFlt3$L_{1013}$, nCaFlt3$L_{882}$, nCaFlt3$L_{804}$, nCaFlt$3_{828}$, nCaFlt3$L_{985}$, nCaFlt3$L_{1019}$, nCaFlt3$L_{93}$, nCaFlt3$L_{750}$, nFeFlt3$L_{395}$, nFeFlt3$L_{793}$, nFeFlt3$L_{942}$, nFeFlt3$L_{873}$, nFeFlt3$L_{795}$, nCaCD$40_{321}$, nCaCD$40_{1425}$, nCaCD$40_{822}$, nCaCD$40_{765}$, nFeCD$40_{336}$, nCaCD$154_{390}$, nCaCD$1541_{878}$, nCaCD$154_{780}$, nCaCD$154_{633}$, nFeCD$154_{885}$, nFeCD$154_{780}$, nFeCD$154_{633}$, nCaIL-$5_{610}$, nCaIL-$5_{402}$, nCaIL-$5_{345}$, nCaIL-$13_{166}$, nCaIL-$13_{272}$, nCaIL-$13_{278}$, nCaIL-$13_{1302}$, nCaIL-$13_{393}$, nCaIL-$13_{333}$, nCaIL-$13_{1269}$, nCaIL-$13_{390}$, nCaIL-$13_{330}$, nFeIFN$\alpha_{567a}$, nFeIFN$\alpha_{567b}$, nFeIFN$\alpha_{567c}$, nFeIFN$\alpha_{498a}$, nFeIFN$\alpha_{498b}$, nFeIFN$\alpha_{498c}$, nFeIFN$\alpha_{528d}$, nFeIFN$\alpha_{513d}$, nFeIFN$\alpha_{567e}$, nFeIFN$\alpha_{498e}$, nFeGMCS$F_{444}$, nFeGMCS$F_{432}$, and/or nFeGMCS$F_{381}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing immunoregulatory proteins of the present invention or can be capable of producing such proteins after being transformed with at least one nucleic acid molecule of the present invention. Host cells of the present invention can be any cell capable of producing at least one protein of the present invention, and include bacterial, fingal (including yeast), parasite (including helminth, protozoa and ectoparasite), other insect, other animal and plant cells. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, chinese hamster ovary (CHO) cells, Ltk cells and Vero cells. Particularly preferred host cells are *Escherichia coli*, including *E. coli* K-12 derivatives; *Salmonella typhi*; *Salmonella typhimurium*, including attenuated strains such as UK-1 $_0$3987 and SR-11 $_0$4072; *Spodoptera frugiperda*; Trichoplusia ni; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including any of canine interleukin-4, canine or feline Flt-3 ligand, canine or feline CD40, canine or feline CD154, canine interleukin-5, canine interleukin-13, feline interferon alpha, or feline GM-CSF nucleic acid molecule encoding one or more proteins of the present invention and/or one or more other nucleic acid molecules encoding other therapeutic compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgamo sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated immunoregulatory proteins of the present invention can be produced in a variety of ways, including production and/or recovery of natural proteins, production and/or recovery of recombinant proteins, and/or chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce an immunoregulatory protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and/or differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to an immunoregulatory protein of the present invention and/ ora mimetope thereof (e.g., anti-IL-4 antibodies, anti-Flt-3 ligand antibodies, anti-CD40 antibodies, anti-CD154 antibodies, anti-IL-5 antibodies, anti-IL-13 antibodies, anti-IFNα antibodies, and/or anti-GM-CSF antibodies). As used herein, the term "selectively binds to" an immunoregulatory protein of the present invention, refers to the ability of antibodies of the present invention to preferentially bind to specified proteins and/or mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual*, Cold Spring Harbor Labs Press; Harlow et al., ibid., is incorporated by this reference herein in its entirety. An anti-IL-4 antibody of the present invention preferably selectively binds to an IL-4 protein in such a way as to inhibit the function of that protein. An anti-Flt-3 ligand antibody of the present invention preferably selectively binds to a Flt-3 ligand- protein in such a way as to inhibit the function of that protein. An anti-CD40 antibody of the present invention preferably selectively binds to a CD40 protein in such a way as to inhibit the function of that protein. An anti-CD154 antibody of the present invention preferably selectively binds to a CD154 protein in such a way as to inhibit the function of that protein. An anti-IL-5 antibody of the present invention preferably selectively binds to an IL-5 protein in such a way as to inhibit the function of that protein. An anti-IL-13 antibody of the present invention preferably selectively binds to an IL-13 protein in such a way as to inhibit the function of that protein. An anti-IFNα antibody of the present invention preferably selectively binds to an IFNα protein in such a way as to inhibit the function of that protein. An anti-GM-CSF antibody of the present invention preferably selectively binds to a GM-CSF protein in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and/or genetically-engineered antibodies, including single chain antibodies or chimeric antibodies that can bind to one or more epitopes.

A preferred method to produce antibodies of the present invention includes (a) administering to an animal an effective amount of a protein, peptide and/ormimetope thereof of the present invention to produce the antibodies and (b) recovering the antibodies. In another method, antibodies of the present invention are produced recombinantly using techniques as heretofore disclosed to produce any of the immunoregulatory proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as reagents in assays to detect an immunoregulatory protein of the present invention, (b) as reagents in assays to modulate cellular activity through an immunoregulatory protein of the present invention (e.g., mimicking ligand binding to a canine interleukin-4, canine or feline Flt-3 ligand, canine or feline CD40, canine or feline CD154, canine interleukin-5, canine interleukin-13, feline interferon alpha, or feline GM-CSF protein, as appropriate), and/or (c) as tools to screen expression libraries and/or to recover desired proteins of the present invention from a mixture of proteins and other contaminants. Furthermore, antibodies of the present invention can be used to target compounds (e.g., nucleic acid molecules, drugs or proteins) to antigen presenting cells. Targeting can be accomplished by conjugating (i.e., stably joining) such antibodies to the compounds using techniques known to those skilled in the art. Suitable compounds are known to those skilled in the art.

One embodiment of the present invention is a therapeutic composition that, when administered to an animal in an effective manner, is capable of regulating an immune response in an animal. Therapeutic compositions of the present invention can include at least one of the following therapeutic compounds: an isolated IL-4, Flt-3 ligand, CD40, CD154, IL-5, IL-13, IFNα, and/or GM-CSF protein of the present invention and/or a mimetope thereof; an isolated IL-4, Flt-3 ligand, CD40, CD154, IL-5, IL-13, IFNα, and/or GM-CSF nucleic acid molecule of the present invention; an isolated antibody that selectively binds to an IL-4, Flt-3 ligand, CD40, CD154, IL-5, IL-13, IFNα, and/or GM-CSF protein of the present invention; an inhibitor of canine IL-4, Flt-3 ligand, CD40, CD154, IL-5, IL-1 3, IFNα, and/or GM-CSF function identified by its ability to bind to an IL-4, Flt-3 ligand, CD40, CD154, IL-5, IL-13, IFNα, and/or GM-CSF protein, respectively, of the present invention; such an inhibitor can inhibit binding of the respective immunoregulatory protein with its respective receptor, or inhibit the activity the respective protein. Methods to perform such assays to measure binding and/or activity of an immunoregulatory protein of the present invention are known to those of skill in the art, and are described, for example, in Janeway et al., ibid. As used herein, a therapeutic compound refers to a compound that, when administered to an animal in an effective manner, is able to treat, ameliorate, and/or prevent a disease. Examples of proteins, nucleic acid molecules, antibodies and/or inhibitors of the present invention are disclosed herein.

The present invention also includes a therapeutic composition comprising at least one IL-4-, Flt-3 ligand-, CD40-, CD154-, IL-5-, IL-13-, IFNα-, and/or GM-CSF-based compound of the present invention in combination with at least one additional therapeutic compound. Examples of such compounds are disclosed herein.

Therapeutic compositions of the present invention can be administered to any animal susceptible to such therapy, preferably to mammals, and more preferably to dogs, cats, humans, ferrets, horses, cattle, sheep and/or other pets, economic food animals and/or zoo animals. Preferred animals include dogs, cats, horses and/or humans.

A therapeutic composition of the present invention is administered to an animal in an effective manner such that the composition is capable of regulating an immune response in that animal. Therapeutic compositions of the present invention can be administered to animals prior to onset of a disease (i.e., as a preventative vaccine) and/or can be administered to animals after onset of a disease in order to treat the disease (i.e., as a therapeutic vaccine). Preferred diseases to prevent and/or treat include autoimmune diseases, allergic reactions, infectious diseases, tumor development, inflammatory diseases and/or graft rejection. In one embodiment, a therapeutic composition of the present invnetion is administered with an antigen to enhance an immune response against that antigen.

Therapeutic compositions of the present invention can be formulated in an excipient that the animal to be treated can tolerate. Examples of such excipients include water, saline, Ringer's solution, dextrose solution, Hank's solution, and/or other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and/or Tris buffer, while examples of preservatives include thimerosal, o-cresol, formalin and/or benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and/or compounds that induce the production of cytokines and/or chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 5 (IL-5), interleukin 6 (IL-6), interleukin 7 (IL-7), interleukin 8 (IL-8), interleukin 10 (IL-10), interleukin 12 (IL-1 2), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to regulate an immune response in an animal. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Therapeutic compositions of the present invention can be administered to animals prior to and/or after onset of disease. Acceptable protocols to administer therapeutic compositions in an effective manner include individual dose size, number of doses, frequency of dose administration, and/or mode of administration. Determination of such protocols can be accomplished by those skilled in the art. A suitable single dose is a dose that is capable of regulating the immune response in an animal when administered one or more times over a suitable time period. For example, a preferred single dose of a protein, mimetope or antibody therapeutic composition is from about 1 microgram ($\mu$g) to about milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, intraoccular, oral, transdermal and/or intramuscular routes.

According to one embodiment, a nucleic acid molecule of the present invention can be administered to an animal in a fashion to enable expression of that nucleic acid molecule into a therapeutic protein or therapeutic RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid as a genetic vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. Preferred genetic vaccines include at least a ortion of a viral genome (i.e., a viral vector). Preferred viral vectors include those based on alphaviruses, poxviruses, adenoviruses, herpesviruses, picomaviruses, and/or retroviruses, with those based on alphaviruses (such as sindbis or Semliki forest virus), species-specific herpesviruses and/or poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, with intramuscular, subcutaneous, intradermal, transdermal, intranasal and/or oral routes of administration being preferred. A preferred single dose of a genetic vaccine ranges from about 1 nanogram (ng) to about 600 $\mu$g, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picomaviruses, and/or retroviruses. Preferred recombinant virus vaccines are those based on alphaviruses (such as Sindbis virus), raccoon poxviruses, species-specific herpesviruses and/or species-specific poxviruses. An example of methods to produce and use alphavirus recombinant virus vaccines are disclosed in U.S. Pat. No. 5,766,602 by Xiong et al., issued Jun. 16, 1998, which is incorporated by this reference herein in its entirety.

When administered to an animal, a recombinant virus vaccine of the present invention infects cells within the immunized animal and directs the production of a therapeutic protein or RNA nucleic acid molecule that is capable of protecting the animal from disease caused by a parasitic helminth as disclosed herein. For example, a recombinant virus vaccine comprising an immunoregulatory nucleic acid molecule of the present invention is administered according to a protocol that results in the regulation of an immune response in an animal. A preferred single dose of a recombinant virus vaccine of the present invention is from about $1\times10^4$ to about $1\times10^8$ virus plaque forming units (pfu) per kilogram body weight of the animal. Administration protocols are similar to those described herein for protein-based vaccines, with subcutaneous, intramuscular, intranasal, intraocular and/or oral administration routes being preferred.

A recombinant cell vaccine of the present invention includes recombinant cells of the present invention that express at least one protein of the present invention. Preferred recombinant cells for this embodiment include Salmonella, *E. coli*, Listeria, Mycobacterium, *S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to regulate the immune response in an animal can be tested in a variety of ways including, but not limited to, detection of cellular immunity within the treated animal, determining lymphocyte or dendritic cell activity, detection of immunoglobulin levels, determining hematopoietic stem cell or hematopoietic early progenitor cell development, determining dendritic cell development or challenge of the treated animal with an infectious agent to determine whether the treated animal is resistant to disease. In one embodiment, therapeutic compositions can be tested in animal models such as mice. Such techniques are known to those skilled in the art.

One embodiment of the present invention is an inhibitory compound. Preferably, such an inhibitory compound is derived from an IL-4, Flt-3 ligand, CD40, CD154, IL-5, IL-13, IFNα, and/or GM-CSF protein of the present invention. Examples of inhibitory compounds include an antibody of the present invention, that is administered to an animal in an effective manner (i.e., is administered in an amount so as to be present in the animal at a titer that is sufficient, upon interaction of that antibody with a native IL-4, Flt-3 ligand, CD40, CD154, IL-5, IL-13, IFNα, and/or GM-CSF protein, to decrease the activity of such proteins in an animal, at least temporarily). Oligonucleotide nucleic acid molecules of the present invention can also be administered in an effective manner, thereby reducing expression of either an IL-4, Flt-3 ligand, CD40, CD154, IL-5, IL-13, IFNα, and/or GM-CSF protein, in order to interfere with the protein activity targeted in accordance with the present invention. Peptides of an IL-4, Flt-3 ligand, CD40, CD154, IL-5, IL-13, IFNα, and/or GM-CSF protein of the present invention can also be administered in an effective manner, thereby reducing binding of IL-4, Flt-3 ligand, CD40, CD154, IL-5, IL-13, IFNα, and/or GM-CSF proteins to the appropriate receptor, in order to interfere with the protein activity targeted in accordance with the present invention. An inhibitory compound of an IL-4, Flt-3 ligand, CD40, CD154, IL-5, IL-13, IFNα, and/or GM-CSF function can be identified using IL-4, Flt-3 ligand, CD40, CD154, IL-5, IL-13, IFNα, and/or GM-CSF proteins of the present invention, respectively.

One embodiment of the present invention is a method to identify a compound capable of inhibiting IL-4 function. Such a method includes the steps of: (a) contacting (e.g., combining, mixing) an isolated IL-4 protein of the present invention, with a putative inhibitory compound under conditions in which, in the absence of the compound, the IL-4 protein binds to IL-4 receptor or stimulates T cells in a T cell proliferation assay, and (b) determining if the putative inhibitory compound inhibits the binding of IL-4 protein to IL-4 receptor or the stimulation of T cells in a T cell proliferation assay. Another embodiment of the present invention is a method to identify a compound capable of inhibiting Flt-3 ligand function. Such a method includes the steps of: (a) contacting an isolated Flt-3 ligand protein of the present invention, with a putative inhibitory compound under conditions in which, in the absence of the compound, the Flt-3 ligand protein binds to Flt-3 receptor or stimulates dendritic precursor cells in a proliferation assay, and (b) determining if the putative inhibitory compound inhibits the binding of Flt-3 ligand protein to Flt-3 receptor or the stimulation of dendritic precursor cells in a proliferation assay. Another embodiment of the present invention is a method to identify a compound capable of inhibiting CD40 function. Such a method includes the steps of (a) contacting an isolated CD40 protein of the present invention, with a putative inhibitory compound under conditions in which, in the absence of the compound, the CD40 protein binds to a CD40 binding partner (e.g., CD154) and (b) determining if the putative inhibitory compound inhibits the binding of CD40 protein to the CD40 binding partner. A CD40 binding partner is a molecule that selectively binds to CD40 protein. Likewise, a binding partner for any other immunoregulatory protein of the present invention includes molecules that selectively bind to that particular immunoregulatory protein. Another embodiment of the present invention is a method to identify a compound capable of inhibiting CD154 function. Such a method includes the steps of (a) contacting an isolated CD154 protein of the present invention, with a putative inhibitory compound under conditions in which, in the absence of the compound, the CD154 protein binds to a CD154 binding partner (e.g., CD40) and (b) determining if the putative inhibitory compound inhibits the binding of CD154 protein to the CD154 binding partner. Yet another embodiment of the present invention is a method to identify a compound capable of inhibiting IL-5 function. Such a method includes the steps of: (a) contacting an isolated IL-5 protein of the present invention, with a putative inhibitory compound under conditions in which, in the absence of the compound, the IL-5 protein binds to IL-5 receptor or stimulates T cells in a T cell proliferation assay, and (b) determining if the putative inhibitory compound inhibits the binding of IL-5 protein to IL-5 receptor or the stimulation of T cells in a T cell proliferation assay. Another embodiment of the present invention is a method to identify a compound capable of inhibiting IL-13 function. Such a method includes the steps of: (a) contacting an isolated IL-13 protein of the present invention, with a putative inhibitory compound under conditions in which, in the absence of the compound, the IL-13 protein binds to IL-13 receptor or stimulates T cells in a T cell proliferation assay, and (b) determining if the putative inhibitory compound inhibits the binding of IL-13 protein to IL-13 receptor or the stimulation of T cells in a T cell proliferation assay. Another embodiment of the present invention is a method to identify a compound capable of inhibiting IFNα function. Such a method includes the steps of: (a) contacting an isolated IFNα protein of the present invention, with a putative inhibitory compound under conditions in which, in the absence of the compound, the IFNA protein binds to IFNα receptor or inhibits proliferation of GM-CSF stimulated TF-1 cells, and (b) determining if the putative inhibitory compound inhibits the binding of IFNα protein to IFNα receptor or inhibits proliferation of GM-CSF stimulated TF-1 cells. Another embodiment of the present invention is a method to identify a compound capable of inhibiting GM-CSF function. Such a method includes the steps of: (a) contacting an isolated GM-CSF protein of the present invention, with a putative inhibitory compound under conditions in which, in the absence of said compound, the GM-CSF protein binds to GM-CSF receptor or stimulates T cells in a T cell proliferation assay, and (b) determining if the putative inhibitory compound inhibits the binding of GM-CSF protein to GM-CSF receptor or the stimulation of T cells in a T cell proliferation assay.

Putative inhibitory compounds to screen include small organic molecules, antibodies (including mimetopes thereof), and/or ligand analogs. Such compounds are also screened to identify those that are substantially not toxic in host animals.

Preferred IL-4, Flt-3 ligand, CD40, CD154, IL-5, IL-1 3, IFNα, and/or GM-CSF, proteins to inhibit are those produced by dogs, cats, horses or humans, even more preferred IL-4, Flt-3 ligand, CD40, CD154, IL-5, IL-13, IFNα, and/or GM-CSF proteins to inhibit are those produced by domestic dogs or cats. A particularly preferred inhibitor of the present invention is capable of regulating an immune response in an animal. It is also within the scope of the present invention to use inhibitors of the present invention to target diseases involving undesired immune activity in animals. Compositions comprising inhibitors of IL-4, Flt-3 ligand, CD40, CD154, IL-5, IL13, IFNα, and/or GM-CSF function can be administered to animals in an effective manner to regulate the immune response in the animals, and preferably to prevent autoimmune disease, allergy, infectious disease, inflammation or prevent graft rejection in animals, or to treat animals with such diseases. Effective amounts and/or dosing regimens can be determined using techniques known to those skilled in the art.

It is also within the scope of the present invention to use isolated proteins, mimetopes, nucleic acid molecules and/or antibodies of the present invention as diagnostic reagents. Methods to use such diagnostic reagents are well known to those skilled in the art, see, for example, Janeway, et al., ibid., and/or PCT Publication No. WO 98/23964, published Jun. 4, 1998.

The following examples are provided for the purposes of illustration and are not intended to limit the scope of the present invention.

EXAMPLES

It is to be noted that the examples include a number of molecular biology, microbiology, immunology and biochemistry techniques considered to be familiar to those skilled in the art. Disclosure of such techniques can be found, for example, in Sambrook et al., ibid. and Ausubel, et al., 1993*, Current Protocols in Molecular Biology*, Greene/Wiley Interscience, New York, N.Y., and related references. Ausubel, et al, ibid. is incorporated by reference herein in its entirety.

Example 1

This example describes the isolation and sequencing of canine interleukin-4 (IL-4) nucleic acid molecules of the present invention. This example also describes expression of recombinant canine IL-4 in *E. coli* and mammalian cells; development of monoclonal and polyclonal antibodies to *E. coli* expressed canine IL-4; and bioactivity of mammalian-expressed and *E. coli*-expressed canine IL-4.

A. Isolation and Sequencing of a Canine IL-4 Nucleic Acid Molecule.

Initial attempts to isolate a canine IL-4 nucleic acid molecule using various primers corresponding to putative conserved regions of IL-4 nucleic acid molecules failed. Forward and reverse primers were then designed using a sequence tag site (IL-4sts) described by Venta et al. in GenBank. The forward primer was designated as EL-4stsA, having the nucleic acid sequence 5' CTATTAATGG GTCTCACCTC CCAA CT 3', designated herein as SEQ ID NO:11. The reverse primer was designated as prIL-4stsB, having the nucleic acid sequence 5' TCAACTCGGT GCACAGAGTC TTGG 3', designated herein as SEQ ID NO:12. The primers were used to amplify PCR products from a *C. familiaris* mitogen activated PBMC cDNA library that was constructed in the Uni-ZAP® XR vector (available from Stratagene Cloning Systems, La Jolla, Calif.), using Stratagene's ZAP-cDNA® Synthesis Kit and the manufacturer's protocol. The mRNA was isolated from *C. familiaris* peripheral blood mononuclear cells about 4 hours after they were activated by a polyclonal activating agent in culture. Four PCR products were produced that had the expected size range. The PCR products were cloned and sequenced using standard techniques. A portion of one of the four products was found to be somewhat homologous with an IL-4 nucleic acid sequence reported in GenBank.

To identify a cDNA encoding a full-length canine IL-4 protein, the PCR product showing some homology with the IL-4 sequence reported in GenBank was used to generate an about 549 base pair DNA fragment as follows. The PCR product was labeled with $^{32}P$ and used as a probe to screen the canine PBMC cDNA library. Hybridization was done at about 6×SSC, 5×Denhardt's solution, 0.5% SDS, 100 μg/ml of ssDNA and 100 μg/ml of tRNA, at about 68° C., for about 36 hr. (the compositions of SSC and Denhardt's are described in Sambrook et al., ibid.). The filters were washed 3 times, for about 30 minutes per wash, at about 55° C. in about 2×SSC, 0.2% SDS, followed by a final wash of about 30 minutes in the same buffer except using about 1×SSC. Positive clones were isolated and the cDNA inserts were sequenced for both strands using vector flanking primers and gene-specific internal primers. Sequence analysis was performed using the GAP program of GCG (available from the University of Wisconsin) using the alignment settings of: gap weight set at 50, length weight set at 3, and average match set at 10 for nucleic acid sequence comparisons; and gap weight set at 12, length weight set at 4, and average match set at 2.912 for amino acid sequence comparisons.

A cDNA nucleic acid molecule was isolated, referred to herein as nCaIL-$4_{549}$, the coding strand of which was shown to have a nucleic acid sequence denoted herein as SEQ ID NO:1. The complement of SEQ ID NO:1 is represented herein by SEQ ID NO:3. Translation of SEQ ID NO:1 suggests that nucleic acid molecule nCaIL-$4_{549}$ encodes a full-length IL-4 protein of about 132 amino acids, denoted herein as PCaIL-$4_{132}$, the amino acid sequence of which is presented in SEQ ID NO:2, assuming an open reading frame having an initiation codon spanning from nucleotide 43 through nucleotide 45 of SEQ ID NO:1 and a stop codon spanning from nucleotide 439 through nucleotide 441 of SEQ ID NO:1. The coding region encoding PCaIL-$4_{132}$ is presented herein as nCaIL-$4_{396}$, which has the nucleotide sequence SEQ ID NO:4 (the coding strand) and SEQ ID NO:5 (the complementary strand). A putative signal sequence coding region extends from nucleotide 43 through nucleotide 114 of SEQ ID NO:1. The proposed mature protein (i.e., canine IL-4 protein from which the signal sequence has been cleaved), denoted herein as PCaIL-$4_{108}$, contains about 108 amino acids, extending from residue 25 through residue 132 of SEQ ID NO:2; PCaIL-$4_{108}$ amino acid sequence is represented herein as SEQ ID NO:20. The nucleic acid molecule encoding PCaIL-$4_{108}$ is denoted herein as nCaIL-$4_{324}$, extending from nucleotide 115 through nucleotide 438 of SEQ ID NO:1. nCaIL-$4_{324}$ has a coding sequence denoted SEQ ID NO:19 and a complementary sequence denoted SEQ ID NO:21.

Comparison of nucleic acid sequence SEQ ID NO:1 with nucleic acid sequences reported in GenBank indicates that SEQ ID NO:1 showed the most homology, i.e., about 89.3% identity, with a feline IL-4 gene. Comparison of amino acid sequence SEQ ID NO:2 with amino acid sequences reported in GenBank indicates that SEQ ID NO:2 showed the most homology, i.e., about 82.6% identity, with a feline IL-4 protein. Sequence analysis was performed using the GCG GAP program as described above.

B. Expression of Recombinant Canine L-4 in *E. coli* and Mammalian Cells i. *E. coli* expression A recombinant molecule capable of expressing the mature form of canine IL-4, denoted herein as pGEX-nCaIL-$4_{327}$, was produced as follows. A 340-nucleotide fragment was PCR amplified from nucleic acid molecule nCaIL-$4_{549}$ (having coding strand SEQ ID NO:1) using the following primer sequences: positive strand 5' TGAATTCGGA CATAACTTCA ATATTAC 3' (SEQ ID NO:38) (EcoRI site in bold) and 5' TCTCGAGATT CAGCTTCATG CCTGTA 3' (SEQ ID NO39) (XhoI site in bold). The resulting 340-base pair fragment was digested with EcoRI and XhoI restriction enzymes (available from New England Biolabs, Beverly, Mass.), according to the manufacturer's directions, and gel-purified using standard techniques. The digested 340-base pair fragment, now 327 base pairs, was then ligated into pGEX-6P-1 (available from Amersham Phartnacia, Piscataway, N.J.), which had been previously digested with EcoRI and XhoI and gel purified, to produce recombinant molecule pGEX-nCaIL-$4_{327}$. Recombinant molecules of pGEX produce the protein of interest as a glutathione s-transferase (GST) fusion protein. The recombinant molecule pGEX-nCaIL-$4_{327}$ was transformed into DH5alpha cells (available from Life Technologies, Gaithersburg, Md.), a recombination deficient strain of *E. coli*, to produce recombinant cell DH5-pGEX-nCaIL-$4_{327}$. The recombinant cells were screened for presence of insert by PCR and confirmed by enzyme restriction analysis and nucleic acid sequencing, using standard techniques. Several clonal recombinant molecules were transformed into BL21 cells (available from Amersham Pharmacia, Piscataway, N.J.), a protease deficient strain of *E. coli*, to produce recombinant cell BL21 -pGEX-nCaIL-$4_{327}$. These recombinant cells were screened, and the clone with the highest level of protein yield was selected for scaling up for larger-scale protein production. The resultant recombinant protein is referred to herein as *E. coli*PCaIL-$4_{109}$.

To produce and purify *E. coli*PCaIL-$4_{109}$, bacterial cultures of recombinant cell BL21: pGEX-nCaIL-$4_{327}$ were grown in shake flasks at 37° C. and induced with 0.1 mM IPTG (isopropyl-β-D-thiogalactopyranoside), (available from Sigma Chemical Company, St. Louis, Mo.) when $OD_{600nm}$ reached about 0.8 units. Growth was allowed to continue for about 4 hours; then bacteria were harvested by centrifugation at 4000×g (times gravity) for 20 minutes. The bacterial pellet was washed and resuspended in phosphate buffered saline (PBS) (for recipe, see Sambrook et al, ibid.), then lysed by exposure to gaseous nitrogen pressure in a Parr pressure vessel (available from Parr Instrument Co., Moline, Ill.), according to the manufacturer's instructions. Cell debris was removed by centrifligation at 10,000×g for 20 minutes. The IL-4-GST fusion protein *E. coli*PCaIL-$4_{109}$ was purified from the supernatant by allowing incubation with glutathione-conjugated resin, removing unbound proteins and then removing the GST tag with PRESCISSION™ protease; all reagents were available from Amersham Pharmacia and all were used according to the manufacturer's directions.

Concentration and purity of *E. coli*PCaIL-$4_{109}$ were estimated by BCA Protein Assay kit (available from Pierce, Rockford, Ill.) and SDS-PAGE followed by Coomassie staining, respectively. The purified material exhibited a single band of approximately 14 kilodaltons (kD) by Coomassie stained SDS-PAGE.

ii. CHO cell expression

A recombinant molecule denoted herein as pCMV-nCaIL-$4_{399}$, capable of expressing a full length form of canine IL-4 (including signal sequence) was produced as follows. A 422-nucleotide fragment was PCR amplified from nucleic acid molecule nCaIL-$4_{549}$ using the following primers: 5' CCCAAGCTTA TGGGTCTCACC TCCCAAC (HindIII site in bold), denoted SEQ ID NO:40, and 3' CCTCGAGATT CAGCTTTCAA TGCCTGTA (XhoI site in bold), denoted SEQ ID NO:127. The 422-base pair PCR product was digested with the restriction endonucleases HindIII and XhoI, both available from New England Biolabs. The resulting 399-base pair product encoding full-length canine IL-4 was gel purified using standard techniques and ligated into the cytomegalovirus (CMV) immediate-early transcription control region of the pCMV-Int A plasmid vector that had been digested with HindIII and XhoI (available from New England Biolabs), and gel purified, to produce the recombinant molecule pCMV-nCaIL-$4_{399}$. The pCMV-Int A plasmid vector was generated as referenced by J. E. Osorio et al., 1999, *Vaccine* 17, 1109-1116. Briefly, vector pRc/RSV, (available from Invitrogen Corp., San Diego, Calif.) was cleaved with restriction enzyme PvuII (available from New England Biolabs), and the 2963-base pair PvuII fragment was gel purified. The fragment was self-ligated to form the vector pRc/RSV(Pvu), which contains a Rous Sarcoma Virus (RSV) long terminal repeat, a multiple cloning site, a bovine growth hormone polyadenylation sequence, a bacterial origin of replication, and an ampicillin resistance gene. Vector pRc/RSV(Pvu) was restriction enzyme digested using HindIII and NruI. A HindIII/SspI fragment containing the HCMV intermediate early promoter and first intron (i.e. intron A) was ligated into the digested pRc/RSV(Pvu) vector to produce the vector pCMV-Int A.

Stable expression of CaIL-4 in mammalian cells was carried out by transfecting the recombinant molecule pCMV-nCaIL-$4_{399}$ into Chinese Hamster Ovary cells, (CHO, available from ATCC) as follows. Six-well polystyrene tissue culture plates (available from Coming Costar, Acton, Mass.) were seeded with approximately $5\times10^5$ cells/well in 2 milliliter (ml) cell culture media, consisting of Minimal Essential Media (MEM) supplemented with 100 mM L-glutamine, 100 mM gentamicin, and 10% fetal bovine serum (FBS), (all available from Life Technologies). Cells were grown to about 80% confluence (for about 18 hours) before transfection. The recombinant molecules to be transfected were purified using the Plasmid Midi Kit (available from Qiagen, Valencia, Calif.) and used according to the manufacturer's instructions. The recombinant molecule pCMV-nCaIL-$4_{399}$ was linearized using the restriction enzyme PvuI (available from New England Biolabs). The plasmid pcDNA3, (available from Invitrogen), which contains the neomycin resistance gene, was linearized using the restriction enzyme EcoRI. Approximately 2 $\mu$g of pCMV-nCaIL-$4_{399}$ was mixed with about 2 ng of linearized pcDNA3 in about 100 $\mu$l OPTIMEM™ media, available from Life Technologies. About 10 $\mu$l Lipofectamine, (available from Life Technologies) was mixed with 100 $\mu$l OPTIMEM. The nucleic acid molecule-containing mixture was then added to the Lipofectamine mixture and incubated at room temperature for about 45 minutes. After incubation, about 0.8 ml OPTIMEM was added, and the mixture was overlaid onto the CHO cells which had been previously rinsed with OPTIMEM. Cells were incubated for about 5 hours at 37° C. 5% $CO_2$, 95% relative humidity. Approximately 1 ml of cell culture media as described previously, with 20% FBS, was added and the cells were incubated overnight. The media was changed at 24 hours, and at 72 hours post transfection, the cells were split 1:4 and put into fresh cell culture media containing about 500 $\mu$g/ml geneticin (G418, available from Life Technologies). The media was changed every 3–5 days. After several weeks, G418 resistant colonies were trypsinized using sterile filter papers, 5–6 mm in diameter that were soaked in trypsin, which were then placed over individual wells of 24 well plates that contained separated widely spaced colonies of CHO cells. After 3 days, the papers were removed. The resulting recombinant cells are referred to herein as CHO-pCMV-nCaIL-$4_{399}$. The recombinant cells were then expanded and tested for the presence of nIL-$4_{399}$ RNA by RT-PCR and tested for the presence of PCaIL-$4_{133}$ protein by Western blot analysis. Westerns were developed with rabbit anti-*E. coli*PCaIL-$4_{109}$ serum and 607.1 monoclonal antibody, a monoclonal antibody that selectively binds to *E. coli*PCaIL-$4_{109}$ protein. See Example 1C for a description of how these antibodies were produced.

C. Monoclonal and Polyclonal Antibodies to Recombinant Canine IL-4 (i.e. Anti-canine IL-4 Antibodies)

The following describes the development of monoclonal and polyclonal antibodies that selectively bind to *E. coli*PCaIL-$4_{109}$.

Female Balb/C mice, 6–8 weeks old, were injected subcutaneously, at about 4 sites, with a total of 25 $\mu$g *E. coli*PCaIL-$4_{109}$ (produced as described in Example 1B) in Freund's Complete Adjuvant (day 0). Fourteen days later, the mice received an intraperitoneal boost of 25 $\mu$g *E. coli*PCaIL-$4_{109}$ in Freund's Incomplete Adjuvant (day 14). Fourteen days later, serum was tested for antibody titer to *E. coli*PCaIL-$4_{109}$ by ELISA (day 28). Three days prior to fusion, mice were boosted intravenously with 20 $\mu$g *E. coli*PCaIL-$4_{109}$ in PBS (day 35). Splenocytes were harvested from mice demonstrating the highest serum titer by ELISA and depleted of CD4+ and CD8+ cells. This depletion was achieved by incubation of the splenocytes with biotinylated rat anti-mouse CD4 and anti-mouse CD8 monoclonal antibodies, available from PharMingen, San Diego, Calif. Antibody-labeled cells were then removed by incubation with M-280 streptavidin coated magnetic beads, available from Dynal, Oslo, Norway. Depleted splenocytes were fused to SP2/0 cells (available from ATCC) using 50% polyethylene glycol in unsupplemented Iscove's Modified Dulbecco's Media (IMDM), following established protocols; see, for example, Harlow E., and Lane D., eds., 1995, *Antibodies. A Laboratory Manual*, Monoclonal Antibodies, Cold Spring Harbor Laboratories; Harlow et al, ibid., is incorporated by reference herein in its entirety. Fused cells were plated in 96-well plates using IMDM cell culture media, (available from Life Technologies, Inc., Rockville, Md.), which was supplemented with 10% fetal bovine serum, 2 mM L-glutamine, 1 mM sodium pyruvate, 1×nonessential amino acids, 1×MEM amino acids, 0.05 mg/ml gentamicin, and 0.5 mM β-mercaptoethanol (all reagents available from Life Technologies). Additionally, 100 $\mu$M hypoxanthine, 0.4 $\mu$M aminopterin, and 16 $\mu$M thymidine, all available from Sigma Chemical Corporation, St Louis, Mo., were added.

After about 7 days, wells positive for hybridoma growth were screened by ELISA to *E. coli*PCaIL-$4_{109}$. Immulon II 96-well plates (available from VWR, Denver, Colo.) were coated, overnight, with 100 ng/ml *E. coli*PCaIL-$4_{109}$ in 0.1 M carbonate/bicarbonate buffer, Ph 9.6. After blocking the wells with 20% FBS in Tris buffered saline (TBS), culture supernatants were allowed to bind. Presence of anti-*E. coli*PCaIL-$4_{109}$ mouse antibody was detected with polyclonal goat anti-mouse IgG conjugated to horseradish peroxidase, (available from KPL, Gaithersburg, Md.), and color developed with 3,3',5,5' -tetramethylbenzidine dihydrochloride (TMB), available from Pierce, Rockford, Ill. Specificity of the ELISA reactivity was verified by Western blot analysis to *E. coli*PCaIL-$4_{109}$, developed with polyclonal goat anti-mouse IgG conjugated to alkaline phosphatase and nitro-blue tetrazolium/5-bromo-4-chloro-3'-indolyphosphate p-toluidine salt substrate (NBT/BCIP, available from Sigma). Western blots exhibited a single band of approximately 14 kD. Immunoglobulin isotype of the monoclonal antibodies was determined using IsoStrips, available from Boehringer Mannheim, Indianapolis, Ind. Twenty-three monoclonal antibodies were generated to *E. coli*PCaIL-$4_{109}$, 22 of which were of the IgM isotype and one of which was IgG1, and is referred to herein as 607.1.

Polyclonal rabbit serum was produced by repeated immunization (over a 10 month period) of a male, New Zealand White rabbit 12–16 months old. Initial immunization was 50 ug *E. coli*PCaIL-$4_{109}$ (prepared as described in Example 1bi) in Freund's Complete Adjuvant, at several sites subcutaneously and intradermally. One month later, and at one month intervals thereafter, the rabbit was boosted intradermally with 50 ug *E. coli*PCaIL-$4_{109}$ in Freund's Incomplete Adjuvant. Serum was collected bi-weekly and titers monitored by ELISA and Western blot to *E. coli*PCaIL-$4_{109}$. Serum that selectively bound to *E. coli*PCaIL-$4_{109}$ protein is referred to as anti-*E. coli*PCaIL-$4_{109}$ serum.

D. Bioactivity of Mammalian-Expressed Canine IL-4

The following describes a bioassay to detect the expression of canine IL-4 protein expressed in the supernatants from CHO-pCMV-nCaIL-$4_{399}$ recombinant cells by screening for production of CD23.

About 100 μl Ramos cells, available from ATCC, at a concentration of about $3.5 \times 10^3$ cells/ml were seeded into 96-well flat bottom plates, available from Becton Dickinson, Franklin Lakes, N.J.). These cells were grown in RPMI media supplemented with 100 mM L-glutamine, gentamicin, and 10% FBS (called TCM). The Ramos cells were then treated in 5% $CO_2$ for 37° C. for approximately 48 h. with one of the following:

| Group | Treatment |
|---|---|
| 1 | TCM |
| 2 | CHO-pCMV (a transfectant cell line containing the empty pCMV vector) supernatant (1:4 final dilution in TCM) |
| 3 | CHO-pCMV-nCaIL-$4_{399}$ supernatant (1:20 final dilution in TCM) |

Triplicate samples for each treatment group were pooled for staining to look for increased expression of CD23 (one of the reported effects of IL-4). Briefly, $1 \times 10^5$ cells from each treatment group were incubated in phosphate buffered saline (PBS) containing 30% FBS for 15–30 min on ice. The cells were collected and incubated with the following:

| Condition | Primary Incubation | Secondary Incubation |
|---|---|---|
| A | PBS | Goat anti mouse PE |
| B | Mouse anti human CD23 | Goat anti mouse PE |

Mouse anti-human CD23 monoclonal antibody, available from Pharmingen, was used at about 10 μg/ml. Goat (Fab'2) anti mouse IgG PE, available from Southern Biotechnologies was used at about 2.5 μg/ml. These reagents were diluted in PBS with 5% FBS . Primary incubations were performed for 30–60 minutes on ice, and secondary incubations were performed for 20–30 min on ice. Three washes of PBS/5% FBS were performed in between each incubation. Cells were then analyzed on a flow cytometer (e.g., MoFlow Desk Top System, available from Cytomation, Ft. Collins, Colo.) with the fluorescein gate set at $10^1$. The results are shown in Table 2.

TABLE 2

Induction of CD23 on Ramos cells post-treatment with supernatants from CHO-pCMV-nCaIL-$4_{399}$.

| Treatment | Condition | % positive |
|---|---|---|
| 1 | A | 0 |
| | B | 1 |
| 2 | A | 8 |
| | B | 1 |
| 3 | A | 3 |
| | B | 99 |

Table 2 shows that the canine 11–4 expressed by the CHO transfectant CHO-pCMV-nCaIL-$4_{399}$is biologically active, demonstrated by its ability to induce expression of CD23 in Ramos cells.

E. Bioactivity of *E. coli*-expressed Canine IL-4

The following describes a bioassay to detect the expression of canine IL-4 by stimulating the proliferation of TF-1 cells.

TF-1 cells (a human erytliroleukaemia cell line, available from R&D Systems, Minneapolis, Minn.), were grown and maintained in TCM-TF-1 medium (RPMI-1640 media supplemented with 2 mM L-glutamine, 5 μg/ml gentamicin, 5% FBS and 2 ng/ml recombinant human GM-CSF (rhuGM-CSF, available from R&D Systems)) in 5% $CO_2$ at 37° C.

For assay, TF-1 cells were extensively washed to remove rhuGM-CSF, then added at approximately $1 \times 10^4$ cells per well to 96-well flat bottom plates. Refolded and HPLC-purified *E. coli*-expressed PCaIL-$4_{109}$, produced as described in Example 1Bi, was diluted to the appropriate concentration in TCM-TF-1 without rhuGM-CSF and filter sterilized. Cells and *E. coli*-expressed PCaIL-$4_{109}$ were incubated for 48 hours in 5% $CO_2$ at 37° C., then pulsed with 1 μCi/well tritiated thymidine (available from ICN Pharmaceuticals, Irvine, Calif.), and incubated for an additional 18 hours. Contents of the wells were harvested onto glass fiber filters and counted in a Wallac Trilux 1450 scintillation counter (available from Wallac Inc., Gaithersburg, Md.). The results are shown in Table 3.

TABLE 3

Stimulation of proliferation of TF-1 cells with *E coli*-expressed PCaIL-$4_{109}$

| Concentration *E. coli* PcaIL-$4_{109}$ (ng/ml) | Counts per minute |
|---|---|
| 1000 | 33,216 |
| 500 | 26,297 |
| 250 | 27,283 |
| 125 | 23,804 |
| 62.5 | 26,225 |
| 31.3 | 19,803 |
| 15.6 | 9,818 |
| 7.8 | 6,475 |
| 0 | 165 |

Table 3 shows that canine IL-4 expressed by *E. coli* is biologically active, as demonstrated by its ability to stimulate proliferation of TF-1 cells.

Example 2

This example describes the isolation and sequencing of certain canine Flt-3 ligand and feline Flt-3 nucleic acid molecules and proteins of the present invention. The example also describes expression of a canine Flt-3 ligand protein of the present invention in CHO cells, as well as detection of the expressed canine Flt-3 ligand protein.

A. Canine Flt-3 Ligand Nucleic Acid Molecules and Proteins.

i. This example describes the isolation and sequencing of certain canine Flt-3 ligand nucleic acid molecules and proteins of the present invention.

A canine Flt-3 ligand nucleic acid molecule was produced as follows. A pair of primers was initially used to amplify DNA from the *C. familiaris* mitogen activated PBMC cDNA library described above in Example 1. A forward primer referred to as FLT3F1, having the nucleic acid sequence 5' CTGGCGCCAG CCTGGAGCCC 3', designated herein as SEQ ID NO:13 was used in combination with a reverse primer referred to herein as FLT3B1, having the nucleic acid sequence 5' GGGAGATGTT GGTCTGGACG 3', referred to herein as SEQ ID NO:14 to amplify Flt-3 ligand DNA from the cDNA library by polymerase chain reaction (PCR). The primers were designed using conserved regions of IL-4 cDNA sequences from other species in the public databases corresponding to the positions shown below:

| Database | Accession number | Nucleotides | Animal |
|---|---|---|---|
| gb | U04806 | 102–121 | human |
| gb | L23636 | 41–60 | mouse |
| gb | U04806 | 77–458 | human |
| gb | L23636 | 419–400 | mouse |

A 360-base pair (bp) PCR product was generated in the above reaction that was purified, radiolabeled and used as a probe to screen the cDNA library. Hybridization was performed in 6×SSC, 5×Denhardt's solution, 0.5% SDS, 100 $\mu$g/ml ssDNA and 100 $\mu$g/ml of tRNA, at 68° C., for about 36 hr. The filters were washed 3 times, for about 30 minutes per wash, at 55° C. in 2×SSC, 0.1% SDS, followed by a final wash in 0.25×SSC, for about 30 minutes, at 55° C. Several positive phage clones were identified and shown to produce PCR products when used as templates in combination with the FLT3F1 and FLT3B1 primers. The DNA inserts in the phage clones were sequenced using standard techniques and failed to yield any clones containing DNA inserts having a portion homologous to published Flt-3 ligand sequences. The 360-bp PCR fragment generated above was then cloned into the vector pcDNA 2.1 (available from Invitrogen Corp., San Diego, Calif.). Several independent colonies were generated and the sequences of their inserts determined. One clone was identified that which contained insert sequence having a portion that was somewhat homologous to published human or murine Flt-3 ligand sequence.

Two canine Flt-3 ligand-specific primers were then designed using the nucleic acid sequence obtained using the 360-bp PCR product described above.

| Primer | Sequence | SEQ ID NO |
|---|---|---|
| DFLB1 | 5' GACCAGGCGCCAGAACGC 3' | SEQ ID NO:15 |
| DFLF1 | 5' CGGTCACCATCCGCAAGC 3' | SEQ ID NO:16 |

The 5' region of a Flt-3 ligand nucleic acid molecule was PCR amplified from the cDNA library using the DFLB1 primer in combination with the 5' T3 vector primer from the Uni-ZAP® XR vector (available from Stratagene). The 3' region of a Flt-3 ligand nucleic acid molecule was PCR amplified from the cDNA library using the DFLF1 in combination with the 3' T7 primer from the Uni-ZAP® XR vector (available from Stratagene). A 855-bp PCR product was obtained representing the 5' region of a Flt-3 ligand nucleic acid molecule. A 265-bp PCR product was obtained representing the 3' region of a Flt-3 ligand nucleic acid molecule. Both the 855-bp PCR product and 265-bp PCR product were cloned and sequenced using standard methods. Additional canine Flt-3 ligand-specific primers were designed using the nucleic acid sequence obtained from the sequence of the 855-bp PCR product and 265-bp PCR products.

| Primer | Sequence | SEQ ID NO |
|---|---|---|
| DFLB2 | 5' TGGCAAGGCAGTGGCCTC 3' | SEQ ID NO: 17 |
| DFLF2 | 5' GCCGAGATGATAGTGCTGGC 3' | SEQ ID NO: 18 |

A 546-bp PCR product was generated using the primer DFLF2 in combination with the primer DFLB2 to amplify a PCR product from the cDNA library. The 546-bp PCR product was then purified, radiolabelled and used as a probe to screen the cDNA library. Hybridization was performed in 6×SSC, 5×Denhardt's solution, 0.5% SDS, 100 $\mu$g/ml of ssDNA and 100 $\mu$g/ml of tRNA, at 68° C., for about 36 hr. The filters were washed in 1.25×SSC, for about 30 minutes, at 55° C. Four cDNA clones encoding full-length canine Flt-3 ligand were isolated. Nucleic acid sequence was obtained using standard techniques.

A Flt-3 ligand clone was isolated, referred to herein as $nCaFlt3L_{1013}$, the coding strand of which was shown to have a nucleic acid sequence denoted herein as SEQ ID NO:6. The complement of SEQ ID NO:6 is represented herein by SEQ ID NO:8. Translation of SEQ ID NO:6 suggests that nucleic acid molecule $nCaFlt3L_{1013}$ encodes a full-length Flt-3 ligand protein of about 294 amino acids, denoted herein as $PCaFlt3L_{294}$, the amino acid sequence of which is presented in SEQ ID NO:7, assuming an open reading frame having an initiation codon spanning from nucleotide 35 through nucleotide 37 of SEQ ID NO:6 and a stop codon spanning from nucleotide 917 through nucleotide 919 of SEQ ID NO:6. The coding region encoding $PCaFlt3L_{294}$ is presented herein as $nCaFlt3L_{882}$, which has the nucleotide sequence SEQ ID NO:9 (the coding strand) and SEQ ID NO:10 (the complementary strand). A putative signal sequence coding region extends from nucleotide 35 through nucleotide 112 of SEQ ID NO:6. The proposed mature protein (i.e., canine Flt-3 ligand protein from which the signal sequence has been cleaved), denoted herein as $PCaFlt3L_{268}$ (SEQ ID NO:23), contains about 268 amino acids, extending from residue 27 through residue 294 of SEQ ID NO:7. The nucleic acid molecule encoding $PCaFlt3L_{268}$ is denoted herein as $nCaFlt3L_{804}$, extending from nucleotide 113 through nucleotide 916 of SEQ ID NO:6. $nCaFlt3L_{804}$ has a coding sequence denoted SEQ ID NO:22 and a complementary sequence denoted SEQ ID NO:24.

Below is a description of the identification of alternatively spliced Canis Flt3 ligand transcripts. Besides cDNA clones such as nucleic acid molecule $nCaFlt3L_{1013}$ encoding the full-length canine Flt3 ligand protein, two splice variants of canine Flt3 ligand cDNA clones were also isolated, using the same hybridization conditions as mentioned previously in this Example. One such variant (Clone 1), denoted herein as $nCaFlt3L_{985}$, has a coding strand the nucleic acid sequence of which is represented as SEQ ID NO:25. The complement of SEQ ID NO:25 is represented herein by SEQ ID NO:27. Translation of SEQ ID NO:25 suggests that nucleic acid molecule $nCaFlt3L_{985}$ encodes a Flt-3 ligand protein of 276 amino acids, denoted herein as $PCaFlt3L_{276}$, the amino acid sequence of which is represented by SEQ ID NO:26, assuming an open reading frame having an initiation codon spanning from nucleotide 74 through nucleotide 76 of SEQ ID NO:25 and a stop codon spanning from nucleotide 902 through nucleotide 904 of SEQ ID NO:25. The coding region encoding $PCaFlt3L_{276}$ is represented herein as nCaFlt3L828, which has the nucleotide sequence SEQ ID NO:28 (the coding strand) and SEQ ID NO:29 (the complementary strand). Alignment of nucleic acid molecules $nCaFlt3L_{882}$ and $nCaFlt3L_{828}$ indicates that the nucleic acid molecules are identical except for a deletion in $nCaFlt3L_{828}$, which spans from nucleotide 343 through nucleotide 396 of $nCaFlt3L_{882}$. Accordingly, $nCaFlt3L_{828}$ encodes 18 fewer amino acids than $nCaFlt3L_{882}$. The deletion in $PCaFlt3L_{276}$, which spans from residue 115 through residue 132 of $PCaFlt3L_{294}$, occurs between helix III and helix IV of the canine Flt3 ligand protein inferred from alignment with the human and mouse Flt3 ligand protein (Lyman et al., *Cell*, vol. 75, pp. 1157–1167, 1993; Hannum et al., *Nature*, vol. 368, pp. 643–648, 1994; Lyamn et al., *Blood*, vol. 83, pp. 2795–2801, 1994). In addition, the alignment shows that there are 39 more nucleotides in the 5' untranslated region of nucleic acid molecule $nCaFlt3L_{985}$ (nucleotides 1 to 39) than nucleic acid molecule $nCaFlt3L_{1013}$ and there are 2 more nucleotides in the 3' untranslated region of nucleic acid molecule nCaFlt3 $L_{985}$ (nucleotides 922 to 923) than nucleic acid molecule $nCaFlt3L_{1013}$. The remaining sequences between $nCaFlt3L_{985}$ and $nCaFlt3L_{1013}$ are identical. A putative mature form of $nCaFlt3L_{985}$ (without the signal sequence) is predicted. The putative signal sequence coding region extends from nucleotide 74 to nucleotide 151 of SEQ ID NO:25. The proposed mature protein, denoted herein as $PCaFlt3L_{250}$, represented by SEQ ID NO:31, contains about 250 amino acids, extending from residue 27 through residue 276 of SEQ ID NO:26. The nucleic acid molecule encoding $PCaFlt3L_{250}$, extending from nucleotide 152 through nucleotide 901 of SEQ ID NO:6, denoted herein as $nCaFlt3L_{750}$, is represented by SEQ ID NO:30 (the coding strand) and SEQ ID NO:32 (the complement strand).

A second variant (Clone 19) is represented by nucleic acid molecule $nCaFlt3L_{1019}$, the coding strand of which is denoted herein as SEQ ID NO:33. The complement of SEQ ID NO:33 is denoted herein as SEQ ID NO:35. Translation of SEQ ID NO:33 suggests that $nCaFlt3L_{1019}$ encodes a Flt-3 ligand protein of 31 amino acids, $PCaFlt3L_{31}$, denoted SEQ ID NO:34, assuming an initiation codon spanning from nucleotide 74 through nucleotide 76 and a stop codon spanning nucleotide 167 through nucleotide 169 of SEQ ID NO:33. The coding region encoding $PCaFlt3L_{31}$ is represented herein as $nCaFlt3L_{93}$, which has the nucleotide sequence SEQ ID NO:36 (the coding strand) and SEQ ID NO:37 (the complementary strand). Alignment of nucleic acid molecules $nCaFlt3L_{985}$ and $nCaFlt3L_{1019}$ indicates the presence of an insertion of 91 nucleotides in $nCaFl3L_{1019}$. The insertion spans nucleotide 107 through nucleotide 198 of $nCaFlt3L_{1019}$. A stop codon is found in this insertion in frame with the predicted initiation codon, which span nucleotide 74 through nucleotide 76 of SEQ ID NO:6. Since this insertion (with an inframe stop codon) occurs in or close to the signal peptide, it is likely that nucleic acid molecule $nCaFlt3L_{1019}$ encodes a nonfunctional Flt-3 ligand protein.

Comparison of nucleic acid sequence SEQ ID NO:6 with nucleic acid sequences reported in GenBank indicates that SEQ ID NO:6 showed the most homology, i.e., about 69.8% identity, with a human Flt-3 ligand gene. Comparison of amino acid sequence SEQ ID NO:7 with amino acid sequences reported in GenBank indicates that SEQ ID NO:7 showed the most homology, i.e. about 71% identity, with a human Flt-3 ligand protein. Sequence analysis was performed with DNAsis™ using the alignment settings of: gap penalty set at 5; number of top diagonals set at 5; fixed gap penalty set at 10; K-tuple set at 2; window size set at 5 and floating gap penalty set at 10.

ii. This example describes the production of a recombinant molecule encoding a full length canine Flt-3 ligand protein and expression of that protein by a recombinant cell of the present invention.

A recombinant molecule, denoted herein as pCMV-$nCaFlt3L_{882}$ and capable of expressing a full length form of Flt-3 ligand, was produced as follows. Nucleic acid molecule $nCaFlt3L_{882}$ was digested with the restriction endonucleases EcoRI and XbaI, gel purified and ligated into pCMV-Int A (prepared by methods described in Example 1) to produce recombinant molecule pCMV-$nCaFlt3L_{882}$. Insert size and identity were confirmed by restriction digestion, PCR, and sequencing analyses.

Stable transfectants expressing the recombinant molecule pCMV-$nCaFlt3L_{882}$ were established in Chinese Hamster Ovary cells (CHO, available from ATCC) as follows. Briefly, six-well polystyrene tissue culture plates were seeded with approximately $4\times10^5$ cells per well in 2 ml of MEM (available from Life Technologies, Gaithersburg, Md.) supplemented with 100 mM L-glutamine, gentamicin, and 10% FBS (TCM). Cells were grown to about 80% confluence (about 18 hr). The recombinant molecule to be transfected was prepared using the Qiagen Endotoxin-Free Plasmid Maxi Kit as per the manufacturer's instructions. The recombinant molecule was linearized with the restriction enzyme PvuI, extracted with phenol, and precipitated with isopropanol. The plasmid pcDNA 3, available from Invitrogen, which contains the neomycin resistance gene, was linearized with the restriction enzyme EcoRI. Approximately 1 $\mu$g of recombinant plasmid DNA and 100 ng of pcDNA3 were mixed with about 100 $\mu$l OptiMEM medium, available from Life Technologies. About 10 $\mu$l Lipofectamine (available from Life Technologies) was mixed with 100 $\mu$l OptiMEM. The DNA-containing mixture was then added to the Lipofectamine mixture and incubated at room temperature for about 30 min. After incubation, about 800 $\mu$l of OptiMEM was added, and the entire mixture was overlaid onto the CHO cells that had been rinsed with OptiMEM. Cells were incubated for 6 hours at 37° C., 5% $CO_2$, 95% relative humidity. Approximately 1 ml of TCM with 20% FBS was added, and the cells were incubated overnight. The media was changed after about 24 hr. About 72 hr post transfection, the cells were split 1:4 and put into selection TCM containing 500 $\mu$g/ml Geneticin (G418), available from Life Technologies. The medium was changed every 3–5 days. After several weeks, G418-resistant colonies were trypsinized, and the cells were plated into 24 well plates. The resulting recombinant cells are referred to herein as CHO-pCMV-$nCaFlt3L_{882}$. The recombinant cells were then expanded for testing.

iii. The following describes the detection of expression of a canine Flt-3 ligand protein of the present invention by CHO-pCMV-$nCaFlt3L_{882}$, a recombinant cell of the present invention.

Recombinant cells CHO-pCMV-$nCaFlt3L_{882}$, produced as described in Example 2, part (B)(ii) above, were tested for surface expression of canine Flt-3 ligand using a cross-reactive goat anti-human Flt-3 ligand polyclonal antibody as follows. Briefly, $1\times10^5$ CHO-pCMV-$nCaFlt3L_{882}$ cells or CHO-pCMV cells (i.e., cells transfected with an empty vector as described in Example 1) were incubated in phosphate buffered saline (PBS) containing 30% fetal bovine serum (FBS) for about 30 min on ice. The cells were then spun down and treated with the following:

| Condition | Primary Incubation | Secondary Incubation |
|---|---|---|
| 1 | PBS | Rabbit (Fab'2) anti sheep (H + L) FITC |
| 2 | Goat anti-human Flt3 ligand | Rabbit (Fab'2) anti sheep (H + L) FITC |

Goat anti-human Flt3 ligand, available from R and D Systems, Minneapolis, Minn. was used at about 20 μg/ml. Rabbit (Fab'2) anti sheep (H+L) FITC, available from Southern Biotechnology Associates, Inc., was used at about 10 μg/ml. These reagents were diluted in PBS/5%FBS. All incubations were in 50 μl for about 1 hr on ice with 2 washes of PBS/5%FBS in between each incubation. Cells were then analyzed on a flow cytometer (e.g., MoFlow Desk Top System, available from Cytomation, Ft. Collins, Colo.) with the fluorescein gate set at $10^1$. The results are shown be low in Table 4.

TABLE 4

Expression of canine Flt3 ligand on CHO transfectants.

| | % positive | |
|---|---|---|
| Cells | Condition 1 | Condition 2 |
| CHO-pCMV | 1 | 1 |
| CHO-pCMV nCaFlt3$L_{882}$ | 2 | 48 |
| CHO-pCMV nCaFlt3$L_{882}$ | 1 | 20 |

Table 4 shows that canine Flt3 ligand is expressed on the surface of the CHO transfectants.

B. Feline Flt-3 Ligand Nucleic Acid Molecules and Proteins.

This example describes the production of certain feline Flt-3 ligand nucleic acid molecules and proteins of the present invention.

A nucleic acid molecule encoding a feline Flt 3 ligand was isolated from a feline PBMC cDNA library as follows. A *Felis catus* mitogen activated PBMC cDNA library was constructed in the Uni-Zap-R XR™ vector, available from Stratagene, La Jolla, Calif., using Stratagene's Zap-cDNA-R™ Synthesis Kit and the manufacturer's protocol using mRNA isolated from *F. catus* peripheral blood mononuclear cells about 4 hours after they were activated by a polyclonal activating agent in culture. PCR amplification to isolate a feline Flt 3 ligand nucleic acid molecule was conducted according to the following set of steps: one initial denaturation step at 95° C. for 3 minutes; then 35 cycles of the following: 94° C. for 30 seconds, 53.8° C. for 30 seconds, and 72° C. for 105 seconds; then one final extension step at 72° C. for 8 minutes. A 395-nucleotide cDNA fragment containing the 5' end of feline Flt3 ligand coding region, denoted c eFlt3$L_{395}$,was amplified from the feline PMBC cDNA library using the following primers: vector primer T3 having nucleic acid sequence 5' AATTAACCCT CACTAAAGGG 3, (SEQ ID NO:142) (available from Stratagene) and the antisense primer having SEQ ID NO:14, described in Example 2A. The nucleic ac id sequence of the coding strand of nFeFlt3$L_{395}$ is denoted SEQ ID NO:41. A 793-nucleotide cDNA fragment containing the3' end of feline Flt3 ligand coding region, denoted nFeFlt3$L_{793}$, was isolated using sense primer 2 having the nucleic acid sequence 5' CACAGYCCCA TCTCCTCC 3, (where Y was either T or C) denoted herein as SEQ ID NO:151, in conjunction with vector primer T7 having the nucleic acid sequence 5' GTAATACGAC TCACTATAGG GC 3' (SEQ ID NO:152). The nuclei c acid sequence of the coding strand of nFeFlt3$L_{793}$ is denoted SEQ ID NO:42. Nucleic acid molecules feFlt3$L_{395}$ and nFeFlt3$L_{793}$ overlap by 246 nucleotides and form a composite sequence encoding a Flt3 ligand protein that is similar in length to that of PCaFlt3$L_{294}$. This composite feline Flt3 ligand cDNA is referred to herein as nFeFlt3$L_{942}$, the coding strand of which was shown to have nucleic acid sequence SEQ ID NO:43. The reverse complement of SEQ ID NO:43 is referred to herein as SEQ ID NO:45. Translation of SEQ ID NO:43 suggests that nucleic acid molecule nFeFlt3$L_{942}$ encodes a Flt3 ligand protein of 291 amino acids, denoted herein as PeFlt3$L_{291}$, the amino acid sequence of which is presented in SEQ ID NO:44, assuming an open reading frame having an initiation codon spanning from nucleotide 31 through nucleotide 33 of SEQ ID NO:43 and a stop codon spanning from nucleotide 904 through nucleotide 906 of SEQ ID NO:43. The coding region encoding PFeFlt3$L_{291}$, not including the termination codon, is presented herein as nFeFlt3$L_{873}$, which has the nucleotide sequence SEQ ID NO:46 (the coding strand) and SEQ ID NO:47 (the complementary strand). A putative signal sequence coding region extends from nucleotide 31 to nucleotide 108 of SEQ ID NO:43. The proposed mature protein, denoted herein as PFeFlt3$L_{265}$, denoted SEQ ID NO:49, contains about 265 amino acids, extending from residue 27 though residue 291 of SEQ ID NO:44. The nucleic acid molecule encoding PFeFlt3$L_{265}$ is denoted herein as nFeFlt3$L_{795}$, (SEQ ID NO:48) extending from nucleotide 109 through nucleotide 903 of SEQ ID NO:43. SEQ ID NO:48 has a complementary strand denoted SEQ ID NO:50.

Sequence alignment indicates that nucleic acid sequence SEQ ID NO:43 shares the highest (67.8%) identity with the nucleic acid sequence of human Flt-3 ligand (GenBank accession numbers U04806 and U03858). Amino acid sequence SEQ ID NO:44 shares the highest (70.2%) identity with human Flt-3 ligand protein (GenBank accession numbers U04806 and U03858).

Example 3

This example describes the isolation and sequencing of certain canine CD40 and feline CD40 nucleic acid molecules and proteins of the present invention.

A. Canine CD40 Nucleic Acid Molecules and Proteins

This example describes the production of certain canine CD40 nucleic acid molecules and proteins of the present invention.

A canine CD40 nucleic acid molecule of the present invention was produced by PCR amplification as follows. A 321-nucleotide canine CD40 nucleic acid molecule, denoted nCaCD$40_{321}$, was amplified from a canine PBMC cDNA library, prepared as described in Example 1, using two degenerate oligonucleotide primers designed in accordance with conserved regions of human, bovine, rabbit, and mouse CD40 gene sequences available in GenBank: sense primer, 5' TGCCCRSTCG GCTTCTTCTC C 3', denoted herein as SEQ ID NO:128; and antisense primer, 5' CGACTCTCTT TRCCRTCCTC CTG 3', denoted herein as SEQ ID NO:129, where R was either A or G and S was either G or C. PCR conditions were as follows: one initial denaturation step at 95° C. for 3 minutes; then 35 cycles of the following: 94° C. for 30 seconds, then 53° C. for 30 seconds, then 72° C. for 105 seconds; followed by one final extension at 72° C. for 5 minutes. The resulting PCR product, i.e., $nCaCD40_{321}$, with a coding strand represented by SEQ ID NO:51, was radiolabeled using standard techniques and used to screen the canine PBMC cDNA library, under the following hybridization conditions: hybridized in 6×SSC, 5×Denhardt's solution, 0.5% SDS, 100 μg/ml single stranded DNA, 100 μg/ml tRNA for 36 hours at 68° C., followed by a wash of 0.1% SDS, 1×SSC at 55° C. for 60 minutes. A clone (Clone 18B) containing a 1425-nucleotide canine CD40 nucleic acid molecule, denoted $nCaCD40_{1425}$, was obtained. The nucleic acid sequence of the coding strand of $nCaCD40_{1425}$ is represented as SEQ ID NO:52. The reverse complement of SEQ ID NO:52 is referred to herein as SEQ ID NO:54. Translation of SEQ ID NO:52 suggests that nucleic acid molecule $nCaCD40_{1425}$ encodes a canine CD40 protein of 274 amino acids, denoted herein as $PCaCD40_{274}$, the amino acid sequence of which is presented in SEQ ID NO:53, assuming an open reading frame having an initiation codon spanning from nucleotide 196 through nucleotide 198 of SEQ ID NO:52 and a stop codon spanning from nucleotide 1018 through nucleotide 1020 of SEQ ID NO:52. The coding region encoding $PCaCD40_{274}$, not including the termination codon, is presented herein as $nCaCD40_{822}$, which has the nucleotide sequence SEQ ID NO:55 (the coding strand) and SEQ ID NO:56 (the complementary strand).

A putative signal sequence coding region extends from nucleotide 196 through nucleotide 252 of SEQ ID NO:52. The proposed mature protein, denoted herein as $PCaCD40_{255}$, represented by SEQ ID NO:58, contains about 255 amino acids, extending from residue 20 through residue 274 of SEQ ID NO:53. The nucleotide sequence encoding $PCaCD402_{55}$, which extends from nucleotide 253 through nucleotide 1017 of SEQ ID NO:52, is denoted herein as nucleic acid molecule $nCaCD40_{765}$, represented by SEQ ID NO:57 (the coding strand) and SEQ ID NO:59 (the complement strand).

Sequence analysis was performed with DNAsis™ using the alignment settings of: gap penalty set at 5; number of top diagonals set at 5; fixed gap penalty set at 10; k-tuple set at 2; window size set at 5 and floating gap penalty set at 10. At the amino acid level, $PCaCD40_{274}$ shares 65.3%, 50.1%, and 42.3% identity with the CD40 proteins of human, bovine, and mouse, respectively (Stamenkovic et al., *EMBO J.*, vol. 8:1403–1410, 1989; Hirano et al., *Immunology*, vol. 90, pp. 294–300, 1997; Grimaldi et al., *J. Immunol.*, vol. 143, pp.3921–3926; Torres and Clark, *J. Immuno.*, vol. 148, pp. 620–626). At the nucleotide level, $nCaCD40_{1425}$ shares 69.3%, 69.4%, and 40.4% identity with the cDNA sequences of human, bovine, and mouse CD40, respectively.

B. Feline CD40 Nucleic Acid Molecules and Proteins

This example describes the isolation and sequencing of certain nucleic acid molecules of the present invention that encode certain feline CD40 proteins of the present invention.

A 336-nucleotide feline CD40 nucleic acid molecule, denoted $nFeCD40_{336}$, was amplified from a feline PBMC cDNA library, prepared as described in Example 2, using PCR conditions and primers as described in Example 3A, i.e., a sense primer having SEQ ID NO:128; and an antisense primer having SEQ ID NO:129. The resulting PCR product, i.e., $nFeCD40_{336}$, was shown to have a coding strand the nucleic acid sequence of which is represented as SEQ ID NO:60. The reverse complement of SEQ ID NO:60 is referred to herein as SEQ ID NO:62. Translation of SEQ ID NO:60 suggests that nucleic acid molecule $nFeCD40_{336}$ encodes a partial CD40 protein of 112 amino acids, denoted herein as $PFeCD40_{112}$, the amino acid sequence of which is presented in SEQ ID NO:61, assuming an open reading frame spanning from nucleotide 1 through nucleotide 336 of SEQ ID NO:60.

Comparison of nucleic acid sequence SEQ ID NO:60 with nucleic acid molecules reported in GenBank indicates that SEQ ID NO:60 showed the most homology, i.e. 67.2% identity, with a human CD40 gene. Comparison of amino acid sequence SEQ ID NO:61 with amino acid sequences reported in GenBank indicates that SEQ ID NO:61 showed the most homology, i.e. about 54.4% identity, with a human CD40 protein. Sequence analysis was performed using the GCG GAP program as described above.

Example 4

This example describes the isolation and sequencing of certain canine CD154 (canine CD40 ligand) and feline CD154 (feline CD40 ligand) nucleic acid molecules and proteins of the present invention.

A. Canine CD154 (CD40 ligand) Nucleic Acid Molecules and Proteins

The following describes the isolation and sequencing of certain cDNA nucleic acid molecules encoding certain canine CD154 (CD40 ligand) proteins of the present invention.

A canine CD154 nucleic acid molecule of the present invention was produced by PCR amplification as follows. A 390-nucleotide canine CD40 nucleic acid molecule, denoted $nCaCD154_{390}$, was amplified from a canine PBMC cDNA library, prepared as described in Example 1, using two degenerate oligonucleotide primers designed in accordance with human CD154 gene sequences available in GenBank: sense primer, 5' CCTCAAATTG CGGCACATGT C 3', denoted herein as SEQ ID NO:130; and antisense primer, 5' CTGTTCAGAG TTTGAGTAAG CC 3', denoted herein as SEQ ID NO:131. PCR conditions used for canine CD154 cDNA amplification were standard conditions for PCR amplification (Sambrook, et al., ibid.). The resulting PCR product, i.e., $nCaCD154_{390}$, with a coding strand represented by SEQ ID NO:63, was radiolabeled using standard techniques and used to screen the canine PBMC cDNA library, under the hybridization conditions described in Example 3. A clone containing a 1878-nucleotide canine CD154 nucleic acid molecule, denoted $nCaCD154_{1878}$, was obtained. The nucleic acid sequence of the coding strand of $nCaCD154_{1878}$ is represented as SEQ ID NO:64. The reverse complement of SEQ ID NO:64 is referred to herein as SEQ ID NO:66. Translation of SEQ ID NO:64 suggests that nucleic acid molecule $nCaCD154_{,878}$ encodes a CD154 protein of 260 amino acids, denoted herein as $PCaCD154_{260}$, the amino acid sequence of which is presented in SEQ ID NO:65, assuming an open reading frame having an initiation codon spanning from nucleotide 284 through nucleotide 286 of SEQ ID NO:64 and a stop codon spanning from nucleotide 1064 through nucleotide 1066 of SEQ ID NO:64. The coding region encoding $PCaCD154_{260}$, not including the termination codon, is presented herein as $nCaCD154_{780}$, which has the nucleotide sequence SEQ ID NO:67 (the coding strand) and SEQ ID NO:68 (the complementary strand).

A putative signal/membrane anchor sequence coding region extends from nucleotide 284 through nucleotide 430 of SEQ ID NO:64. The proposed soluble CD154 protein, denoted herein as $PCaCD154_{211}$, represented by SEQ ID NO:70, contains about 211 amino acids, extending from residue 50 though residue 260 of SEQ ID NO:65. The nucleotide sequence encoding $PCaCD154_{211}$, which extends from nucleotide 431 through nucleotide 1063 of SEQ ID NO:64, is denoted herein as nucleic acid molecule nCaCD154$_{633}$, represented by SEQ ID NO:69 (the coding strand) and SEQ ID NO:71 (the complement strand).

Sequence analysis was performed with DNAsis™ using the alignment settings of: gap penalty set at 5; number of top diagonals set at 5; fixed gap penalty set at 10; k-tuple set at 2; window size set at 5 and floating gap penalty set at 10. At the amino acid level, PCaCD154$_{260}$ shares 78.0%, 77.6%, and 67.6% identity with the CD154 proteins of human, bovine, and mouse, respectively (Graf et al., *Eur. J. Immunol., vol.* 22, pp. 3191–3194, 1992; Hollenbaugh, et al., *EMBO J.*, vol. 11:4313–4321, 1992; Gauchat et al., *FEBS lett.*, vol., 315, pp. 259–266, 1993; Mertens et al., *Immunogenetics*, vol. 42, pp. 430–431; Armitage et al., *Nature*, vol. 357, pp. 80–82; 1992). At the nucleotide level, nCaCD154$_{1878}$ shares 81.1%, 81.5%, and 74.4% identity with the sequences of human, bovine, and mouse CD154 cDNAs, respectively.

B. Feline CD154 (CD40 ligand) Nucleic Acid Molecules and Proteins

This example describes the isolation and sequencing of certain nucleic acid molecules encoding certain feline CD154 (CD40 ligand) proteins of the present invention.

A feline CD154 nucleic acid molecule was isolated by PCR amplification from a feline PBMC cDNA library, prepared as described in Example 2, using Amplitaq DNA polymerase (available from PE Applied Biosystems Inc, Foster City, Calif.) under the following PCR protocol: one initial denaturation step at 95° C. for 5 minutes; then 40 cycles of the following: 94° C. for 45 seconds, then 48° C. for 45 seconds, then 72° C.; for 120 seconds; followed by a final extension at 72° C. for 7 minutes. The forward and reverse primers used were based on human CD154 cDNA sequences outside the open reading frame in the 5' and 3' untranslated regions, respectively, so that the open reading frame in the PCR product contained only feline sequences. The sequence of the forward primer was 5' GAAGATACCA TTTCAACTTT AACACAGC 3' SEQ ID NO:132, and that of the reverse primer was 5' TGCTGTATTG TGAA-GACTCC CAGC 3' SEQ ID NO:133. PCR products were cloned into the TA cloning vector (available from Invitrogen Corporation, Carlsbad, Calif.), and the resulting clones were sequenced using an ABI Prism™ Model 377 Automatic DNA Sequencer (available from PE Applied Biosystems Inc.). DNA sequencing reactions were performed using Prism™ dRhodamine Terminator Cycle Sequencing Ready Reaction kits (available from PE Applied Biosystems Inc.).

The PCR product was sequenced and found to contain 885 nucleotides, and is denoted as nFeCD154$_{885}$. The nucleotide sequence of the coding strand of nFeCD154$_{885}$ is represented herein as SEQ ID NO:72, and its complement is denoted SEQ ID NO:74. Translation of the open reading frame in SEQ ID NO:72 suggests that nFeCD154$_{885}$ encodes a protein containing 260 amino acids, referred to herein as PFeCD154$_{260}$, the amino acid sequence of which is presented as SEQ ID NO:73, assuming an open reading frame in which the first codon spans from nucleotide 29 through nucleotide 31 of SEQ ID NO:72, and the stop codon spans from nucleotide 809 through nucleotide 811 of SEQ ID NO:72. The encoded protein has a predicted molecular weight of 28.6 kDa for the precursor protein and 27.2 kDa for the mature protein. The coding region encoding PFeCD154$_{260}$, not including the termination codon, is presented herein as nFeCD154780, which has the nucleotide sequence SEQ ID NO:75 (the coding strand) and SEQ ID NO:76 (the complementary strand)

A putative signal/membrane anchor sequence coding region extends from nucleotide 29 through nucleotide 175 of SEQ ID NO:72. The proposed soluble feline CCD154 protein, denoted herein as PFeCD154$_{211}$, represented by SEQ ID NO:78, contains about 211 amino acids, extending from residue 50 though residue 260 of SEQ ID NO:73. The nucleotide sequence encoding PFeCD154$_{211}$, denoted herein as nFeCD154$_{633}$ which extends from nucleotide 176 through nucleotide 808 of SEQ ID NO:72, is represented herein by SEQ ID NO:77 (the coding strand) and SEQ ID NO:79 (the complementary strand).

Comparison of feline CD154 nucleotide and amino acid sequences with those of other species published in GenBank reveals that the feline CD154 nucleotide sequence SEQ ID NO:75 is 86%, 88% and 75% identical to the human, bovine and murine CD154 gene sequences, respectively (Genbank accession number L07414, Z48469 and X56453 respectively). At the amino acid sequence level, SEQ ID NO:73 is 81%, 82%, and 67% identical to the human, bovine and murine CD154 amino acid sequences, respectively. Hydrophobicity analysis of feline CD154 proteins results in a pattern similar to those of human, bovine and murine CD154 proteins. A putative N-glycosylation site was identified at position 239 in PFeCD154$_{260}$that is conserved in the human, bovine and murine amino acid sequences. Five cysteine residues are present in the feline CD154 protein sequence SEQ ID NO:73. Four of the five residues, located at positions 72, 84, 177 and 217 of PFeCD154$_{260}$, are conserved in all four species and are likely involved in disulfide bond formation. The cysteine residue located at position 193 of PFeCD154$_{260}$ is present in all but the murine sequence.

Example 5

This example describes the isolation and sequencing of certain canine IL-5 nucleic acid molecules and proteins of the present invention. This example also describes expression of canine IL-5 in a Pichia expression system and the bioactivity of such an expressed protein.

A. Isolation and Sequencing of Canine IL-5 Nucleic Acid Molecules and Proteins

A canine IL-5 cDNA nucleic acid molecule encoding a canine IL-5 protein was isolated by PCR amplification from a canine PBMC cDNA library (prepared as described in Example 1) using PCR conditions as described in Example 4B and the following primers. Degenerate oligonucleotide primers were designed in accordance with conserved regions of human and cat IL-5 gene sequences available in GenBank: sense primer, 5' ATGCACTTTC TTTGCC 3', denoted herein as SEQ ID NO:134; antisense primer 1, 5' CTGGAG-GAAA AKACTTCRAT GATTCTGATA TCTGAAATAT AT 3', denoted herein as SEQ ID NO:135; and antisense primer 2, 5' CTGACYCTTK STTGGSCCTC ATTCTCA 3', denoted herein as SEQ ID NO:136, where K was G or T, R was either A or G, S was either G or C, and Y was either T or C.

An about 610-nucleotide canine IL-5 nucleic acid molecule, denoted nCaIL-5$_{610}$, was obtained using primers having SEQ ID NO:134 and SEQ ID NO:135, respectively. The sequence of the coding strand of nCaIL-5$_{610}$ is represented herein as SEQ ID NO:80. The reverse complement of SEQ ID NO:80 is referred to herein as SEQ ID NO:82. Translation of SEQ ID NO:80 suggests that nucleic acid molecule nCaIL-5$_{610}$ encodes an IL-5 protein of 134 amino acids, denoted herein as PCaIL-5$_{134}$, the amino acid sequence of which is presented in SEQ ID NO:81, assuming an open reading frame having an initiation codon spanning from nucleotide 29 through nucleotide 31 of SEQ ID NO:80 and a stop codon spanning from nucleotide 431 through nucleotide 433 of SEQ ID NO:80. The coding region encoding PCaIL-$13_{134}$, not including the termination codon, is presented herein as nCaIL-$5_{402}$, which has the nucleotide sequence SEQ ID NO:83 (the coding strand) and SEQ ID NO:84 (the complementary strand).

An about 488-nucleotide fragment, denoted herein as nCaIL-$5_{488}$, isolated by PCR with primers having SEQ ID NO:134 and SEQ ID NO:136, respectively, corresponds to nucleotide 1 through nucleotide 488 of nCaIL-$5_{610}$.

A putative signal sequence coding region extends from nucleotide 29 through nucleotide 85 of SEQ ID NO:80. The proposed mature protein, denoted herein as PCaIL-$5_{115}$, represented by SEQ ID NO:86, contains about 115 amino acids, extending from residue 20 though residue 134 of SEQ ID NO:81. The nucleotide sequence encoding PCaIL-$5_{115}$, which extends from nucleotide 86 through nucleotide 430 of SEQ ID NO:80, is denoted herein as nucleic acid molecule nCaIL-$5_{345}$, represented by SEQ ID NO:85 (coding strand) and SEQ ID NO:87 (the complement strand).

Sequence analysis was performed with DNAsis™ using the alignment settings of: gap penalty set at 5; number of top diagonals set at 5; fixed gap penalty set at 10; k-tuple set at 2; window size set at 5 and floating gap penalty set at 10. At the amino acid level, PCaIL-$5_{134}$ shared 82.8% and 57.4% identity with feline and human IL-5 proteins, respectively (Padrid et al., *Am. J. Vet. Res.*, vol. 59, pp. 1263–1269, 1998; Azuma et al., *Nucleic Acids Res.*, vol. 14, pp. 9149–9158, 1986). At the nucleotide level, nCaIL-$5_{610}$ shared 81.7% and 75% identity with the cDNA sequences of the feline and human IL-5, respectively.

B. Expression of Canine IL-5 in Pichia

This example describes the expression in Pichia of a canine IL-5 cDNA fragment, namely a canine IL-5 nucleic acid molecule denoted nCaIL-$5_{348}$, the coding strand of which consists of nucleotides 86–433 of SEQ ID NO:80, and as such, encodes a predicted mature canine IL-5 protein having SEQ ID NO:86. Nucleic acid molecule nCaIL-$5_{348}$, was PCR amplified from nCaIL-$5_{610}$ using sense primer 5' GGGCTCGAGA AAAGATTTGC TGTAGAAAAT CCCATG 3' denoted herein as SEQ ID NO:137, with nucleotides 16–36 corresponding to nucleotides 86–106 of SEQ ID NO:80; and antisense primer 5' CCCGCGGCCG CTCAACTTTC CGGTGTCCAC TC 3', denoted herein as SEQ ID NO:138, with nucleotides 12–32 corresponding to the reverse complement of nucleotides 413–433 of SEQ ID NO:80. To facilitate cloning, an XhoI site (shown in bold) was added to the sense primer and a NotI site (shown in bold) was added to the antisense primer. The PCR-amplified fragment was digested with restriction endonucleases XhoI and NotI, gel purified and ligated into pPICZαA plasmid vector, available from Invitrogen, that had been digested by Xho I and Not I and gel purified, to produce recombinant molecule pPICZαA-nCaIL-$5_{348}$. The insert in the recombinant molecule was verified by DNA sequencing The recombinant molecule was used to transform Pichia pastoris strain X-33 by electroporation to produce recombinant cell Pichia-pPICZαA-nCaIL-$5_{348}$. Recombinant cell Pichia-pPICZαA-nCaIL-$5_{348}$ was cultured using techniques known to those skilled in the art and IL-5 expression was induced with methanol. The supernatant was recovered and submitted to SDS-PAGE. Silver staining of the resultant gel indicated a band of about 18 kDa only seen in the supernatant of Pichia transformed with recombinant molecule pPICZαA-nCaIL-$5_{348}$.

C. Bioactivity of Pichia-expressed Canine IL-5

The following describes a bioassay to detect the expression of canine IL-5 by stimulating the proliferation of TF-1 cells.

TF-1 cells, grown and maintained as described in Example 1E, were extensively washed to remove rhuGM-CSF, and then added at approximately $1\times10^4$ cells per well to 96-well flat bottom plates. Pichia-expressed canine IL-5, produced as described in Example 5B, was dialyzed overnight at 4° C. against Phosphate Buffered Saline, diluted to the appropriate concentration in TCM-TF-1 without rhuGM-CSF and filter sterilized. Cells and Pichia-produced canine IL-5 were incubated for 48 hours in 5% $CO_2$ at 37° C., then pulsed, incubated, harvested and counted as described in Example 1E. The results are shown in Table 5.

TABLE 5

Stimulation of proliferation of TF-1 with Pichia-expressed canine IL-5

| 1/dilution | Counts per minute |
|---|---|
| 2 | 44,885 |
| 4 | 101,564 |
| 8 | 81,161 |
| 16 | 59,384 |
| 32 | 40,508 |
| 64 | 15,948 |
| 128 | 6,634 |
| 256 | 2,441 |
| Media (no IL-5) | 172 |

Table 5 shows that canine IL-5 expressed by Pichia is biologically active, as demonstrated by its ability to stimulate proliferation of TF-1 cells.

Example 6

This example describes the isolation and sequencing of certain canine IL-13 nucleic acid molecules and proteins of the present invention. This example also describes expression of canine IL-13 in *E. coli* and bioactivity of such an expressed protein.

A. Isolation and Sequencing of Canine IL-13 Nucleic Acid Molecules and Proteins

A canine IL-13 cDNA nucleic acid molecule encoding a canine IL-13 protein was isolated by PCR amplification from a canine PBMC cDNA library (prepared as described in Example 1) using the following primers and PCR conditions: Degenerate oligonucleotide primers were designed in accordance with conserved regions of human and cat IL-5 gene sequences available in GenBank: sense primer, 5' GTCMTKGCTC TYRCTTGCCT TGG 3', denoted herein as SEQ ID NO:139; antisense primer 1, 5' AAASTGGGCY ACYTCGATTT TGG 3', denoted herein as SEQ ID NO:140; antisense primer 2, 5' GTGATGTTGM YCAGCTCCTC 3', denoted herein as SEQ ID NO:141, where M was either A or C, K was G or T, R was either A or G, S was either G or C, and Y was either T or C. PCR conditions used were as follows: One initial denaturation step at 95° C. for 3 minutes; then 38 cycles of the following: 94° C. for 30 seconds, 51.8° C. for 45 seconds, then 72° C. for 105 seconds; then a final extension at 72° C. for 5 minutes.

An about 272-nucleotide canine IL-13 nucleic acid molecule, denoted nCaIL-$13_{272}$ and having a coding strand represented by SEQ ID NO:89, was PCR amplified using primers having nucleic acid sequences of SEQ ID NO:139 and SEQ ID NO:140, respectively. An about 166-nucleotide canine IL-13 nucleic acid molecule, denoted nCaIL-$13_{166}$ and having a coding strand represented by SEQ ID NO:88, was isolated using primers having nucleic acid sequences of SEQ ID NO:142 (see Example 2B) and SEQ ID NO:141, respectively. Nucleic acid molecules nCaIL-$13_{272}$ and nCaIL-$13_{272}$ form a overlapping composite fragment of 383 nucleotides, denoted nCaIL-$13_{383}$. Two canine IL-13 specific primers (i.e., sense primer, 5' ATGGCGCTCT GGTTGACTGT 3', denoted herein as SEQ ID NO:143; and antisense primer, 5' GGCTTTTGAG AGCACAGTGC 3', denoted herein as SEQ ID NO:144) were derived from nCaIL-$13_{383}$ and were used to isolate a 278-nucleotide fragment, denoted nCaIL-$13_{278}$ and having a coding strand represented by SEQ ID NO:90. Nucleic acid molecule nCaIL-$13_{278}$ was radiolabeled and used to screen the canine PBMC cDNA library under the following hybridization conditions: hybridization took place in 6×SSC, 5×Denhardt's solution, 0.5% SDS, 100 $\mu$g/ml single stranded DNA, 100 $\mu$g/ml tRNA, for 36 hours at 60° C.; the final wash solution was 0.1% SDS, 0.125×SSC at 60° C. for 30 minutes. Two clones were selected, namely clone 80 and clone 78.

Sequence analysis of Clone 80 indicated that the clone includes an about 1302-nucleotide canine IL-13 nucleic acid molecule referred to herein as nCaIL-$13_{1302}$, the coding strand of which was shown to have nucleic acid sequence SEQ ID NO:91. The reverse complement of SEQ ID NO:91 is referred to herein as SEQ ID NO:93. Translation of SEQ ID NO:91 suggests that nucleic acid molecule n nCaIL-$13_{1302}$encodes an IL-13 protein of 131 amino acids, denoted herein as PCaIL-$13_{131}$, the amino acid sequence of which is presented in SEQ ID NO:92, assuming an open reading frame having an initiation codon spanning from nucleotide 52 through nucleotide 54 of SEQ ID NO:91 and a stop codon spanning from nucleotide 445 through nucleotide 447 of SEQ ID NO:91. The coding region encoding PCaIL-$13_{131}$, not including the termination codon, is presented herein as nCaIL-$13_{393}$, which has the nucleotide sequence SEQ ID NO:94 (the coding strand) and SEQ ID NO:95 (the complementary strand).

A putative signal sequence coding region extends from nucleotide 52 to nucleotide 111 of SEQ ID NO:91. The proposed mature protein, denoted herein as PCaIL-$13_{111}$, represented by SEQ ID NO:97, contains 111 amino acids, extending from residue 21 through residue 131 of SEQ ID NO:91. The nucleotide sequence encoding PCaIL-$13_{111}$, which extends from nucleotide 112 through nucleotide 444 of SEQ ID NO:91, is denoted herein as nucleic acid molecule nCaIL-$13_{333}$, represented by SEQ ID NO:96 (coding strand) and SEQ ID NO:98 (the complement strand).

Sequence analysis of Clone 78 indicated that the clone includes an about 1269-nucleotide canine IL-13 nucleic acid molecule referred to herein as nCaIL-$13_{1269}$, the coding strand of which was shown to have nucleic acid sequence SEQ ID NO:99. The reverse complement of SEQ ID NO:99 is referred to herein as SEQ ID NO:101. Translation of SEQ ID NO:99 suggests that nucleic acid molecule nCaIL-$13_{1269}$ encodes an IL-13 protein of 130 amino acids, denoted herein as PCaIL-$13_{130}$, the amino acid sequence of which is presented in SEQ ID NO:100, assuming an open reading frame having an initiation codon spanning from nucleotide 57 through nucleotide 59 of SEQ ID NO:99 and a stop codon spanning from nucleotide 447 through nucleotide 449 of SEQ ID NO:99. The coding region encoding PCaIL-$13_{130}$, not including the termination codon, is represented herein as nCaIL-$13_{390}$, which has the nucleotide sequence SEQ ID NO:102 (the coding strand) and SEQ ID NO:103 (the complementary strand). PCaIL-$13_{130}$ is missing one amino acid compared to PCaIL-$13_{133}$, namely amino acid position Q97 of PCaIL-$13_{133}$.

A putative signal sequence coding region extends from nucleotide 57 to nucleotide 116 of SEQ ID NO:99. The proposed mature protein, denoted herein as PCaIL-$13_{110}$, represented by SEQ ID NO:105, contains 110 amino acids, extending from residue 21 though residue 130 of SEQ ID NO:100. The nucleotide sequence encoding PCaIL-$13_{110}$, which extends from nucleotide 117 through nucleotide 446 of SEQ ID NO:99, is denoted herein as nucleic acid molecule nCaIL-$13_{330}$, represented by SEQ ID NO:104 (coding strand) and SEQ ID NO:106 (the complement strand).

Sequence analysis was performed with DNAsis™ using the alignment settings of: gap penalty set at 5; number of top diagonals set at 5; fixed gap penalty set at 10; k-tuple set at 2; window size set at 5 and floating gap penalty set at 10. At the amino acid level, PCaIL-$13_{131}$ shared 61.7%, 39.6%, 36.6% identity with the IL-13 proteins of human, mouse, and rat (Brown et al., *J. Immunol*., vol. 142, pp. 679–687, 1989; Lakkis et al., *Biochem. Biophys. Res. Commun*., Vol. 197, pp. 612–618, 1993; McKenzie et al., *Proc. Natl Acad. Sci. USA*, vol. 90, pp. 3735–3739, 1993; Minty et al., *Nature*, vol. 362, pp. 248–250, 1993), respectively. At the nucleotide level, nCaIL-$13_{1302}$ shared 56.0%, 57.1%, and 45.9% identity with the sequences of human, rat, and mouse IL-13 cDNAs, respectively.

B. Expression of Canine IL-13 in *E. coli*

This example describes the expression in *E. coli* of a canine IL-13 cDNA fragment, namely a canine IL-13 nucleic acid molecule denoted nCaIL-$13_{336}$, the coding strand of which consists of nucleotides 112–447 of SEQ ID NO:91, and as such, encodes a predicted mature canine IL-13 protein having SEQ ID NO:97. Nucleic acid molecule nCaIL-$13_{336}$ was PCR amplified from nCaIL-$13_{1302}$ using sense primer 5' CCCCATATGA GCCCTGTGAC TCCCTCCCC 3' denoted herein as SEQ ID:145, with nucleotides 10–29 corresponding to nucleotides 112–1131 of SEQ ID NO:91; and antisense primer 5' GGGGAATTCT CATCTGAAAT TTCCATGGCG 3', denoted herein as SEQ ID NO:146, with nucleotides 10–30 corresponding to the reverse complement of nucleotides 427–447 of SEQ ID NO:91. To facilitate cloning, an NdeI site (shown in bold) was added to the sense primer and an EcoRI site (shown in bold) was added to the antisense primer. The resulting PCR fragment was digested with restriction endonucleases NdeI and EcoRI, gel purified and ligated into λcro plasmid vector, the production of which is described in U.S. Pat. No. 5,569,603 by Tripp et al., issued Oct. 29, 1996, that had been digested by NdeI and EcoRI and gel purified to produce recombinant molecule pλcro-nCaIL-$13_{336}$. The insert in the recombinant molecule was verified by DNA sequencing. Recombinant molecule pλcro-nCaIL-$13_{336}$ was used to transform *E. coli* strain HCE101 (BL21), thereby producing BL21-pλcro-nCaIL-$13_{336}$. PCaIL-$13_{111}$ was produced under conditions as described in U.S. Pat. No. 5,569,603, ibid., protein expression being induced by switching the fermentation temperature from 32° C. to 42° C. SDS-PAGE and Commassie blue staining analysis indicated that a band of about 11 kD was only produced by induced BL21-pλcro-nCaIL-$13_{336}$ recombinant cells. The 11-kD band showed a positive reaction with a rabbit polyclonal antibody against human IL-13 (available from PeproTech Inc, Rocky Hill, N.J.), indicating expression of canine IL-13 in *E. coli.*

C. Bioactivity of *E. coli*-expressed Canine IL-13

The following describes a bioassay to detect the expression of canine IL-13 by stimulating the proliferation of TF-1 cells.

TF-1 cells, grown and maintained as described in Example 1E, were extensively washed to remove rhuGM- CSF, and then added at approximately $1\times10^4$ cells per well to 96-well flat bottom plates. *E. coli*-produced PCaIL-$13_{111}$, produced as described in Example 6B, was dialyzed overnight at 4° C. against Phosphate Buffered Saline, diluted to the appropriate concentration inTCM-TF-1 without rhuGM-CSF and filter sterilized. Cells and *E. coli*-produced PCaIL-$13_{111}$ were incubated for 48 hours in 5% $CO_2$ at 37° C., then pulsed, incubated, harvested and counted as described in Example 1E. The results are shown in Table 6.

TABLE 6

Stimulation of proliferation of TF-1 with *E. coli* PCaIL-$13_{111}$

| Concentration *E. coli* PCaIL-$13_{111}$ (ng/ml) | Counts per minute |
|---|---|
| 1000 | 126,203 |
| 500 | 77,893 |
| 250 | 57,781 |
| 125 | 40,491 |
| 62.5 | 26,115 |
| 31.3 | 7,042 |
| 15.6 | 8,713 |
| 0 | 991 |

Table 6 shows that canine IL-13 expressed by *E. coli* is biologically active, as demonstrated by its ability to stimulate proliferation of TF-1 cells.

Example 7

This example describes the isolation and sequencing of feline interferon alpha nucleic acid molecules and proteins of the present invention. This example also describes expression of feline interferon alpha proteins of the present invention in *E. coli* and mammalian cells as well as the bioactivities of the resulting proteins.

A. Isolation and Sequencing of Feline IFN-alpha Nucleic Acids and Proteins

Feline IFN-alpha nucleic acid molecules were PCR amplified from a feline cDNA library as follows. Total RNA was isolated from cat (kitten) mesenteric lymph node cells stimulated with PMA (phorbol myristate acetate) for 48 hours using Tri Reagent™ (available from Molecular Research Center, Cincinnati, Ohio). cDNA was made from the RNA using the cDNA synthesis kit containing Ready to Go -You Prime First-Strand Beads™ (available from Amersham Pharmacia Biotech, Piscataway, N.J.). An aliquot of this cDNA was used as a template to isolate a feline IFN-alpha nucleic acid molecule by PCR amplification using Amplitaq DNA polymerase™ (available from PE Applied Biosystems Inc, Foster City, Calif.) and the following primers and conditions. The sequence of the forward primer was 5' ATGGCGCTGC CCTCTTCCTT CTTG 3' (SEQ ID NO:143), and that of the reverse primer was 5' TCATTTCTCG CTCCTTAATC TTTTCTGC 3' (SEQ ID NO:148). The following PCR protocol was used: one initial denaturation step at 95° C. for 5 minutes; then 43 cycles of the following: 94° C. for 45 seconds, then 47° C. for 45 seconds, then 72° C. for 120 seconds; followed by a final extension at 72° C. for 7 minutes. PCR products were cloned into the TA cloning vector (available from Invitrogen Corporation) and the clones were sequenced using an ABI Prism™ Model 377 Automatic DNA Sequencer (available from PE Applied Biosystems Inc.). DNA sequencing reactions were performed using Prism™ dRhodamine Terminator Cycle Sequencing Ready Reaction kits (available from PE Applied Biosystems Inc.). Five PCR products were generated and sequenced. These products were included, respectively, in Clones #1, #2, #3, #5, and #6.

Clone #2 includes a feline IFN-alpha nucleic acid molecule that is represented herein as nFeIFN$\alpha_{567a}$, the coding strand of which was shown to have a nucleic acid sequence denoted herein as SEQ ID NO:107. The complement of SEQ ID NO:107 is represented herein by SEQ ID NO:109. Translation of SEQ ID NO:107 suggests that nFeIFN$\alpha_{567a}$ encodes a protein containing 189 amino acids, referred to herein as PFeIFN$\alpha_{189a}$, with an amino acid sequence denoted SEQ ID NO:108. The open reading frame of SEQ ID NO:107 is assumed to be the following: the first codon spans from nucleotide 1 through nucleotide 3 and the last codon before the stop codon spans from nucleotide 565 to nucleotide 567 of SEQ ID NO:107. The encoded protein has a predicted molecular weight of 21 kDa. The putative signal peptide cleavage site occurs between amino acid positions 23 and 24, based on homology with the human and canine interferon-alpha proteins. The proposed mature protein (i.e. feline IFNα protein from which the signal sequence has been cleaved), denoted herein as PFeIFN$\alpha_{166a}$, contains about 166 amino acids, extending from residue 24 to residue 166 of SEQ ID NO:108; the amino acid sequence is denoted herein as SEQ ID NO:114. The nucleic acid molecule encoding PFeIFN$\alpha_{166a}$ is denoted herein as nFeIFN$\alpha_{498a}$, the coding strand of which is represented by SEQ ID NO:113, and the complementary strand of which is represented by SEQ ID NO:115. A putative N-glycosylation site and an interferon alpha-beta-delta family signature motif are present at amino acid positions 102 and 145, respectively, of PfeIFN$\alpha_{189a}$.

Clone #3 includes a feline IFN-alpha nucleic acid molecule that is represented herein as nFeIFN$\alpha_{567b}$, the coding strand of which was shown to have a nucleic acid sequence denoted herein as SEQ ID NO:110. The complement of SEQ ID NO:110 is represented herein by SEQ ID NO:112. Translation of SEQ ID NO:110 suggests that nFeIFN$\alpha_{567b}$ encodes a protein containing 189 amino acids, referred to herein as PFeIFN$\alpha_{189b}$, with an amino acid sequence denoted SEQ ID NO:111. The open reading frame of SEQ ID NO:110 is assumed to be the following: the first codon spans from nucleotide 1 through nucleotide 3 and the last codon before the stop codon spans from nucleotide 565 through nucleotide 567 of SEQ ID NO:110. The encoded protein has a predicted molecular weight of 21 kDa. The putative signal peptide cleavage site occurs between amino acid positions 23 and 24, based on homology with the human and canine interferon-alpha proteins. The proposed mature protein (i.e. feline IFNα protein from which the signal sequence has been cleaved), denoted herein as PFeIFN$\alpha_{166b}$, contains about 166 amino acids, extending from residue 24 to residue 166 of SEQ ID NO:111; the amino acid sequence is denoted herein as SEQ ID NO:117. The nucleic acid molecule encoding PFeIFN$\alpha_{166b}$ is denoted herein as nFeIFN$\alpha_{498b}$, the coding strand of which is represented by SEQ ID NO:116, and complementary strand of which is represented by SEQ ID NO:118. A putative N-glycosylation site and an interferon alpha-beta-delta family signature motif are present at amino acid positions 102 and 145, respectively, of PFeIFN$\alpha_{189b}$.

Clone #1 includes a feline IFN-alpha nucleic acid molecule that is represented herein as nFeIFN$\alpha_{567c}$, the coding strand of which was shown to have a nucleic acid sequence denoted herein as SEQ ID NO:155. The complement of SEQ ID NO:155 is represented herein by SEQ ID NO:157. Translation of SEQ ID NO:155 suggests that nFeIFN$\alpha_{567c}$ encodes a protein containing 189 amino acids, referred to herein as PFeIFN$\alpha_{890c}$, with an amino acid sequence denoted SEQ ID NO:156. The open reading frame of SEQ ID NO:155 is assumed to be the following: the first codon spans from nucleotide 1 through nucleotide 3 and the last codon before the stop codon spans from nucleotide 565 to nucleotide 567 of SEQ ID NO:155. The encoded protein has a predicted molecular weight of 21 kDa. The putative signal peptide cleavage site occurs between amino acid positions 23 and 24, based on homology with the human and canine interferon-alpha proteins. The proposed mature protein (i.e. feline IFNa protein from which the signal sequence has been cleaved), denoted herein as PFeIFNa$_{166c}$, contains about 166 amino acids, extending from residue 24 to residue 166 of SEQ ID NO:156; the amino acid sequence is denoted herein as SEQ ID NO:159. The nucleic acid molecule encoding PFeIFNa$_{166c}$ is denoted herein as nFeIFNa$_{498c}$, the coding strand of which is represented by SEQ ID NO:158, and the complementary strand of which is represented by SEQ ID NO:160. A putative N-glycosylation site and an interferon alpha-beta-delta family signature motif are present at amino acid positions 102 and 145, respectively, of PfeIFNa$_{189c}$.

Clone #5 includes a feline IFN-alpha nucleic acid molecule that is represented herein as nFeIFNa$_{582d}$, the coding strand of which was shown to have a nucleic acid sequence denoted herein as SEQ ID NO:161. The complement of SEQ ID NO:161 is represented herein by SEQ ID NO:163. Translation of SEQ ID NO:161 suggests that nFeIFNa$_{582d}$ encodes a protein containing 194 amino acids, referred to herein as PFeIFNa$_{194d}$, with an amino acid sequence denoted SEQ ID NO:162. The open reading frame of SEQ ID NO:161 is assumed to be the following: the first codon spans from nucleotide 1 through nucleotide 3 and the last codon before the stop codon spans from nucleotide 580 through nucleotide 582 of SEQ ID NO:161. The encoded protein has a predicted molecular weight of 21.5 kDa. The putative signal peptide cleavage site occurs between amino acid positions 23 and 24, based on homology with the human and canine interferon-alpha proteins. The proposed mature protein (i.e. feline IFNa protein from which the signal sequence has been cleaved), denoted herein as PFeIFNa$_{171d}$, contains about 171 amino acids, extending from residue 24 to residue 171 of SEQ ID NO:162; the amino acid sequence is denoted herein as SEQ ID NO:165. The nucleic acid molecule encoding PFeIFNa$_{171d}$ is denoted herein as nFeIFNa$_{513d}$, the coding strand of which is represented by SEQ ID NO:164, and the complementary strand of which is represented by SEQ ID NO:166. A putative N-glycosylation site and an interferon alpha-beta-delta family signature motif are present at amino acid positions 102 and 145, respectively, of PFeIFNa$_{194d}$.

Clone #6 includes a feline IFN-alpha nucleic acid molecule that is represented herein as nFeIFNa$_{567e}$, the coding strand of which was shown to have a nucleic acid sequence denoted herein as SEQ ID NO:167. The complement of SEQ ID NO:167 is represented herein by SEQ ID NO:169. Translation of SEQ ID NO:167 suggests that nFeIFNa$_{567e}$ encodes a protein containing 189 amino acids, referred to herein as PFeIFNa$_{189e}$, with an amino acid sequence denoted SEQ ID NO:168. The open reading frame of SEQ ID NO:167 is assumed to be the following: the first codon spans from nucleotide 1 through nucleotide 3 and the last codon before the stop codon spans from nucleotide 565 to nucleotide 567 of SEQ ID NO:167. The encoded protein has a predicted molecular weight of 21 kDa. The putative signal peptide cleavage site occurs between amino acid positions 23 and 24, based on homology with the human and canine interferon-alpha proteins. The proposed mature protein (i.e. feline IFNa protein from which the signal sequence has been cleaved), denoted herein as PFeIFNa$_{166e}$, contains about 166 amino acids, extending from residue 24 to residue 166 of SEQ ID NO:167; the amino acid sequence is denoted herein as SEQ ID NO:171. The nucleic acid molecule encoding PFeIFNa$_{166e}$ is denoted herein as nFeIFNa$_{498e}$, the coding strand of which is represented by SEQ ID NO:170, and the complementary strand of which is represented by SEQ ID NO:172. A putative N-glycosylation site and an interferon alpha-beta-delta family signature motif are present at amino acid positions 102 and 145, respectively, of PfeIFNa$_{189e}$.

Comparison of the nucleic acid sequences of the five feline IFN-alpha nucleic acid molecules of the present invention indicated that the sequences, while being very similar (i.e., encoded proteins sharing from about 96% to 99% identity), exhibited several differences. The differences in nucleic acid sequences and deduced amino acid sequences are summarized in Table 7. The left hand column indicates the change at the nucleotide or amino acid level, as appropriate, and the "X"s in the other columns indicate which clones include such changes. For example, feline IFN-alpha protein PfeIFNa$_{194d}$ (having SEQ ID NO:161) has five extra amino acids (namely IHPED) inserted at position at 139 as compared to feline IFN-alpha proteins PfeIFNa$_{189a}$ (SEQ ID NO:108), PfeIFNa$_{189b}$ (SEQ ID NO:111), PfeIFNa$_{189c}$ (SEQ ID NO:155) or PfeIFNa$_{189e}$ (SEQ ID NO:167). Other variations, i.e., nucleotide substitutions, some of which lead to amino acid variations, are also indicated in Table 7.

TABLE 7

Comparison of feline IFN-alpha nucleic acid molecules and proteins

| Amino acid Changes | Clone #1 | Clone #2 | Clone #3 | Clone #5 | Clone #6 |
|---|---|---|---|---|---|
| 5 amino acid deletion | X | X | X | | X |
| $S_{18}$ to $S_{18}$ (TCC to TCT) | | | | | X |
| $C_{52}$ to $C_{52}$ (TGT to TGC) | | | | | X |
| $R_{56}$ to $R_{56}$ (AGA to AGG) | | | X | | |
| $N_{57}$ to $S_{57}$ (AAT to AGT) | X | | | X | |
| $F_{66}$ to $F_{66}$ (TTC to TTT) | X | X | | | |
| $A_{74}$ to $A_{74}$ (GCC to GCT) | | | X | | |
| $K_{86}$ to $E_{86}$ (AAG to GAG) | | | X | | |
| $R_{115}$ to $W_{115}$ (CGG to TGG) | X | X | | | |
| $L_{125}$ to $V_{125}$ (CTG to GTG) | | | X | X | X |
| $L_{125}$ to $M_{125}$ (CTG to ATG) | X | X | | | |
| $L_{135}$ to $L_{135}$ (CTG to CTC) | X | X | X | | X |
| $I_{141}$ to $L_{141}$ (ATC to CTC) | | | X | | |

Feline IFN-alpha proteins of the present invention PFeIFNα$_{189a}$, PfeIFNα$_{189b}$, PFeIFNα$_{189c}$, and PFeIFN$\alpha_{189e}$ are five amino acids shorter than the GenBank entry for feline IFN-omega, accession #E02521, while IFN-alpha protein PFeIFN$\alpha_{194d}$ of the present invention has the same number of amino acids as the feline IFN-omega reported in GenBank. In addition, there are: 3 non-conservative and 2 conservative changes at the amino acid level between this GenBank entry and SEQ ID NO:108 (PFeIFN$\alpha_{189a}$); 4 non-conservative and 3 conservative changes at the amino acid level between this GenBank entry and SEQ ID NO:111 (PfeIFN$\alpha_{189b}$); 4 non-conservative and 3 conservative changes at the amino acid level between this GenBank entry and SEQ ID NO:156 (PFeIFNa$_{189c}$); 2 non-conservative and 2 conservative changes at the amino acid level between this GenBank entry and SEQ ID NO:162 (PfeIFNa$_{194d}$; and 1 non-conservative and 5 conservative changes at the amino acid level between this GenBank entry and SEQ ID NO:168 (PFeIFNa$_{189e}$).

The lengths of SEQ ID NO:108 and SEQ ID NO:111, when compared with those of IFN-alpha proteins of other species, are two amino acids longer than published canine interferon-alpha subtype 1, 2 and 3 sequences, two amino acids longer than published human interferon-alpha type 1,B,D, F, and J sequences, three amino acids longer than the published human interferon-alpha sequence type A sequence and two amino acids longer than published murine interferon-alpha type B, 8, 7, 11, and 19 sequences. The lengths of SEQ ID NO:156 and SEQ ID NO:168, when compared with those of IFN-alpha proteins of other species, are two amino acids longer than published canine interferon-alpha subtype 1, 2 and 3 sequences, two amino acids longer than published human interferon-alpha type 1,B,D, F, and J sequences, three amino acids longer than the published human interferon-alpha sequence type A sequence and two amino acids longer than published murine interferon-alpha type B, 8, 7, 11, and 19 sequences. The length of SEQ ID NO:162, when compared with those of IFN-alpha proteins of other species, are seven amino acids longer than published canine interferon-alpha subtype 1, 2 and 3 sequences, seven amino acids longer than published human interferon-alpha type 1,B,D, F, and J sequences, eight amino acids longer than the published human interferon-alpha sequence type A sequence and seven amino acids longer than published murine interferon-alpha type B, 8, 7, 11, and 19 sequences.

B. Expression of Feline IFN-alpha Proteins in Mammalian Cells

This example describes the expression of the feline IFN-alpha proteins of the present invention in Chinese hamster ovary (CHO) cells.

Feline IFN-alpha nucleic acid molecule PCR products were amplified from nFeIFN$\alpha_{567a}$, nFeIFN$\alpha_{567b}$, nFeIFN$\alpha_{567c}$, nFeIFN$\alpha_{582d}$, and nFeIFN$\alpha_{567e}$ using Pfu DNA polymerase™ (available from Stratagene, La Jolla, Calif.) and the following primers and conditions. The sequence of the forward primer was 5' ATTAGGATCC ATGGCGCTGC CCTCTTCCT 3' (SEQ ID NO:173), and that of the reverse primer was 5' GCCTCTAGAC TGT-CATTTCT CGCTCCTTAA TCTTTTCTGC 3' (SEQ ID NO:174). The following PCR protocol was used: one initial denaturation step at 95° C. for 5 minutes; then 30 cycles of the following: 94° C. for 30 seconds, then 50° C. for 30 seconds, then 72° C. for 90 seconds; followed by a final extension at 72° C. for 7 minutes.

Each of the five PCR products was ligated into a CMV-Int A-kan+(amp) expression vector using techniques similar to those described in Example 1Bii to produce recombinant molecules in which feline IFN-alpha nucleic acid molecules were operatively linked to transcription control sequences. It is to be noted that CMV-Int A-kan$^+$(amp) vector is similar to the pCMV-Int A plasmid vector described in Example 1Bii except that the ampicillin resistance gene open reading frame has been disrupted by the insertion of the kanamycin resistance gene. The feline IFN-alpha nucleic acid molecules in the recombinant molecules were sequenced using an ABI Prism™ Model 377 Automatic DNA Sequencer (available from PE Applied Biosystems Inc.). DNA sequencing reactions were performed using Prism™ dRhodamine Terminator Cycle Sequencing Ready Reaction kits (available from PE Applied Biosystems Inc.). The sequence data indicated that there was no changes introduced during the PCR amplification or ligation in any of the nucleic acid molecules.

Using techniques similar to those described elsewhere herein, CHO cells were transiently transfected with each of the five recombinant molecules encoding a subtype of feline IFN-alpha protein using Lipofectamine™ (available from Life technologies, Inc.) resulting in recombinant cells expressing feline IFN-alpha subtype proteins of the present invention. The cells and culture supernatants were harvested 48 hours later and Western analysis was done using both pellets and the supernatants from each transfection. The detecting antibody was an anti-human IFN-alpha-A antibody (available from Accurate Chemical and Scientific Corporation, Westbury, N.Y.). The Western analysis indicated that each of the five feline IFN-alpha nucleic acid molecule-containing recombinant cells expressed a corresponding feline IFN-alpha subtype protein which was secreted into the tissue culture supernatant and recognized by the antibody against human IFN-alpha-A. The migration patterns of each of the CHO cell-expressed feline IFN-alpha subtype proteins suggested that each of the proteins is glycosylated.

C. Bioactivity of Mammalian-expressed Feline-IFN Alpha Proteins (i) The antiviral activity of the five CHO-expressed feline IFN-alpha subtype proteins, produced as described in Example 7B, was tested using the following protocol: Crandell feline kidney (CRFK) cells were treated for 24 hours, using procedures known to those skilled in the art, with or without IFN-alpha tissue culture supernatants, produced as described in Example 7B. The cells were then infected with feline calicivirus and cytopathic effects induced by the virus were assessed 12 to 14 hours later using techniques known to those skilled in the art. The cell layers were fixed in methanol, stained with crystal violet and examined under the microscope or processed for the MTT (3-[4,5-dimethylthiazol-2-yl]-2,5-diphenyltetrazolium bromide) assay. The MTT assay was conducted as follows. After viral infection, the infected cells were washed with PBS. A volume of MTT stock solution (5 mg/ml in PBS) equal to one-tenth of the original culture volume was added to each well being assayed and incubated at 37° C. for 3 to 4 hr. The MTT solution was removed, and acidified isopropanol ( ). 1 N HCl in absolute isopropanol) was added to the wells to solubilize the converted dye. The absorbance of the converted dye was measured at 570 nm using a plate reader. Each of the five IFN-alpha subtype proteins demonstrated anti-viral activity. Pre-treatment with any of the subtypes of IFN-alpha proteins of the present invention resulted in significant reduction in the virus-induced cytopathic effect.

(ii) The CHO cell-expressed feline IFN-alpha subtype proteins were also tested for their ability to inhibit granulocyte-macrophage colony stimulating factor-induced proliferation of TF-1 cells using an assay similar to that described in Example 1E, but with the following modification:. For the assay, the cells were washed and TCM-TF-1 medium containing a suboptimal amount of GM-CSF (i.e., 0.4 ng/ml) was added along with the appropriate dilutions of the designated IFN-alpha proteins. The results are shown in Table 8 for feline IFN-alpha proteins expressed as described in Example 7B, lanes labeled Clone #1, Clone #2, Clone #3, Clone #5 and Clone #6, respectively; supernatant from a culture of CHO cells transfected with only the vector described in Example 7B, lane labeled vector; *E. coli*-expressed feline IFN-alpha protein PFeIFNa$_{166e}$ produced as described in Example 7D, lane labeled *E. coli*-expressed; and recombinant human IFN-alpha, lane labeled human IFN-alpha. Media alone gave a reading of 128 and recombinant GM-CSF alone gave a reading of 96080.

TABLE 8

Inhibition of TF-1 cell production by CHO cell-expressed feline IFN-alpha proteins

| Dilution | Clone #1 | Clone #2 | Clone #3 | Clone #5 | Clone #6 | Vector | *E. coli* expressed | Human IFN alpha |
|---|---|---|---|---|---|---|---|---|
| 2 | 15077 | 7914 | 21173 | 15218 | 13256 | 53585 | 19541 | 559 |
| 4 | 18318 | 23515 | 41488 | 43449 | 31618 | 64722 | 56315 | 10412 |
| 8 | 22484 | 25823 | 48487 | 40438 | 43896 | 83092 | 80646 | 21710 |
| 16 | 42138 | 34274 | 72145 | 66266 | 48775 | 102423 | 97255 | 23585 |
| 32 | 81248 | 52847 | 63264 | 95256 | | | | |
| 64 | 74613 | 43848 | 58533 | 88172 | 70596 | 141821 | 129556 | 45907 |
| 128 | 59360 | 48901 | 48701 | 54623 | 90092 | 155960 | 151946 | 40402 |
| 256 | 75788 | 54017 | 37391 | 59849 | 83022 | 119491 | 123794 | 39299 |

Table 8 demonstrates that CHO cell-expressed and *E. coli*-expressed feline IFN-alpha subtype proteins inhibited granulocyte-macrophage colony stimulating factor-induced proliferation of TF-1 cells.

D. Expression of Feline IFN-alpha in *E. coli* and Bioactivity Thereof

The nucleic acid molecule encoding the mature feline IFN-alpha protein having SEQ ID NO:171 was ligated into the λcro plasmid vector, using techniques as described in Example 6B, to produce recombinant molecule pλcro-nFeIFNa$_{498e}$. The recombinant molecule was transformed into *E. coli*, using techniques similar to those described in Example 6B to produce recombinant cell *E. coli*:pλcro-nFeIFNa$_{498e}$. The recombinant cell was grown and induced as described in Example 6B. The resulting feline IFN-alpha protein, *E. coli*-expressed PFeIFNa$_{166e}$. which was expressed as an insoluble form, was solubilized using urea and DTT and refolded using techniques known to those skilled in the art. The refolded *E. coli*-expressed feline IFN-alpha protein PFeIFNa$_{166e}$ when tested for antiviral activity as described in Example 7C was found to have significant antiviral activity.

Example 8

This example describes the isolation and sequencing of feline granulocyte-macrophage colony-stimulating factor (GMCSF) nucleic acid molecules and proteins of the present invention. This example also describes expression of a feline GMCSF protein of the present invention.

Nucleic acid molecules encoding feline GMCSF were isolated as follows. A cDNA library was prepared from feline PBMCs stimulated with Con A for 12 hours, as previously described in Example 2. An aliquot of this library was used as a template to amplify feline GMCSF nucleic acid molecules by PCR using Amplitaq DNA polymerase ™ (PE Applied Biosystems Inc, Foster City, Calif.) and the following primers and conditions The sequence of the forward primer was 5' CAGGGATCCA CCATGTGGCT GCAGAACCTG CTTTTCC 3' (SEQ ID NO:149), and that of the reverse primer was 5' TTACTTCTGG TCTGGTCCCC AGCAGTCAAA GGGGTTGTTA AACAGAAAAT 3' (SEQ ID NO:150). The following PCR protocol was used: one initial denaturation step at 95° C. for 5 minutes; then 35 cycles of the following: 94° C. for 30 seconds, then 50° C. for 30 seconds, then 72° C. for 90 seconds; followed by a final extension at 72° C. for 7 minutes. PCR products were cloned into the CMV-Intron A vector and the clones were sequenced as described in Example 7.

A PCR product was isolated, referred to herein as nFeGMCSF$_{444}$, the coding strand of which is represented herein as SEQ ID NO:119, and its complement is denoted SEQ ID NO:121. Translation of the open reading frame in SEQ ID NO:119 suggests that nucleic acid molecule nFeGMCSF$_{444}$ encodes a protein containing 144 amino acids, referred to herein as PFeGMCSF$_{144}$, with an amino acid sequence denoted SEQ ID NO:120, assuming an open reading frame in which the first codon spans from nucleotide 10 through nucleotide 12 of SEQ ID NO:119, and the stop codon spans from nucleotide 442 through nucleotide 444 of SEQ ID NO:121. The encoded protein has a predicted molecular weight of 16 kDa. The coding region encoding PFeGMCSF$_{144}$ is presented herein as nFeGMCSF$_{432}$ which has the nucleotide sequence SEQ ID NO:122 (the coding strand) and SEQ ID NO:123 (the complementary strand). A putative signal peptide cleavage site is between amino acid positions 17 and 18, based on homology with human, mouse and ovine GMCSF proteins. The nucleic acid molecule encoding the proposed mature protein is denoted as nFeGMCSF$_{381}$ and has a nucleotide sequence represented herein as SEQ ID NO:124 and a complementary sequence represented herein as SEQ ID NO:126. The amino acid sequence of the putative mature protein, referred to herein as PFeGMCSF$_{127}$ has an amino acid sequence represented herein as SEQ ID NO:125. The number of amino acids in the feline GMCSF protein is the same compared to human, porcine, ovine and canine GMCSF proteins. The feline GMCSF protein is one amino acid longer than bovine GMCSF and three amino acid longer than murine GMCSF.

The deduced amino acid sequence of the full-length feline GMCSF protein of the present invention has four non-conservative changes and one conservative change compared to a GenBank entry for feline GMCSF (accession # AF053007). Amino acids asparagine, methionine, threonine, and lysine at positions 10, 36, 56 and 126 of the GenBank entry have been changed to glycine, isoluecine, alanine and asparagine, respectively, in PfeGMCSF$_{144}$. PFeGMCSF$_{144}$, containing the above-noted amino acid substitutions, appears to have GMCSF activity, as demonstrated by an experiment in which supernatant collected from Chinese Hamster Ovary (CHO) cells that were transiently transfected with a recombinant molecule encoding a feline GMCSF protein of the present invention was able to induce proliferation of TF-1 cells.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated protein selected from the group consisting of:

(a) an isolated protein of at least about 20 amino acids in length, wherein said 20 amino acids are encoded by a nucleic acid molecule that has an at least 60 contiguous nucleotide region identical in sequence to a 60 contiguous nucleotide region of a nucleic acid sequence selected from the group consisting of SEQ ID NO:88, SEQ ID NO:89, SEQ ID NO:90, SEQ ID NO:91, SEQ ID NO:94, SEQ ID NO:96, SEQ ID NO:99, SEQ ID NO:102, and SEQ ID NO:104; and (b) an isolated protein of at least about 20 amino acids in length, wherein said protein has an at least 20 contiguous amino acid region identical in sequence to a 20 contiguous amino acid region selected from the group consisting of SEQ ID NO:92, SEQ ID NO:97, SEQ ID NO:100, and SEQ ID NO:105, wherein said isolated protein of (a) or (b) elicits an immune response against a canine IL-13 protein or has IL-13 activity.

2. The isolated protein of claim 1, wherein said protein has an amino acid sequence selected from the group consisting of SEQ ID NO:92, SEQ ID NO:97, SEQ ID NO:100, and SEQ ID NO:105.

3. The isolated protein of claim 2, wherein the protein has the amino acid sequence of SEQ ID NO:92.

4. The isolated protein of claim 2, wherein the protein has the amino acid sequence of SEQ ID NO:97.

5. The isolated protein of claim 2, wherein the protein has the amino acid sequence of SEQ ID NO:100.

6. The isolated protein of claim 2, wherein the protein has the amino acid sequence of SEQ ID NO:105.

7. An isolated protein having an amino acid sequence that is at least about 85 percent identical to an amino acid sequence selected from the group consisting of SEQ ID NO:92, SEQ ID NO:97, SEQ ID NO:100, and SEQ ID NO:105, wherein said isolated protein elicits an immune response against a canine IL-13 protein or has IL-13 activity.

8. A therapeutic composition comprising the isolated protein of claim 1.

9. The composition of claim 8, wherein said composition further comprises a component selected from the group consisting of an excipient, an adjuvant and a carrier.

10. A method to regulate an immune response in an animal comprising administering to the animal the therapeutic composition of claim 8.

11. The method of claim 10, wherein said animal is a canid.

12. The method of claim 10, wherein said composition further comprises a component selected from the group consisting of an excipient, an adjuvant and a carrier.

* * * * *

UNITED STATES PATENT AND TRADEMARK OFFICE

CERTIFICATE OF CORRECTION

PATENT NO. : 6,482,403 B1
DATED : November 19, 2002
INVENTOR(S) : Gek-Kee Sim et al.

It is certified that error appears in the above-identified patent and that said Letters Patent is hereby corrected as shown below:

Title page,
Item [54], Title, please delete "CANINEY" and replace with -- CANINE --.

Signed and Sealed this

Thirty-first Day of August, 2004

JON W. DUDAS
*Director of the United States Patent and Trademark Office*